US012655474B2

(12) United States Patent  (10) Patent No.: US 12,655,474 B2
Wang et al.  (45) Date of Patent:  Jun. 16, 2026

(54) SPATIOTEMPORALLY RESOLVED TRANSCRIPTOMICS AT SUBCELLULAR RESOLUTION

(71) Applicants: The Broad Institute, Inc., Cambridge, MA (US); Massachusetts Institute of Technology, Cambridge, MA (US)

(72) Inventors: Xiao Wang, Cambridge, MA (US); Jingyi Ren, Cambridge, MA (US); Hu Zeng, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 409 days.

(21) Appl. No.: 18/559,322

(22) PCT Filed: May 6, 2022

(86) PCT No.: PCT/US2022/028012
§ 371 (c)(1),
(2) Date: Nov. 6, 2023

(87) PCT Pub. No.: WO2022/236011
PCT Pub. Date: Nov. 10, 2022

(65) Prior Publication Data
US 2024/0254545 A1  Aug. 1, 2024

Related U.S. Application Data

(60) Provisional application No. 63/314,873, filed on Feb. 28, 2022, provisional application No. 63/185,511, filed on May 7, 2021.

(51) Int. Cl.
| | |
|---|---|
| *C12Q 1/6841* | (2018.01) |
| *C12N 15/10* | (2006.01) |
| *C12Q 1/6876* | (2018.01) |
| *G01N 21/64* | (2006.01) |

(52) U.S. Cl.
CPC ....... *C12Q 1/6841* (2013.01); *C12N 15/1093* (2013.01); *C12Q 1/6876* (2013.01); *G01N 21/6458* (2013.01); *G01N 21/6486* (2013.01); *C12Q 2600/118* (2013.01); *C12Q 2600/136* (2013.01)

(58) Field of Classification Search
CPC ............... C12Q 1/6841; C12Q 1/6876; C12Q 2600/118; C12Q 2600/136; C12Q 2523/109; C12Q 2525/117; C12Q 2525/307; C12Q 2531/125; C12Q 2563/185; C12N 15/1093; G01N 21/6458; G01N 21/6486
See application file for complete search history.

(56) References Cited

U.S. PATENT DOCUMENTS

| | | | |
|---|---|---|---|
| 3,687,808 | A | 8/1972 | Merigan, Jr. et al. |
| 4,318,846 | A | 3/1982 | Khanna et al. |
| 4,663,161 | A | 5/1987 | Mannino et al. |
| 4,757,141 | A | 7/1988 | Fung et al. |
| 4,797,368 | A | 1/1989 | Carter et al. |
| 4,849,336 | A | 7/1989 | Miyoshi et al. |
| 4,871,488 | A | 10/1989 | Mannino et al. |
| 4,945,050 | A | 7/1990 | Sanford et al. |
| 4,946,778 | A | 8/1990 | Ladner et al. |
| 5,034,506 | A | 7/1991 | Summerton et al. |
| 5,036,006 | A | 7/1991 | Sanford et al. |
| 5,066,580 | A | 11/1991 | Lee |
| 5,067,805 | A | 11/1991 | Corle et al. |
| 5,091,519 | A | 2/1992 | Morrison et al. |
| 5,100,792 | A | 3/1992 | Sanford et al. |
| 5,135,855 | A | 8/1992 | Moss et al. |

(Continued)

FOREIGN PATENT DOCUMENTS

| | | |
|---|---|---|
| CN | 110933725 A | 3/2020 |
| EP | 2 270 205 A2 | 1/2011 |

(Continued)

OTHER PUBLICATIONS

Alpert, N.M et al., "The principal axes transformation—a method for image registration," Journal of nuclear Medicine: official publication, Society of Nuclear Medicine, 1990, vol. 31, No. 10 (pp. 1717-1722).
Asp, et al., "Spatially Resolved Transcriptomes—Next Generation Tools for Tissue Exploration," BioEssays. Oct. 2020, vol. 42, No. 10 (pp. 1-16).
Avey, et al., "Single-cell RNA-seq uncovers a robust transcriptional response to morphine by glia," Cell Reports, Sep. 2018, vol. 24, No. 13 (pp. 3619-3629, e1-e4).
Bagasra, Omar, "Protocols for the in situ PCR-amplification and detection of mRNA and DNA sequences," Nature Protocols, Nov. 2007, vol. 2, No. 11 (pp. 2782-2795).

(Continued)

*Primary Examiner* — Cynthia B Wilder
(74) *Attorney, Agent, or Firm* — Foley & Lardner LLP; Sunit Talapatra

(57) ABSTRACT

The present disclosure provides methods for profiling spatiotemporal gene expression, including methods for profiling spatiotemporal gene expression in vivo in a subject. The present disclosure also provides methods for profiling the role of post-transcriptional modification in spatiotemporal gene expression, methods for studying the role of spatiotemporal gene expression in the development or progression of a disease or disorder, methods for screening for an agent capable of modulating spatiotemporal gene expression, methods for diagnosing a disease or disorder in a subject, and methods for treating a disease or disorder in a subject. Oligonucleotide probes useful in the methods described herein are also provided by the present disclosure. The present disclosure also provide kits comprising the oligonucleotide probes disclosed herein. Systems for profiling spatiotemporal gene expression are also provided by the present disclosure.

20 Claims, 66 Drawing Sheets

(56) References Cited

U.S. PATENT DOCUMENTS

| | | | |
|---|---|---|---|
| 5,139,941 | A | 8/1992 | Muzyczka et al. |
| 5,151,507 | A | 9/1992 | Hobbs et al. |
| 5,173,414 | A | 12/1992 | Lebkowski et al. |
| 5,179,022 | A | 1/1993 | Sanford et al. |
| 5,188,934 | A | 2/1993 | Menchen et al. |
| 5,198,537 | A | 3/1993 | Huber et al. |
| 5,219,740 | A | 6/1993 | Miller et al. |
| 5,344,757 | A | 9/1994 | Holtke et al. |
| 5,354,657 | A | 10/1994 | Holtke et al. |
| 5,366,860 | A | 11/1994 | Bergot et al. |
| 5,371,015 | A | 12/1994 | Sanford et al. |
| 5,387,742 | A | 2/1995 | Cordell |
| 5,399,346 | A | 3/1995 | Anderson et al. |
| 5,478,744 | A | 12/1995 | Sanford et al. |
| 5,489,677 | A | 2/1996 | Sanghvi et al. |
| 5,535,052 | A | 7/1996 | Jorgens |
| 5,538,871 | A | 7/1996 | Nuovo et al. |
| 5,539,082 | A | 7/1996 | Nielsen et al. |
| 5,580,859 | A | 12/1996 | Felgner et al. |
| 5,589,466 | A | 12/1996 | Felgner et al. |
| 5,602,240 | A | 2/1997 | De Mesmaeker et al. |
| 5,612,818 | A | 3/1997 | Kumagai et al. |
| 5,619,371 | A | 4/1997 | Pontius |
| 5,676,950 | A | 10/1997 | Small et al. |
| 5,688,648 | A | 11/1997 | Mathies et al. |
| 5,702,888 | A | 12/1997 | Holtke et al. |
| 5,714,331 | A | 2/1998 | Buchardt et al. |
| 5,719,262 | A | 2/1998 | Buchardt et al. |
| 5,789,245 | A | 8/1998 | Dubensky et al. |
| 5,831,005 | A | 11/1998 | Zuckerman et al. |
| 5,843,723 | A | 12/1998 | Dubensky et al. |
| 5,847,162 | A | 12/1998 | Lee et al. |
| 5,990,479 | A | 11/1999 | Weiss et al. |
| 6,054,274 | A | 4/2000 | Sampson et al. |
| 6,094,300 | A | 7/2000 | Kashima et al. |
| 6,207,392 | B1 | 3/2001 | Weiss et al. |
| 6,235,502 | B1 | 5/2001 | Weissman et al. |
| 6,251,303 | B1 | 6/2001 | Bawendi et al. |
| 6,291,187 | B1 | 9/2001 | Kingsmore et al. |
| 6,300,093 | B1 | 10/2001 | Kindsvogel et al. |
| 6,316,229 | B1 | 11/2001 | Lizardi et al. |
| 6,319,426 | B1 | 11/2001 | Bawendi et al. |
| 6,322,901 | B1 | 11/2001 | Bawendi et al. |
| 6,323,009 | B1 | 11/2001 | Lasken et al. |
| 6,344,329 | B1 | 2/2002 | Lizardi |
| 6,368,801 | B1 | 4/2002 | Faruqi |
| 6,423,551 | B1 | 7/2002 | Weiss et al. |
| 6,426,513 | B1 | 7/2002 | Bawendi et al. |
| 6,444,143 | B2 | 9/2002 | Bawendi et al. |
| 6,444,661 | B1 | 9/2002 | Barton et al. |
| 6,558,928 | B1 | 5/2003 | Landegren |
| 6,566,118 | B1 | 5/2003 | Atkinson et al. |
| 6,576,291 | B2 | 6/2003 | Bawendi et al. |
| 6,596,535 | B1 | 7/2003 | Carter |
| 6,649,811 | B2 | 11/2003 | Pasinetti |
| 6,989,264 | B2 | 1/2006 | Atkinson et al. |
| 6,995,006 | B2 | 2/2006 | Atkinson et al. |
| 7,057,026 | B2 | 6/2006 | Barnes et al. |
| 7,335,898 | B2 | 2/2008 | Donders et al. |
| 7,399,845 | B2 | 7/2008 | Seth et al. |
| 7,479,630 | B2 | 1/2009 | Bandura et al. |
| 7,569,686 | B1 | 8/2009 | Bhat et al. |
| 7,632,679 | B2 | 12/2009 | Jessel et al. |
| 7,993,895 | B2 | 8/2011 | Eid et al. |
| 8,497,069 | B2 | 7/2013 | Hutchison, III et al. |
| 8,834,546 | B2 | 9/2014 | Deisseroth et al. |
| 9,175,095 | B2 | 11/2015 | Deisseroth et al. |
| 9,279,973 | B2 | 3/2016 | Takaya |
| 9,359,449 | B2 | 6/2016 | Deisseroth et al. |
| 9,365,628 | B2 | 6/2016 | Deisseroth et al. |
| 9,376,717 | B2 | 6/2016 | Gao et al. |
| 9,423,601 | B2 | 8/2016 | Toda et al. |
| 9,458,208 | B2 | 10/2016 | Deisseroth et al. |
| 9,791,409 | B2 | 10/2017 | Gordon et al. |
| 9,969,783 | B2 | 5/2018 | Deisseroth et al. |
| 10,000,796 | B2 | 6/2018 | Samusik et al. |
| 10,006,082 | B2 | 6/2018 | Samusik et al. |
| 10,052,383 | B2 | 8/2018 | Deisseroth et al. |
| 10,073,259 | B2 | 9/2018 | Garsha et al. |
| 10,138,509 | B2 | 11/2018 | Church et al. |
| 10,196,431 | B2 | 2/2019 | Deisseroth et al. |
| 10,220,092 | B2 | 3/2019 | Deisseroth et al. |
| 10,227,639 | B2 | 3/2019 | Levner et al. |
| 10,266,888 | B2 | 4/2019 | Daugharthy et al. |
| 10,323,272 | B1 | 6/2019 | Rabbani et al. |
| 10,364,457 | B2 | 7/2019 | Wassie et al. |
| 10,445,894 | B2 | 10/2019 | Watanabe et al. |
| 10,478,499 | B2 | 11/2019 | Deisseroth et al. |
| 10,568,307 | B2 | 2/2020 | Deisseroth et al. |
| 10,568,516 | B2 | 2/2020 | Yang et al. |
| 10,583,309 | B2 | 3/2020 | Deisseroth et al. |
| 10,590,484 | B2 | 3/2020 | Korlach et al. |
| RE47,983 | E | 5/2020 | Gao et al. |
| 10,787,701 | B2 | 9/2020 | Chee |
| 10,829,814 | B2 | 11/2020 | Fan et al. |
| 11,008,608 | B2 | 5/2021 | Samusik et al. |
| 11,085,072 | B2 | 8/2021 | Church et al. |
| 11,098,303 | B2 | 8/2021 | Zhuang et al. |
| 11,111,521 | B2 | 9/2021 | Church et al. |
| 11,168,350 | B2 | 11/2021 | Nolan et al. |
| 11,187,581 | B2 | 11/2021 | Kokota et al. |
| 11,299,770 | B2 | 4/2022 | Samusik et al. |
| 11,377,689 | B2 | 7/2022 | Beechem et al. |
| 11,408,094 | B2 | 8/2022 | Fu et al. |
| 11,447,807 | B2 | 9/2022 | Church et al. |
| RE49,304 | E | 11/2022 | Gao et al. |
| 11,566,276 | B2 | 1/2023 | Church et al. |
| 11,649,485 | B2 | 5/2023 | Yin et al. |
| 11,656,447 | B2 | 5/2023 | Tsia et al. |
| 12,060,603 | B2 | 8/2024 | Bava |
| 12,157,124 | B2 | 12/2024 | Cox et al. |
| 12,188,085 | B2 | 1/2025 | Bava |
| 12,359,253 | B2 | 7/2025 | Wang et al. |
| 2002/0045045 | A1 | 4/2002 | Adams et al. |
| 2003/0017264 | A1 | 1/2003 | Treadway et al. |
| 2003/0092624 | A1 | 5/2003 | Wang et al. |
| 2005/0112639 | A1 | 5/2005 | Wang et al. |
| 2005/0239184 | A1 | 10/2005 | Ohara et al. |
| 2006/0141501 | A1 | 6/2006 | Friend et al. |
| 2008/0124735 | A1 | 5/2008 | Schuster et al. |
| 2009/0011943 | A1 | 1/2009 | Drmanac et al. |
| 2009/0093403 | A1 | 4/2009 | Zhang et al. |
| 2009/0262183 | A1 | 10/2009 | Hayashi et al. |
| 2010/0055733 | A1 | 3/2010 | Lutolf et al. |
| 2010/0120129 | A1 | 5/2010 | Amshey et al. |
| 2011/0256183 | A1 | 10/2011 | Frank et al. |
| 2012/0003657 | A1 | 1/2012 | Myllykangas et al. |
| 2013/0045872 | A1 | 2/2013 | Zhou et al. |
| 2013/0178372 | A1 | 7/2013 | Geiss et al. |
| 2013/0266512 | A1 | 10/2013 | Fox et al. |
| 2013/0338038 | A1 | 12/2013 | Dubridge et al. |
| 2014/0162892 | A1 | 6/2014 | Mir |
| 2014/0170654 | A1 | 6/2014 | Landegren et al. |
| 2015/0144490 | A1 | 5/2015 | Deisseroth et al. |
| 2015/0377886 | A1 | 12/2015 | Ciceri et al. |
| 2016/0080632 | A1 | 3/2016 | Iwase et al. |
| 2016/0129437 | A1 | 5/2016 | Kayyem et al. |
| 2016/0169923 | A1 | 6/2016 | Holmes et al. |
| 2016/0252715 | A1 | 9/2016 | Nakano et al. |
| 2016/0258003 | A1 | 9/2016 | Celedon et al. |
| 2016/0377524 | A1 | 12/2016 | Martin et al. |
| 2017/0068086 | A1 | 3/2017 | Tomer et al. |
| 2017/0145510 | A1 | 5/2017 | Oliphant et al. |
| 2017/0211133 | A1 | 7/2017 | Landegren et al. |
| 2018/0094320 | A1 | 4/2018 | Li |
| 2018/0119219 | A1 | 5/2018 | Chen et al. |
| 2018/0208975 | A1 | 7/2018 | Peterson et al. |
| 2018/0216161 | A1 | 8/2018 | Chen et al. |
| 2018/0267283 | A1 | 9/2018 | Matsumoto |
| 2018/0340221 | A1 | 11/2018 | Davis et al. |
| 2019/0002971 | A1 | 1/2019 | Koslover et al. |
| 2019/0055594 | A1 | 2/2019 | Samusik et al. |
| 2019/0085383 | A1 | 3/2019 | Church et al. |
| 2019/0110281 | A1 | 4/2019 | Zhou et al. |

(56) References Cited

U.S. PATENT DOCUMENTS

| | | |
|---|---|---|
| 2019/0154679 A1 | 5/2019 | Doyle et al. |
| 2019/0179127 A1 | 6/2019 | Mertz et al. |
| 2019/0284603 A1 | 9/2019 | Shema-Yaacoby et al. |
| 2020/0199667 A1 | 6/2020 | Erickstad et al. |
| 2020/0277663 A1 | 9/2020 | Iyer et al. |
| 2020/0341259 A1 | 10/2020 | Chan et al. |
| 2021/0130810 A1 | 5/2021 | Schwartz et al. |
| 2021/0164039 A1 | 6/2021 | Wang et al. |
| 2021/0238662 A1 | 8/2021 | Bava et al. |
| 2021/0238665 A1 | 8/2021 | Samusik et al. |
| 2021/0238674 A1 | 8/2021 | Bava |
| 2021/0262018 A1 | 8/2021 | Bava et al. |
| 2021/0293693 A1 | 9/2021 | Bharadwaj et al. |
| 2021/0340621 A1 | 11/2021 | Daugharthy et al. |
| 2021/0388424 A1 | 12/2021 | Bava |
| 2022/0015638 A1 | 1/2022 | Zeng et al. |
| 2022/0016624 A1 | 1/2022 | Daugharthy et al. |
| 2022/0083832 A1 | 3/2022 | Shah |
| 2022/0084628 A1 | 3/2022 | Shah |
| 2022/0084629 A1 | 3/2022 | Shah |
| 2022/0119871 A1 | 4/2022 | Regev et al. |
| 2022/0251642 A1 | 8/2022 | Church et al. |
| 2022/0290228 A1 | 9/2022 | Hauling et al. |
| 2022/0316004 A1 | 10/2022 | Miller et al. |
| 2022/0364160 A1 | 11/2022 | Nolan et al. |
| 2022/0372570 A1 | 11/2022 | Costa |
| 2022/0380838 A1 | 12/2022 | Kåœhnemund et al. |
| 2022/0403458 A1 | 12/2022 | Bava |
| 2023/0012607 A1 | 1/2023 | Kåœhnemund et al. |
| 2023/0013775 A1 | 1/2023 | Chen et al. |
| 2023/0026886 A1 | 1/2023 | Chen |
| 2023/0034039 A1 | 2/2023 | Shahjamali |
| 2023/0037182 A1 | 2/2023 | Bava et al. |
| 2023/0061542 A1 | 3/2023 | Kåœhnemund |
| 2023/0077364 A1 | 3/2023 | Patterson et al. |
| 2023/0081232 A1 | 3/2023 | Weisenfeld et al. |
| 2023/0109070 A1 | 4/2023 | Richman et al. |
| 2023/0115903 A1 | 4/2023 | Hernández Neuta et al. |
| 2023/0126825 A1 | 4/2023 | Nagendran et al. |
| 2023/0143569 A1 | 5/2023 | Iyer et al. |
| 2023/0227894 A1 | 7/2023 | Nilsson et al. |
| 2023/0238078 A1 | 7/2023 | Gonzalez Lozano et al. |
| 2023/0242974 A1 | 8/2023 | Costa et al. |
| 2023/0279480 A1 | 9/2023 | Kåœhnemund |
| 2023/0314327 A1 | 10/2023 | Hoffman |
| 2023/0314328 A1 | 10/2023 | Costa |
| 2023/0323437 A1 | 10/2023 | Chen et al. |
| 2023/0324421 A1 | 10/2023 | Zhang et al. |
| 2023/0351619 A1 | 11/2023 | Tentori et al. |
| 2024/0019353 A1 | 1/2024 | Wang et al. |
| 2024/0033743 A1 | 2/2024 | Tentori et al. |
| 2024/0132938 A1 | 4/2024 | Kåœhnemund |
| 2024/0144704 A1 | 5/2024 | Wang et al. |
| 2024/0150816 A1 | 5/2024 | Feng et al. |
| 2024/0151937 A1 | 5/2024 | Hoffman |
| 2024/0167081 A1 | 5/2024 | Bava et al. |
| 2024/0167956 A1 | 5/2024 | Hoffman et al. |
| 2024/0168273 A1 | 5/2024 | Monkowski et al. |
| 2024/0171723 A1 | 5/2024 | Shutov et al. |
| 2024/0171833 A1 | 5/2024 | Hoffman et al. |
| 2024/0177348 A1 | 5/2024 | Shutov et al. |
| 2024/0209346 A1 | 6/2024 | Shastry |
| 2024/0233415 A1 | 7/2024 | Hoffman |
| 2024/0248038 A1 | 7/2024 | Deisseroth et al. |
| 2024/0254545 A1 | 8/2024 | Wang et al. |
| 2024/0254553 A1 | 8/2024 | Deisseroth et al. |
| 2024/0254554 A1 | 8/2024 | Deisseroth et al. |
| 2024/0257912 A1 | 8/2024 | Deisseroth et al. |
| 2024/0263228 A1 | 8/2024 | Deisseroth et al. |
| 2024/0271138 A1 | 8/2024 | Hacohen et al. |
| 2024/0305314 A1 | 9/2024 | Hoffman et al. |
| 2024/0369471 A1 | 11/2024 | Hoffman et al. |
| 2024/0376530 A1 | 11/2024 | Wang et al. |
| 2024/0428880 A1 | 12/2024 | Marks et al. |
| 2025/0012786 A1 | 1/2025 | Skrynnyk et al. |
| 2025/0052979 A1 | 2/2025 | Miller et al. |
| 2025/0061732 A1 | 2/2025 | Li et al. |

FOREIGN PATENT DOCUMENTS

| | | | |
|---|---|---|---|
| EP | 2 794 928 B1 | 2/2019 | |
| EP | 2 971 184 B1 | 4/2019 | |
| EP | 3 578 666 A1 | 12/2019 | |
| EP | 4 045 887 A1 | 8/2022 | |
| EP | 4 108 782 B1 | 6/2023 | |
| EP | 4 513 431 A2 | 2/2025 | |
| WO | WO-98/39352 A1 | 9/1998 | |
| WO | WO-99/14226 A2 | 3/1999 | |
| WO | WO-01/61037 A1 | 8/2001 | |
| WO | WO-2005/033340 A2 | 4/2005 | |
| WO | WO-2010/062775 A2 | 6/2010 | |
| WO | WO-2012/005595 A2 | 1/2012 | |
| WO | WO-2012/110899 A2 | 8/2012 | |
| WO | WO-2012/160083 A1 | 11/2012 | |
| WO | WO-2013/173774 A2 | 11/2013 | |
| WO | WO-2014/030066 A2 | 2/2014 | |
| WO | WO-2015031691 A1 * | 3/2015 | ........... C12Q 1/6876 |
| WO | WO-2015/200139 A1 | 12/2015 | |
| WO | WO-2017/019481 A1 | 2/2017 | |
| WO | WO-2017/096248 A1 | 6/2017 | |
| WO | WO-2017/147483 A1 | 8/2017 | |
| WO | WO-2017/149550 A1 | 9/2017 | |
| WO | WO-2018/033528 A1 | 2/2018 | |
| WO | WO-2018/136856 A1 | 7/2018 | |
| WO | WO-2019/016048 A1 | 1/2019 | |
| WO | WO-2019199579 A1 * | 10/2019 | ........... C12Q 1/6841 |
| WO | WO-2019/222284 A1 | 11/2019 | |
| WO | WO-2020/030162 A1 | 2/2020 | |
| WO | WO-2020/148769 A1 | 7/2020 | |
| WO | WO 2020/160044 A1 | 8/2020 | |
| WO | WO-2020/176788 A1 | 9/2020 | |
| WO | WO-2020/214885 A1 | 10/2020 | |
| WO | WO-2020/240025 A1 | 12/2020 | |
| WO | WO-2021/076770 A1 | 4/2021 | |
| WO | WO-2022/246269 A1 | 11/2022 | |
| WO | WO-2022/246279 A1 | 11/2022 | |
| WO | WO-2022/261255 A1 | 12/2022 | |
| WO | WO-2024/103007 A1 | 5/2024 | |
| WO | WO-2025/014828 A1 | 1/2025 | |
| WO | WO-2025/189030 A1 | 9/2025 | |

OTHER PUBLICATIONS

Bandura, et al., "Mass cytometry: technique for real time single cell multitarget immunoassay based on inductively coupled plasma time-of-flight mass spectrometry," Analytical Chemistry, Aug. 2009, vol. 81, No. 16 (6813-6822).

Baner, et al., "Signal amplification of padlock probes by rolling circle replication," Nucleic Acids Research, Nov. 1998, vol. 26, No. 22 (pp. 5073-5078).

Battich, et al., "Control of Transcript Variability in Single Mammalian Cells," Cell, Dec. 2015, vol. 163 (pp. 1596-1610).

Battich, et al., "Sequencing metabolically labeled transcripts in single cells reveals mRNA turnover strategies," Science, Mar. 2020, vol. 367 (pp. 1151-1156).

Bergen, et al., "Generalizing RNA velocity to transient cell states through dynamical modeling," bioRxiv, URL: https://www.biorxiv.org/content/10.1101/820936v1, 2019 (26 pages).

Berry, et al., "Nuclear RNA concentration coordinates RNA production with cell size in human cells," bioRxiv preprint doi: https://doi.org/10.1101/2021.05.17.444432; this version posted May 17, 2021 (pp. 1-41).

Bevis, et al., "Rapidly maturing variants of the Discosoma red fluorescent protein (DsRed)," Nature Biotechnology, Jan. 2002, vol. 20, No. 1 (pp. 83-87).

Bhatt, et al., "Transcript Dynamics of Proinflammatory Genes Revealed by Sequence Analysis of Subcellular RNA Fractions," Cell, Jul. 2012, vol. 150 (pp. 279-290).

(56) References Cited

OTHER PUBLICATIONS

Bleton, et al., "Cognitive Tasks and Cerebral Blood Flow Through Anterior Cerebral Arteries: a Study via Functional Transcranial Doppler Ultrasound Recordings," BMC Medical Imaging, 2016, vol. 16 (pp. 1-12).

Borden, et al., "Neoantigen fitness model predicts lower immune recognition of cutaneous squamous cell carcinomas than actinic keratoses," Frontiers in Immunology, Nov. 2019, vol. 10 No. 2799, (pp. 1-11).

Braasch, et al., "Novel antisense and peptide nucleic acid strategies for controlling gene expression," Biochemistry, Mar. 2002, vol. 41, No. 14 (pp. 4503-4510).

Buchwalow, et al., "Immunohistochemistry: Basics and Methods," Springer-Verlag Berlin Heidelberg, 2010, vol. 4, No. 13 (pp. 109-127).

Buxbaum, et al., "In the right place at the right time: Visualizing and understanding mRNA localization," Nature Reviews Molecular Cell Biology, Feb. 2015, vol. 16, No. 2 (pp. 95-109).

Chan, Ken Y., et al. "Engineered AAVs for efficient noninvasive gene delivery to the central and peripheral nervous systems," Nature Neuroscience, Aug. 2017, vol. 20, No. 8 (1172-1179).

Chen, et al., "Comprehensive analysis of nucleocytoplasmic dynamics of mRNA in *Drosophila* cells," PLOS Genetics, Aug. 2017, vol. 13, No. 8, e1006929 (pp. 1-25).

Chen, et al., "Efficient in situ barcode sequencing using padlock probe-based BaristaSeq," Nucleic Acids Research, Feb. 2018, vol. 46, No. 4 (10 pages).

Chen, et al., "High-Throughput Mapping of Long-Range Neuronal Projection Using In Situ Sequencing," Oct. 2019, Cell, vol. 179, No. 3 (pp. 772-786).

Chen, et al., "Nanoscale Imaging of RNA with Expansion Microscopy," Nature Methods, Jul. 2016, vol. 13 (pp. 679-684).

Chen, et al., "Decoding molecular and cellular heterogeneity of mouse nucleus accumbens," Nature Neuroscience, Dec. 2021, vol. 24, No. 12 (pp. 1757-1771).

Cheng, et al., "Sequencing-free whole-genome spatial transcriptomics at single-molecule resolution," Cell, Nov. 2025, vol. 188, No. 24 (pp. 6953-6970).

Clausson, et al., "Compaction of rolling circle amplification products increases signal integrity and signal-to-noise ratio," Scientific Reports, Jul. 2015, vol. 5, No. 12317 (pp. 1-10).

Data Portal: Allen Mouse Brain Atlas Data Portal 2004; [retrieved on Oct. 3, 2025], Available at URL:https://mouse.brain-map.org/ (pp. 1-2).

Deng, et al., "DNA-Sequence-Encoded Rolling Circle Amplicon for Single-Cell RNA Imaging," Chem, Jun. 2018, vol. 4, No. 6 (pp. 1373-1386).

Dixit, et al., "Perturb-Seq: Dissecting Molecular Circuits with Scalable Single-Cell RNA Profiling of Pooled Genetic Screens," Cell, Dec. 15, 2016, vol. 167, No. 7 (pp. 1853-1866).

Djebali, et al., "Landscape of transcription in human cells," Nature, Sep. 2012, vol. 489, No. 7414 (pp. 101-108).

El-Nachef, et al., "High-resolution 3D fluorescent imaging of intact tissues," International Journal of Cardiology and Cardiovascular Diseases, 2021, vol. 1, No. 1 (pp. 1-14).

Englisch, et al., "Chemically Modified Oligonucleotides as Probes and Inhibitors," Angewandte Chemie, International Edition, Jun. 1991, vol. 30, No. 6 (pp. 613-629).

Fang, et al., "Three-dimensional single-cell transcriptome imaging of thick tissues," Elife, Dec. 2024, vol. 12, RP90029 (pp. 1-18).

Faruqi, et al., "High-throughput genotyping of single nucleotide polymorphisms with rolling circle amplification," BMC Genomics, Aug. 2001, vol. 2, No. 4 (pp. 1-10).

Ferkowicz, et al., "Large-scale, three-dimensional tissue cytometry of the human kidney: a complete and accessible pipeline," Laboratory Investigation, Jan. 2021, vol. 101, No. 5 (pp. 661-676).

Fredriksson, et al., "Protein detection using proximity-dependent DNA ligation assays," Nature Biotechnology, May 2002, vol. 20 (pp. 473-477).

Fujimoto, et al., "Site-specific cytosine to uracil transition by using reversible DNA-crosslinking," ChemBioChem, 2010, vol. 11, No. 12 (pp. 1661-1664).

Fujita, et al., "Langerhans cells from human cutaneous squamous cell carcinoma induce strong type 1 immunity," Journal of Investigative Dermatology, 2012, vol. 132, No. 6 (pp. 1645-1655).

Gandin, et al., "Deep-tissue spatial omics: imaging whole-embryo transcriptomics and subcellular structures at high spatial resolution," bioRxiv, Dec. 2024, https://doi.org/10.1101/2024.05.17.594641 (137 pages).

Gao, et al., "Tracing the temporal-spatial transcriptome landscapes of the human fetal digestive tract using single-cell RNA-sequencing," Nature Cell Biology, 2018 vol. 20 (pp. 1-17).

Gao, Xin et al., "ClusterMap—Compare multiple Single cell RNA-seq profiling," Jul. 12, 2023 [Retrieved Jul. 15, 2025]. Available at URL:https://xgaoo.github.io/ClusterMap/ClusterMap.html.(pp. 1-54).

Guenthner, et al., "Permanent genetic access to transiently active neurons via TRAP: targeted recombination in active populations," Neuron, Jun. 2013, vol. 78, No. 5 (pp. 773-784).

Halpern, et al. "Nuclear Retention of mRNA in Mammalian Tissues," Cell Reports, Dec. 2015, vol. 13 (pp. 2653-2662).

Hein et al., "Click chemistry, a powerful tool for pharmaceutical sciences," Pharmaceutical Research, Oct. 10, 2008, vol. 25, No. 10 (pp. 2216-2230).

Hendriks, et al., NASC-seq monitors RNA synthesis in single cells. Nature Communications, Jul. 2019, vol. 10, No. 1 (pp. 1-9).

Hong, et al., "DNA interstrand cross-link formation initiated by reaction between singlet oxygen and a modified nucleotide," Journal of the American Chemical Society, 2005, vol. 127, No. 30 (pp. 10510-10511).

Hrvatin, et al., "Single-cell analysis of experience-dependent transcriptomic states in the mouse visual cortex," Nature Neuroscience, 2018, vol. 21, No. 1 (pp. 120-129).

Huh, Kang Moo, et al., "Synthesis and characterization of poly (ethylene glycol)/poly (L-lactic acid) alternating multiblock copolymers," Polymer, 1999, vol. 40, No. 22 (pp. 6147-6155).

International Preliminary Report on Patentability for Appl. Ser. No. PCT/US2017/019443 dated Sep. 7, 2018 (8 pages).

International Preliminary Report on Patentability for Appl. Ser. No. PCT/US2019/025835 dated Oct. 22, 2020 (8 pages).

International Preliminary Report on Patentability for Appl. Ser. No. PCT/US2020/055800 dated Apr. 28, 2022 (8 pages).

International Preliminary Report on Patentability for Appl. Ser. No. PCT/US2022/017016 mail date Aug. 31, 2023 (10 pages).

International Preliminary Report on Patentability for Appl. Ser. No. PCT/US2022/028012 mail date Nov. 16, 2023 (8 pages).

International Preliminary Report on Patentability for Appl. Ser. No. PCT/US2022/030232 dated Nov. 30, 2023 (11 pages).

International Preliminary Report on Patentability for Appl. Ser. No. PCT/US2022/030321 dated Nov. 30, 2023 (7 pages).

International Preliminary Report on Patentability for Appl. Ser. No. PCT/US2022/030363 dated Nov. 30, 2023 (7 pages).

International Preliminary Report on Patentability for Appl. Ser. No. PCT/US2022/030370 dated Nov. 30, 2023 (9 pages).

International Preliminary Report on Patentability for Appl. Ser. No. PCT/US2022/030374 dated Nov. 30, 2023 (7 pages).

International Preliminary Report on Patentability for Appl. Ser. No. PCT/US2022/031275 dated Dec. 7, 2023 (11 pages).

International Preliminary Report on Patentability for Appl. Ser. No. PCT/US2022/035271 dated Jan. 11, 2024 (8 pages).

International Search Report and Written Opinion for Appl. Ser. No. PCT/US2017/019443 dated May 19, 2017 (10 pages).

International Search Report and Written Opinion for Appl. Ser. No. PCT/US2020/055800 dated Feb. 22, 2021 (10 pages).

International Search Report and Written Opinion for Appl. Ser. No. PCT/US2022/017016 mail date May 24, 2022 (15 pages).

International Search Report and Written Opinion for Appl. Ser. No. PCT/US2022/028012 dated Aug. 17, 2022 (11 pages).

International Search Report and Written Opinion for Appl. Ser. No. PCT/US2022/030232 dated Oct. 26, 2022 (15 pages).

International Search Report and Written Opinion for Appl. Ser. No. PCT/US2022/030321 dated Oct. 6, 2022 (9 pages).

(56)　　　　　References Cited

OTHER PUBLICATIONS

International Search Report and Written Opinion for Appl. Ser. No. PCT/US2022/030363 dated Sep. 1, 2022 (9 pages).
International Search Report and Written Opinion for Appl. Ser. No. PCT/US2022/030370 dated Sep. 1, 2022 (9 pages).
International Search Report and Written Opinion for Appl. Ser. No. PCT/US2022/030374 dated Sep. 1, 2022 (9 pages).
International Search Report and Written Opinion for Appl. Ser. No. PCT/US2022/031275 dated Oct. 31, 2022 (16 pages).
International Search Report and Written Opinion for Appl. Ser. No. PCT/US2022/035271 dated Oct. 11, 2022 (11 pages).
International Search Report and Written Opinion for Appl. Ser. No. PCT/US2024/060469 dated May 7, 2025 (16 pages).
International Search Report and Written Opinion for Appl. Ser. No. PCT/US2025/018783 dated Jun. 27, 2025 (10 pages).
International Search Report and Written Opinion for Appl. Ser. No. PCT/US2025/030656 dated Aug. 7, 2025 (15 pages).
International Search Report and Written Opinion for Appl. Ser. PCT/US2024/036943 dated Oct. 18, 2024 (14 pages).
International Search Report and Written Opinion for Application No. PCT/US2022/039895, mailed Nov. 17, 2022.
International Search Report for Appl. Ser. No. PCT/US2019/025835 dated Jul. 1, 2019 (3 pages).
Invitation to Pay Additional Fees for Appl. Ser. No. PCT/US2022/031275 dated Sep. 8, 2022 (10 pages).
Jao, et al., "Exploring RNA transcription and turnover in vivo by using click chemistry," Proceedings of the National Academy of Sciences, USA, Oct. 2008, vol. 105, No. 41 (pp. 15779-15784).
Jerby-Arnon et al., "A Cancer Cell Program Promotes T Cell Exclusion and Resistance to Checkpoint Blockade," Cell, Nov. 1, 2018, vol. 175, No. 4 (pp. 984-997).
Ji, et al., "Multimodal Analysis of Composition and Spatial Architecture in Human Squamous Cell Carcinoma," Cell, Jul. 2020, vol. 182, No. 6 (pp. 1661-1662).
Jones, et al., "Glowing jellyfish, luminescence and a molecule called coelenterazine," Trends in Biotechnology, Dec. 1999, vol. 17, No. 12 (pp. 477-481).
Joost, et al., "The molecular anatomy of mouse skin during hair growth and rest," Cell Stem Cell, Mar. 2020, vol. 26, No. 3 (pp. 441-457).
Klechevsky, et al., "Functional specializations of human epidermal Langerhans cells and CD14+ dermal dendritic cells," Immunity, Sep. 2008, vol. 29, No. 3 (pp. 497-510).
Klein, et al., "elastix: a toolbox for intensity-based medical image registration," IEEE transactions on medical imaging, Published Online Nov. 17, 2009, vol. 29, No. 1 (pp. 196-205).
Koos, et al., "Analysis of protein interactions in situ by proximity ligation assays," Current Topics in Microbiology and Immunology, 2013, vol. 377 (pp. 111-126).
Korsunsky et al., "Fast, sensitive and accurate integration of single-cell data with Harmony," Nature Methods, Dec. 2019, vol. 16, No. 12 (pp. 1289-1296).
Koshkin, et al., "LNA (Locked Nucleic Acids): Synthesis of the Adenine, Cytosine, Guanine, 5-methylcytosine, Thymine and Uecognition," Tetrahedron, 1998, vol. 54, No. 14 (pp. 3607-3630).
Kroschwitz, I. J., "Polynuclieotids. The Concise Encyclopedia of Polymer Science and Engineering," A Wiley-Interscience Publication John Wiley & Sons, 1990 (pp. 858-859).
La Manno et al., "RNA velocity of single cells," Nature, 2018, vol. 560, No. 7719 (36 pages).
Lee et al., "Highly multiplexed subcellular RNA sequencing in situ," Science, Mar. 21, 2014, vol. 343, No. 6177 (pp. 1360-1363).
Lee, et al., "Hydrophobic nanoparticles improve permeability of cell-encapsulating poly (ethylene glycol) hydrogels while maintaining patternability," Proceedings of the National Academy of Sciences, USA, Nov. 2010, vol. 107, No. 48 (pp. 20709-20714).
Li, et al., "High-dimensional cell-level analysis of tissues with Ce3D multiplex volume imaging," Nature Protocols, Apr. 2019, vol. 14, No. 6 (pp. 1708-1733).

Lizardi et al. "Mutation detection and single-molecule counting using isothermal rolling-circle amplification," Nature Genetics, Jul. 1998, vol. 19 (pp. 225-232).
Lowe, et al. "Transcriptomics technologies," PLoS Computational Biology, May 2017, vol. 13, No. 5 (pp. 1-23).
Lubeck, et al., "Single-cell systems biology by super-resolution imaging and combinatorial labeling," Nature Methods, Jun. 2012, vol. 9, No. 7 (pp. 743-748).
Maintz, et al., "A survey of medical Image Registration," Medical Image Analysis, Mar. 1998, vol. 2, No. 1 (pp. 1-36).
Martin, P., "ChemInform Abstract: A New Access to 2'-O-Alkylated Ribonucleosides and Properties of 2'-O-Alkylated Oligoribonucleotides," Aug. 1, 1995 || Martin et al., "Ein neuer Zugang zu 2'-O-Alkylribonucleosiden and Eigenschaften deren Oligonucleotide," Helvetica Chimica Acta, Mar. 1995, vol. 78 (pp. 486-504).
Matz, et al. "Fluorescent proteins from nonbioluminescent Anthozoa species," Nature Biotechnology, Oct. 1999, vol. 17, No. 10 (969-973).
Moffitt, J. R. et al., "Molecular, spatial, and functional single-cell profiling of the hypothalamic preoptic region," Science, Nov. 2018, vol. 362, No. 6416 (pp. 1-31).
Mondal, et al., "Highly multiplexed single-cell in situ RNA and DNA analysis with bioorthogonal cleavable fluorescent oligonucleotides," Chemical Science, Feb. 2018, vol. 9, No. 11 (pp. 2909-2917).
Moon, K. R. et al., "Visualizing structure and transitions in high-dimensional biological data," Nature Biotechnology, Dec. 2019, vol. 37, No. 12 (pp. 1482-1492).
Mount, et al., "Cell-based therapy technology classifications and translational challenges," Philosophical Transactions of the Royal Society B: Biological Sciences, 2015, vol. 370, No. 1680 (pp. 1-16).
Nagai et al., "A variant of yellow fluorescent protein with fast and efficient maturation for cell-biological applications," Nature Biotechnology, 2002, vol. 20 (pp. 87-90).
Nawy, Tal., "In situ sequencing," Nature Methods, Jan. 2014, vol. 11, No. 1 (p. 29).
Nejad, et al., "Interstrand DNA cross-links derived from reaction of a 2-aminopurine residue with an abasic site," ACS Chemical Biology, Jun. 2019, vol. 14, No. 7 (pp. 1481-1489).
Nguyen, et al., "Evolutionary optimization of fluorescent proteins for intracellular FRET," Nature Biotechnology, Mar. 2005, vol. 23, No. 3 (pp. 355-360).
Norris, et al., "Whole Tissue Imaging of Cellular Boundaries at Sub-Micron Resolutions for Automatic Cell Segmentation: Applications in Epithelial Bending of Ectodermal Appendages," bioRxiv, Oct. 2024 (pp. 1-18).
Definition—Oligonucleotide Definition. Merriam-Webster, [retrieved on Aug. 23, 2017]. Available at URL: https://www.merriam-webster.com/dictionary/oligonucleotide (p. 1).
Wikipedia—Oligonucleotide. Wikipedia, [retrieved on Feb. 17, 2019]. Available at URL: https://en.wikipedia.org/wiki/Oligonucleotide (pp. 1-3).
Ornatsky, et al., "Highly multiparametric analysis by mass cytometry," Journal of Immunological Methods, Sep. 2010, vol. 361 Nos. 1-2 (pp. 1-20).
Padovan-Merhar, 0., et al., "Single Mammalian Cells Compensate for Differences in Cellular Volume and DNA Copy Number through Independent Global Transcriptional Mechanisms," Molecular Cell, Apr. 2015, vol. 58 (pp. 339-352).
Pelizzari, et al., "Accurate three-dimensional registration of CT, PET, and/or MR images of the brain," Journal of Computer Assisted Tomography, Jan. 1989, vol. 13, No. 1 (pp. 20-26).
Player, et al., "Single-copy gene detection using branched DNA (bDNA) in situ hybridization," The Journal of Histochemistry and Cytochemistry, May 2001, vol. 49, No. 5 (pp. 603-612).
Qian, et al., "Probabilistic cell typing enables fine mapping of closely related cell types in situ," Nature Methods, 2020, vol. 17, No. 1 (pp. 101-106).
Qiu et al., "Mapping transcriptomic vector fields of single cells," Cell, Feb. 2022, vol. 185, No. 4 (pp. 690-711).
Qiu et al., "Massively parallel and time-resolved RNA sequencing in single cells with scNT-seq," Nature Methods Oct. 2020, vol. 17, No. 10 (pp. 991-1001).

(56)         References Cited

OTHER PUBLICATIONS

Rabani, et al., "A Metabolic labeling of RNA uncovers principles of RNA production and degradation dynamics in mammalian cells," Nature biotechnology, May 2011, vol. 29, No. 5 (pp. 436-442).

Rizzo, et al., "An improved cyan fluorescent protein variant useful for FRET," Nature Biotechnology, Feb. 2004, vol. 22, No. 4 (pp. 445-449).

Robles-Remacho, et al., "Spatial Transcriptomics: Emerging Technologies in Tissue Gene Expression Profiling," Analytical Chemistry, Oct. 2023, vol. 95, No. 42 (pp. 15450-15460).

Rosales, et al., "The design of reversible hydrogels to capture extracellular matrix dynamics," Nature Reviews Materials, Feb. 2016, vol. 1 No. 15012 (pp. 1-15).

Roundtree, et al., "Dynamic RNA Modifications in Gene Expression Regulation," Cell, Jun. 2017, vol. 169 (1187-1200).

Roundtree, et al., "YTHDC1 mediates nuclear export of N6-methyladenosine methylated mRNAs," Elife, Oct. 2017, vol. 6 (pp. 1-28).

Sakaguchi, et al., "Bright multicolor labeling of neuronal circuits with fluorescent proteins and chemical tags," Elife, Nov. 2018, vol. 7 (pp. 1-28).

Samusik, et al., "Automated mapping of phenotype space with single-cell data," Nature Methods, Jun. 2016, vol. 13, No. 6 (pp. 493-496).

Sanz, et al., "Cell-type-specific isolation of ribosome-associated mRNA from complex tissues," Proceedings of the National Academy of Sciences, USA, Aug. 2009, vol. 106, No. 33 (pp. 13939-13944).

Savell, et al., "A dopamine-induced gene expression signature regulates neuronal function and cocaine response," Science Advances, Jun. 2020, vol. 6, No. 26 (pp. 1-15).

Scheffer, et al. "A connectome and analysis of the adult *Drosophila* central brain," elife, Sep.-Oct. 2020, No. 57443 (pp. 1-83).

Schwanhausser, et al., "Global quantification of mammalian gene expression control," Nature, May 2011, Author transcript (21 pages).

Schweitzer, et al. "Multiplexed protein profiling on microarrays by rolling-circle amplification," Nature Biotechnology, Apr. 2002, vol. 20 (pp. 359-365).

Schweitzer, et al., "Immunoassays with rolling circle DNA amplification: A versatile platform for ultrasensitive antigen detection," Proceedings of the National Academy of Sciences, USA, Aug. 29, 2000, vol. 97, No. 18 (pp. 10113-10119).

Shah, et al., "In Situ Transcription Profiling of Single Cells Reveals Spatial Organization of Cells in the Mouse Hippocampus," Neuron, Oct. 2016, vol. 92, No. 2 (pp. 342-357).

Shah, et al., "Single-molecule RNA detection at depth by hybridization chain reaction and tissue hydrogel embedding and clearing," Development, 2016, vol. 143, No. 15 (pp. 2862-2867).

Shaner, et al., "A guide to choosing fluorescent proteins," Nature Methods, 2005, vol. 2, No. 12 (pp. 905-909).

Sharp, et al., "Cell division requires RNA eviction from condensing chromosomes," Journal of Cell Biology, 2020, vol. 219, No. 11 (pp. 1-26).

Shi, et al., "Where, When, and How: Context-Dependent Functions of RNA Methylation Writers, Readers, and Erasers," Molecular Cell, 2019, vol. 74, (pp. 640-650).

Shkrob, et al., "Far-red fluorescent proteins evolved from a blue chromoprotein from Actinia equina," The Biochemical Journal, Dec. 2005, vol. 392, No. 3 (pp. 649-654).

Singh, et al., "LNA (locked nucleic acids): Synthesis and High-affinity Nucleic Acid Recognition," Chemical Communications, 1998, vol. 4 (pp. 455-456).

Soderberg, et al., "Direct observation of individual endogenous protein complexes in situ by proximity ligation," Nature Methods, Oct. 2006, vol. 3, No. 12 (pp. 995-1000).

Stahl, et al., "Visualization and analysis of gene expression in tissue sections by spatial transcriptomics" Science, Jul. 2016, vol. 353, No. 6294 (pp. 78-82).

Stevens, et al., "Furan-modified oligonucleotides for fast, high-yielding and site-selective DNA inter-strand cross-linking with non-modified complements," Nucleic Acids Research, Jan. 2009, vol. 37, No. 5 (pp. 1555-1565).

Stickels et al., "Highly sensitive spatial transcriptomics at near-cellular resolution with SlideseqV2," Nature Biotechnology, Mar. 2021, vol. 39, No. 3 (pp. 313-319).

Sui, et al., "Scalable Spatial Single-cell Transcriptomics and Translatomics in 3d Thick Tissue Blocks," Biorxiv : the Preprint Server for Biology, Aug. 2024 (pp. 1-37).

Sui, et al., "Scalable spatial single-cell transcriptomics and translatomics in 3D thick tissue blocks," Nature Methods, Nov. 2025, vol. 22 (pp. 2574-2584).

Tainaka, et al., "Whole-body imaging with single-cell resolution by tissue decolorization," Cell, Nov. 2014, vol. 159, No. 4 (pp. 911-924).

Takko, et al., "ShapeMetrics: A userfriendly pipeline for 3D cell segmentation and spatial tissue analysis," Developmental Biology, Jun. 2020, vol. 462, No. 1 (7-19).

Tam, et al., "Engineering cellular microenvironments with photo—and enzymatically responsive hydrogels: toward biomimetic 3D cell culture models," Accounts of Chemical Research, Mar. 2017 vol. 50, No. 4 (pp. 703-713).

Tanenbaum, et al., "Regulation of mRNA translation during mitosis," Elife, Aug. 2015, vol. 4 (pp. 1-19).

Taranda, et al., "Combined whole-organ imaging at single-cell resolution and immunohistochemical analysis of prostate cancer and its liver and brain metastases," Cell Reports, Nov. 2021, vol. 37, No. 7, 110027 (pp. 1-14).

Tasic, et al., "Shared and distinct transcriptomic cell types across neocortical areas," Nature, Oct. 2018, vol. 563, No. 7729 (pp. 72-78).

Tepper, et al., "Heterogeneity and diversity of striatal GABAergic interneurons: update 2018," Frontiers in Neuroanatomy, Nov. 2018, vol. 12, No. 91 (pp. 1-14).

Thirumurugan, P. et al., "Click Chemistry for Drug Development and Diverse Chemical-Biology Applications," Chemical Reviews, 2013, vol. 113, No. 7 (pp. 4905-4979).

Tirosh, et al., "Dissecting the Multicellular Ecosystem of Metastatic Melanoma by Single-Cell RNA-Seq," Science, Apr. 8, 2016, vol. 352, No. 6282 (pp. 189-196).

Tomer, et al., "Advanced Clarity for rapid and high-resolution imaging of intact tissues," Nature Protocols, Jun. 2014, vol. 9 (pp. 1682-1697).

US Non-Final Office Action for U.S. Appl. No. 17/768,996 dated Aug. 22, 2025 (pages).

US Non-final Office Action for U.S. Appl. No. 18/561,643 dated Dec. 4, 2025 (68 pages).

US Non-Final Office Action for U.S. Appl. No. 19/230,050 dated Sep. 4, 2025 (14 pages).

US Non-Final Office Action for U.S. Appl. No. 19/236,720 dated Aug. 7, 2025 (pages).

US Non-final Office Action for U.S. Appl. No. 18/277,950 dated Oct. 1, 2025 (30 pages).

US Notice of Allowance for U.S. Appl. No. 19/270,264 dated Sep. 8, 2025 (9 pages).

US Non-Final Office Action for U.S. Appl. No. 19/236,732 dated Aug. 8, 2025 (32 pages).

Van't Sant, et al., "In vivo 5-ethynyluridine (EU) labelling detects reduced transcription in Purkinje cell degeneration mouse mutants, but can itself induce neurodegeneration," Acta Neuropathological Communications, May 2021, vol. 9, No. 94 (pp. 1-20).

Vickovic, et al., "High-Definition Spatial Transcriptomics for in Situ Tissue Profiling," Nature Methods, Oct. 2019, vol. 16, No. 10 (pp. 987-990).

Wahlestedt, et al., "Potent and nontoxic antisense oligonucleotides containing locked nucleic acids," Proceedings of the National Academy of Sciences, USA, May 2000, vol. 97, No. 10 (pp. 5633-5638).

Wang, et al. Supplementary Material: "Three-dimensional Intact-tissue Sequencing of Single-cell Transcriptional States," Science, Jul. 2018, vol. 361, No. 6400 (pp. 1-39).

(56)                    References Cited

OTHER PUBLICATIONS

Wang, et al., "Cyclohexene nucleic acids (CeNA): serum stable oligonucleotides that activate RNase H and increase duplex stability with complementary RNA," Journal of the American Chemical Society 122(36):8595-8602 (2000).

Wang, et al., "EASI-FISH for thick tissue defines lateral hypothalamus spatio-molecular organization," Cell, Dec. 2021, vol. 184, No. 26 (pp. 6361-6377, e1-e24).

Wang, et al., "Evolution of new nonantibody proteins via iterative somatic hypermutation," Proceedings of the National Academy of Sciences, USA, Nov. 2004, vol. 101, No. 48 (pp. 16745-16749).

Wang, et al., "Human CD4+ lymphocytes for antigen quantification: characterization using conventional flow cytometry and mass cytometry," Cytometry Part A, 2012, vol. 81, No. 7 (pp. 567-575).

Wang, et al., "Three-dimensional intact-tissue sequencing of single-cell transcriptional states," Science, Jul. 27, 2018, vol. 361, No. 6400 (22 pages).

Wang, et al., N6-methyladenosine-dependent regulation of messenger RNA stability, Nature, Jan. 2014, vol. 505, No. 7481 (pp. 117-120; 22 total pages).

Weibrecht, et al., "In situ detection of individual mRNA molecules and protein complexes or post-translational modifications using padlock probes combined with the in situ proximity ligation assay," Nature protocols, Jan. 2013, vol. 8, No. 2 (pp. 355-372).

Weibrecht, et al., "Visualising individual sequence-specific protein-DNA interactions in situ," New Biotechnology, Jun. 2012, vol. 29, No. 5 (pp. 589-598).

West, et al., "Polymeric Biomaterials with Degradation Sites for Proteases Involved in Cell Migration," Macromolecules, 1999 vol. 32, No. 1 (pp. 241-244).

Wetmur, James G., "DNA probes: applications of the principles of nucleic acid hybridization," Critical Reviews in Biochemistry and Molecular Biology, 1991, vol. 26, Nos. 3-4 (pp. 227-259).

Wiedenmann, et al., "A far-red fluorescent protein with fast maturation and reduced oligomerization tendency from Entacmaea quadricolor (Anthozoa, Actinaria)," Proceedings of the National Academy of Sciences, USA, 2002, vol. 99, No. 18 (pp. 11646-11651).

Woods, et al., "MRI-PET registration with automated algorithm," Journal of Computer Assisted Tomography, 1993, vol. 17, No. 4 (pp. 536-546).

Wu, et al., "Translation dynamics of single mRNAs in live cells and neurons", Science, Jun. 2016, vol. 352, No. 6292 (pp. 1430-1435).

Xia, et al., "Spatial transcriptome profiling by MERFISH reveals subcellular RNA compartmentalization and cell cycledependent gene expression," Proceedings of the National Academy of Sciences, USA, 2019, vol. 116 (pp. 19490-19499).

Xu, et al., "Enhanced FIB-SEM systems for large-volume 3D imaging," elife, May 2017 6, e25916 (pp. 1-36).

Yang, et al., "Single-cell phenotyping within transparent intact tissue through whole-body clearing," Cell, Aug. 2014, vol. 158, No. 4 (pp. 945-958).

Yapp, et al., "Highly Multiplexed 3D Profiling of Cell States and Immune Niches in Human Tumours," bioRxiv, Apr. 2025, bioRxiv: doi: 10.1101/2023.11.10.566670 (pp. 1-53).

Yoshimura, et al., "A New Approach for Reversible RNA Photocrosslinking Reaction: Application to Sequence-Specific RNA Selection," ChemBioChem, Jun. 2009, vol. 10, No. 9 (pp. 1473-1476).

Yoshimura, et al., "Ultrafast reversible photo-cross-linking reaction: toward in situ DNA manipulation," Organic letters, Jun. 2008, vol. 10, No. 15 (pp. 3227-3230).

Zechel, et al., "Topographical transcriptome mapping of the mouse medial ganglionic eminence by spatially resolved RNA-seq" Genome Biology, 2014, vol. 15, No. 486 (pp. 1-12).

Zeisel et al., Brain Strcuture: "Cell Types in The Mouse Cortex and Hippocampus Revealed by Single-cell RNA-seq," Science, Mar. 6, 2015, vol. 347, No. 6226 (pp. 1138-1142).

Zeng, et al., "Neuronal cell-type classification: challenges, opportunities and the path forward," Nature Reviews Neuroscience, 2017, vol. 18, No. 9 (pp. 530-546).

Zhang, et al., "Detection of nucleic acids with a novel stem-loop primer rolling circle amplification technique," Biotechniques, Feb. 2018, vol. 64, No. 2 (pp. 69-80).

Zhang, et al., "Proximity-dependent Assay for Specific RNA-protein Interactions in Intact Cells," RNA, 2016, vol. 22, No. 11 (pp. 1785-1792).

Zhong, et al., "Visualization of oligonucleotide probes and point mutations in interphase nuclei and DNA fibers using rolling circle DNA amplification," Proceedings of the National Academy of Sciences, USA, Mar. 2001, vol. 98, No. 7 (pp. 3940-3945).

International Preliminary Report on Patentability for Application No. PCT/US2022/039895, mailed Feb. 22, 2024.

Erhard et al., scSLAM-seq reveals core features of transcription dynamics in single cells. bioRxiv. Jan. 21, 2019; 1-29. doi: https://doi.org/10.1101/486852. Published as: Nature. Jul. 2019;571(7765):419-423. doi: 10.1038/s41586-019-1369-y. Epub Jul. 10, 2019.

Halstead et al., Translation. An RNA biosensor for imaging the first round of translation from single cells to living animals. Science. Author manuscript; available in PMC Jun. 2, 2015. Published in final edited form as: Science. Mar. 20, 2015; 347(6228): 1367-1671. doi: 10.1126/science.aaa3380.

Mahdessian et al., Spatiotemporal dissection of the cell cycle with single-cell proteogenomics. bioRxiv. Mar. 26, 2020; 1-51. doi: https://doi.org/10.1101/543231. Published as: Nature. Feb. 2021;590(7847):649-654. doi: 10.1038/s41586-021-03232-9. Epub Feb. 24, 2021.

Morisaki et al., Real-time quantification of single RNA translation dynamics in living cells. Science. Jun. 17, 2016;352(6292):1425-9. doi: 10.1126/science.aaf0899. Epub May 5, 2016. With supplemental materials.

Vaninsberghe et al., Single-cell Ribo-seq reveals cell cycle-dependent translational pausing. Nature. Sep. 2021;597(7877):561-565. doi: 10.1038/s41586-021-03887-4. Epub Sep. 8, 2021.

Wang et al., N6-methyladenosine modulates messenger RNA translation Efficiency. Cell. Jun. 4, 2015;161(6):1388-99. doi: 10.1016/j.cell.2015.05.014.

Widagdo et al., The m6A-epitranscriptomic signature in neurobiology: from neurodevelopment to brain plasticity. J Neurochem. Oct. 2018;147(2):137-152. doi: 10.1111/jnc.14481. Epub Aug. 1, 2018.

Williams et al., Targeting and plasticity of mitochondrial proteins revealed by proximity-specific ribosome profiling. Science. Author manuscript; available in PMC Dec. 11, 2014. Published in final edited form as: Science. Nov. 7, 2014;346(6210): 748-751. doi: 10.1126/science.1257522.

Zhu et al., Single-cell multimodal omics: the power of many. Nat Methods. Jan. 2020;17(1):11-14. doi: 10.1038/s41592-019-0691-5.

International Search Report and Written Opinion for Application No. PCT/US2022/028012, mailed Aug. 17, 2022.

International Preliminary Report on Patentability for Application No. PCT/US2022/028012, mailed Nov. 16, 2023.

International Search Report and Written Opinion for Application No. PCT/US2021/05682, mailed Feb. 10, 2022.

International Preliminary Report on Patentability for Application No. PCT/US2021/05682, mailed May 11, 2023.

International Search Report and Written Opinion for Application No. PCT/US2022/035271, mailed Oct. 11, 2022.

International Preliminary Report on Patentability for Application No. PCT/US2022/035271, mailed Jan. 11, 2024.

International Search Report and Written Opinion for Application No. PCT/US2022/017016, mailed May 24, 2022.

International Preliminary Report on Patentability for Application No. PCT/US2022/017016, mailed Aug. 31, 2023.

Invitation to Pay Additional Fees for Application No. PCT/US2022/031275, mailed Sep. 8, 2022.

International Search Report and Written Opinion for Application No. PCT/US2022/031275, mailed Oct. 31, 2022.

International Preliminary Report on Patentability for Application No. PCT/US2022/031275, mailed Dec. 7, 2023.

No Author Listed, Starfish: Open-Source Image Based Transcriptomics and Proteomics Tools. 2018. http://github.com/spacetx/starfish [Online; accessed Feb. 1, 2023].

(56) References Cited

OTHER PUBLICATIONS

Abbott et al., A nanoelectrode array for obtaining intracellular recordings from thousands of connected neurons. Nat Biomed Eng. Feb. 2020;4(2):232-241. doi: 10.1038/s41551-019-0455-7. Epub Sep. 23, 2019.

Abdelaal et al., SpaGE: spatial gene enhancement using scRNA-seq. Nucleic Acids Res. Oct. 9, 2020;48(18):e107. doi: 10.1093/nar/gkaa740.

Achim et al., High-throughput spatial mapping of single-cell RNA-seq data to tissue of origin. Nat Biotechnol. May 2015;33(5):503-9. doi: 10.1038/nbt.3209. Epub Apr. 13, 2015.

Akbalik et al., Visualization of newly synthesized neuronal RNA in vitro and in vivo using click-chemistry. RNA Biol. Jan. 2, 2017;14(1):20-28. doi: 10.1080/15476286.2016.1251541. Epub Nov. 1, 2016.

Alfaro et al., The emerging landscape of single-molecule protein sequencing technologies. Nat Methods. Jun. 2021;18(6):604-617. doi: 10.1038/s41592-021-01143-1. Epub Jun. 7, 2021.

Arganda-Carreras et al., Trainable Weka Segmentation: a machine learning tool for microscopy pixel classification. Bioinformatics. Aug. 1, 2017;33(15):2424-2426. doi: 10.1093/bioinformatics/btx180.

Asakura et al., Improvement of acquisition and analysis methods in multi-electrode array experiments with iPS cell-derived cardiomyocytes. J Pharmacol Toxicol Methods. Sep.-Oct. 2015;75:17-26. doi: 10.1016/j.vascn.2015.04.002. Epub Apr. 22, 2015.

Asp et al., Spatially Resolved Transcriptomes—Next Generation Tools for Tissue Exploration. Bioessays. Oct. 2020;42(10):e1900221. doi: 10.1002/bies.201900221. Epub May 4, 2020.

Axelrod et al., starfish: scalable pipelines for image-based transcriptomics. Journal of Open Source Software. 2021; 6(61): 2440. https://doi.org/10.21105/joss.02440.

Blondel et al., Fast unfolding of communities in large networks. arXiv. Oct. 2008; 2008: 1-12. DOI 10.1088/1742-5468/2008/10/P10008.

Bolanos-Burgos et al., Thiamine Deficiency Increases Intrinsic Excitability of Mouse Cerebellar Purkinje Cells. Cerebellum. Apr. 2021;20(2):186-202. doi: 10.1007/s12311-020-01202-x. Epub Oct. 24, 2020.

Braselmann et al., Illuminating RNA Biology: Tools for Imaging RNA in Live Mammalian Cells. Cell Chem Biol. Aug. 20, 2020;27(8):891-903. doi: 10.1016/j.chembiol.2020.06.010. Epub Jul. 7, 2020.

Burke et al., A Fluorescence in Situ Hybridization Method To Quantify mRNA Translation by Visualizing Ribosome-mRNA Interactions in Single Cells. ACS Cent Sci. May 24, 2017;3(5):425-433. doi: 10.1021/acscentsci.7b00048. Epub May 3, 2017.

Buxbaum et al., In the right place at the right time: Visualizing and understanding mRNA localization. Nat Rev Mol Cell Biol. Author manuscript; available in PMC Jun. 29, 2015. Published in final edited form as: Nat Rev Mol Cell Biol. Feb. 2015; 16(2): 95-109. Published online Dec. 30, 2014. doi: 10.1038/nrm3918.

Cadwell et al., Electrophysiological, transcriptomic and morphologic profiling of single neurons using Patch-seq. Nat Biotechnol. Feb. 2016;34(2):199-203. doi: 10.1038/nbt.3445. Epub Dec. 21, 2015.

Cao et al., Sci-fate characterizes the dynamics of gene expression in single cells. Nat Biotechnol. Author manuscript; available in PMC Oct. 13, 2020. Published in final edited form as: Nat Biotechnol. Aug. 2020; 38(8): 980-988. Published online Apr. 13, 2020. doi: 10.1038/s41587-020-0480-9.

Cao et al., The single-cell transcriptional landscape of mammalian organogenesis. Nature. Feb. 2019;566(7745):496-502. doi: 10.1038/s41586-019-0969-x. Epub Feb. 20, 2019.

Chatterjee et al., Nontoxic, double-deletion-mutant rabies viral vectors for retrograde targeting of projection neurons. Nat Neurosci. Apr. 2018;21(4):638-646. doi: 10.1038/s41593-018-0091-7. Epub Mar. 5, 2018.

Chen et al., Spatial Transcriptomics and In Situ Sequencing to Study Alzheimer's Disease. Cell. Aug. 20, 2020;182(4):976-991.e19. doi: 10.1016/j.cell.2020.06.038. Epub Jul. 22, 2020.

Chen et al., Spatially resolved, highly multiplexed RNA profiling in single cells. Science. Apr. 24, 2015;348(6233):aaa6090. doi: 10.1126/science.aaa6090. Epub Apr. 9, 2015.

Codeluppi et al., Spatial organization of the somatosensory cortex revealed by osmFISH. Nat Methods. Nov. 2018;15(11):932-935. doi: 10.1038/s41592-018-0175-z. Epub Oct. 30, 2018.

Coelho et al., Nuclear segmentation in microscope cell images: a hand-segmented dataset and comparison of algorithms. Proc IEEE Int Symp Biomed Imaging. 2009:5193098:518-521. doi: 10.1109/ISBI.2009.5193098.

Crosetto et al., Spatially resolved transcriptomics and beyond. Nat Rev Genet. Jan. 2015;16(1):57-66. doi: 10.1038/nrg3832. Epub Dec. 2, 2014.

Cui et al., Single-Cell Transcriptome Analysis Maps the Developmental Track of the Human Heart. Cell Rep. Feb. 12, 2019;26(7):1934-1950.e5. doi: 10.1016/j.celrep.2019.01.079.

Dixit et al., Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.

Djebali et al., Landscape of transcription in human cells. Nature. Sep. 6, 2012;489(7414):101-8. doi: 10.1038/nature11233.

Dominissini et al., The topology of the human and mouse m6A RNA methylomes revealed by m6A-seq. Nature. Apr. 29, 2012;485(7397):201-6. doi: 10.1038/nature11112.

Eng et al., Transcriptome-scale super-resolved imaging in tissues by RNA seqFISH. Nature. Apr. 2019;568(7751):235-239. doi: 10.1038/s41586-019-1049-y. Epub Mar. 25, 2019.

Fazal et al., Atlas of Subcellular RNA Localization Revealed by APEX-Seq. Cell. Jul. 11, 2019;178(2):473-490.e26. doi: 10.1016/j.cell.2019.05.027. Epub Jun. 20, 2019.

Feiner et al., Engineered hybrid cardiac patches with multifunctional electronics for online monitoring and regulation of tissue function. Nat Mater. Jun. 2016;15(6):679-85. doi: 10.1038/nmat4590. Epub Mar. 14, 2016.

Franti et al., K-means properties on six clustering benchmark datasets. Applied Intelligence. Dec. 2018; 48(2): 4743-4759. DOI:10.1007/s10489-018-1238-7.

Friedman et al., Diverse Brain Myeloid Expression Profiles Reveal Distinct Microglial Activation States and Aspects of Alzheimer's Disease Not Evident in Mouse Models. Cell Rep. Jan. 16, 2018;22(3):832-847. doi: 10.1016/j.celrep.2017.12.066.

Friedman et al., Single-Cell Transcriptomic Analysis of Cardiac Differentiation from Human PSCs Reveals HOPX-Dependent Cardiomyocyte Maturation. Cell Stem Cell. Oct. 4, 2018;23(4):586-598.e8. doi: 10.1016/j.stem.2018.09.009.

Fu et al., Stable long-term chronic brain mapping at the single-neuron level. Nat Methods. Oct. 2016;13(10):875-82. doi: 10.1038/nmeth.3969. Epub Aug. 29, 2016.

Fuzik et al., Integration of electrophysiological recordings with single-cell RNA-seq data identifies neuronal subtypes. Nat Biotechnol. Feb. 2016;34(2):175-183. doi: 10.1038/nbt.3443. Epub Dec. 21, 2015.

Gao et al., Intracellular neuronal recording in awake nonhuman primates. Nature Protoc. Nov. 2020;15(11):3615-3631. doi: 10.1038/s41596-020-0388-3. Epub Oct. 12, 2020.

Gao, ClusterMap—Compare multiple Single cell RNA-seq profiling. May 22, 2018. 57 pages. Retrieved from the Internet: https://xgaoo.github.io/ClusterMap/ClusterMap.html. [last accessed: Jul. 12, 2023].

Goddard et al., UCSF ChimeraX: Meeting modern challenges in visualization and analysis. Protein Sci. Jan. 2018;27(1):14-25. doi: 10.1002/pro.3235. Epub Sep. 6, 2017.

Goddard et al., Visualizing density maps with UCSF Chimera. J Struct Biol. Jan. 2007;157(1):281-7. doi: 10.1016/j.jsb.2006.06.010. Epub Jul. 15, 2006.

Goltsev et al., Deep profiling of mouse splenic architecture with CODEX multiplexed imaging. Cell. Aug. 9, 2018;174(4):968-981.e15. doi: 10.1016/j.cell.2018.07.010. Epub Aug. 2, 2018.

Han et al., Mapping the Mouse Cell Atlas by Microwell-Seq. Cell. Feb. 22, 2018;172(5):1091-1107.e17. doi: 10.1016/j.cell.2018.02.001.

(56) References Cited

OTHER PUBLICATIONS

Hao et al., Integrated analysis of multimodal single-cell data. Cell. Jun. 24, 2021;184(13):3573-3587.e29. doi: 10.1016/j.cell.2021.04. 048. Epub May 31, 2021.

He et al., ClusterMap: multi-scale clustering analysis of spatial gene expression. Nat Commun. Oct. 8, 2021;12(1):5909. doi: 10.1038/ s41467-021-26044-x.

He et al., Integrating spatial gene expression and breast tumor morphology via deep learning. Nat Biomed Eng. Aug. 2020;4(8):827-834. doi: 10.1038/s41551-020-0578-x. Epub Jun. 22, 2020.

Heideman et al., Gauss and the history of the fast Fourier transform. IEEE ASSP Magazine. Oct. 1994; 1(4): 14-21. 10.1109/MASSP. 1984.1162257.

Hendriks et al., NASC-seq monitors RNA synthesis in single cells. Nat Commun. Jul. 17, 2019;10(1):3138. doi: 10.1038/s41467-019-11028-9.

Hernandez-Ochoa et al., Voltage clamp methods for the study of membrane currents and SR Ca(2+) release in adult skeletal muscle fibres. Prog Biophys Mol Biol. Apr. 2012;108(3):98-118. doi: 10.1016/j.pbiomolbio.2012.01.001. Epub Jan. 26, 2012.

Higham et al., Linear Algebra. Chapter 9 in: MATLAB Guide. 3rd Edition. Siam, Eds. 2016. pp. 135-158.

Hunter, Matplotlib: a 2D graphics environment. Comput Sci Eng. May-Jun. 2007; 9(3): 90-95. DOI: 10.1109/MCSE.2007.55.

Ingolia et al., Genome-wide analysis in vivo of translation with nucleotide resolution using ribosome profiling. Science. Apr. 10, 2009;324(5924):218-23. doi: 10.1126/science.1168978. Epub Feb. 12, 2009.

Ingolia, Ribosome Footprint Profiling of Translation throughout the Genome. Cell. Mar. 24, 2016;165(1):22-33. doi: 10.1016/j.cell.2016. 02.066.

Jan et al., Principles of ER cotranslational translocation revealed by proximity-specific ribosome profiling. Science. Nov. 7, 2014;346(6210):1257521. doi: 10.1126/science.1257521. Epub Nov. 6, 2014.

Jao et al., Exploring RNA transcription and turnover in vivo by using click chemistry. Proc Natl Acad Sci U S A. Oct. 14, 2008;105(41):15779-84. doi: 10.1073/pnas.0808480105. Epub Oct. 7, 2008.

Jonkhout et al., The RNA modification landscape in human disease. RNA. Dec. 2017;23(12):1754-1769. doi: 10.1261/rna.063503.117. Epub Aug. 30, 2017.

Jun et al., Fully integrated silicon probes for high-density recording of neural activity. Nature. Nov. 8, 2017;551(7679):232-236. doi: 10.1038/nature24636.

Katz et al., Mapping translation "hot-spots" in live cells by tracking single molecules of mRNA and ribosomes. Elife. Jan. 13, 2016;5:e10415. doi: 10.7554/eLife.10415.

Ke et al., In situ sequencing for RNA analysis in preserved tissue and cells. Nat Methods. Sep. 2013;10(9):857-60. doi: 10.1038/ nmeth.2563. Epub Jul. 14, 2013.

Keller et al., Visualizing whole-brain activity and development at the single-cell level using light-sheet microscopy. Neuron. Feb. 4, 2015;85(3):462-83. doi: 10.1016/j.neuron.2014.12.039.

Kishi et al., SABER amplifies FISH: enhanced multiplexed imaging of RNA and DNA in cells and tissues. Nat Methods. Jun. 2019;16(6):533-544. doi: 10.1038/s41592-019-0404-0. Epub May 20, 2019.

Kodandaramaiah et al., Automated whole-cell patch-clamp electrophysiology of neurons in vivo. Nat Methods. Jun. 2012;9(6):585-7. doi: 10.1038/nmeth.1993. Epub May 6, 2012.

Koh et al., Quantitative FastFUCCI assay defines cell cycle dynamics at single-cell level. J Cell Sci. Jan. 15, 2017;130(2):512-520. doi: 10.1242/jcs.195164. Epub Nov. 25, 2016.

Koos et al., Analysis of protein interactions in situ by proximity ligation assays. Curr Top Microbiol Immunol. 2014;377:111-26. doi: 10.1007/82_2013_334.

Lau et al., Single-nucleus transcriptome analysis reveals dysregulation of angiogenic endothelial cells and neuroprotective glia in Alzheimer's disease. Proc Natl Acad Sci U S A. Oct. 13, 2020;117(41):25800-25809. doi: 10.1073/pnas.2008762117. Epub Sep. 28, 2020.

Lee et al., Highly multiplexed subcellular RNA sequencing in situ. Science. Mar. 21, 2014;343(6177):1360-3. doi: 10.1126/science. 1250212. Epub Feb. 27, 2014.

Lee et al., Fluorescent in situ sequencing (FISSEQ) of RNA for gene expression profiling in intact cells and tissues. Nat Protoc. Mar. 2015;10(3):442-58. doi: 10.1038/nprot.2014.191. Epub Feb. 12, 2015.

Lein et al., The promise of spatial transcriptomics for neuroscience in the era of molecular cell typing. Science. Oct. 6, 2017;358(6359):64-69. doi: 10.1126/science.aan6827.

Li et al., Cyborg Organoids: Implantation of Nanoelectronics via Organogenesis for Tissue-Wide Electrophysiology. Nano Lett. Aug. 14, 2019;19(8):5781-5789. doi: 10.1021/acs.nanolett.9b02512. Epub Aug. 2, 2019.

Li et al., Epitranscriptome sequencing technologies: decoding RNA modifications. Nat Methods. Dec. 29, 2016;14(1):23-31. doi: 10.1038/ nmeth.4110.

Liu et al., Intrinsically stretchable electrode array enabled in vivo electrophysiological mapping of atrial fibrillation at cellular resolution. Proc Natl Acad Sci U S A. Jun. 30, 2020;117(26):14769-14778. doi: 10.1073/pnas.2000207117. Epub Jun. 15, 2020.

Liu et al., Multifunctional three-dimensional macroporous nanoelectronic networks for smart materials. Proc Natl Acad Sci U S A. Apr. 23, 2013;110(17):6694-9. doi: 10.1073/pnas.1305209110. Epub Apr. 8, 2013.

Liu et al., Probing N6-methyladenosine RNA modification status at single nucleotide resolution in mRNA and long non-coding RNA. RNA. Dec. 2013;19(12):1848-56. doi: 10.1261/rna.041178.113. Epub Oct. 18, 2013.

Liu et al., Syringe-injectable electronics. Nat Nanotechnol. Jul. 2015;10(7):629-636. doi: 10.1038/nnano.2015.115. Epub Jun. 8, 2015.

Machiraju et al., Current methods for the maturation of induced pluripotent stem cell-derived cardiomyocytes. World J Stem Cells. Jan. 26, 2019;11(1):33-43. doi: 10.4252/wjsc.v11.i1.33.

Macqueen, Some methods for classification and analysis of multivariate observations. Berkeley Symp on Math Statist and Prob. 1967; 5.1: 281-297.

Mathys et al., Single-cell transcriptomic analysis of Alzheimer's disease. Nature. Author manuscript; available in PMC Dec. 1, 2019. Published in final edited form as: Nature. Jun. 2019; 570(7761): 332-337. Published online May 1, 2019. doi: 10.1038/s41586-019-1195-2.

Mccabe et al., Automated quantitative analysis (AQUA) of in situ protein expression, antibody concentration, and prognosis. J Natl Cancer Inst. Dec. 21, 2005;97(24):1808-15. doi: 10.1093/jnci/ dji427.

Mcinnes et al., UMAP: Uniform Manifold Approximation and Projection. Journal of Open Source Software. Sep. 2, 2018; 3(29): 861. https://doi.org/10.21105/joss.00861.

Mcinnes et al., UMAP: Uniform Manifold Approximation and Projection for Dimension Reduction. ArXiv. Sep. 21, 2020; 1-63. https://arxiv.org/pdf/1802.03426.pdf [last accessed Jun. 11, 2023].

Mckinney, Data structures for statistical computing in Python. Proc of the 9th Python in Science Conference. Jan. 2010; 56-61. DOI:10. 25080/Majora-92bf1922-00a.

Moen et al., Deep learning for cellular image analysis. Nat Methods. Dec. 2019;16(12):1233-1246. doi: 10.1038/s41592-019-0403-1. Epub May 27, 2019.

Moffitt et al., Molecular, spatial, and functional single-cell profiling of the hypothalamic preoptic region. Science. Nov. 16, 2018;362(6416):eaau5324. doi: 10.1126/science.aau5324. Epub Nov. 1, 2018.

Nitzan et al., Gene expression cartography. Nature. Dec. 2019;576(7785):132-137. doi: 10.1038/s41586-019-1773-3. Epub Nov. 20, 2019.

Oliphant, Guide to NumPy. 1st Edition. Trelgol Publishing USA, Eds. 2006, 378 pages.

(56)          References Cited

OTHER PUBLICATIONS

Park et al., Segmentation-free inference of cell types from in situ transcriptomics data. Nat Commun. Jun. 10, 2021;12(1):3545. doi: 10.1038/s41467-021-23807-4.

Pedregosa et al., Scikit-learn: machine learning in Python. J Machine Learn Res. Oct. 2011; 12: 2825-2830.

Perez et al., Python: an ecosystem for scientifc computing. Comput Sci Eng. May 2011; 13(2): 13-21. DOI:10.1109/MCSE.2010.119.

Perkel, Starfish enterprise: finding RNA patterns in single cells. Nature. Aug. 2019;572(7770):549-551. doi: 10.1038/d41586-019-02477-9.

Petukhov et al., Bayesian segmentation of spatially resolved transcriptomics data. bioRxiv. Oct. 6, 2020. 34 pages. doi: https://doi.org/10.1101/2020.10.05.326777.

Qian et al., Probabilistic cell typing enables fine mapping of closely related cell types in situ. Nat Methods. Jan. 2020;17(1):101-106. doi: 10.1038/s41592-019-0631-4. Epub Nov. 18, 2019.

Qiu et al., Mapping transcriptomic vector fields of single cells. Cell. Feb. 17, 2022;185(4):690-711.e45. doi: 10.1016/j.cell.2021.12.045. Epub Feb. 1, 2022.

Qiu et al., Massively parallel and time-resolved RNA sequencing in single cells with scNT-seq. Nat Methods. Author manuscript; available in PMC May 7, 2021. Published in final edited form as: Nat Methods. Oct. 2020; 17(10): 991-1001. Published online Aug. 31, 2020. doi: 10.1038/s41592-020-0935-4.

Qu et al., Layer-Enriched Tissue Dissection Of The Mouse Placenta In Late Gestation. In: The Guide To Investigation Of Mouse Pregnancy. Academic Press, Eds. 2014; 529-535. DOI:10.1016/B978-0-12-394445-0.00044-8.

Rabani et al., Metabolic labeling of RNA uncovers principles of RNA production and degradation dynamics in mammalian cells. Nat Biotechnol. Author manuscript; available in PMC Nov. 1, 2011. Published in final edited form as: Nat Biotechnol. May 2011; 29(5): 436-442. Published online Apr. 24, 2011. doi: 10.1038/nbt.1861.

Rodriguez et al., Clustering by fast search and find of density peaks. Science. Jun. 27, 2014;344(6191):1492-6. doi: 10.1126/science.1242072.

Rokach et al., Clustering Methods. Chapter 15 in: Data Mining and Knowledge Discovery Handbook. 2005; 321-352.

Rosenberg et al., Single-cell profiling of the developing mouse brain and spinal cord with split-pool barcoding. Science. Apr. 13, 2018;360(6385):176-182. doi: 10.1126/science.aam8999. Epub Mar. 15, 2018.

Roundtree et al., Dynamic RNA Modifications in Gene Expression Regulation. Cell. Jun. 15, 2017;169(7):1187-1200. doi: 10.1016/j.cell.2017.05.045.

Rueden et al., ImageJ2: ImageJ for the next generation of scientific image data. BMC Bioinformatics. Nov. 29, 2017;18(1):529. doi: 10.1186/s12859-017-1934-z.

Sakaue-Sawano et al., Visualizing spatiotemporal dynamics of multicellular cell-cycle progression. Cell. Feb. 8, 2008;132(3):487-98. doi: 10.1016/j.cell.2007.12.033.

Schlegel et al., Charged pore-lining residues are required for normal channel kinetics in the eukaryotic mechanosensitive ion channel MSL1. Channels. (Austin). Dec. 2020;14(1):310-325. doi: 10.1080/19336950.2020.1818509.

Schmidt et al., Cell detection with star-convex polygons. Medical Image Computing and Computer Assisted Intervention Conference (MICCAI). Lecture Notes in Computer Science book series. Sep. 26, 2018;11071: 265-273.

Schwanhausser et al., Global quantification of mammalian gene expression control. Nature. May 19, 2011;473(7347):337-42. doi: 10.1038/nature10098.

Shah et al., In Situ Transcription Profiling of Single Cells Reveals Spatial Organization of Cells in the Mouse Hippocampus. Neuron. Oct. 19, 2016;92(2):342-357. doi: 10.1016/j.neuron.2016.10.001.

Shah et al., seqFISH accurately detects transcripts in single cells and reveals robust spatial organization in the hippocampus. Neuron. May 17, 2017;94(4):752-758.e1. doi: 10.1016/j.neuron.2017.05.008.

Stahl et al., Visualization and analysis of gene expression in tissue sections by spatial transcriptomics. Science. Jul. 1, 2016;353(6294):78-82. doi: 10.1126/science.aaf2403.

Stark et al., RNA sequencing: the teenage years. Nat Rev Genet. Nov. 2019;20(11):631-656. doi: 10.1038/s41576-019-0150-2. Epub Jul. 24, 2019.

Stickels et al., Highly sensitive spatial transcriptomics at near-cellular resolution with Slide-seqV2. Nat Biotechnol. Author manuscript; available in PMC Nov. 21, 2021. Published in final edited form as: Nat Biotechnol. Mar. 2021;39(3): 313-319. Published online Dec. 7, 2020. doi: 10.1038/s41587-020-0739-1.

Strell et al., Placing RNA in context and space—methods for spatially resolved transcriptomics. FEBS J. Apr. 2019;286(8):1468-1481. doi: 10.1111/febs.14435. Epub Mar. 31, 2018.

Stuart et al., Comprehensive integration of single-cell data. Cell. Jun. 13, 2019;177(7):1888-1902.e21. doi: 10.1016/j.cell.2019.05.031. Epub Jun. 6, 2019.

Stuart et al., Integrative single-cell analysis. Nat Rev Genet. May 2019;20(5):257-272. doi: 10.1038/s41576-019-0093-7.

Thomas et al., A review on cell detection and segmentation in microscopic images. 2017 International Conference on Circuit, Power and Computing Technologies (ICCPCT). Date of Conference: Apr. 20-21, 2017. 5 pages. 10.1109/ICCPCT.2017.8074189.

Tian et al., Macroporous nanowire nanoelectronic scaffolds for synthetic tissues. Nat Mater. Nov. 2012;11(11):986-94. doi: 10.1038/nmat3404. Epub Aug. 26, 2012.

Tirosh et al., Dissecting the multicellular ecosystem of metastatic melanoma by single-cell RNA-seq. Science. Author manuscript; available in PMC Jul. 14, 2016. Published in final edited form as: Science. Apr. 8, 2016; 352(6282): 189-196. doi: 10.1126/science.aad0501.

Toga et al., Towards multimodal atlases of the human brain. Nat Rev Neurosci. Dec. 2006;7(12):952-66. doi: 10.1038/nrn2012.

Traag et al., From Louvain to Leiden: guaranteeing well-connected communities. Sci Rep. Mar. 26, 2019;9(1):5233. doi: 10.1038/s41598-019-41695-z.

Van Den Berge et al., Trajectory-based differential expression analysis for single-cell sequencing data. Nat Commun. Mar. 5, 2020;11(1):1201. doi: 10.1038/s41467-020-14766-3.

Van Der Walt et al., scikit-image: image processing in Python. Peer J. Jun. 19, 2014:2:e453. doi: 10.7717/peerj.453. eCollection 2014.

Van'T Sant et al., In vivo 5-ethynyluridine (EU) labelling detects reduced transcription in Purkinje cell degeneration mouse mutants, but can itself induce neurodegeneration. Acta Neuropathol Commun. May 21, 2021;9(1):94. doi: 10.1186/s40478-021-01200-y.

Viventi et al., Flexible, foldable, actively multiplexed, high-density electrode array for mapping brain activity in vivo. Nat Neurosci. Nov. 13, 2011;14(12):1599-605. doi: 10.1038/nn.2973.

Wang et al., N6-methyladenosine-dependent regulation of messenger RNA stability. Nature. Author manuscript; available in PMC Jul. 2, 2014. Published in final edited form as: Nature. Jan. 2, 2014; 505(7481): 117-120. Published online Nov. 27, 2013. doi: 10.1038/nature12730.

Wang et al., Spatial organization of the transcriptome in individual neurons. bioRxiv. Dec. 7, 2020; 1-45. doi: https://doi.org/10.1101/2020.12.07.414060.

Wang et al., Three-dimensional intact-tissue sequencing of single-cell transcriptional states. Science. Jul. 27, 2018;361(6400):eaat5691. doi: 10.1126/science.aat5691. Epub Jun. 21, 2018.

Weibrecht et al., Visualising individual sequence-specific protein-DNA interactions in situ. N Biotechnol. Jun. 15, 2012;29(5):589-98. doi: 10.1016/j.nbt.2011.08.002. Epub Aug. 31, 2011.

Wolf et al., SCANPY: large-scale single-cell gene expression data analysis. Genome Biol. Feb. 6, 2018;19(1):15. doi: 10.1186/s13059-017-1382-0.

Xia et al., Spatial transcriptome profiling by MERFISH reveals subcellular RNA compartmentalization and cell cycle-dependent gene expression. Proc Natl Acad Sci U S A. Sep. 24, 2019;116(39):19490-19499. doi: 10.1073/pnas.1912459116. Epub Sep. 9, 2019.

Zechel et al., Topographical transcriptome mapping of the mouse medial ganglionic eminence by spatially resolved RNA-seq. Genome Biol. 2014;15(10):486. doi: 10.1186/s13059-014-0486-z.

(56)          References Cited

OTHER PUBLICATIONS

Zhou et al., Encoding Method of Single-cell Spatial Transcriptomics Sequencing. Int J Biol Sci. 2020; 16(14): 2663-2674. Published online Jul. 30, 2020. doi: 10.7150/ijbs.43887.

Zhou et al., Human and mouse single nucleus transcriptomics reveal TREM2-dependent and TREM2-independent cellular responses in Alzheimer's disease. Nat Med. Author manuscript; available in PMC Jul. 13, 2020. Published in final edited form as: Nat Med. Jan. 2020; 26(1): 131-142. Published online Jan. 13, 2020. doi: 10.1038/s41591-019-0695-9.

* cited by examiner

FIG. 2A
CONTINUED $d_1$ - the shortest distance to nuclear membrane in 3D $d_2$ - the shortest distance to *cell membrane* in 3D $$\text{distance ratio (DR)} = \frac{d_1}{d_1 + d_2}$$

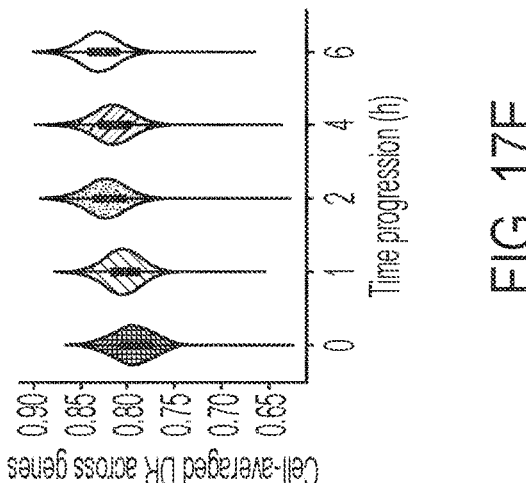
FIG. 17E
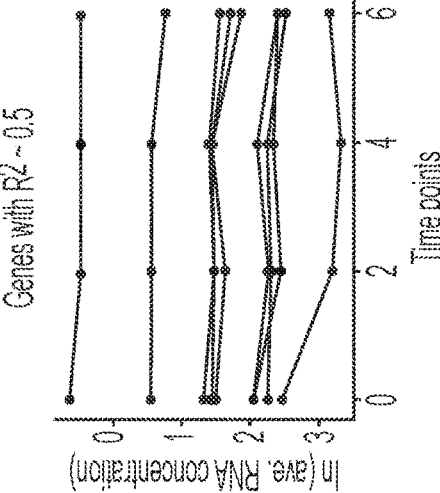
FIG. 17D
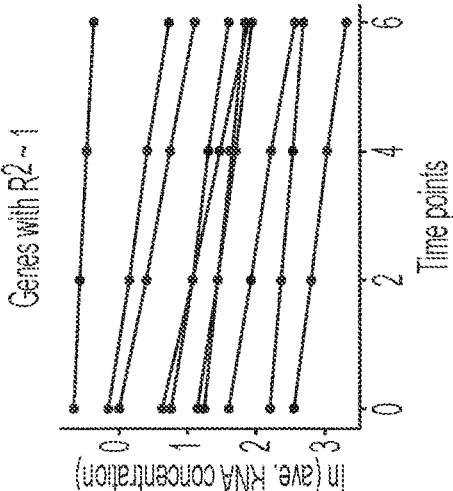

SPATIOTEMPORALLY RESOLVED TRANSCRIPTOMICS AT SUBCELLULAR RESOLUTION

RELATED APPLICATIONS

This application is a national stage filing under 35 U.S.C. § 371 of International PCT Application PCT/US2022/028012, filed May 6, 2022, which claims priority under 35 U.S.C. § 119(e) to U.S. Provisional Application, U.S. Ser. No. 63/185,511, filed May 7, 2021, and U.S. Provisional Application, U.S. Ser. No. 63/314,873, filed on Feb. 28, 2022, each of which is incorporated herein by reference.

BACKGROUND OF THE INVENTION

The regulated flow of gene expression shapes the most fundamental processes of life and influences the development and progression of many diseases and disorders. These highly controlled processes include transcription, RNA processing, translation, and degradation of messenger RNAs (mRNAs) and proteins. The development of methods for spatial transcriptomics has created a rapid paradigm shift to the technology of single cell sequencing by retaining genetic information in a spatial context, allowing cell organization and tissue structure to be directly visualized. However, current methods for spatial transcriptomics only detect mRNAs as static pictures of transcriptomes, obscuring their highly dynamic nature. In addition, most current methods focus on the pan-cellular level, determining heterogenous cell types and mapping them back to tissue, but ignoring the rich information in the intracellular environment. Accordingly, methods for linking spatial transcriptomics with the temporal dimension are needed to study gene expression in a spatial context over time and understand the links between spatiotemporal gene expression and cellular development, as well as the development and progression of various diseases and disorders.

SUMMARY OF THE INVENTION

The present disclosure describes methods for profiling spatiotemporal gene expression in a cell or multiple cells (including, for instance, cells present in a tissue). In one aspect, a method, referred to herein as "TEMPOmap" (temporally resolved in situ sequencing and mapping), is described. The TEMPOmap method resolves nascently transcribed RNAs at subcellular resolution and can be used to track the dynamics of gene expression (i.e., the transcriptome) by incorporating temporal resolution into spatial transcriptomic workflows. The method provides imaged-based single-cell descriptions at the subcellular level and can be used to study intracellular activities, such as epitranscriptomic processing, mRNA trafficking, localized translation, kinetic parameters of RNA translation, and others. TEMPOmap may also be used to study intact tissues and to understand and identify causes in the development and progression of various diseases and disorders linked to alterations in gene expression. The methods described herein facilitate understanding of RNAs, proteins, and their interactions, providing a valuable tool to visualize how genomic information is processed in time and space. Any of these methods can also be performed in vivo, as is described further herein.

Thus, in one aspect, the present disclosure provides methods for profiling spatiotemporal gene expression in a cell comprising the steps of:

a) incubating a cell in the presence of a pool of nucleoside analogs for an amount of time $t_1$ to metabolically label nucleic acids synthesized by the cell, wherein each nucleoside analog in the pool of nucleoside analogs comprises a reactive chemical moiety;

b) contacting the metabolically labeled nucleic acids with a population of first oligonucleotide probes, wherein each first oligonucleotide probe in the population of first oligonucleotide probes comprises a chemical moiety that reacts with the reactive chemical moiety of the nucleoside analogs;

c) contacting the metabolically labeled nucleic acids with one or more pairs of oligonucleotide probes comprising a second oligonucleotide probe and a third oligonucleotide probe, wherein:
  i) the second oligonucleotide probe comprises a barcode sequence and a portion that is complementary to a metabolically labeled nucleic acid of interest; and
  ii) the third oligonucleotide probe comprises a portion that is complementary to the metabolically labeled nucleic acid of interest, a first barcode sequence, a portion that is complementary to a first oligonucleotide probe in the population of first oligonucleotide probes, and a second barcode sequence, wherein the first barcode sequence of the third oligonucleotide probe is complementary to the barcode sequence of the second oligonucleotide probe;

d) ligating the 5' end and the 3' end of the third oligonucleotide probe together to produce a circular oligonucleotide;

e) performing rolling circle amplification to amplify the circular oligonucleotide using the second oligonucleotide probe as a primer to produce one or more concatenated amplicons;

f) embedding the one or more concatenated amplicons in a polymer matrix;

g) contacting the one or more concatenated amplicons embedded in the polymer matrix with a fourth oligonucleotide probe comprising a sequence that is complementary to the second barcode sequence of the third oligonucleotide probe; and h) imaging the fourth oligonucleotide probe to determine the location of the one or more concatenated amplicons embedded in the polymer matrix.

In some embodiments, steps (a)-(h) are performed one or more additional times. In some embodiments, steps (a)-(h) are repeated at least one time using a different amount of time, $t_2$, in the incubation of step (a). In certain embodiments, steps (a)-(h) are optionally repeated for a third amount of time $t_3$, optionally repeated for a fourth amount of time $t_4$, optionally repeated for a fifth amount of time $t_5$, optionally repeated for a sixth amount of time $t_6$, optionally repeated for a seventh amount of time $t_7$, optionally repeated for an eight amount of time $t_8$, optionally repeated for a ninth amount of time $t_9$, and optionally repeated for a tenth amount of time $t_{10}$.

In some embodiments, any of the methods disclosed herein are useful in diagnosing and/or treating a disease or disorder. In some embodiments, any of the methods disclosed herein are useful for studying the kinetic parameters of RNA translation. In some embodiments, any of the methods described herein are useful for studying post-transcriptional RNA modifications. In some embodiments, any of the methods disclosed herein are useful for studying spatiotemporal gene expression at various stages of the cell cycle and cell replication.

In another aspect, the present disclosure provides methods for profiling the role of post-transcriptional modification in spatiotemporal gene expression. In some embodiments, the methods for profiling spatiotemporal gene expression described herein may be performed in a cell comprising a knockdown of a gene involved in post-transcriptional modification of one or more nucleic acids of interest (e.g., one or more RNA transcripts). The spatiotemporal expression of various nucleic acids of interest in the knockdown cell can then be compared to the spatiotemporal expression of the same nucleic acids of interest in a wild-type cell. Any alteration in the expression of the nucleic acids of interest relative to expression in a wild-type cell may indicate that the post-transcriptional modification is involved in regulating spatiotemporal expression of the nucleic acid of interest.

In another aspect, the present disclosure provides methods for studying the role of spatiotemporal gene expression in the development or progression of a disease or disorder. For example, the methods for profiling spatiotemporal gene expression described herein may be performed in a cell from a diseased tissue (e.g., a diseased tissue taken from a subject). The spatiotemporal expression of various nucleic acids of interest in the cell from the diseased tissue can then be compared to the spatiotemporal expression of the same nucleic acids of interest in a cell from a non-diseased tissue. Any alteration in the expression of the nucleic acid of interest relative to expression in a non-diseased cell may indicate that spatiotemporal expression of the nucleic acid of interest may be involved in the development or progression of the disease or disorder.

In another aspect, the present disclosure provides methods for screening for an agent capable of modulating spatiotemporal gene expression of a nucleic acid of interest, or of multiple nucleic acids of interest. For example, the methods for profiling spatiotemporal gene expression described herein may be performed in a cell (e.g., a normal cell, or a diseased cell) in the presence of one or more candidate agents. The spatiotemporal expression of various nucleic acids of interest in the cell can then be compared to the spatiotemporal expression of the same nucleic acids of interest in a cell that was not exposed to the one or more candidate agents. Any alteration in the expression of the nucleic acid(s) of interest relative to expression in the cell that was not exposed to the candidate agent(s) may indicate that spatiotemporal expression of the nucleic acid(s) of interest is modulated by the candidate agent(s).

In another aspect, the present disclosure provides methods for diagnosing a disease or disorder in a subject. For example, the methods for profiling spatiotemporal gene expression described herein may be performed in a cell from a sample taken from a subject (e.g., a subject who is thought to have or is at risk of having a disease or disorder). The spatiotemporal expression of various nucleic acids of interest in the cell can then be compared to the spatiotemporal expression of the same nucleic acids of interest in a cell from a non-diseased tissue sample. Any alteration in the expression of the nucleic acid of interest relative to expression in a non-diseased cell may indicate that the subject has the disease or disorder.

In another aspect, the present disclosure provides methods for treating a disease or disorder in a subject. For example, the methods for profiling spatiotemporal gene expression described herein may be performed in a cell from a sample taken from a subject (e.g., a subject who is thought to have or is at risk of having a disease or disorder). The spatiotemporal expression of various nucleic acids of interest in the cell can then be compared to the spatiotemporal expression of the same nucleic acids of interest in a cell from a non-diseased tissue sample. A treatment for the disease or disorder may then be administered to the subject if any alteration in the expression of the nucleic acids of interest relative to expression in a non-diseased cell is observed.

In another aspect, the present disclosure provides methods for profiling spatiotemporal gene expression in a subject in vivo comprising the steps of:

a) administering a pool of nucleoside analogs to a subject in vivo for an amount of time $t_1$ to metabolically label nucleic acids synthesized by one or more cells in the subject, wherein each nucleoside analog in the pool of nucleoside analogs comprises a reactive chemical moiety;

b) harvesting a tissue sample from the subject;

c) contacting the metabolically labeled nucleic acids in the harvested tissue sample with a population of first oligonucleotide probes, wherein each first oligonucleotide probe in the population of first oligonucleotide probes comprises a chemical moiety that reacts with the reactive chemical moiety of the nucleoside analogs;

d) contacting the metabolically labeled nucleic acids with one or more pairs of oligonucleotide probes comprising a second oligonucleotide probe and a third oligonucleotide probe, wherein:

i) the second oligonucleotide probe comprises a barcode sequence and a portion that is complementary to a metabolically labeled nucleic acid of interest; and ii) the third oligonucleotide probe comprises a portion that is complementary to the metabolically labeled nucleic acid of interest, a first barcode sequence, a portion that is complementary to a first oligonucleotide probe in the population of first oligonucleotide probes, and a second barcode sequence, wherein the first barcode sequence of the third oligonucleotide probe is complementary to the barcode sequence of the second oligonucleotide probe;

e) ligating the 5' end and the 3' end of the third oligonucleotide probe together to produce a circular oligonucleotide;

f) performing rolling circle amplification to amplify the circular oligonucleotide using the second oligonucleotide probe as a primer to produce one or more concatenated amplicons;

g) embedding the one or more concatenated amplicons in a polymer matrix;

h) contacting the one or more concatenated amplicons embedded in the polymer matrix with a fourth oligonucleotide probe comprising a sequence that is complementary to the second barcode sequence of the third oligonucleotide probe; and i) imaging the fourth oligonucleotide probe to determine the location of the one or more concatenated amplicons embedded in the polymer matrix.

In another aspect, the present disclosure provides a plurality of oligonucleotide probes comprising a first oligonucleotide probe, a second oligonucleotide probe, and a third oligonucleotide probe, wherein:

i) the first oligonucleotide probe comprises a reactive chemical moiety;

ii) the second oligonucleotide probe comprises a barcode sequence and a portion that is complementary to a nucleic acid of interest; and iii) the third oligonucleotide probe comprises a portion that is complementary to the nucleic acid of interest, a first barcode sequence, a portion that is complementary to the first oligonucleotide probe, and a second barcode sequence, wherein the first barcode sequence of the third oligonucleotide probe is complementary to the barcode sequence of the second oligonucleotide probe.

In some embodiments, the present disclosure provides an oligonucleotide probe comprising the structure 5'-[reactive chemical moiety]-[poly-A linker sequence]-[portion complementary to third oligonucleotide probe]-[polymerization blocker]-3', wherein ]-[ comprises an optional nucleotide linker. In some embodiments, the present disclosure provides an oligonucleotide probe comprising the structure 5'-[portion complementary to nucleic acid of interest]-[barcode sequence]-3', wherein ]-[ comprises an optional nucleotide linker. In some embodiments, the present disclosure provides an oligonucleotide probe comprising the structure 5'-[first portion complementary to first oligonucleotide probe]-[first barcode sequence]-[portion complementary to nucleic acid of interest]-[second barcode sequence]-[second portion complementary to first oligonucleotide probe]-3', wherein ]-[ comprises an optional nucleotide linker.

In another aspect, the present disclosure provides kits comprising one or more of the oligonucleotide probes described herein.

In another aspect, the present disclosure provides systems for profiling spatiotemporal gene expression in a cell. In some embodiments, the systems comprise a) a cell; b) a pool of nucleoside analogs, wherein each nucleoside analog in the pool of nucleoside analogs comprises a reactive chemical moiety (e.g., a bioorthogonal functional group such as a click chemistry handle); c) a first oligonucleotide probe, wherein the first oligonucleotide probe comprises a chemical moiety that reacts with the reactive chemical moiety of the nucleoside analogs; and d) one or more pairs of oligonucleotide probes comprising a second oligonucleotide probe and a third oligonucleotide probe, wherein:

i) the second oligonucleotide probe comprises a barcode sequence and a portion that is complementary to a nucleic acid of interest; and ii) the third oligonucleotide probe comprises a portion that is complementary to the nucleic acid of interest, a first barcode sequence, a portion that is complementary to the first oligonucleotide probe, and a second barcode sequence, wherein the first barcode sequence of the third oligonucleotide probe is complementary to the barcode sequence of the second oligonucleotide probe.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 2A provides a schematic showing an overview of TEMPOmap. After 5-ethynyl uridine (5-EU) labeled cells are prepared, the custom 3-part probes are conjugated or hybridized to cellular mRNAs, resulting in the enzymatic replication of each padlock sequence into cDNA amplicons. The amplicons are anchored in situ via a functionalized acrylic group to a hydrogel mesh to create a DNA-gel hybrid (wavy lines). The five-base barcode on each amplicon is read out by five rounds of SEDAL sequencing. Thus, multiplexed RNA quantification reveals gene expression in nascent subcellular locations. FIG. 2B shows a reconstruction of the spatiotemporal trajectory of RNAs by integrating different time points. FIG. 2C provides a schematic of the three-part DNA probe design. The DNA splint probe conjugates to the labeled RNAs in a non-targeted way, and pairing of the splint probe and the padlock probe is required to circularize the padlock. A second pairing of the primer probe and the padlock probe amplifies target-specific signals. FIG. 2D shows that signal amplification requires the presence of all three probes. mRNA_I represents ACTB and mRNA_II represents GAPDH. All four images show ACTB (light gray) mRNA and HeLa cell nuclei (dark gray). EU-treated cells compared with untreated cells results in signal-to-noise ratios of 30. FIG. 2E shows the design of the pulse-chase experiment (left) and a set of fluorescent images (right) from the experiment, showing the translocation of ACTB mRNAs when washed after 1 h EU treatment with different times.

FIG. 4A provides a clustered heat map of gene expression when each cell is knocked down with one siRNA compared to a wild-type cell. FIG. 4B provides a histogram of counts of reads (left) and counts of genes per cell (right).

FIG. 6A shows the principle of STARmap. After the cells or tissues are fixed, the DNA probes that hybridize to intracellular mRNAs within the cells are enzymatically replicated as cDNA amplicons. Each pair of DNA probes contain a barcode (as labeled on the probes) which encodes gene identity and is read-out through in situ sequencing as fluorescent colors. FIG. 6B shows temporally resolved STARmap. Transcription, nuclear export, and degradation rates are measured at transcriptome scale. Ethynyl-uridine (EU) is used to label newly transcribed RNAs in short pulses, and the samples are fixed after different case durations. The labeled RNAs are modified in situ with a polymerizable moiety via click chemistry, then copolymerized with acrylamide to embed within a hydrogel network (wavy lines), followed by clearance of unlabeled RNAs. The spatiotemporal trajectory of RNAs inside cells is reconstructed by integrating the STARmap results at multiple time points.

FIG. 8A provides raw fluorescent images of 5-EU labeled human HeLa cells. HeLa cells were labeled for two hours (pulse) and then cultured for various amounts of hours without 5-EU (chase: 0, 2, 4, or 6 hours) before fixation and in situ sequencing quantification. The spatial localization of nascently transcribed hACTB RNAs is shown in light gray, while the spatial localization of cell nuclei is shown in dark gray. FIG. 8B shows quantification of the ratio of hACTB RNA versus cell nuclei (DAPI staining) fluorescent intensities under different conditions.

FIG. 9A provides raw fluorescent images of 5-EU labeled human HeLa cells. HeLa cells were labeled for 12 hours and fixed immediately after labeling, followed by in situ sequencing. Four channels show the localizations of four human RNAs, respectively. Cells in the negative control were cultured without 5-EU labeling. FIG. 9B provides raw fluorescent images of 1-hour labeled HeLa cells, followed by various numbers of hours of cell culture without 5-EU (chase: 0-6 hours) before fixation. Each channel represents the spatial information of one type of RNA. The legend is indicated in FIG. 9A.

FIG. 10A provides an overview of the TEMPOmap workflow: in situ nascent RNA sequencing of multiple time points followed by spatiotemporal RNA analyses. FIG. 10B provides a schematic of the TEMPOmap experimental workflow showing the procedure of TEMPOmap amplicon library preparation and in situ SEDAL sequencing. FIG. 10C shows the rationale for the three-part DNA probe design. The generation of an amplicon requires the presence of the splint probe, the circularized padlock probe, and the primer probe. FIG. 10D (left) provides schematics and representative fluorescent cell images of negative control experiments of FIG. 10C, showing three-part probe requirement for signal amplification. mRNA_I represents ACTB, and mRNA_II represents GAPDH. All four images show ACTB (light gray) mRNA in HeLa cells (DAPI in dark gray). Right: quantification of cell images showing the average amplicon reads per cell (each condition measured 5 images containing ~300 cells). ****p<1e-04. Scale bars: 10 μm.

FIG. 11A shows the design of TEMPOmap pulse-chase experiments. FIG. 11B shows reads (amplicons)-per-cell count for each pulse-chase time point normalized by STARmap probe-targeting gene expression. FIG. 11C shows 3D fluorescent images of in-process TEMPOmap with zoomed views of representative single cells of cycle 1 in each time point. Z-stack range: 10 μm. FIG. 11D shows subcellular region assignment (nuclear, middle, and periphery) of one representative cell (bottom) and a boxplot summarizing the fraction of reads in each subcellular region of all cells in each time point (top). **P<0.001 (n=1000-2000). FIG. 11E** shows TEMPOmap single-cell (top row) or nucleocytoplasmic (middle row) RNA measurements rendered as a visualization by Potential of Heat-diffusion for Affinity-based Trajectory Embedding (PHATE) and colored by pulse-chase time points (I, III) or cell-cycle marker gene expression (II, IV). Black arrows inferred by RNA degradation vector field mainly show the transition directions of chase time progression. Representative raw images of G2/M phase cells separated on PHATE coordinates are provided on the bottom row. Scale bars: 15 μm.

FIG. 12A shows the dynamic model for estimating RNA kinetic parameters. For each gene, RNA synthesis ($\alpha$) and whole-cell degradation constant ($\beta$) were estimated using single-cell RNA concentration. The export constant ($\lambda$), nuclear degradation constant ($\beta n$), and cytoplasm ($\beta c$) were estimated using subcellular RNA concentrations. FIG. 12B shows the dynamic model for estimating cytoplasmic translocation ($\gamma$) using DR-based analysis. FIG. 12C shows a mathematical model of RNA life cycle and kinetic assumptions used for the estimation (bottom right). FIG. 12C also shows the histogram of the six parameters for all genes that passed QC and the scatter plots depicting the pairwise correlation of parameters with R value (Pearson correlation) and linear fitting curve (bottom left). The pair of parameters that showed correlation are highlighted with an asterisk (R>0.1). Intensity of the dots indicates local density. FIG. 12D provides a heat map depicting pairwise correlation matrix of the six parameters estimated using single-cells from three cell-cycle phase (G1, G1/S, G2/M). Shading according to the legend provided indicates the value of Pearson correlation. Boxed regions indicate the correlations of each parameter across cell cycle. FIG. 12E provides a UMAP representation (left) and heatmap (right) showing gene clustering using all 18 estimated parameters across cell cycle. Shading according to the legend provided in the heatmap represents the parameter-wise z-score normalized value. FIG. 12F shows pathway enrichment analysis of genes in each cluster in FIG. 12E using DAVID. FIG. 12G provides a visualization of the four kinetic clusters in representative cells across pulse-chase time points. Scale bar: 10 μm.

FIG. 13A provides a heat map depicting the pairwise correlation of all genes by single-cell RNA co-variation when combining all time points, where the shading indicates the value of Pearson correlation. The four kinetic clusters from FIG. 12E are shaded on the right side, indicating the cluster to which each gene belongs. Groups 1 and 2 are highlighted for highly correlated gene modules. FIG. 13B shows zoomed-in views of Groups 1 (top) and 2 (bottom), showing the correlation of RNA co-variation of each gene module across individual time points. The complete heat maps of individual time points are shown in FIG. 19A. FIG. 13C shows pathway enrichment analysis results of genes in Groups 1 and 2. FIG. 13D provides box plots showing the distribution of RNA synthesis (a, left) and whole-cell degradation constants (0, right) in Groups 1 and 2. FIG. 13E provides box plots showing the distribution of six parameters estimated for DNA-binding, RNA-binding, and cell-cell junction-related genes. FIG. 13F provides heat maps showing the parameter correlation matrix for DNA-binding, RNA-binding, and cell-cell junction related genes across cell cycle. Shading indicates the value of Pearson correlation. Boxed regions indicate the correlations of each parameter across cell cycle. FIG. 13G shows a box plot comparing the six parameters estimated for $m^6A$ and non-$m^6A$ RNAs. p<0.05, *p<0.01, ****p<0.001. The range of y-axes was selected for 25-75% quartile of values in FIGS. 13E and 13G.

FIG. 14A shows the use of CuAAC-mediated click chemistry to conjugate azide-modified splint and EU-labeled nascent transcript. FIG. 14B shows a comparison of TEMPOmap two-probe and three-probe design. Left, probe design schematics. Middle, representative fluorescent images of cells treated with sense-targeting and antisense-targeting padlocks and primers. Right, quantification of fluorescence in cell images (n=150-200 for each measurement). FIG. 14C shows DNA sequences of TEMPOmap three-probe system. FIG. 14D shows proof-of-concept pulse-chase experiment (top) followed by raw cell images (bottom) showing the translocation of ACTB mRNAs when chased after 1 h EU treatment with different times. Cell nuclei (dark gray), amplicons (light gray). Scale bar: 10 μm. FIG. 14E shows simultaneous mapping and sequencing of nascent RNAs by TEMPOmap and total RNAs by STARmap in the experimental workflow. TEMPOmap-targeted amplicon reads were normalized against the reads of STARmap-targeted RNAs.

FIG. 15A shows the TEMPOmap data analysis pipeline. FIG. 15B provides schematics of read assignment in subcellular compartments. FIG. 15C provides histograms showing detected reads (DNA amplicons) per cell (left), and genes per cell (right). FIG. 15D provides schematics of distance ratio (DR)-based subcellular segmentation in the cytoplasm. Two values for each amplicon were computed in 3D: $d_1$, the shortest distance to nuclear membrane; $d_2$, the shortest distance to cell membrane. "Middle" is the region defined between DR=0 and 10. "Periphery" is defined as DR>10.

FIG. 16A shows nuclear-to-cytoplasmic ratio of amplicon reads of 991 genes at 6 h chase time point. Genes were ranked from top to bottom according to the ratios. FIG. 16B shows cell-cycle identification (G1, G1/S, G2/M) by cell-cycle gene marker measured via TEMPOmap labeled RNA expression. The cells were visualized via PCA and shaded by cell-cycle phases (top left). Variations in the raw counts of all cell-cycle gene markers (bottom left) and four representative markers (right) were projected by the pseudotime analysis. FIG. 16C provides a comparison of cell-cycle identification by 1 h labeled reads and total reads using scEU-seq dataset showing no significant difference. The number in each box indicates the number of cells. FIG. 16D provides cell clustering results based on PHATE embedding of the nucleocytoplasmic matrix. Cluster 1 incorporates the cells in M phase by visual inspection of raw images.

FIGS. 17A-17H show RNA kinetic parameter estimation. FIG. 17A shows the correlated relation between cell volume (in voxels) and single-cell reads, indicating the influence of transcript number by cell volume. FIG. 17B provides schematics showing the different concentrations of one RNA species in the nucleus and cytoplasm. FIG. 17C shows mathematical models for estimating RNA kinetic parameters (α, β, βn, λ, βc) and the detailed workflow of calculation and fitting procedure. Note: X(t)=single-cell RNA concentration; N(t)=nuclear RNA concentration; C(t)=cytoplasmic RNA concentration; p (nuclear processing constant)=βn+λ. For the purpose of clarity, $\beta_n=\beta n$, $\beta_c=\beta c$. FIG. 17D shows changes in the natural log of X(t) across time points of genes with $R^2 \sim 1$ (left) and $R^2 \sim 0.5$ (right). The estimated β and p were filtered with a threshold of $R^2 > 0.5$ as a quality control. FIG. 17E shows the distribution of single cell-averaged DR values for all 991 genes across 0-6 h chase time points. FIG. 17F provides a histogram of estimated 7 (cytoplasmic translocation) values for all genes. Dashed line separates the genes with γ>0 and γ<0, which indicates the opposite direction of observed translocation. FIG. 17G shows, on the left, that 12 genes of 7<0 ($R^2 > 0.5$) were strongly enriched in extracellular exosome and transmembrane proteins (9/12). FIG. 17G shows, in the middle, time-lapsed DR values of representative genes. FIG. 17H provides schematics showing the observed inward direction of RNA translocation of genes with 7<0.

FIGS. 18A-18F provide examples of pairwise correlation in FIG. 12D, showing scatter plots of the relationships between G1 and G2/M. Correlation coefficients from left to right: α (R=0.99), β (R=0.77), βn (R=0.70), λ (R=0.65), βc (R=0.36), γ (R=0.07). R indicates the value of Pearson correlation. FIGS. 18G-18H show that RNA synthesis (α) and degradation (β) were estimated from single-cell RNA expression (FIG. 18G) and from the published scEU-seq dataset (FIG. 18H) for each cell-cycle phase (G1, G1/S, G2/M). FIG. 18I provides density plots showing the distribution of each of the six parameters (left to right: α, β, βn, λ, βc, γ) estimated in each cell-cycle state. The first five parameters were estimated from RNA concentrations and γ from DR values, showing no overall changes across the three states. FIG. 18J provides violin plots showing the distribution of βn, λ, βc of cells in G2 and M phase. M phase was identified in FIG. 16D; G2 phase were the rest of G2/M cells. FIG. 18K provides boxplots showing the subcellular distribution of RNA reads across time in each kinetic cluster.

FIG. 19A provides heat maps showing matrices of the pairwise correlation coefficients from single-cell variation in TEMPOmap-measured gene expression of 0 h, 2 h, 4 h, and 6 h (from left to right) chase time points. Gene order along each matrix was the same and determined by the hierarchical clustering tree of the matrix combining the four time points (FIG. 13A). Side bar of each matrix shows the shaded annotation of gene clusters from FIG. 12E. FIG. 19B provides a pie chart describing the major molecular functions of 991 genes analyzed by gene ontology. FIG. 19C provides a pie chart describing $m^6A$-RNA methylation in the gene pool. FIG. 19D provides a pie chart describing the relationship to YTHDC1 in the gene pool. FIG. 19E provides box plots comparing the six parameters estimated for $m^6A$ and non-$m^6A$ RNAs across three cell-cycle phases. **p<0.05,

*p<0.01. The range of y-axes was selected for 25-75% quartile of values. FIG. 19F shows the expression of YTHDC1 normalized by the expression of the other six STARmap-targeted genes (METTL3/14, YTHDC2, YTHDF1-3) in control cells and siYTHDC1 cells. FIG. 19G shows the cumulative distribution of log 2 fold changes in nuclear-to-cytoplasmic expression ratio following knock-down of YTHDC1 in 0-6 h chase time point (from left to right). FIG. 19H** shows the cumulative distribution of log 2 fold changes in the six parameters following knockdown of YTHDC1.

FIG. 20A shows in vivo TEMPOmap workflow. Tissues from an EU-injected mouse (1 mg EU) and a PBS-injected control were harvested and fixed 2 hours post-administration. Tissues were sectioned and chemically processed by TEMPOmap workflow for DNA amplicon library preparation. The DNA amplicons were then in situ sequenced by rounds of fluorescent imag-ing. FIG. 20B (left) EU-injected heart sections showed strong enrichment in the signals of amplicons compared to PBS-injected control, demonstrating the high signal-to-noise ratio of in vivo TEMPOmap. FIG. 20B (right) Rep-resentative fluorescent images of heart sections showing the signals of nascent transcription of four genes (Myh6, Flt1, Dach1, Lamc1) in the 2-hour EU-labeling window in mouse heart and minimal background signals in PBS-injected mouse heart.

DEFINITIONS

Figure 1:
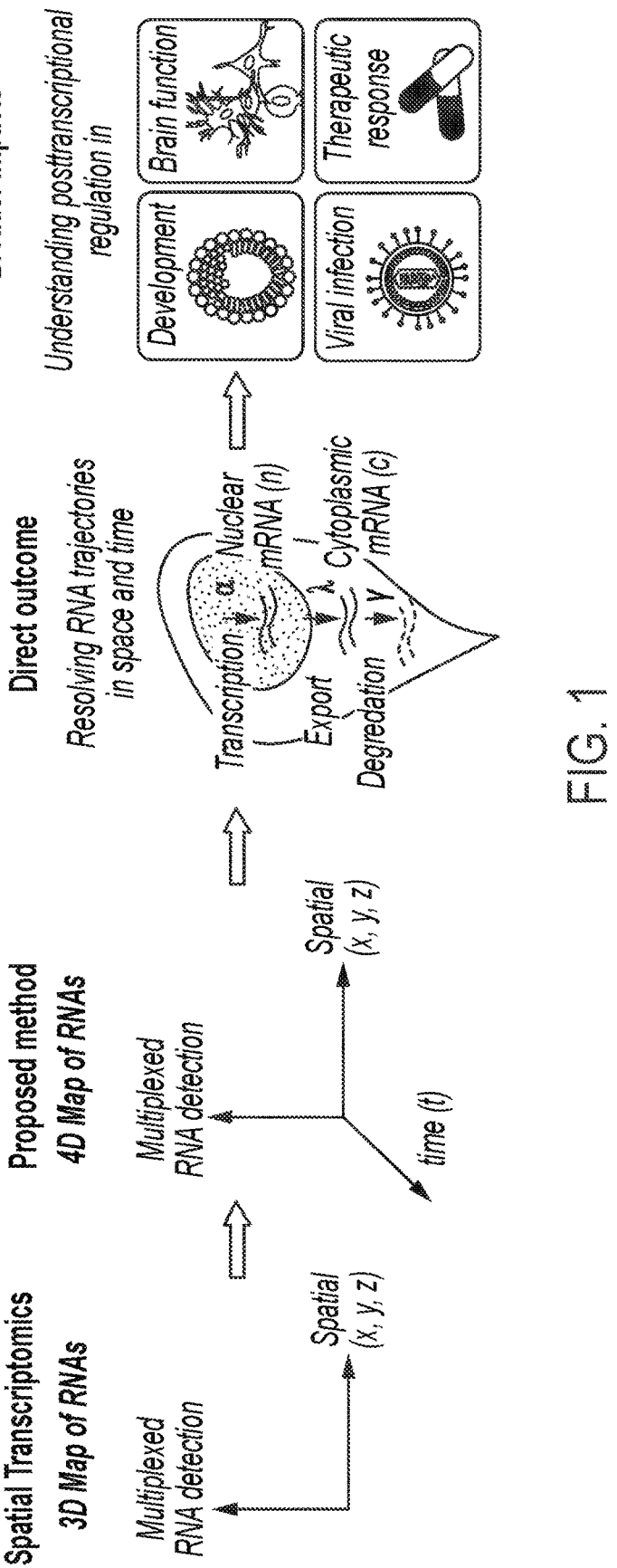
FIG. 1 provides a schematic of the temporally resolved in situ sequencing and mapping (TEMPOmap) method for dissecting gene regulation mechanisms in cells and tissues at subcellular resolution. TEMPOmap integrates temporal resolution with spatial transcriptomics to create a 4D map of RNAs. This method maps the trajectory of RNA in 3D space across tunable time periods and enables a deeper understanding of gene regulation in various biological and physiological processes.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); *The Cambridge Dictionary of Science and Technology* (Walker ed., 1988); *The Glossary of Genetics,* 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

The terms "administer," "administering," and "adminis-tration" refer to implanting, absorbing, ingesting, injecting, inhaling, or otherwise introducing a treatment or therapeutic agent, or a composition of treatments or therapeutic agents, in or on a subject.

The term "amplicon" as used herein refers to a nucleic acid (e.g., DNA or RNA) that is the product of an amplifi-cation reaction (i.e., the production of one or more copies of a genetic fragment or target sequence) or replication reac-tion. Amplicons can be formed artificially using, for example, PCR or other polymerization reactions. The term "concatenated amplicons" refers to multiple amplicons that are joined together to form a single nucleic acid molecule. Concatenated amplicons can be formed, for example, by rolling circle amplification (RCA), in which a circular oligonucleotide is amplified to produce multiple linear cop-ies of the oligonucleotide as a single nucleic acid molecule comprising multiple amplicons that are concatenated.

The term "angiogenesis" refers to the physiological pro-cess through which new blood vessels form from pre-existing vessels. Angiogenesis is distinct from vasculogen-esis, which is the de novo formation of endothelial cells from mesoderm cell precursors. The first vessels in a devel-oping embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., exces-sive or insufficient) angiogenesis that amounts to and/or is associated with a disease.

An "antibody" refers to a glycoprotein belonging to the immunoglobulin superfamily. The terms antibody and immunoglobulin are used interchangeably. With some exceptions, mammalian antibodies are typically made of basic structural units each with two large heavy chains and two small light chains. There are several different types of antibody heavy chains, and several different kinds of anti-bodies, which are grouped together into different isotypes based on which heavy chain they possess. Five different antibody isotypes are known in mammals (IgG, IgA, IgE, IgD, and IgM), which perform different roles, and help direct the appropriate immune response for each different type of foreign object they encounter. The term "antibody" as used herein also encompasses antibody fragments and nanobodies, as well as variants of antibodies. The term "antibody variants" may also be used to encompass antibody fragments. In some embodiments, an antibody or antibody variant is administered as a treatment for a disease or disorder (e.g., one that is associated with a change in the profile of spatiotemporal gene expression in a cell taken from a subject).

"Anti-cancer agents" encompass biotherapeutic anti-can-cer agents as well as chemotherapeutic agents. Exemplary biotherapeutic anti-cancer agents include, but are not limited to, interferons, cytokines (e.g., tumor necrosis factor, inter-feron α, interferon γ), vaccines, hematopoietic growth fac-tors, monoclonal serotherapy, immunostimulants and/or immunomodulatory agents (e.g., IL-1, 2, 4, 6, or 12), immune cell growth factors (e.g., GM-CSF) and antibodies (e.g. HERCEPTIN (trastuzumab), T-DM1, AVASTIN (beva-cizumab), ERBITUX (cetuximab), VECTIBIX (panitu-mumab), RITUXAN (rituximab), BEXXAR (tositumo-mab)). Exemplary chemotherapeutic agents include, but are not limited to, anti-estrogens (e.g. tamoxifen, raloxifene, and megestrol), LHRH agonists (e.g. goserelin and leuprolide), anti-androgens (e.g. flutamide and bicalutamide), photody-namic therapies (e.g. vertoporfin (BPD-MA), phthalocya-nine, photosensitizer Pc4, and demethoxy-hypocrellin A (2BA-2-DMHA)), nitrogen mustards (e.g. cyclophosph-amide, ifosfamide, trofosfamide, chlorambucil, estramus-tine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of pacli-taxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis*), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genentech), SF1126 (Semafoe), and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, antiphospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "bioorthogonal functional groups," as used herein, refers to functional groups that can be used in a chemical reaction inside of a living system (e.g., inside a cell) without interfering with any of the native biochemical processes inside the system.

Bioorthogonal functional groups include, for example, click chemistry handles. The term "click chemistry handle," as used herein, refers to a reactant, or a reactive group, that can partake in a click chemistry reaction. Exemplary click chemistry handles are demonstrated in U.S. Patent Publication 20130266512, which is incorporated by reference herein. For example, a strained alkyne, e.g., a cyclooctyne, is a click chemistry handle, since it can partake in a strain-promoted cycloaddition. In general, click chemistry reactions require at least two molecules comprising click chemistry handles that can react with each other. Such click chemistry handle pairs that are reactive with each other are sometimes referred to herein as partner click chemistry handles. For example, an azide is a partner click chemistry handle with an alkyne. Exemplary click chemistry handles include, but are not limited to, alkenes, dienes, tetrazines, trans-cyclooctenes, alkynes, azides, nitrones, and tetrazoles. For two molecules to be conjugated via click chemistry, the click chemistry handles of the molecules have to be reactive with each other, for example, in that the reactive moiety of one of the click chemistry handles can react with the reactive moiety of the second click chemistry handle to form at least one covalent bond. Such reactive pairs of click chemistry handles are well known to those of skill in the art.

The term "cancer" refers to a class of diseases characterized by the development of abnormal cells that proliferate uncontrollably and have the ability to infiltrate and destroy normal body tissues. See e.g., *Stedman's Medical Dictionary*, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer;

skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

A "cell," as used herein, may be present in a population of cells (e.g., in a tissue, an organ, or an organoid). In some embodiments, a population of cells is composed of a plurality of cell types. Cells for use in the methods of the present disclosure can be present within an organism, a single cell type derived from an organism, or a mixture of cell types. Included are naturally occurring cells and cell populations, genetically engineered cell lines, cells derived from transgenic animals, etc. Virtually any cell type and size can be accommodated in the methods and systems described herein. Suitable cells include bacterial, fungal, plant, and animal cells. In some embodiments, the cells are mammalian cells (e.g., complex cell populations such as naturally occurring tissues). In some embodiments, the cells are from a human. In certain embodiments, the cells are collected from a subject (e.g., a human) through a medical procedure such as a biopsy. Alternatively, the cells may be a cultured population (e.g., a culture derived from a complex population or a culture derived from a single cell type where the cells have differentiated into multiple lineages).

Cell types contemplated for use in the methods of the present disclosure include, but are not limited to, stem and progenitor cells (e.g., embryonic stem cells, hematopoietic stem cells, mesenchymal stem cells, neural crest cells, etc.), endothelial cells, muscle cells, myocardial cells, smooth and skeletal muscle cells, mesenchymal cells, epithelial cells, hematopoietic cells, lymphocytes such as T-cells (e.g., Th1 T cells, Th2 T cells, Th0 T cells, cytotoxic T cells) and B cells (e.g., pre-B cells), monocytes, dendritic cells, neutrophils, macrophages, natural killer cells, mast cells, adipocytes, immune cells, neurons, hepatocytes, and cells involved with particular organs (e.g., thymus, endocrine glands, pancreas, brain, neurons, glia, astrocytes, dendrocytes, and genetically modified cells thereof). The cells may also be transformed or neoplastic cells of different types (e.g., carcinomas of different cell origins, lymphomas of different cell types, etc.) or cancerous cells of any kind (e.g., from any of the cancers disclosed herein). Cells of different origins (e.g., ectodermal, mesodermal, and endodermal) are also contemplated for use in the methods of the present disclosure.

As used herein, the term "gene" refers to a nucleic acid fragment that expresses a protein, including regulatory sequences preceding (5' non-coding sequences) and following (3' non-coding sequences) the coding sequence. "Native gene" refers to a gene as found in nature with its own regulatory sequences.

As used herein, "gene expression" refers to the process by which information from a gene is used in the synthesis of a gene product. Gene products include proteins and RNA transcripts (e.g., messenger RNA, transfer RNA, or small nuclear RNA). Gene expression includes transcription and translation. Transcription is the process by which a segment of DNA is transcribed into RNA by an RNA polymerase. Translation is the process by which an RNA is translated into a peptide or protein by a ribosome. The term "genetic information" as used herein refers to one or more genes and/or one or more RNA transcripts (e.g., any number of genes and/or RNA transcripts).

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism.

The terms "inflammatory disease" and "inflammatory condition" are used interchangeably herein, and refer to a disease or condition caused by, resulting from, or resulting in inflammation. Inflammatory diseases and conditions include those diseases, disorders or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

Additional exemplary inflammatory conditions include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, Type II diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatistis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease).

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver, Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic porphyria, hepatic porphyria (e.g., acute intermittent porphyria, porphyria cutanea tarda), and Zellweger syndrome.

The term "lung disease" or "pulmonary disease" refers to a disease of the lung. Examples of lung diseases include, but are not limited to, bronchiectasis, bronchitis, bronchopulmonary dysplasia, interstitial lung disease, occupational lung disease, emphysema, cystic fibrosis, acute respiratory distress syndrome (ARDS), severe acute respiratory syndrome (SARS), asthma (e.g., intermittent asthma, mild persistent asthma, moderate persistent asthma, severe persistent asthma), chronic bronchitis, chronic obstructive pulmonary disease (COPD), emphysema, interstitial lung disease, sarcoidosis, asbestosis, aspergilloma, aspergillosis, pneumonia (e.g., lobar pneumonia, multilobar pneumonia, bronchial pneumonia, interstitial pneumonia), pulmonary fibrosis, pulmonary tuberculosis, rheumatoid lung disease, pulmonary embolism, and lung cancer (e.g., non-small-cell lung carcinoma (e.g., adenocarcinoma, squamous-cell lung carcinoma, large-cell lung carcinoma), small-cell lung carcinoma).

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

"Neurodegenerative diseases" refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. In some embodiments, a neurodegenerative disease is Alzheimer's disease. Causes of Alzheimer's disease are poorly understood but in the majority of cases are thought to include a genetic basis. The disease is characterized by loss of neurons and synapses in the cerebral cortex, resulting in atrophy of the affected regions. Biochemically, Alzheimer's is characterized as a protein misfolding disease caused by plaque accumulation of abnormally folded amyloid beta protein and tau protein in the brain. Symptoms of Alzheimer's disease include, but are not limited to, difficulty remembering recent events, problems with language, disorientation, mood swings, loss of motivation, self-neglect, and behavioral issues. Ultimately, bodily functions are gradually lost, and Alzheimer's disease eventually leads to death. Treatment is currently aimed at treating cognitive problems caused by the disease (e.g., with acetylcholinesterase inhibitors or NMDA receptor antagonists), psychosocial interventions (e.g., behavior-oriented or cognition-oriented approaches), and general caregiving. There are no treatments currently available to stop or reverse the progression of the disease completely.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA and mean any chain of two or more nucleotides. The polynucleotides can be chimeric mixtures or derivatives or modified versions thereof, and single-stranded or double-stranded. The oligonucleotide can be modified at the base moiety, sugar moiety, or phosphate backbone, for example, to improve stability of the molecule, its hybridization parameters, etc. In some embodiments, a nucleic acid is a metabolically labeled nucleic acid. A "metabolically labeled nucleic acid" refers herein to a nucleic acid that has incorporated one or more unnatural nucleoside analogs, such as 5-ethynyl uridine, into its oligonucleotide chain during transcription.

The term "post-transcriptional modification" as used herein refers to a chemical modification or alteration of an RNA (e.g., an RNA primary transcript) following transcription. Post-transcriptional modifications are common in eukaryotic cells (e.g., human cells) and are often important for producing a mature, functional RNA molecule, and/or for the translocation of the RNA molecule from the nucleus to various locations in a cell where it can perform different functions. Post-transcriptional modification also plays an important role in the conversion of mRNA transcripts into mature mRNA that the cell can translate into protein. Post-transcriptional modifications include, but are not limited to, those involved in 5' processing of an RNA transcript (e.g., 5' capping of an mRNA with, for example, 7-methylguanosine), 3' processing of an RNA transcript (e.g., cleavage or polyadenylation of the 3' end of the RNA transcript), intron splicing (i.e., the removal of non-coding regions (introns) from pre-mRNA), and histone mRNA processing. Specific post-transcriptional modifications include, but are not limited to 7-methylguanosine ($m^7G$), $N^6$-methyladenosine ($m^6A$), poly(A) tails, intron splicing, and histone mRNA processing A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

An "RNA transcript" is the product resulting from RNA polymerase-catalyzed transcription of a DNA sequence. When the RNA transcript is a complimentary copy of the DNA sequence, it is referred to as the primary transcript, or it may be an RNA sequence derived from post-transcriptional processing of the primary transcript and is referred to as the mature RNA. "Messenger RNA (mRNA)" refers to the RNA that is without introns and can be translated into polypeptides by the cell. "cRNA" refers to complementary RNA, transcribed from a recombinant cDNA template. "cDNA" refers to DNA that is complementary to and derived from an mRNA template. "Nascent RNA" refers to RNA that is actively being transcribed by the cell, and RNA that has recently been transcribed by the cell but has not yet undergone any kind of post-transcriptional modification.

The term "sample" or "biological sample" refers to any sample including tissue samples (such as tissue sections, surgical biopsies, and needle biopsies of a tissue); cell samples (e.g., cytological smears (such as Pap or blood smears) or samples of cells obtained by microdissection); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. In some embodiments, a biological sample is a surgical biopsy taken from a subject, for example, a biopsy of any of the tissues described herein. In certain embodiments, a biological sample is a tumor biopsy (e.g., from a subject diagnosed with, suspected of having, or thought to have cancer).

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In some embodiments, the non-human animal is a mammal (e.g., primate (e.g., cynomolgus monkey or rhesus monkey) or mouse). The term "patient" refers to a subject in need of treatment of a disease. In some embodiments, the subject is human. In some embodiments, the patient is human. The human may be a male or female at any stage of development. A subject or patient "in need" of treatment of a disease or disorder includes, without limitation, those who exhibit any risk factors or symptoms of a disease or disorder. In some embodiments, a subject is a non-human experimental animal (e.g., a mouse, rat, dog, or pig).

A "therapeutically effective amount" of a treatment or therapeutic agent is an amount sufficient to provide a therapeutic benefit in the treatment of a condition or to delay or minimize one or more symptoms associated with the condition. A therapeutically effective amount of a treatment or therapeutic agent means an amount of the therapy, alone or in combination with other therapies, that provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

As used herein, a "tissue" is a group of cells and their extracellular matrix from the same origin. Together, the cells carry out a specific function. The association of multiple tissue types together forms an organ. The cells may be of different cell types. In some embodiments, a tissue is an epithelial tissue. Epithelial tissues are formed by cells that cover an organ surface (e.g., the surface of the skin, airways, soft organs, reproductive tract, and inner lining of the digestive tract). Epithelial tissues perform protective functions and are also involved in secretion, excretion, and absorption. Examples of epithelial tissues include, but are not limited to, simple squamous epithelium, stratified squamous epithelium, simple cuboidal epithelium, transitional epithelium, pseudostratified epithelium, columnar epithelium, and glandular epithelium. In some embodiments, a tissue is a connective tissue. Connective tissues are fibrous tissues made up of cells separated by non-living material (e.g., an extracellular matrix). Connective tissues provide shape to organs and hold organs in place. Connective tissues include fibrous connective tissue, skeletal connective tissue, and fluid connective tissue. Examples of connective tissues include, but are not limited to, blood, bone, tendon, ligament, adipose, and areolar tissues. In some embodiments, a tissue is a muscular tissue. Muscular tissue is an active contractile tissue formed from muscle cells. Muscle tissue functions to produce force and cause motion. Muscle tissue includes smooth muscle (e.g., as found in the inner linings of organs), skeletal muscle (e.g., as typically attached to bones), and cardiac muscle (e.g., as found in the heart, where it contracts to pump blood throughout an organism). In some embodiments, a tissue is a nervous tissue. Nervous tissue includes cells comprising the central nervous system and peripheral nervous system. Nervous tissue forms the brain, spinal cord, cranial nerves, and spinal nerves (e.g., motor neurons). In certain embodiments, a tissue is brain tissue. In certain embodiments, a tissue is placental tissue. In some embodiments, a tissue is heart tissue.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed (e.g., prophylactically (as may be further described herein) or upon suspicion or risk of disease). In other embodiments, treatment may be administered in the absence of signs or symptoms of the disease. For example, treatment may be administered to a susceptible subject prior to the onset of symptoms (e.g., in light of a history of symptoms in the subject, or family members of the subject). Treatment may also be continued after symptoms have resolved, for example, to delay or prevent recurrence. In some embodiments, treatment may be administered after using the methods disclosed herein and observing an alteration in spatiotemporal gene expression of one or more nucleic acids of interest in a cell or tissue in comparison to a healthy cell or tissue.

The terms "tumor" and "neoplasm" are used herein refers to an abnormal mass of tissue wherein the growth of the mass surpasses and is not coordinated with the growth of a normal tissue. A tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

DETAILED DESCRIPTION OF CERTAIN EMBODIMENTS

The aspects described herein are not limited to specific embodiments, systems, compositions, methods, or configurations, and as such can, of course, vary. The terminology used herein is for the purpose of describing particular aspects only and, unless specifically defined herein, is not intended to be limiting.

The present disclosure provides methods for profiling spatiotemporal gene expression, including methods for profiling spatiotemporal gene expression in a subject in vivo. The present disclosure also provides methods for profiling the role of post-transcriptional modification in spatiotemporal gene expression, methods for studying the role of spatiotemporal gene expression in the development or progression of a disease or disorder, methods for identifying an agent capable of modulating gene expression, methods for diagnosing a disease or disorder in a subject, and methods for treating a disease or disorder in a subject. Oligonucleotide probes useful in the methods and systems described herein are also provided by the present disclosure. The present disclosure also provides kits comprising the oligonucleotide probes disclosed herein. Systems for profiling spatiotemporal gene expression are also provided by the present disclosure.

Methods for Profiling Spatiotemporal Gene Expression

In one aspect, the present disclosure provides methods for profiling spatiotemporal gene expression in a cell (see, for example, FIG. 1). In the methods disclosed herein, a cell may be metabolically labeled through incubation in the presence of a pool of nucleoside analogs, where each nucleoside analog comprises a reactive chemical moiety (e.g., any reactive bioorthogonal functional group, such as a click chemistry handle, as described further herein) for an amount of time (referred to herein as "$t_1$"). The metabolically labeled nucleic acids may then be contacted with a first oligonucleotide probe comprising a reactive chemical moiety (e.g., any bioorthogonal functional group capable of reacting with the reactive chemical moiety of the nucleoside analogs that has been incorporated into the transcripts of the cell). The reactive chemical moieties of the nucleoside analogs and the first oligonucleotide probe react with one another, linking the first oligonucleotide probe to the metabolically labeled transcripts produced by the cell. The metabolically labeled nucleic acids may then be contacted with one or more pairs of oligonucleotide probes, which are described further herein and may be used to amplify the transcripts produced by the cell to produce one or more concatenated amplicons. The one or more concatenated amplicons may then be embedded in a polymer matrix and sequenced to determine the identity of the transcripts (e.g., through SEDAL sequencing (Sequencing with Error-reduction by Dynamic Annealing and Ligation) as described further herein) and their location within the polymer matrix. Using the locations of the transcripts, individual cells, subcellular locations, and organelles can be identified. The method may then be repeated one or more additional times, incubating the cell and the nucleoside analogs for different amounts of time (i.e., $t_2$, $t_3$, $t_4$, etc.) to determine how expression of one or more nucleic acids varies over time.

In some embodiments, the present disclosure provides a method for profiling spatiotemporal gene expression in a cell comprising the steps of:

a) incubating a cell in the presence of a pool of nucleoside analogs for an amount of time $t_1$ to metabolically label nucleic acids synthesized by the cell, wherein each nucleoside analog in the pool of nucleoside analogs comprises a reactive chemical moiety;

b) contacting the metabolically labeled nucleic acids with a population of first oligonucleotide probes, wherein each first oligonucleotide probe in the population of first oligonucleotide probes comprises a chemical moiety that reacts with the reactive chemical moiety of the nucleoside analogs;

c) contacting the metabolically labeled nucleic acids with one or more pairs of oligonucleotide probes comprising a second oligonucleotide probe and a third oligonucleotide probe, wherein:

i) the second oligonucleotide probe comprises a barcode sequence and a portion that is complementary to a metabolically labeled nucleic acid of interest; and ii) the third oligonucleotide probe comprises a portion that is complementary to the metabolically labeled nucleic acid of interest, a first barcode sequence, a portion that is complementary to a first oligonucleotide probe in the population of first oligonucleotide probes, and a second barcode sequence, wherein the first barcode sequence of the third oligonucleotide probe is complementary to the barcode sequence of the second oligonucleotide probe;

d) ligating the 5' end and the 3' end of the third oligonucleotide probe together to produce a circular oligonucleotide;

e) performing rolling circle amplification to amplify the circular oligonucleotide using the second oligonucleotide probe as a primer to produce one or more concatenated amplicons;

f) embedding the one or more concatenated amplicons in a polymer matrix;

g) contacting the one or more concatenated amplicons embedded in the polymer matrix with a fourth oligonucleotide probe comprising a sequence that is complementary to the second barcode sequence of the third oligonucleotide probe; and h) imaging the fourth oligonucleotide probe to determine the location of the one or more concatenated amplicons embedded in the polymer matrix.

In some embodiments, steps (a)-(h) are performed one or more additional times. Repeating steps (a)-(h) and incubating the cell and the pool of nucleoside analogs together in step (a) for varying amounts of time allows the expression of a metabolically labeled nucleic acid of interest, or multiple metabolically labeled nucleic acids of interest, to be observed over time, allowing the spatiotemporal expression of the labeled nucleic acids of interest to be profiled. In some embodiments, steps (a)-(h) are repeated at least one time for a different amount of time $t_2$. In certain embodiments, steps (a)-(h) are optionally repeated for a third amount of time $t_3$, optionally repeated for a fourth amount of time $t_4$, optionally repeated for a fifth amount of time $t_5$, optionally repeated for a sixth amount of time $t_6$, optionally repeated for a seventh amount of time $t_7$, optionally repeated for an eighth amount of time $t_8$, optionally repeated for a ninth amount of time $t_9$, and optionally repeated for a tenth amount of time $t_{10}$. There is no limit to the number of times that steps (a)-(h) may be repeated. There is also no limit on the amount of time that the cell and the pool of nucleoside analogs are incubated together in step (a). In some embodiments, the incubation of step (a) is performed for an amount of time on the order of minutes (e.g., about 1 minute, about 2 minutes, about 5 minutes, about 10 minutes, about 20 minutes, about 30 minutes, about 40 minutes, about 50 minutes, or about 60 minutes). In some embodiments, the incubation of step (a) is performed for an amount of time on the order of hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours). In certain embodiments, the incubation of step (a) is performed for more than 24 hours. In some embodiments, the incubation of step (a) is performed for an amount of time on the order of days (e.g., for about 1 day, about 2 days, about 3 days, about 4 days, about 5 days, about 6 days, about 7 days, or for more than 7 days).

The use of any type of cell in the methods disclosed herein is contemplated by the present disclosure (e.g., any of the cell types described in the Definitions herein). In some embodiments, the cell is a mammalian cell. In certain embodiments, the cell is a human cell. In some embodiments, the cell is a cancer cell. The present disclosure also contemplates performing the methods described herein on multiple cells simultaneously. In some embodiments, spatiotemporal gene expression is profiled in more than 10 cells, more than 20 cells, more than 50 cells, more than 100 cells, more than 200 cells, more than 300 cells, more than 400 cells, more than 500 cells, or more than 1000 cells simultaneously. In some embodiments, the method is performed on multiple cells of the same cell type. In some embodiments, the method is performed on multiple cells comprising cells of different cell types (e.g., stem cells, progenitor cells, neuronal cells, astrocytes, dendritic cells, endothelial cells, microglia, oligodendrocytes, muscle cells, myocardial cells, mesenchymal cells, epithelial cells, immune cells, hepatic cells, smooth and skeletal muscle cells, hematopoietic cells, lymphocytes, monocytes, neutrophils, macrophages, natural killer cells, mast cells, adipocytes, neurons, etc.). In certain embodiments, the cells are HeLa cells. In certain embodiments, the cell or cells are permeabilized cells (e.g., the cells are permeabilized prior to the step of contacting with a population of first oligonucleotide probes). In certain embodiments, the cell or cells are present within an intact tissue (e.g., of any of the tissue types described herein, such as epithelial tissue, connective tissue, muscular tissue, and nervous tissue). In some embodiments, the tissue is in vivo prior to the step of contacting the metabolically labeled nucleic acids with a population of first oligonucleotide probes (i.e., the tissue is in vivo during the step of incubating the cell in the presence of a pool of nucleoside analogs). In some embodiments, one or more cells in a tissue are incubated in the presence of a pool of nucleoside analogs in vivo, and the tissue is then harvested prior to the step of contacting the metabolically labeled nucleic acids with a population of first oligonucleotide probes. Harvesting the tissues may involve harvesting entire organs from the subject (e.g., a non-human experimental animal), or it may involve a tissue biopsy. In certain embodiments, the tissue is in a non-human experimental animal (e.g., a mouse, rat, dog, pig, or non-human primate (e.g., a monkey, an ape, etc.). In some embodiments, the tissue is plant tissue.

In some embodiments, any of the methods described herein may be performed in vivo. Thus, in some embodiments, the present disclosure provides methods for profiling spatiotemporal gene expression in a subject comprising steps of:

a) administering a pool of nucleoside analogs to a subject in vivo for an amount of time $t_1$ to metabolically label nucleic acids synthesized by one or more cells in the subject, wherein each nucleoside analog in the pool of nucleoside analogs comprises a reactive chemical moiety;

b) harvesting a tissue sample from the subject;

c) contacting the metabolically labeled nucleic acids in the harvested tissue sample with a population of first oligonucleotide probes, wherein each first oligonucleotide probe in the population of first oligonucleotide probes comprises a chemical moiety that reacts with the reactive chemical moiety of the nucleoside analogs;

d) contacting the metabolically labeled nucleic acids with one or more pairs of oligonucleotide probes comprising a second oligonucleotide probe and a third oligonucleotide probe, wherein:

i) the second oligonucleotide probe comprises a barcode sequence and a portion that is complementary to a metabolically labeled nucleic acid of interest; and ii) the third oligonucleotide probe comprises a portion that is complementary to the metabolically labeled nucleic acid of interest, a first barcode sequence, a portion that is complementary to a first oligonucleotide probe in the population of first oligonucleotide probes, and a second barcode sequence, wherein the first barcode sequence of the third oligonucleotide probe is complementary to the barcode sequence of the second oligonucleotide probe;

e) ligating the 5' end and the 3' end of the third oligonucleotide probe together to produce a circular oligonucleotide;

f) performing rolling circle amplification to amplify the circular oligonucleotide using the second oligonucleotide probe as a primer to produce one or more concatenated amplicons;

g) embedding the one or more concatenated amplicons in a polymer matrix;

h) contacting the one or more concatenated amplicons embedded in the polymer matrix with a fourth oligonucleotide probe comprising a sequence that is complementary to the second barcode sequence of the third oligonucleotide probe; and i) imaging the fourth oligonucleotide probe to determine the location of the one or more concatenated amplicons embedded in the polymer matrix.

In some embodiments, the harvested tissue is epithelial tissue, connective tissue, muscular tissue, or nervous tissue. In certain embodiments, the harvested tissue is heart tissue. In some embodiments, the subject is a non-human experimental animal (e.g., a mouse, rat, dog, pig, or non-human primate). The nucleoside analogs may be administered to the subject by any appropriate means, for example, by injection. In some embodiments, the nucleoside analogs are administered by retro-orbital administration. In some embodiments, harvesting a tissue sample from the subject comprises taking a tissue biopsy. In some embodiments, harvesting a tissue sample from the subject comprises harvesting one or more whole organs from the subject.

The use of labeled cells (i.e., a cell that has been metabolically labeled) in the methods described herein is also contemplated by the present disclosure. In some embodiments, the cell has been labeled with nucleoside analogs. In some embodiments, the nucleoside analogs are analogs of adenosine, guanosine, thymidine, cytidine, uridine, and/or inosine. In some embodiments, the nucleoside analog is 3'-azido-3'-deoxythymidine, C8-alkyne-deoxyuridine, (2'S)-2'-deoxy-2'-fluoro-5-ethynyluridine, or 5-ethynyl-2'-deoxycytidine. In certain embodiments, the metabolically labeled nucleic acids are 5-ethynyl uridine labeled nucleic acids. In some embodiments, multiple cells are profiled simultaneously using the methods described herein.

The methods described herein may be used to profile spatiotemporal gene expression for one metabolically labeled nucleic acid of interest at a time, or for multiple metabolically labeled nucleic acids of interest simultaneously. In some embodiments, spatiotemporal gene expression is profiled for up to 100, up to 200, up to 500, up to 1000, up to 2000, up to 3000, or for more than 3000 metabolically labeled nucleic acids of interest simultaneously. In certain embodiments, spatiotemporal gene expression is profiled for up to 1000 metabolically labeled nucleic acids of interest simultaneously. The metabolically labeled nucleic acid of interest may be a transcript that has been expressed from the genomic DNA of the cell. In some embodiments, the metabolically labeled nucleic acid of interest is nascent RNA, messenger RNA (mRNA), transfer RNA (tRNA), or ribosomal RNA (rRNA). In some embodiments, the metabolically labeled nucleic acid of interest is nascent RNA (i.e., RNA that is being newly produced by the cell, or that has been newly produced by the cell but has not yet undergone any kind of post-transcriptional modification). In certain embodiments, the metabolically labeled nucleic acid of interest is mRNA.

Nucleoside analogs with various reactive chemical moieties are contemplated for use in the methods described herein. The reactive chemical moiety on the nucleoside analogs can be any reactive bioorthogonal functional group (e.g., any of the click chemistry handles described herein). One of ordinary skill in the art will readily appreciate that other bioorthogonal functional groups besides those disclosed herein are suitable for use in the methods disclosed herein and that the bioorthogonal functional groups described herein can be substituted with any others known in the art. See, for example, those described in U.S. Patent Publication 20130266512 and Thirumurugan, P. et al. Click Chemistry for Drug Development and Diverse Chemical-Biology Applications. *Chem. Rev.* 2013, 113(7), 4905-4979. In some embodiments, the reactive chemical moiety of the nucleoside analog comprises an azide, an alkyne, a nitrone, an alkene, a tetrazine, or a tetrazole. In certain embodiments, the reactive chemical moiety of the nucleoside analog comprises an alkyne. In some embodiments, the nucleoside analog is 3'-azido-3'-deoxythymidine, C8-alkyne-deoxyuridine, (2'S)-2'-deoxy-2'-fluoro-5-ethynyluridine, or 5-ethynyl-2'-deoxycytidine. In some embodiments, the nucleoside analog is 5-ethynyl uridine. In some embodiments, a nucleoside analog is at the 5' end of an oligonucleotide probe. In some embodiments, a nucleoside analog is at the 3' end of an oligonucleotide probe.

The methods described herein contemplate the use of a first oligonucleotide probe (also referred to herein as the "splint probe") comprising a reactive chemical moiety. The reactive chemical moiety of the first oligonucleotide probe should be reactive with the reactive chemical moiety of the nucleoside analogs used to metabolically label the cell, such that upon contact with the cell, the first oligonucleotide probe becomes conjugated to the metabolically labeled transcripts present in the cell. The reactive chemical moiety of the first oligonucleotide probe may be any bioorthogonal functional group described herein or that is known in the art. In some embodiments, the chemical moiety of the first oligonucleotide probe comprises an azide, an alkyne, a nitrone, an alkene, a tetrazine, or a tetrazole. In certain embodiments, the chemical moiety of the first oligonucleotide probe comprises an azide. In some embodiments, reaction of the chemical moiety of the nucleoside analogs and the chemical moiety of the first oligonucleotide probe comprises a click chemistry reaction (e.g., a copper(I)-catalyzed azide-alkyne cycloaddition (CuAAC) reaction).

The first oligonucleotide probe may also comprise various other components. In some embodiments, the first oligonucleotide probe further comprises a polymerization blocker. The polymerization blocker can be any moiety capable of preventing the use of the first oligonucleotide probe as a primer in the amplification of step (e) of the methods described herein. In some embodiments, the polymerization blocker is at the 3' end of the first oligonucleotide probe. The polymerization blocker can be, for example, any chemical moiety that prevents a polymerase from using the first oligonucleotide probe as a primer for polymerization. In some embodiments, the polymerization blocker is a nucleic acid residue comprising a blocked 3' hydroxyl group (e.g., comprising an oxygen protecting group on the 3' hydroxyl group). In some embodiments, the polymerization blocker comprises a hydrogen in place of the 3' hydroxyl group. In some embodiments, the polymerization blocker comprises any chemical moiety in place of the 3' hydroxyl group that prevents an additional nucleotide from being added. In some embodiments, the polymerization blocker comprises an inverted nucleic acid residue. In some embodiments, the polymerization blocker is an inverted adenosine, thymine, cytosine, guanosine, or uridine residue. In certain embodiments, the polymerization blocker is an inverted thymine residue. In some embodiments, the first oligonucleotide probe further comprises a poly-adenosine (poly-A) linker sequence. In some embodiments, the poly-A linker sequence is about 2 to about 100, about 10 to about 90, about 30 to about 70, or about 40 to about 60 nucleotides long. In certain embodiments, the poly-A linker sequence is about 50 nucleotides long.

In some embodiments, the first oligonucleotide probe is about 30, about 35, about 40, about 45, about 50, about 55, about 60, about 65, about 70, or about 75 nucleotides long. In some embodiments, the portion of the first oligonucleotide probe that is complementary to the third oligonucleotide probe is about 3-20, about 4-19, about 5-18, about 6-17, about 7-16, about 8-15, about 9-14, about 10-13, or about 11-12 nucleotides in length. In some embodiments, the portion of the first oligonucleotide probe that is complementary to the third oligonucleotide probe is about 3, about 4, about 5, about 6, about 7, about 8, about 9, about 10, about 11, about 12, about 13, about 14, about 15, about 16, about 17, about 18, about 19, or about 20 nucleotides long. In certain embodiments, the portion of the first oligonucleotide probe that is complementary to the third oligonucleotide probe is about 12 nucleotides long. In some embodiments, the first oligonucleotide probe comprises the structure:

5'-[reactive chemical moiety]-[poly-A linker sequence]-[portion complementary to third oligonucleotide probe]-[polymerization blocker]-3', wherein ]-[ comprises an optional nucleotide linker. Each instance of the optional nucleotide linker may independently be 1, 2, 3, 4, 5, 6, 7, 8, 9, or 10 nucleotides long. In some embodiments, ]-[ comprises an optional non-nucleotide linker (e.g., a chemical or peptide-based linker).

The methods disclosed herein also include the use of a second and third oligonucleotide probe, provided as a pair of oligonucleotide probes. The second oligonucleotide probe (also referred to herein as the "primer" probe) includes a barcode sequence made up of a specific sequence of nucleotides. In some embodiments, the barcode sequence of the second oligonucleotide probe is about 1 to about 10 nucleotides long. In some embodiments, the barcode sequence of the second oligonucleotide probe is about 5 to about 10 nucleotides long. In some embodiments, the barcode sequence is greater than about 10, greater than about 15, or greater than about 20 nucleotides long. In certain embodiments, the barcode sequence of the second oligonucleotide probe is 5 nucleotides long. In some embodiments, the portion of the second oligonucleotide probe that is complementary to a metabolically labeled nucleic acid of interest is about 10-30, about 11-29, about 12-28, about 13-27, about 14-26, about 15-25, about 16-24, about 17-23, about 18-22, or about 19-21 nucleotides in length. In some embodiments, the portion of the second oligonucleotide probe that is complementary to a metabolically labeled nucleic acid of interest is about 10, about 11, about 12, about 13, about 14, about 15, about 16, about 17, about 18, about 19, about 20, about 21, about 22, about 23, about 24, about 25, about 26, about 27, about 28, about 29, or about 30 nucleotides long. In certain embodiments, the portion of the second oligonucleotide probe that is complementary to a nucleic acid of interest is 20 nucleotides long. In some embodiments, the second oligonucleotide probe is about 20, about 21, about 22, about 23, about 24, about 25, about 26, about 27, about 28, about 29, about 30, about 31, about 32, about 33, about 34, about 35, about 36, about 37, about 38, about 39, or about 40 nucleotides long. In certain embodiments, the second oligonucleotide probe is 32 nucleotides long. In some embodiments, the second oligonucleotide probe comprises the structure:

> 5'-[portion complementary to metabolically labeled nucleic acid of interest]-[barcode sequence]-3', wherein ]-[ comprises an optional nucleotide linker. Each instance of the optional nucleotide linker may independently be 1, 2, 3, 4, 5, 6, 7, 8, 9, or 10 nucleotides long. In some embodiments, ]-[ comprises an optional non-nucleotide linker (e.g., a chemical or peptide-based linker).

The third oligonucleotide probe used in the methods described herein (also referred to herein as the "padlock" probe) includes a first barcode sequence and a second barcode sequence, each made up of a specific sequence of nucleotides. In some embodiments, the first barcode sequence of the third oligonucleotide probe is about 1 to about 10 nucleotides long. In some embodiments, the first barcode sequence of the third oligonucleotide probe is about 5 to about 10 nucleotides long. In some embodiments, the barcode sequence is greater than about 10, greater than about 15, or greater than about 20 nucleotides long. In certain embodiments, the first barcode sequence of the third oligonucleotide probe is about 5 nucleotides long. In some embodiments, the second barcode sequence of the third oligonucleotide probe is about 1 to about 10 nucleotides long. In some embodiments, the second barcode sequence of the third oligonucleotide probe is about 5 to about 10 nucleotides long. In some embodiments, the barcode sequence is greater than about 10, greater than about 15, or greater than about 20 nucleotides long. In certain embodiments, the second barcode sequence of the third oligonucleotide probe is about 5 nucleotides long. The third oligonucleotide probe also comprises a portion that is complementary to the first oligonucleotide probe. In some embodiments, the portion of the third oligonucleotide probe that is complementary to the first oligonucleotide probe is about 3-20, about 4-19, about 5-18, about 6-17, about 7-16, about 8-15, about 9-14, about 10-13, or about 11-12 nucleotides in length. In some embodiments, the portion of the third oligonucleotide probe that is complementary to the first oligonucleotide probe is about 3, about 4, about 5, about 6, about 7, about 8, about 9, about 10, about 11, about 12, about 13, about 14, about 15, about 16, about 17, about 18, about 19, or about 20 nucleotides in length. In some embodiments, the portion of the third oligonucleotide probe that is complementary to the first oligonucleotide probe is split between the 5' end and the 3' end of the third oligonucleotide probe. In some embodiments, the portion of the third oligonucleotide probe that is complementary to the metabolically labeled nucleic acid of interest is about 10-30, about 11-29, about 12-28, about 13-27, about 14-26, about 15-25, about 16-24, about 17-23, about 18-22, or about 19-21 nucleotides in length. In some embodiments, the portion of the third oligonucleotide probe that is complementary to the metabolically labeled nucleic acid of interest is about 10, about 11, about 12, about 13, about 14, about 15, about 16, about 17, about 18, about 19, about 20, about 21, about 22, about 23, about 24, about 25, about 26, about 27, about 28, about 29, about 30, or more than 30 nucleotides in length. In some embodiments, the third oligonucleotide probe comprises the structure:

> 5'-[first portion complementary to first oligonucleotide probe]-[first barcode sequence]-[portion complementary to metabolically labeled nucleic acid of interest]-[second barcode sequence]-[second portion complementary to first oligonucleotide probe]-3', wherein ]-[ comprises an optional nucleotide linker. Each instance of the optional nucleotide linker may independently be 1, 2, 3, 4, 5, 6, 7, 8, 9, or 10 nucleotides long. In some embodiments, ]-[ comprises an optional non-nucleotide linker (e.g., a chemical or peptide-based linker).

In some embodiments, the barcodes of the oligonucleotide probes described herein comprise gene-specific sequences used to identify metabolically labeled nucleic acids of interest. The use of the barcodes on the oligonucleotide probes described herein is further described in, for example, International Patent Application Publication No. WO 2019/199579, published Oct. 17, 2019, and Wang et al., *Science* 2018, 361, 380, both of which are incorporated by reference herein in their entireties.

In some embodiments, the step of ligating cannot be performed in the absence of the third oligonucleotide probe. In some embodiments, the step of performing rolling circle amplification to amplify the circular oligonucleotide to produce one or more concatenated amplicons further comprises providing nucleotides modified with reactive chemical groups. In some embodiments, the step of performing rolling circle amplification to amplify the circular oligonucleotide to produce one or more concatenated amplicons further comprises providing amine-modified nucleotides. During the amplification process, the amine-modified nucleotides are incorporated into the one or more concatenated amplicons as they are produced. The resulting amplicons are functionalized with primary amines, which can be further reacted with another compatible chemical moiety (e.g., N-hydroxysuccinimide) to facilitate the step of embedding the amplicons in the polymer matrix. In some embodiments, the step of embedding the one or more concatenated amplicons in a polymer matrix comprises reacting the amine-modified nucleotides of the one or more concatenated amplicons with methacrylic acid N-hydroxysuccinimide and co-polymerizing the one or more concatenated amplicons and the polymer matrix.

The use of various polymer matrices is contemplated by the present disclosure, and any polymer matrix in which the one or more concatenated amplicons can be embedded is suitable for use in the methods described herein. In some embodiments, the polymer matrix is a hydrogel (i.e., a network of crosslinked polymers that are hydrophilic). In some embodiments, the hydrogel is a polyvinyl alcohol hydrogel, a polyethylene glycol hydrogel, a sodium polyacrylate hydrogel, an acrylate polymer hydrogel, or a polyacrylamide hydrogel. In certain embodiments, the hydrogel is a polyacrylamide hydrogel.

The methods disclosed herein also include the use of a fourth oligonucleotide probe. In some embodiments, the fourth oligonucleotide probe comprises a fluorophore. As described herein, the fourth oligonucleotide probe is complementary to the second barcode sequence of the third oligonucleotide probe. In some embodiments, the second barcode sequence of the third oligonucleotide probe is a gene-specific sequence used to identify a metabolically labeled nucleic acid of interest. In some embodiments, the step of contacting the one or more concatenated amplicons embedded in the polymer matrix with the fourth oligonucleotide probe is performed to identify the metabolically labeled nucleic acid of interest. This method for identifying a metabolically labeled nucleic acid of interest is known as sequencing with error-reduction by dynamic annealing and ligation (SEDAL sequencing) and is described further in Wang, X. et al. Three-dimensional intact-tissue sequencing of single-cell transcriptional states. *Science* 2018, 36, eaat5691 and International Patent Application Publication No. WO 2019/199579, each of which is incorporated herein by reference. In some embodiments, SEDAL sequencing is performed two, three, four, five, or more than five times to identify one or more metabolically labeled nucleic acids of interest.

The fourth oligonucleotide probe used in the methods described herein (e.g., as used in SEDAL sequencing) may be read out using any suitable imaging technique known in the art. For example, in embodiments where the fourth oligonucleotide probe comprises a fluorophore, the fluorophore may be read out using imaging to identify the metabolically labeled nucleic acid of interest. In some embodiments, the step of imaging comprises fluorescent imaging. In certain embodiments, the step of imaging comprises confocal microscopy. In certain embodiments, the step of imaging comprises epifluorescence microscopy.

In various embodiments, the methods described herein may comprise further steps to profile additional molecules besides the nucleic acid of interest. In some embodiments, the methods described herein further comprise profiling additional molecules within the cell. Such additional molecules may include, but are not limited to, RNAs, DNAs, proteins, carbohydrates, small molecules, metabolites, and/or lipids.

In some embodiments, the methods described herein further comprise determining the cell type of the profiled cell by comparing the spatiotemporal gene expression profile of the cell to reference data comprising spatiotemporal gene expression profiles of various cell types.

In some embodiments, the methods described herein further comprise overexpressing or knocking out one or more genes in the cell to determine whether the one or more genes are involved in the spatiotemporal expression of the metabolically labeled nucleic acid of interest.

Methods for Profiling the Role of Post-Transcriptional Modification in Spatiotemporal Gene Expression In another aspect, the present disclosure provides methods for profiling the role of post-transcriptional modification (e.g., 7-methylguanosine, $N^6$-methyladenosine (m⁶A), a poly(A) tail, intron splicing, or histone mRNA processing) in spatiotemporal gene expression. For example, the methods for profiling spatiotemporal gene expression described herein may be performed in a cell comprising a knockdown of a gene involved in post-transcriptional modification of one or more metabolically labeled nucleic acids of interest (e.g., one or more metabolically labeled RNA transcripts). The spatiotemporal expression of various metabolically labeled nucleic acids of interest in the knockdown cell can then be compared to the spatiotemporal expression of the same metabolically labeled nucleic acids of interest in a wild-type cell. Any alteration in the expression of the metabolically labeled nucleic acid of interest relative to expression in a wild-type cell may indicate that the post-transcriptional modification is involved in regulating spatiotemporal expression of the metabolically labeled nucleic acid of interest.

In some embodiments, methods for profiling the role of post-transcriptional modification in spatiotemporal gene expression in a cell comprise the steps of:

a) incubating a cell comprising a knockdown of a gene involved in post-transcriptional modification in the presence of a pool of nucleoside analogs for an amount of time $t_1$ to metabolically label nucleic acids synthesized by the cell, wherein each nucleoside analog in the pool of nucleoside analogs comprises a reactive chemical moiety;

b) contacting the metabolically labeled nucleic acids with a population of first oligonucleotide probes, wherein each first oligonucleotide probe in the population of first oligonucleotide probes comprises a chemical moiety that reacts with the reactive chemical moiety of the nucleoside analogs;

c) contacting the metabolically labeled nucleic acids with one or more pairs of oligonucleotide probes comprising a second oligonucleotide probe and a third oligonucleotide probe, wherein:

i) the second oligonucleotide probe comprises a barcode sequence and a portion that is complementary to a metabolically labeled nucleic acid of interest; and ii) the third oligonucleotide probe comprises a portion that is complementary to the metabolically labeled nucleic acid of interest, a first barcode sequence, a portion that is complementary to a first oligonucleotide probe in the population of first oligonucleotide probes, and a second barcode sequence, wherein the first barcode sequence of the third oligonucleotide probe is complementary to the barcode sequence of the second oligonucleotide probe;

d) ligating the 5' end and the 3' end of the third oligonucleotide probe together to produce a circular oligonucleotide;

e) performing rolling circle amplification to amplify the circular oligonucleotide using the second oligonucleotide probe as a primer to produce one or more concatenated amplicons;

f) embedding the one or more concatenated amplicons in a polymer matrix;

g) contacting the one or more concatenated amplicons embedded in the polymer matrix with a fourth oligonucleotide probe comprising a sequence that is complementary to the second barcode sequence of the third oligonucleotide probe; and h) imaging the fourth oligonucleotide probe to determine the location of the one or more concatenated amplicons embedded in the polymer matrix, wherein an alteration in the expression of the metabolically labeled nucleic acid of interest relative to expression in a wild-type cell indicates that the post-transcriptional modification is involved in regulating spatiotemporal expression of the metabolically labeled nucleic acid of interest.

In some embodiments, more than one cell is analyzed simultaneously using the methods described herein. In some embodiments, steps (a)-(h) are performed one or more additional times. Repeating steps (a)-(h) and incubating the cell and the pool of nucleoside analogs together in step (a) for varying amounts of time allows the expression of a metabolically labeled nucleic acid of interest, or multiple metabolically labeled nucleic acids of interest, to be observed over time, allowing the spatiotemporal expression of the labeled nucleic acids of interest to be profiled. In some embodiments, steps (a)-(h) are repeated at least one time for a different amount of time $t_2$. In certain embodiments, steps (a)-(h) are optionally repeated for a third amount of time $t_3$, optionally repeated for a fourth amount of time $t_4$, optionally repeated for a fifth amount of time $t_5$, optionally repeated for a sixth amount of time $t_6$, optionally repeated for a seventh amount of time $t_7$, optionally repeated for an eighth amount of time $t_8$, optionally repeated for a ninth amount of time $t_9$, and optionally repeated for a tenth amount of time $t_{10}$.

Profiling of various post-transcriptional modifications may be performed using the methods disclosed herein. Any post-transcriptional modification for which a specific gene or set of genes are known or thought to be involved in installing may be profiled using the methods of the present disclosure. In some embodiments, the post-translational modification involves 5' processing of a transcript (e.g., installation of a 5' cap). In some embodiments, the post-transcriptional modification comprises 3' processing of a transcript (e.g., polyadenylation of a transcript or cleavage of the 3' end of a transcript). In some embodiments, the post-transcriptional modification is 7-methylguanosine, $N^6$-methyladenosine ($m^6A$), a poly(A) tail, intron splicing, or histone mRNA processing. In some embodiments, the post-transcriptional modification comprises methylation of adenosine. In certain embodiments, the post-transcriptional modification is $m^6A$.

Various genes involved in post-transcriptional modification of nucleic acids may be knocked down and studied using the methods described herein. In some embodiments, the gene involved in post-transcriptional modification is selected from the group consisting of YTH domain family (YTHDF) 1, YTHDF2, YTHDF 3, YTH domain containing (YTHDC) 1, YTHDC2, methyltransferase like (METTL) 3, and METTL14. The methods disclosed herein may be used to study the role of a gene involved in post-transcriptional modification on the spatiotemporal gene expression of one metabolically labeled nucleic acid of interest at a time, or on multiple metabolically labeled nucleic acids of interest at once. In some embodiments, the role of post-transcriptional modification in spatiotemporal gene expression is profiled for up to 100, up to 200, up to 500, up to 1000, up to 2000, up to 3000, or more than 3000 metabolically labeled nucleic acids of interest simultaneously. In certain embodiments, the role of post-transcriptional modification in spatiotemporal gene expression is profiled for up to 1000 metabolically labeled nucleic acids of interest simultaneously.

In some embodiments, the cell is in a tissue in vivo prior to the step of contacting the metabolically labeled nucleic acids with a population of first oligonucleotide probes (i.e., the tissue is in vivo during the step of incubating the cell in the presence of a pool of nucleoside analogs). In some embodiments, one or more cells in a tissue are incubated in the presence of a pool of nucleoside analogs in a subject in vivo, and the tissue is then harvested from a subject prior to the step of contacting the metabolically labeled nucleic acids with a population of first oligonucleotide probes. Harvesting the tissues may involve harvesting entire organs from the subject (e.g., a non-human experimental animal), or it may involve a tissue biopsy. In certain embodiments, the tissue is in a non-human experimental animal (e.g., a mouse, rat, dog, pig, or non-human primate such as an ape or a monkey).

Methods for Studying the Role of Spatiotemporal Gene Expression in the Development or Progression of a Disease or Disorder In another aspect, the present disclosure provides methods for studying the role of spatiotemporal gene expression in the development or progression of a disease or disorder. For example, the methods for profiling spatiotemporal gene expression described herein may be performed in a cell from a diseased tissue (e.g., a diseased tissue taken from a subject). The spatiotemporal expression of various metabolically labeled nucleic acids of interest in the cell from the diseased tissue can then be compared to the spatiotemporal expression of the same metabolically labeled nucleic acids of interest in a cell from a non-diseased tissue. Any alteration in the expression of the metabolically labeled nucleic acid of interest relative to expression in a non-diseased cell may indicate that spatiotemporal expression of the metabolically labeled nucleic acid of interest may be involved in the development or progression of the disease or disorder.

In some embodiments, methods for studying the role of spatiotemporal gene expression in the development or progression of a disease or disorder comprise steps of:

a) incubating a cell from a diseased tissue in the presence of a pool of nucleoside analogs for an amount of time $t_1$ to metabolically label nucleic acids synthesized by the cell, wherein each nucleoside analog in the pool of nucleoside analogs comprises a reactive chemical moiety;

b) contacting the metabolically labeled nucleic acids with a population of first oligonucleotide probes, wherein each first oligonucleotide prone in the population of first oligonucleotide probes comprises a chemical moiety that reacts with the reactive chemical moiety of the nucleoside analogs;

c) contacting the metabolically labeled nucleic acids with one or more pairs of oligonucleotide probes comprising a second oligonucleotide probe and a third oligonucleotide probe, wherein:

i) the second oligonucleotide probe comprises a barcode sequence and a portion that is complementary to a metabolically labeled nucleic acid of interest; and ii) the third oligonucleotide probe comprises a portion that is complementary to the metabolically labeled nucleic acid of interest, a first barcode sequence, a portion that is complementary to a first oligonucleotide probe in the population of first oligonucleotide probes, and a second barcode sequence, wherein the first barcode sequence of the third oligonucleotide probe is complementary to the barcode sequence of the second oligonucleotide probe;

d) ligating the 5' end and the 3' end of the third oligonucleotide probe together to produce a circular oligonucleotide;

e) performing rolling circle amplification to amplify the circular oligonucleotide using the second oligonucleotide probe as a primer to produce one or more concatenated amplicons;

f) embedding the one or more concatenated amplicons in a polymer matrix;

g) contacting the one or more concatenated amplicons embedded in the polymer matrix with a fourth oligonucleotide probe comprising a sequence that is complementary to the second barcode sequence of the third oligonucleotide probe; and h) imaging the fourth oligonucleotide probe to determine the location of the one or more concatenated amplicons embedded in the polymer matrix, wherein an alteration in the expression of the metabolically labeled nucleic acid of interest relative to expression in a non-diseased cell or a cell from a non-diseased tissue indicates that the alteration in spatiotemporal expression of the metabolically labeled nucleic acid of interest may be involved in the development or progression of the disease or disorder.

In some embodiments, multiple cells are profiled simultaneously using the methods described herein. In some embodiments, steps (a)-(h) are performed one or more additional times. Repeating steps (a)-(h) and incubating the cell and the pool of nucleoside analogs together in step (a) for varying amounts of time allows the expression of a metabolically labeled nucleic acid of interest, or multiple metabolically labeled nucleic acids of interest, to be observed over time, allowing the spatiotemporal expression of the labeled nucleic acids of interest to be profiled. In some embodiments, steps (a)-(h) are repeated at least one time for a different amount of time $t_2$. In certain embodiments, steps (a)-(h) are optionally repeated for a third amount of time $t_3$, optionally repeated for a fourth amount of time $t_4$, optionally repeated for a fifth amount of time $t_5$, optionally repeated for a sixth amount of time $t_6$, optionally repeated for a seventh amount of time $t_7$, optionally repeated for an eighth amount of time $t_8$, optionally repeated for a ninth amount of time $t_9$, and optionally repeated for a tenth amount of time $t_{10}$.

The role of one or more nucleic acids of interest in any disease or disorder that may be associated with alterations in gene expression may be studied using the presently described methods, and the methods described here are not limited to the study of any particular disease or disorder. In some embodiments, the disease or disorder is a genetic disease, a proliferative disease, an inflammatory disease, an autoimmune disease, a liver disease, a spleen disease, a lung disease, a hematological disease, a neurological disease, a gastrointestinal (GI) tract disease, a genitourinary disease, an infectious disease, a musculoskeletal disease, an endocrine disease, a metabolic disorder, an immune disorder, a central nervous system (CNS) disorder, a neurological disorder, an ophthalmic disease, or a cardiovascular disease.

The use of various tissue samples in the methods described here is also contemplated by the present disclosure. Any tissue sample (e.g., a sample of any of the types of tissue listed in the Definitions) may be used when performing the methods described herein. In some embodiments, the diseased tissue is a tissue sample taken from a subject. In some embodiments, the subject is a non-human experimental animal. In certain embodiments, the subject is a mouse, rat, dog, or pig. In some embodiments, the subject is a human (e.g., a patient who has been diagnosed with, is thought to have, or is at risk of having the disease or disorder being studied). In some embodiments, the diseased tissue is in vivo prior to the step of contacting the metabolically labeled nucleic acids with a population of first oligonucleotide probes (i.e., the tissue is in vivo during the step of incubating the cell in the presence of a pool of nucleoside analogs). In some embodiments, one or more cells in a diseased tissue are incubated in the presence of a pool of nucleoside analogs in a subject in vivo, and the diseased tissue is then harvested prior to the step of contacting the metabolically labeled nucleic acids with a population of first oligonucleotide probes. Harvesting the tissues may involve harvesting entire organs from the subject (e.g., a non-human experimental animal), or it may involve a tissue biopsy. In certain embodiments, the diseased tissue is in a non-human experimental animal (e.g., a mouse, rat, dog, pig, or non-human primate such as a monkey or an ape).

Methods of Screening for an Agent Capable of Modulating Spatiotemporal Gene Expression In another aspect, the present disclosure provides methods for screening for an agent capable of modulating spatiotemporal gene expression of a metabolically labeled nucleic acid of interest, or of multiple metabolically labeled nucleic acids of interest. For example, the methods for profiling spatiotemporal gene expression described herein may be performed in a cell in the presence of one or more candidate agents. The spatiotemporal expression of various metabolically labeled nucleic acids of interest in the cell (e.g., a normal cell, or a diseased cell) can then be compared to the spatiotemporal expression of the same metabolically labeled nucleic acids of interest in a cell that was not exposed to the one or more candidate agents. Any alteration in the expression of the metabolically labeled nucleic acid(s) of interest relative to expression in the cell that was not exposed to the candidate agent(s) may indicate that spatiotemporal expression of the metabolically labeled nucleic acid(s) of interest is modulated by the candidate agent(s).

In some embodiments, a method for screening for an agent capable of modulating spatiotemporal gene expression comprises steps of:

a) incubating a cell in the presence of one or more candidate agents and a pool of nucleoside analogs for an amount of time $t_1$ to metabolically label nucleic acids synthesized by the cell, wherein each nucleoside analog in the pool of nucleoside analogs comprises a reactive chemical moiety;

b) contacting the metabolically labeled nucleic acids with a population of first oligonucleotide probe, wherein each first oligonucleotide probe in the population of first oligonucleotide probes comprises a chemical moiety that reacts with the reactive chemical moiety of the nucleoside analogs;

c) contacting the metabolically labeled nucleic acids with one or more pairs of oligonucleotide probes comprising a second oligonucleotide probe and a third oligonucleotide probe, wherein:

i) the second oligonucleotide probe comprises a barcode sequence and a portion that is complementary to a metabolically labeled nucleic acid of interest; and ii) the third oligonucleotide probe comprises a portion that is complementary to the metabolically labeled nucleic acid of interest, a first barcode sequence, a portion that is complementary to a first oligonucleotide probe in the population of first oligonucleotide probes, and a second barcode sequence, wherein the first barcode sequence of the third oligonucleotide probe is complementary to the barcode sequence of the second oligonucleotide probe;

d) ligating the 5' end and the 3' end of the third oligo-nucleotide probe together to produce a circular oligo-nucleotide;

e) performing rolling circle amplification to amplify the circular oligonucleotide using the second oligonucle-otide probe as a primer to produce one or more con-catenated amplicons;

f) embedding the one or more concatenated amplicons in a polymer matrix;

g) contacting the one or more concatenated amplicons embedded in the polymer matrix with a fourth oligo-nucleotide probe comprising a sequence that is comple-mentary to the second barcode sequence of the third oligonucleotide probe; and h) imaging the fourth oligonucleotide probe to determine the location of the one or more concatenated amplicons embedded in the polymer matrix, wherein an alteration in the expression of the metaboli-cally labeled nucleic acid of interest in the presence of the one or more candidate agents relative to expression in the absence of the one or more candidate agents indicates that the one or more candidate agents modu-late spatiotemporal gene expression.

In some embodiments, multiple cells are profiled simul-taneously using the methods described herein. In some embodiments, steps (a)-(h) are performed one or more additional times. Repeating steps (a)-(h) and incubating the cell and the pool of nucleoside analogs together in step (a) for varying amounts of time allows the expression of a metabolically labeled nucleic acid of interest, or multiple metabolically labeled nucleic acids of interest, to be observed over time, allowing the spatiotemporal expression of the labeled nucleic acids of interest to be profiled. In some embodiments, steps (a)-(h) are repeated at least one time for a different amount of time $t_2$. In certain embodiments, steps (a)-(h) are optionally repeated for a third amount of time $t_3$, optionally repeated for a fourth amount of time $t_4$, optionally repeated for a fifth amount of time $t_5$, optionally repeated for a sixth amount of time $t_6$, optionally repeated for a seventh amount of time $t_7$, optionally repeated for an eighth amount of time $t_8$, optionally repeated for a ninth amount of time $t_9$, and optionally repeated for a tenth amount of time $t_{10}$.

In some embodiments, the one or more candidate agents may be provided as a library of candidate agents (e.g., from a screening collection of small molecules or other candidate therapeutic agents). In some embodiments, the library of candidate agents comprises hundreds of candidate agents (e.g., about 100 candidate agents, about 200 candidate agents, about 300 candidate agents, about 400 candidate agents, about 500 candidate agents, about 600 candidate agents, about 700 candidate agents, about 800 candidate agents, or about 900 candidate agents). In some embodi-ments, the screening library comprises thousands of candi-date agents (e.g., about 1000 candidate agents, about 2000 candidate agents, about 3000 candidate agents, about 5000 candidate agents, about 10,000 candidate agents, about 20,000 candidate agents, about 30,000 candidate agents, about 40,000 candidate agents, about 50,000 candidate agents, about 60,000 candidate agents, about 70,000 candi-date agents, about 80,000 candidate agents, about 90,000 candidate agents, about 100,000 candidate agents, or more than 100,000 candidate agents). In some embodiments, one candidate agent per cell is screened. In certain embodiments, only one candidate agent at a time is screened using the methods described herein.

In some embodiments, the one or more candidate agents are selected from the group consisting of small molecules, proteins, peptides, nucleic acids, lipids, and carbohydrates. In certain embodiments, the candidate agents (e.g., small molecules) are anti-cancer therapeutic agents. In some embodiments, the candidate agents (e.g., small molecules) comprise known drugs. In some embodiments, the candidate agents (e.g., small molecules) comprise FDA-approved drugs. In some embodiments, the small molecules comprise libraries of compounds. In certain embodiments, the proteins are antibodies. In certain embodiments, the proteins are antibody fragments. In certain embodiments, the proteins are antibody variants. In certain embodiments, the proteins are receptors. In certain embodiments, the proteins are cytok-ines. In certain embodiments, the nucleic acids are mRNAs, antisense RNAs, miRNAs, siRNAs, RNA aptamers, dsR-NAs, short hairpin RNAs (shRNAs), or antisense oligo-nucleotides (ASOs). Any candidate agent may be screened using the methods described herein. In particular, any can-didate agents thought to be capable of modulating spa-tiotemporal gene expression may be screened using the methods described herein. In some embodiments, modula-tion of spatiotemporal gene expression of a metabolically labeled nucleic acid of interest, or multiple metabolically labeled nucleic acids of interest, by one or more candidate agents is associated with reducing, relieving, or eliminating the symptoms of a disease or disorder, or preventing the development or progression of the disease or disorder. In some embodiments, the disease or disorder modulated by the candidate agent is a genetic disease, a proliferative disease, an inflammatory disease, an autoimmune disease, a liver disease, a spleen disease, a lung disease, a hematologi-cal disease, a neurological disease, a gastrointestinal (GI) tract disease, a genitourinary disease, an infectious disease, a musculoskeletal disease, an endocrine disease, a metabolic disorder, an immune disorder, a central nervous system (CNS) disorder, a neurological disorder, an ophthalmic disease, or a cardiovascular disease.

Methods for Diagnosing a Disease or Disorder in a Subject

In another aspect, the present disclosure provides methods for diagnosing a disease or disorder in a subject. For example, the methods for profiling spatiotemporal gene expression described herein may be performed in a cell from a sample taken from a subject (e.g., a subject who is thought to have or is at risk of having a disease or disorder, or a subject who is healthy or thought to be healthy). The spatiotemporal expression of various metabolically labeled nucleic acids of interest in the cell can then be compared to the spatiotemporal expression of the same metabolically labeled nucleic acids of interest in a non-diseased cell or a cell from a non-diseased tissue sample (e.g., a cell from a healthy individual, or multiple cells from a population of healthy individuals). Any alteration in the expression of the metabolically labeled nucleic acid of interest relative to expression in a non-diseased cell may indicate that the subject has the disease or disorder.

In some embodiments, a method for diagnosing a disease or disorder in a subject comprises steps of:

a) incubating a cell from a sample taken from a subject in the presence of a pool of nucleoside analogs for an amount of time $t_1$ to metabolically label nucleic acids synthesized by the cell, wherein the pool of nucleoside analogs comprises a reactive chemical moiety;

b) contacting the metabolically labeled nucleic acids with a population of first oligonucleotide probes, wherein each first oligonucleotide probe in the population of first oligonucleotide probes comprises a chemical moi-ety that reacts with the reactive chemical moiety of the nucleoside analogs;

c) contacting the metabolically labeled nucleic acids with one or more pairs of oligonucleotide probes comprising a second oligonucleotide probe and a third oligonucleotide probe, wherein:

i) the second oligonucleotide probe comprises a barcode sequence and a portion that is complementary to a metabolically labeled nucleic acid of interest; and ii) the third oligonucleotide probe comprises a portion that is complementary to the metabolically labeled nucleic acid of interest, a first barcode sequence, a portion that is complementary to a first oligonucleotide probe in the population of first oligonucleotide probes, and a second barcode sequence, wherein the first barcode sequence of the third oligonucleotide probe is complementary to the barcode sequence of the second oligonucleotide probe;

d) ligating the 5' end and the 3' end of the third oligonucleotide probe together to produce a circular oligonucleotide;

e) performing rolling circle amplification to amplify the circular oligonucleotide using the second oligonucleotide probe as a primer to produce one or more concatenated amplicons;

f) embedding the one or more concatenated amplicons in a polymer matrix;

g) contacting the one or more concatenated amplicons embedded in the polymer matrix with a fourth oligonucleotide probe comprising a sequence that is complementary to the second barcode sequence of the third oligonucleotide probe; and h) imaging the fourth oligonucleotide probe to determine the location of the one or more concatenated amplicons embedded in the polymer matrix, wherein an alteration in the expression of the metabolically labeled nucleic acid of interest relative to expression in a non-diseased cell or a cell from a non-diseased tissue sample indicates that the subject has the disease or disorder.

In some embodiments, spatiotemporal expression of the metabolically labeled nucleic acid of interest in a non-diseased cell or a cell from a non-diseased tissue sample may be profiled simultaneously as a control experiment. In some embodiments, the spatiotemporal expression profile of the metabolically labeled nucleic acid of interest in a non-diseased cell or a cell from a non-diseased tissue sample comprises reference data.

In some embodiments, multiple cells are profiled simultaneously using the methods described herein. In some embodiments, steps (a)-(h) are performed one or more additional times. Repeating steps (a)-(h) and incubating the cell and the pool of nucleoside analogs together in step (a) for varying amounts of time allows the expression of a metabolically labeled nucleic acid of interest, or multiple metabolically labeled nucleic acids of interest, to be observed over time, allowing the spatiotemporal expression of the nucleic acids of interest to be profiled. In some embodiments, steps (a)-(h) are repeated at least one time for a different amount of time $t_2$. In certain embodiments, steps (a)-(h) are optionally repeated for a third amount of time $t_3$, optionally repeated for a fourth amount of time $t_4$, optionally repeated for a fifth amount of time $t_5$, optionally repeated for a sixth amount of time $t_6$, optionally repeated for a seventh amount of time $t_7$, optionally repeated for an eighth amount of time $t_8$, optionally repeated for a ninth amount of time $t_9$, and optionally repeated for a tenth amount of time $t_{10}$.

Diagnosis of any disease or disorder is contemplated by the methods described herein. In some embodiments, the disease or disorder is a genetic disease, a proliferative disease, an inflammatory disease, an autoimmune disease, a liver disease, a spleen disease, a lung disease, a hematological disease, a neurological disease, a gastrointestinal (GI) tract disease, a genitourinary disease, an infectious disease, a musculoskeletal disease, an endocrine disease, a metabolic disorder, an immune disorder, a central nervous system (CNS) disorder, a neurological disorder, an ophthalmic disease, or a cardiovascular disease. In certain embodiments, the disease or disorder is cancer.

In some embodiments, the subject is a non-human experimental animal (e.g., a mouse, rat, dog, pig, or non-human primate such as an ape or a monkey). In some embodiments, the subject is a domesticated animal. In some embodiments, the subject is a human. In some embodiments, the sample comprises a tissue sample. In certain embodiments, the tissue sample is a biopsy (e.g., a bone, bone marrow, breast, gastrointestinal tract, lung, liver, pancreas, prostate, brain, nerve, renal, endometrial, cervical, lymph node, muscle, or skin biopsy). In certain embodiments, the biopsy is a tumor biopsy.

Methods for Treating a Disease or Disorder in a Subject

In another aspect, the present disclosure provides methods for treating a disease or disorder in a subject. For example, the methods for profiling spatiotemporal gene expression described herein may be performed in a cell from a sample taken from a subject (e.g., a subject who is thought to have or is at risk of having a disease or disorder). The spatiotemporal expression of various metabolically labeled nucleic acids of interest in the cell can then be compared to the spatiotemporal expression of the same metabolically labeled nucleic acids of interest in a cell from a non-diseased tissue sample. A treatment for the disease or disorder may then be administered to the subject if any alteration in the expression of the metabolically labeled nucleic acids of interest relative to expression in a non-diseased cell is observed.

In some embodiments, a method for treating a disease or disorder in a subject comprises steps of:

a) incubating a cell from a sample taken from a subject in the presence of a pool of nucleoside analogs for an amount of time $t_1$ to metabolically label nucleic acids synthesized by the cell, wherein each nucleoside analog in the pool of nucleoside analogs comprises a reactive chemical moiety;

b) contacting the metabolically labeled nucleic acids with a population of first oligonucleotide probes, wherein each first oligonucleotide probe in the population of first oligonucleotide probes comprises a chemical moiety that reacts with the reactive chemical moiety of the nucleoside analogs;

c) contacting the metabolically labeled nucleic acids with one or more pairs of oligonucleotide probes comprising a second oligonucleotide probe and a third oligonucleotide probe, wherein:

i) the second oligonucleotide probe comprises a barcode sequence and a portion that is complementary to a metabolically labeled nucleic acid of interest; and ii) the third oligonucleotide probe comprises a portion that is complementary to the metabolically labeled nucleic acid of interest, a first barcode sequence, a portion that is complementary to a first oligonucleotide probe in the population of first oligonucleotide probes, and a second barcode sequence, wherein the first barcode sequence of the third oligonucleotide probe is complementary to the barcode sequence of the second oligonucleotide probe;

d) ligating the 5' end and the 3' end of the third oligonucleotide probe together to produce a circular oligonucleotide;

e) performing rolling circle amplification to amplify the circular oligonucleotide using the second oligonucleotide probe as a primer to produce one or more concatenated amplicons;

f) embedding the one or more concatenated amplicons in a polymer matrix;

g) contacting the one or more concatenated amplicons embedded in the polymer matrix with a fourth oligonucleotide probe comprising a sequence that is complementary to the second barcode sequence of the third oligonucleotide probe;

h) imaging the fourth oligonucleotide probe to determine the location of the one or more concatenated amplicons embedded in the polymer matrix; and i) administering a treatment for the disease or disorder to the subject if an alteration in spatiotemporal gene expression relative to expression in a non-diseased cell or a cell from a non-diseased tissue sample is observed.

In some embodiments, spatiotemporal expression of the metabolically labeled nucleic acid of interest in a non-diseased cell or a cell from a non-diseased tissue sample may be profiled simultaneously as a control experiment. In some embodiments, the spatiotemporal expression profile of the metabolically labeled nucleic acid of interest in a non-diseased cell or a cell from a non-diseased tissue sample comprises reference data.

In some embodiments, more than one cell is analyzed simultaneously using the methods described herein. In some embodiments, steps (a)-(h) are performed one or more additional times. Repeating steps (a)-(h) and incubating the cell and the pool of nucleoside analogs together in step (a) for varying amounts of time allows the expression of a metabolically labeled nucleic acid of interest, or multiple metabolically labeled nucleic acids of interest, to be observed over time, allowing the spatiotemporal expression of the nucleic acids of interest to be profiled. In some embodiments, steps (a)-(h) are repeated at least one time for a different amount of time $t_2$. In certain embodiments, steps (a)-(h) are optionally repeated for a third amount of time $t_3$, optionally repeated for a fourth amount of time $t_4$, optionally repeated for a fifth amount of time $t_5$, optionally repeated for a sixth amount of time $t_6$, optionally repeated for a seventh amount of time $t_7$, optionally repeated for an eighth amount of time $t_8$, optionally repeated for a ninth amount of time $t_9$, and optionally repeated for a tenth amount of time $t_{10}$.

Any suitable treatment for a disease or disorder may be administered to the subject. In some embodiments, the treatment comprises administering a therapeutic agent. In some embodiments, the treatment comprises surgery. In some embodiments, the treatment comprises imaging. In some embodiments, the treatment comprises performing further diagnostic methods. In some embodiments, the treatment comprises radiation therapy. In some embodiments, the therapeutic agent is a small molecule, a protein, a peptide, a nucleic acid, a lipid, or a carbohydrate. In certain embodiments, the therapeutic agent (e.g., small molecule) is an anti-cancer therapeutic agent. In some embodiments, the therapeutic agents (e.g., small molecules) comprise known drugs. In some embodiments, the therapeutic agents (e.g., small molecules) comprise FDA-approved drugs. In some embodiments, the small molecules comprise libraries of compounds. In certain embodiments, the proteins are antibodies. In certain embodiments, the proteins are antibody fragments. In certain embodiments, the proteins are antibody variants. In certain embodiments, the proteins are receptors. In certain embodiments, the proteins are cytokines. In certain embodiments, the nucleic acid is an mRNA, an antisense RNA, an miRNA, an siRNA, an RNA aptamer, a double stranded RNA (dsRNA), a short hairpin RNA (shRNA), or an antisense oligonucleotide (ASO). In certain embodiments, the nucleic acid is DNA.

Treatment of any disease or disorder is contemplated by the methods described herein. In some embodiments, the disease or disorder is a genetic disease, a proliferative disease, an inflammatory disease, an autoimmune disease, a liver disease, a spleen disease, a lung disease, a hematological disease, a neurological disease, a gastrointestinal (GI) tract disease, a genitourinary disease, an infectious disease, a musculoskeletal disease, an endocrine disease, a metabolic disorder, an immune disorder, a central nervous system (CNS) disorder, a neurological disorder, an ophthalmic disease, or a cardiovascular disease. In certain embodiments, the disease or disorder is cancer.

In some embodiments, the subject is a human. In some embodiments, the sample comprises a biological sample. In some embodiments, the sample comprises a tissue sample. In certain embodiments, the tissue sample is a biopsy (e.g., a bone, bone marrow, breast, gastrointestinal tract, lung, liver, pancreas, prostate, brain, nerve, renal, endometrial, cervical, lymph node, muscle, or skin biopsy). In certain embodiments, the biopsy is a tumor biopsy.

In certain embodiments, the biopsy is a solid tumor biopsy.

Oligonucleotide Probes

The present disclosure also provides oligonucleotide probes for use in the methods and systems described herein. In one aspect, the present disclosure provides a plurality (i.e., set) of oligonucleotide probes comprising a first oligonucleotide probe (also referred to herein as the "splint" probe), a second oligonucleotide probe (also referred to herein as the "primer" probe), and a third oligonucleotide probe (also referred to herein as the "padlock" probe, wherein:

i) the first oligonucleotide probe comprises a reactive chemical moiety;

ii) the second oligonucleotide probe comprises a barcode sequence and a portion that is complementary to a nucleic acid of interest; and iii) the third oligonucleotide probe comprises a portion that is complementary to the nucleic acid of interest, a first barcode sequence, a portion that is complementary to the first oligonucleotide probe, and a second barcode sequence, wherein the first barcode sequence of the third oligonucleotide probe is complementary to the barcode sequence of the second oligonucleotide probe.

All of the oligonucleotide probes described herein may optionally have spacers or linkers of various nucleotide lengths in between each of the recited components, or the components of the oligonucleotide probes may be joined directly to one another. The reactive chemical moiety of the first oligonucleotide probe may be any bioorthogonal functional group described herein or that is known in the art. In some embodiments, the chemical moiety of the first oligonucleotide probe comprises an azide, an alkyne, a nitrone, an alkene, a tetrazine, or a tetrazole. In certain embodiments, the chemical moiety of the first oligonucleotide probe comprises an azide. The first oligonucleotide probe may also comprise various other components. In some embodiments, the first oligonucleotide probe further comprises a polymerization blocker as described herein. In some embodiments, the polymerization blocker is at the 3' end of the first oligonucleotide probe. The polymerization blocker can be, for example, any chemical moiety that prevents a polymerase from using the first oligonucleotide probe as a primer for polymerization. In some embodiments, the polymerization blocker is a nucleic acid residue comprising a blocked 3' hydroxyl group (e.g., comprising an oxygen protecting group on the 3' hydroxyl group). In some embodiments, the polymerization blocker comprises an inverted nucleic acid residue. In some embodiments, the polymerization blocker is an inverted adenosine, thymine, cytosine, guanosine, or uridine residue. In certain embodiments, the polymerization blocker is an inverted thymine residue. In some embodiments, the first oligonucleotide probe further comprises a poly-adenosine (poly-A) linker sequence. In some embodiments, the poly-A linker sequence is about 2 to about 100, about 10 to about 90, about 30 to about 70, or about 40 to about 60 nucleotides long. In certain embodiments, the poly-A linker sequence is about 50 nucleotides long.

In some embodiments, the first oligonucleotide probe is about 30, about 35, about 40, about 45, about 50, about 55, about 60, about 65, about 70, or about 75 nucleotides long. In some embodiments, the portion of the first oligonucleotide probe that is complementary to the third oligonucleotide probe is about 3-20, about 4-19, about 5-18, about 6-17, about 7-16, about 8-15, about 9-14, about 10-13, or about 11-12 nucleotides in length. In some embodiments, the portion of the first oligonucleotide probe that is complementary to the third oligonucleotide probe is about 3, about 4, about 5, about 6, about 7, about 8, about 9, about 10, about 11, about 12, about 13, about 14, about 15, about 16, about 17, about 18, about 19, or about 20 nucleotides long. In certain embodiments, the portion of the first oligonucleotide probe that is complementary to the third oligonucleotide probe is about 12 nucleotides long. In some embodiment, the first oligonucleotide probe comprises the structure:

5'-[reactive chemical moiety]-[poly-A linker sequence]-[portion complementary to third oligonucleotide probe]-[polymerization blocker]-3', wherein ]-[ comprises an optional nucleotide linker. Each instance of the optional nucleotide linker may independently be 1, 2, 3, 4, 5, 6, 7, 8, 9, or 10 nucleotides long. In some embodiments, ]-[ comprises an optional non-nucleotide linker (e.g., a chemical or peptide-based linker).

The plurality of oligonucleotide probes disclosed herein also include a second and a third oligonucleotide probe. The second oligonucleotide probe includes a barcode sequence made up of a specific sequence of nucleotides. In some embodiments, the barcode sequence of the second oligonucleotide probe is about 1 to about 10 nucleotides long. In some embodiments, the barcode sequence of the second oligonucleotide probe is about 5 to about 10 nucleotides long. In some embodiments, the barcode sequence is greater than about 10, greater than about 15, or greater than about 20 nucleotides long. In certain embodiments, the barcode sequence of the second oligonucleotide probe is 5 nucleotides long. In some embodiments, the portion of the second oligonucleotide probe that is complementary to a metabolically labeled nucleic acid of interest is about 10-30, about 11-29, about 12-28, about 13-27, about 14-26, about 15-25, about 16-24, about 17-23, about 18-22, or about 19-21 nucleotides in length. In some embodiments, the portion of the second oligonucleotide probe that is complementary to a metabolically labeled nucleic acid of interest is about 10, about 11, about 12, about 13, about 14, about 15, about 16, about 17, about 18, about 19, about 20, about 21, about 22, about 23, about 24, about 25, about 26, about 27, about 28, about 29, or about 30 nucleotides long. In certain embodiments, the portion of the second oligonucleotide probe that is complementary to a nucleic acid of interest is 20 nucleotides long. In some embodiments, the second oligonucleotide probe is about 20, about 21, about 22, about 23, about 24, about 25, about 26, about 27, about 28, about 29, about 30, about 31, about 32, about 33, about 34, about 35, about 36, about 37, about 38, about 39, or about 40 nucleotides long. In certain embodiments, the second oligonucleotide probe is 32 nucleotides long. In some embodiments, the second oligonucleotide probe comprises the structure:

5'-[portion complementary to nucleic acid of interest]-[barcode sequence]-3', wherein ]-[ comprises an optional nucleotide linker. Each instance of the optional nucleotide linker may independently be 1, 2, 3, 4, 5, 6, 7, 8, 9, or 10 nucleotides long. In some embodiments, ]-[ comprises an optional non-nucleotide linker (e.g., a chemical or peptide-based linker).

The third oligonucleotide probe used in the methods described herein includes a first barcode sequence and a second barcode sequence, each made up of a specific sequence of nucleotides. In some embodiments, the first barcode sequence of the third oligonucleotide probe is about 1 to about 10 nucleotides long. In some embodiments, the first barcode sequence of the third oligonucleotide probe is about 5 to about 10 nucleotides long. In some embodiments, the barcode sequence is greater than about 10, greater than about 15, or greater than about 20 nucleotides long. In certain embodiments, the first barcode sequence of the third oligonucleotide probe is about 5 nucleotides long. In some embodiments, the second barcode sequence of the third oligonucleotide probe is about 1 to about 10 nucleotides long.

In some embodiments, the second barcode sequence of the third oligonucleotide probe is about 5 to about 10 nucleotides long. In some embodiments, the barcode sequence is greater than about 10, greater than about 15, or greater than about 20 nucleotides long. In certain embodiments, the second barcode sequence of the third oligonucleotide probe is about 5 nucleotides long. The third oligonucleotide probe also comprises a portion that is complementary to the first oligonucleotide probe. In some embodiments, the portion of the third oligonucleotide probe that is complementary to the first oligonucleotide probe is split between the 5' end and the 3' end of the third oligonucleotide probe. In some embodiments, the portion of the third oligonucleotide probe that is complementary to the first oligonucleotide probe is about 3-20, about 4-19, about 5-18, about 6-17, about 7-16, about 8-15, about 9-14, about 10-13, or about 11-12 nucleotides in length. In some embodiments, the portion of the third oligonucleotide probe that is complementary to the first oligonucleotide probe is about 3, about 4, about 5, about 6, about 7, about 8, about 9, about 10, about 11, about 12, about 13, about 14, about 15, about 16, about 17, about 18, about 19, or about 20 nucleotides long. In certain embodiments, the portion of the third oligonucleotide probe that is complementary to the first oligonucleotide probe is 12 nucleotides long (e.g., 6 nucleotides on the 5' end of the probe and 6 nucleotides on the 3' end of the probe). In some embodiments, the portion of the third oligonucleotide probe that is complementary to the metabolically labeled nucleic acid of interest is about 10-30, about 11-29, about 12-28, about 13-27, about 14-26, about 15-25, about 16-24, about 17-23, about 18-22, or about 19-21 nucleotides in length. In some embodiments, the portion of the third oligonucleotide probe that is complementary to the metabolically labeled nucleic acid of interest is about 10, about 11, about 12, about 13, about 14, about 15, about 16, about 17, about 18, about 19, about 20, about 21, about 22, about 23, about 24, about 25, about 26, about 27, about 28, about 29, about 30, or more than 30 nucleotides in length. In some embodiments, the third oligonucleotide probe comprises the structure:

5'-[first portion complementary to first oligonucleotide probe]-[first barcode sequence]-[portion complementary to nucleic acid of interest]-[second barcode sequence]-[second portion complementary to first oligonucleotide probe]-3', wherein ]-[ comprises an optional nucleotide linker. Each instance of the optional nucleotide linker may independently be 1, 2, 3, 4, 5, 6, 7, 8, 9, or 10 nucleotides in length. In some embodiments, ]-[ comprises an optional non-nucleotide linker (e.g., a chemical or peptide-based linker).

In some embodiments, the plurality of oligonucleotide probes further comprises a fourth oligonucleotide probe. In some embodiments, the fourth oligonucleotide probe comprises a sequence that is complementary to the second barcode sequence of the third oligonucleotide probe (i.e., the complementary sequence is the same length as the second barcode sequence of the third oligonucleotide probe as defined herein). In certain embodiments, the second barcode sequence of the third oligonucleotide probe is a gene-specific sequence used to identify a nucleic acid of interest (e.g., an RNA such as a nascent RNA or an mRNA). In some embodiments, the fourth oligonucleotide probe comprises a fluorophore. In some embodiments, the fluorophore is attached at the 5' end of the fourth oligonucleotide probe. In some embodiments, the fluorophore is attached at the 3' end of the fourth oligonucleotide probe.

In another aspect, the present disclosure provides an oligonucleotide probe comprising a portion that is complementary to a nucleic acid of interest, a first barcode sequence, a portion that is complementary to an additional oligonucleotide probe, and a second barcode sequence. In some embodiments, the first barcode sequence is complementary to a barcode sequence on the additional oligonucleotide probe. In some embodiments, the lengths of the various components of the presently described probe are the same as those for the third oligonucleotide probe as described herein.

In some embodiments, the first barcode sequence of the oligonucleotide probe is about 1-10 nucleotides long. In some embodiments, the first barcode sequence of the oligonucleotide probe is 5-10 nucleotides long. In some embodiments, the barcode sequence is greater than about 10, greater than about 15, or greater than about 20 nucleotides long. In certain embodiments, the first barcode sequence is 5 nucleotides long. In some embodiments, the second barcode sequence of the oligonucleotide probe is about 1-10 nucleotides long. In some embodiments, the second barcode sequence of the oligonucleotide probe is 5-10 nucleotides long. In some embodiments, the barcode sequence is greater than about 10, greater than about 15, or greater than about 20 nucleotides long. In certain embodiments, the second barcode sequence is 5 nucleotides long. In some embodiments, the portion of the oligonucleotide probe that is complementary to the additional oligonucleotide probe is split between the 5' end and the 3' end of the oligonucleotide probe. In certain embodiments, the oligonucleotide probe comprises the structure:

5'-[first portion complementary to first oligonucleotide probe]-[first barcode sequence]-[portion complementary to nucleic acid of interest]-[second barcode sequence]-[second portion complementary to first oligonucleotide probe]-3', wherein ]-[ comprises an optional nucleotide linker. Each instance of the optional nucleotide linker may independently be 1, 2, 3, 4, 5, 6, 7, 8, 9, or 10 nucleotides long. In some embodiments, ]-[ comprises an optional non-nucleotide linker (e.g., a chemical or peptide-based linker).

Kits

Also encompassed by the disclosure are kits. In one aspect, the kits provided may comprise one or more oligonucleotide probes described herein. In some embodiments, the kits may further comprise a container (e.g., a vial, ampule, bottle, and/or dispenser package, or other suitable container). In some embodiments, the kit comprises any of the pluralities (i.e., sets) of oligonucleotide probes or single oligonucleotide probes described herein. In some embodiments, the kit comprises multiple pluralities of oligonucleotide probes or multiple single oligonucleotide probes described herein, wherein each plurality of oligonucleotide probes or single oligonucleotide probe is used to profile spatiotemporal gene expression of a different metabolically labeled nucleic acid of interest. In some embodiments, the kit comprises more than 1, more than 2, more than 3, more than 4, more than 5, more than 10, more than 20, more than 30, more than 40, more than 50, more than 100, more than 200, more than 500, or more than 1000 pluralities of oligonucleotide probes or single oligonucleotide probes disclosed herein. In some embodiments, the kits may further comprise other reagents for performing the methods disclosed herein (e.g., cells, a pool of nucleoside analogs, wherein each nucleoside analog in the pool of nucleoside analogs comprises a reactive chemical moiety as described further herein, a ligase, a polymerase, amine-modified nucleotides, and/or reagents for making a polymeric matrix (e.g., a polyacrylamide matrix)). In some embodiments, the kits are useful for profiling spatiotemporal gene expression in a cell. In some embodiments, the kits are useful for profiling the role of post-transcriptional modification in spatiotemporal gene expression. In some embodiments, the kits are useful for studying the role of spatiotemporal gene expression in the development or progression of a disease or disorder. In some embodiments, the kits are useful for screening for an agent capable of modulating spatiotemporal gene expression. In some embodiments, the kits are useful for diagnosing a disease or disorder in a subject. In some embodiments, the kits are useful for treating a disease or disorder in a subject. In certain embodiments, a kit described herein further includes instructions for using the kit.

Systems for Profiling Spatiotemporal Gene Expression

The present disclosure also provides systems for profiling spatiotemporal gene expression in a cell. In some embodiments, the systems comprise a) a cell; b) a pool of nucleoside analogs, wherein each nucleoside analog in the pool of nucleoside analogs comprises a reactive chemical moiety; c) a population of first oligonucleotide probes, wherein each first oligonucleotide probe in the population of first oligonucleotide probes comprises a chemical moiety that reacts with the reactive chemical moiety of the nucleoside analogs; and d) one or more pairs of oligonucleotide probes comprising a second oligonucleotide probe and a third oligonucleotide probe, wherein:

i) the second oligonucleotide probe comprises a barcode sequence and a portion that is complementary to a nucleic acid of interest; and ii) the third oligonucleotide probe comprises a portion that is complementary to the nucleic acid of interest, a first barcode sequence, a portion that is complementary to a first oligonucleotide probe in the population of first oligonucleotide probe, and a second barcode sequence, wherein the first barcode sequence of the third oligonucleotide probe is complementary to the barcode sequence of the second oligonucleotide probe.

In some embodiments, the system further comprises a microscope (e.g., a confocal microscope). In some embodiments, the system further comprises a computer. In some embodiments, the system further comprises a CPU. In some embodiments, the system further comprises computer storage and/or memory. In some embodiments, the system further comprises a camera. In some embodiments, the system comprises software for performing microscopy and/or for image analysis. In some embodiments, the system further comprises a ligase. In some embodiments, the system further comprises a polymerase. In some embodiments, the system further comprises amine-modified nucleotides. In some embodiments, the system further comprises reagents for making a polymeric matrix (e.g., a polyacrylamide matrix). The cell in the systems of the present disclosure may be any of the cell types disclosed herein. In some embodiments, the system comprises multiple cells. In some embodiments, the cells are of different cell types. In certain embodiments, the cells are present in a tissue. In some embodiments, the tissue is a tissue sample provided by or from a subject. In certain embodiments, the subject is a human.

EXAMPLES

Example 1: Nascent RNA Labeling Chemistry for Spatiotemporally Resolved Transcriptomics The importance of understanding how cells regulate activities and react to environmental stimuli in their spatial context has become increasingly appreciated. Indeed, biological tissues are composed of an enormous number of spatially confined cells that act coordinately to exert specific functions and control activities. The location of cells within an organism or a tissue affects cell differentiation and activities, and similarly, the landscape of heterogenous cells contributes to the specialized development and the physiological states of tissues.

The rapid advances in studying cell organization in tissues and multicellular organisms began with the development of transcriptomic sequencing technology, or RNA-seq, which has enabled the global detection and quantification of mRNAs in pooled cells. Single-cell RNA sequencing (scRNA-seq) has facilitated assessing an individual cell's transcriptome, allowing biological differences between cell types to be inferred. More recently, spatially resolved transcriptomic methods have gone one step further, examining the single-cell transcriptome while retaining the spatial context within cells. Image-based methods, such as STAR-map, demonstrate an advantage by detecting three-dimensional localization of cells with sequential imaging, a crucial factor for analyzing tissues, organoids, and organs. By taking full advantage of spatial transcriptomes, large consortia such as the Human Cell Atlas and Brain Initiative Cell Census Network are in the process of creating comprehensive reference "maps" of the diverse cell types of tissues in humans as a basis to understand life, health, and disease.

In addition to how tissues are structured by functionalized cell types, the spatial organization of biomolecules in cells is similarly, if not more, crucial to understanding cell function and tissue physiology. Spatial segregation of proteins creates compartmentalized cellular environments, contributing to effective and orderly functioning of a cell. To ensure interaction fidelity and thermodynamic efficiency, such heterogenous organization of proteins also requires spatial control of mRNA and localized protein translation. Known examples of mRNA subcellular localization in animal cells include those observed in fibroblasts, neurons, oligodendrocytes, muscle cells, and cardiomyocytes, suggesting a reoccurring theme of asymmetric distribution of RNA in cell biology. Furthermore, the strong evidence of asymmetric mRNA distribution and on-site protein synthesis allows the decoupling of transcription and translation, demonstrating the important role of mRNA location to cellular functions. In addition to localization, fine-tuning mRNA processing in a time-dependent manner is prevalent, as protein synthesis is oftentimes executed for as long as needed. Prominent examples include mRNA transport and trafficking in neurons and embryonic development. Thus, it is imperative to study not only overall cell organization in tissues but also the specific, compartmentalized activities inside each cell type. As a result, understanding the spatiotemporal control of mRNA, RNA-protein interactions, and protein synthesis at the intracellular level is crucial to reveal how cells differ from each other.

Nevertheless, most spatial transcriptomic strategies still examine on the pan-cellular level, tracking and differentiating single cells but not looking into mRNA spatial information in the intracellular environment. Even with the attempt to look deeper into the subcellular level, the current state of the art in the field only provides snapshots of mRNA localization at the cellular steady state, obscuring the highly regulated balance between transcription and transcript turnover. Since the dynamics of mRNA subcellular location has a wide range of impacts from the fundamental understanding of cell biology to distinguishing healthy and diseased states, there exists a pressing need for a time-resolved spatial sequencing method that tracks the translocation of mRNA from birth to death in single cells to accurately profile gene expression over a defined period of time.

One promising approach for capturing RNA dynamics is through metabolic labeling. The metabolic sequencing of transcriptomes with nucleotide analogs enables the selective labeling of nascently transcribed RNAs. The use of 4-thio-uridine (4SU), 5-bromo-uridine (5BrU), 5-ethynyl uridine (5-EU), as well as adenosine analogs, allows for incorporation of different chemical handles onto the labeled RNAs, which can be further enriched and isolated from the unlabeled transcripts through various means. These approaches have successfully allowed monitoring of the temporal change of gene expression and characterization of the kinetic parameters of nascent transcripts. Specifically, 5-EU-labeled RNAs can be captured and sorted through click chemistry, which demonstrates great potential to achieve bioorthogonality and high signal-to-noise ratio in the chemical processing of cells.

By incorporating metabolic labeling into spatial transcriptomics, TEMPOmap (temporally resolved in situ sequencing and mapping) was developed. TEMPOmap is a new method that resolves single-cell nascent transcriptomics with the temporal dimension. Thus, a "4D map" of RNA within a cell, or multiple cells, can be created (FIG. 1). This method builds on hydrogel-tissue chemistry, DNA barcoding, and a two-base sequencing scheme (SEDAL sequencing). This method includes the incorporation of metabolic labeling, DNA-RNA proximity ligation, and a three-part DNA probe design, which enables the selective capture of nascent transcripts with high efficiency and low background. TEMPOmap is capable of providing spatial, temporal, and single-molecule information about RNA on a transcriptome-wide scale, and the subcellular localization of nascent transcripts can thus be visualized. Like other spatial transcriptomic methods, TEMPOmap can be used to differentiate the heterogeneity of single cells and map them to structured tissues. Thus, the method provides a finer description of single cells' states and intracellular functions by allowing resolution of genome-scale synthesis and degradation rates of mRNAs and simultaneous observation of the spatial translocation constraints of these transcripts over a tunable period of time.

TEMPOmap was first demonstrated by resolving nascent transcripts in HeLa cells and connecting the observed dynamic of a targeted transcriptome with a prevalent epitranscriptomic modification, N6-methyladenosine ($m^6A$). TEMPOmap also allows for studying the biochemical basis of neuroscience since neurons have an elaborate architecture that requires mRNA transport and decentralized protein synthesis. The method is used to determine how neurons adapt and change in response to environmental stimuli from the perspective of RNA localization, RNA-protein interactions, and localized translation. TEMPOmap is a versatile platform and can be used to understand how gene expression is dynamically processed in many different cell and tissue types and to determine the broader impacts of post-transcriptional regulation.

Figure 2A:
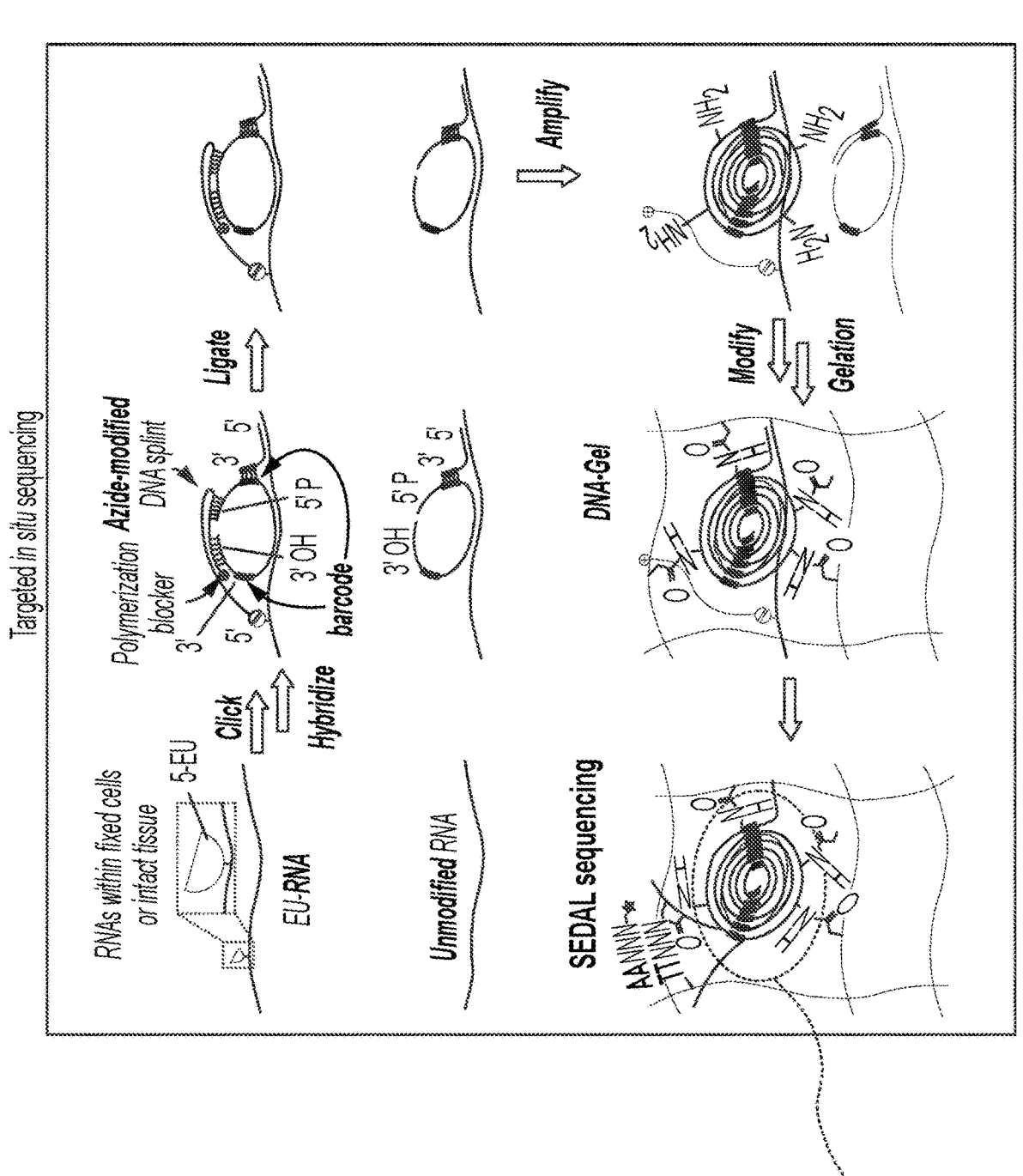
FIGS. 2A-2E show the principles of TEMPOmap and the use of nascent RNA labeling chemistry for spatiotemporally resolved transcriptomics.
Figure 2B:
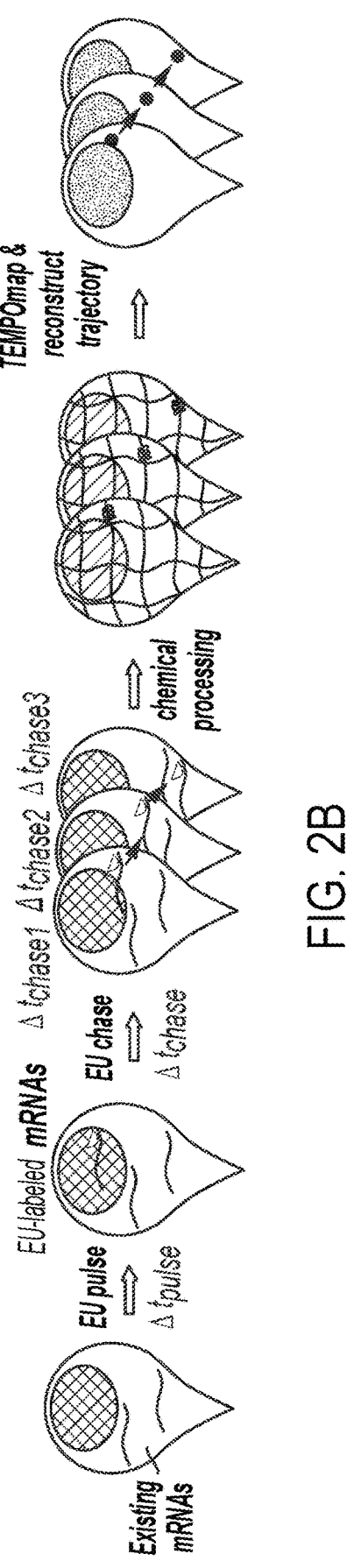
Figure 2C:
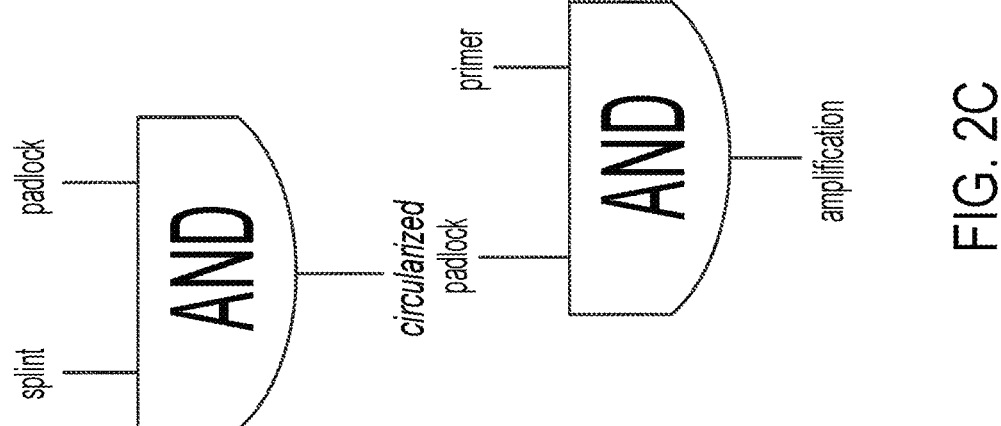

TEMPOmap method design and principles. To demonstrate the selective and efficient capture of the nascent RNAs, HeLa cells were exposed to the nucleoside analog 5-EU to create a chemical handle on the labeled transcripts (FIG. 2A). Next, azide-modified DNA oligos, or DNA "splints," were designed, incubated with the permeabilized cells, and covalently linked to the labeled mRNAs via copper(I)-catalyzed azide-alkyne cycloaddition (CuAAC). This bioorthogonal DNA-RNA conjugation ensures the selective modification of the nascently transcribed RNAs, leaving the transcripts lacking the alkyne-functional group undetected. A library of pairs of primers and padlocks targeting the exonic region of mRNAs was then designed. Upon the hybridization of primers and padlocks to the targeting mRNAs, the 5' phosphorylated padlocks were circularized and concatenated to the RNAs only when a splint was in proximity on the same mRNA. Furthermore, to overcome autofluorescence and scattering in most of fluorescent in situ hybridization (smFISH) experiments, an in situ enzymatic reaction was conducted to amplify the padlock sequences as templates. To this end, the nonspecific hybridization of single probes was further reduced by utilizing pairs of primer and padlock targeting the same gene so that only when the primer and the padlock independently hybridize to the same RNA can rolling cycle amplification (RCA) be allowed, resulting in the formation of cDNA nanoballs (amplicons). Thus, using this three-part DNA probe design (splint, primer, and padlock), the amplification of time- and sequence-controlled transcripts was achieved via a two-step thresholding strategy (FIG. 2c).

During RCA, amine-modified nucleotides were spiked into the amplification reaction to functionalize amplicons with amine groups. An acrylamide functional group was then chemically added to the amine-amplicons by methacrylic acid N-hydroxysuccinimide ester (MA-NHS). To preserve the physical location of endogenous transcripts, a DNA-hydrogel hybrid was created by crosslinking the acrylamide-modified amplicons with hydrogel monomers during polymerization, resulting in the anchoring of amplicons to the hydrogel network. This hybrid builds a molecular scaffold that retains the chemically conjugated amplicons while allowing the unamplified RNAs and DNA probes to be removed. In addition, it also significantly improved sample stability and enabled subsequent high-resolution imaging. Finally, on each padlock, a unique barcode was encoded on two sides of padlock, with one side used for orthogonal-sequence recognition by the respective primer and the other side used for sequential base readout and decoding by SEDAL sequencing, achieving highly multiplexed detection of single-cell transcriptomes.

Figure 2D:
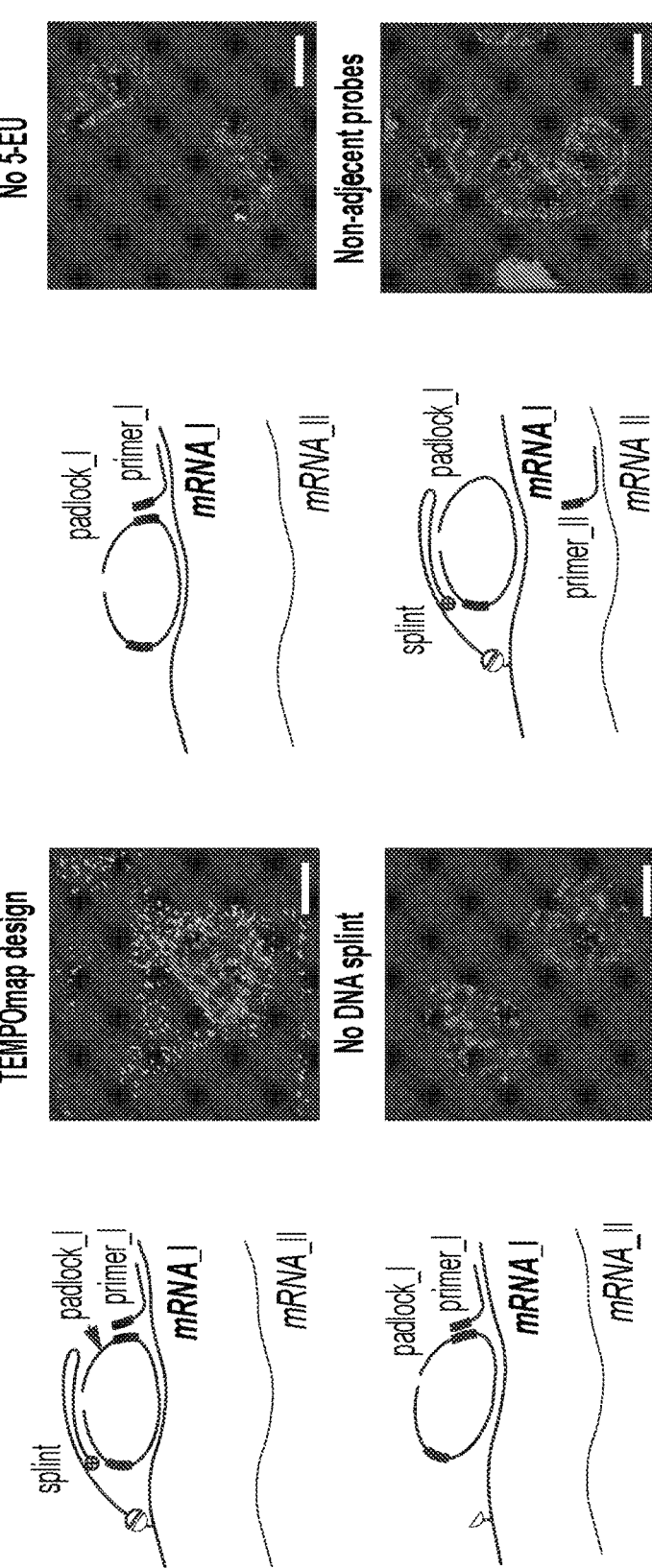
Figure 2E:
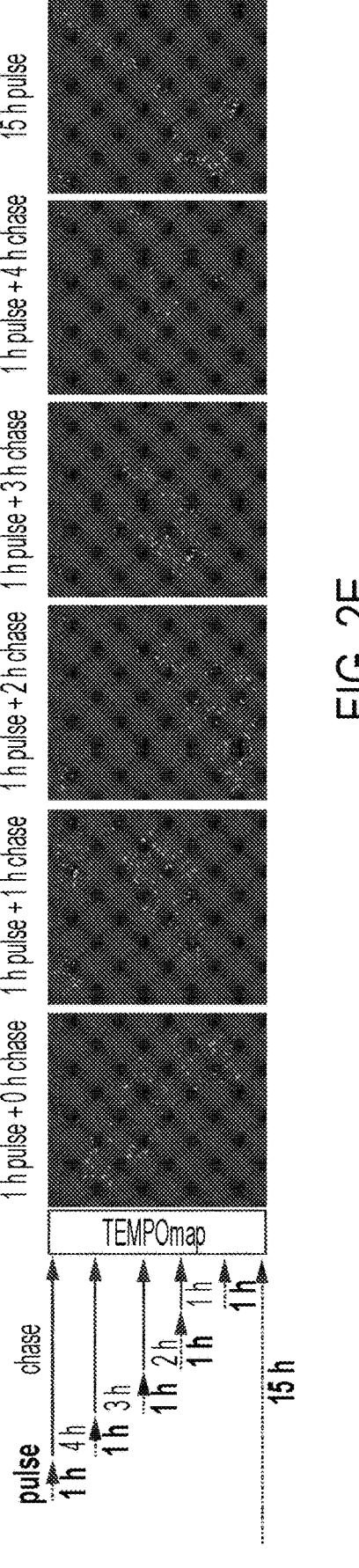

The method was combined with pulse-chase experiments. RNAs encoding approximately 1000 genes were captured after different chase durations and traced to re-build their spatiotemporal trajectory by integrating their locations at different time points (FIG. 2B). It was demonstrated that the method enriched the metabolically labeled transcripts (FIG. 2D) and robustly detected changes in gene expression over tunable time courses (FIG. 2E). Given the strict two-step thresholding principles applied, it was further demonstrated that this approach achieved near-genome-wide transcriptome readout with high signal-to-noise ratio.

Figure 3:
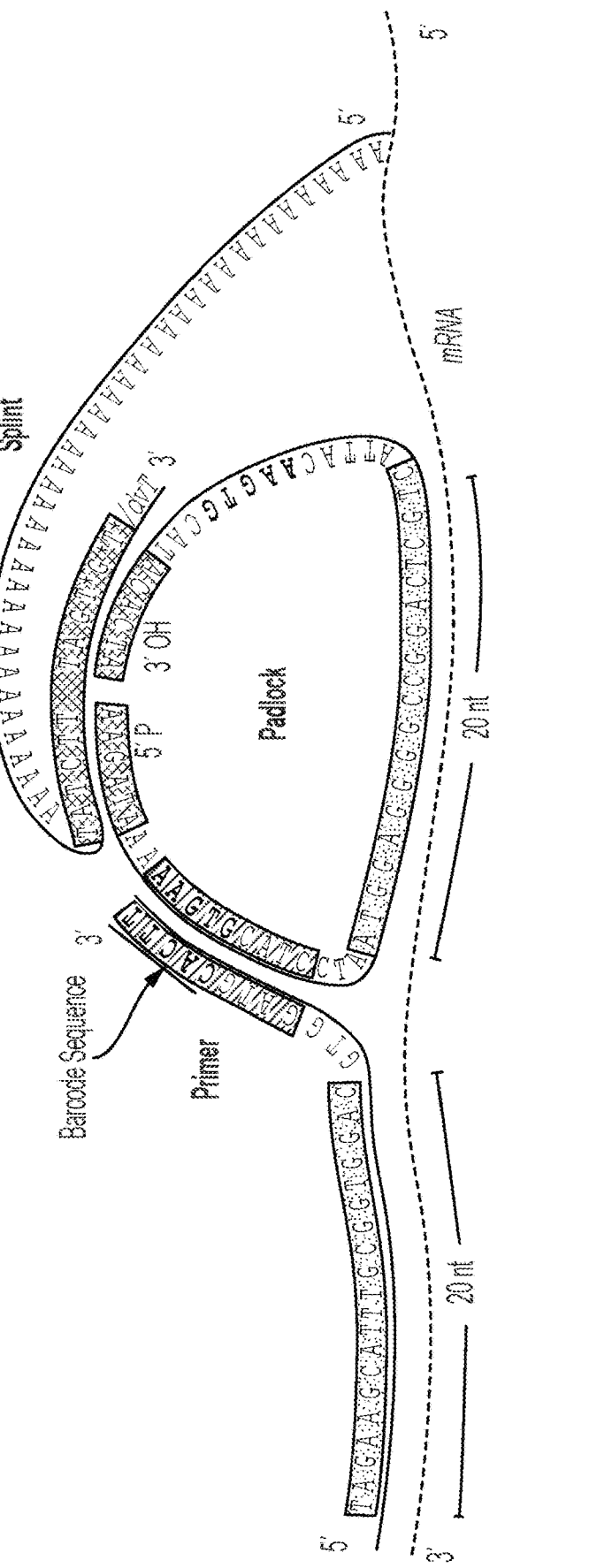
FIG. 3 provides a schematic of the TEMPOmap three-part probes. The splint probe is divided into a polyA segment and a splint-padlock annealing sequence (the nucleotides highlighted in the box on the splint probe). The splint probe ends with an inverted T (as labeled at the 3' end of the probe) to prevent amplification initiation. The padlock probe contains the splint-padlock annealing sequence complementary to the region on the splint probe (the nucleotides complementary to the splint probe highlighted in the boxes on the padlock probe) with a junction, two regions of the same barcodes (labeled "barcode sequence"), a 20 nt hybridization region targeting an mRNA (the nucleotides complementary to the mRNA highlighted in the box on the padlock probe) and a primer-padlock annealing sequence (the nucleotides complementary to the primer probe highlighted in the box on the padlock probe). The primer probe contains a 20 nt hybridization region targeting regions of mRNAs next to the padlock probe (the nucleotides complementary to the mRNA highlighted in the box on the primer probe) and a primer-padlock annealing sequence complementary to the region on the padlock probe (the nucleotides complementary to the padlock highlighted in the box on the primer).

Three-part DNA probe design. Sequence design of the three-part DNA probes used in TEMPOmap is shown in FIG. 3. The three-part probes are comprised of a DNA splint probe, a primer probe, and a padlock probe. The splint is divided into two regions: a poly-A linker and a splint-padlock annealing region. The poly-A linker contains fifty adenosine nucleotides, which provides the splint enough length to reach the nearby padlock. The splint-padlock annealing sequence enables the hybridization of splint with padlock, creating a double-stranded DNA region with a "nick" that can be sealed in the ligation step. The 5' phosphorylated padlock is comprised of a splint-padlock annealing region, two regions of the same barcode, a primer-padlock annealing region, a 20 nt hybridization sequence targeting the mRNA of interest, and several short linkers. Upon ligation, the padlock is circularized and becomes the DNA template for in situ enzymatic amplification. The primer contains a gene-unique region that is reverse complementary to the barcode on the matching padlock, a four-base sequence also complementary to the padlock, and a 20 nt hybridization sequence targeting mRNA. The two 20 nt hybridization regions on the primer and the padlock reside 1-2 bases next to each other on the mRNA. Upon binding of the primer and padlock, the primer serves as the amplification initiator, and the sequence of padlock is amplified, generating cDNA amplicons.

To validate the enrichment of the labeled probe-targeting genes, negative control conditions were compared with test conditions targeting human beta-actin mRNA (ACTB) only. As shown in FIG. 2D, HeLa cells pulsed with 5-EU for 15 h and processed according to TEMPOmap design showed high florescence intensity of quantized amplicon signals, most of which located at the cell periphery. This clear trend of RNA localization reflected the endogenous function and location of beta-actin proteins as a part of the cytoskeleton and also verified the localized translation of the human ACTB gene. In contrast, controls without 5-EU labeling, splint, or matching pairs of primer and padlock showed no or little signal. The signal-to-noise ratios of 5-EU labeled over unlabeled signals demonstrated the significant enrichment of labeled nascent transcripts.

Based on the discovery of ACTB mRNAs in the periphery of HeLa cells, the method was tested for its ability to capture the dynamics of mRNA export and translocation given different pulsing and chasing time courses. Thus, in HeLa cells, newly synthesized RNA was pulse labeled for 1 h with 5-EU, and the cells were washed for varying time periods (FIG. 1D, left). TEMPOmap was then applied to detect the translocation of ACTB transcripts over different lengths of washing time. The images showed a clear trend of nucleus-to-cytoplasm exporting trajectory (FIG. 1D, right). Hence, it was concluded that the method was indeed capable of capturing and enriching nascent transcripts and detecting the translocation and dynamics of these RNAs.

Example 2: Profiling RNA m$^6$A Methylation

The mRNAs of higher eukaryotes are extensively modified by critical post-transcriptional regulations during gene expression. Among these diversely modified nucleotides, N6-methyladenosine (m$^6$A) is the most prevalent internal mark on eukaryotic transcripts. The function and characterization of m$^6$A have been gradually unraveled. RNA-binding proteins, an example of which is a group of m$^6$A "readers" that recognizes m$^6$A site motifs, have been discovered and provide valuable insights into the molecular mechanisms of RNA regulation.

One class of m$^6$A readers includes the YTH domain family 1-3 (YTHDF1-3) and YTH domain containing 1-2 (YTHDC1-2). Despite their shared evolutionary relationship and similar RNA substrates, the biological function of each of these proteins is unique. For example, YTHDF2 regulates the stability of its target RNAs by drawing them to cellular RNA decay sites; YTHDF1 promotes the translation of mRNAs by recruiting translation factors; YTHDF3 is suggested to work in concert with YTHDF1-2 and facilitate both RNA degradation and translation. In contrast, YTHDC1 expedites nuclear export and mRNA splicing by interacting with the splicing factor and nuclear export adaptor protein, whereas YTHDC2 plays a critical role during spermatogenesis. These m$^6$A readers exert their function cooperatively to achieve multi-layer regulation and fine-tune the phenotypical outcomes of m$^6$A-modified transcripts.

The relationship between the regulation of m$^6$A-modified mRNAs and their spatial location in cells has not been systematically addressed. Because the function of RNA is strongly linked to its cellular localization and trafficking, it was investigated whether the TEMPOmap method would be able to provide more insights into the molecular mechanism of epitranscriptomic regulation. To this end, a list of 1000 m$^6$A processing-related genes was curated, from which targeting primer and padlock probes were designed to detect and profile their spatiotemporal dynamics using TEMPOmap. This approach provided an image-based description of RNA m$^6$A methylation processing in space and time and revealed the intricate network that regulates this post-transcriptional modification.

The list of 1000 genes included genes encoding RNAs with extremely high or low m$^6$A abundance and RNAs that are robustly recognized by YTHDF1-3 and YTHDC1-2. The list also incorporates genes relating to m$^6$A processing (addition, recognition, removal, etc.). Furthermore, genes that serve as subcellular location markers were included to help analyze the localization of RNAs, and genes that are active in the cell cycle were also included to help visualize the cells in different time courses. In addition to studying the genes mentioned above in wild-type HeLa cells, seven genes were knocked down independently by treating the cells with short interfering RNA (siRNAs) targeting YTHDF1-3, YTHFC1-2, and m$^6$A writers METTL14 and METTL3, which install the methylation on the RNAs. The expression of these 1000 genes in situ in the control versus the knockdown samples were then compared to capture the changes in the transcriptional and post-transcriptional in situ profiling. Confirmed by the independent roles of METTL14/3, YTHDF1-3, and YTHDC1-2, it was assumed that mRNA transport and trafficking should be more or less influenced by the gene knockdown.

Figure 4A:
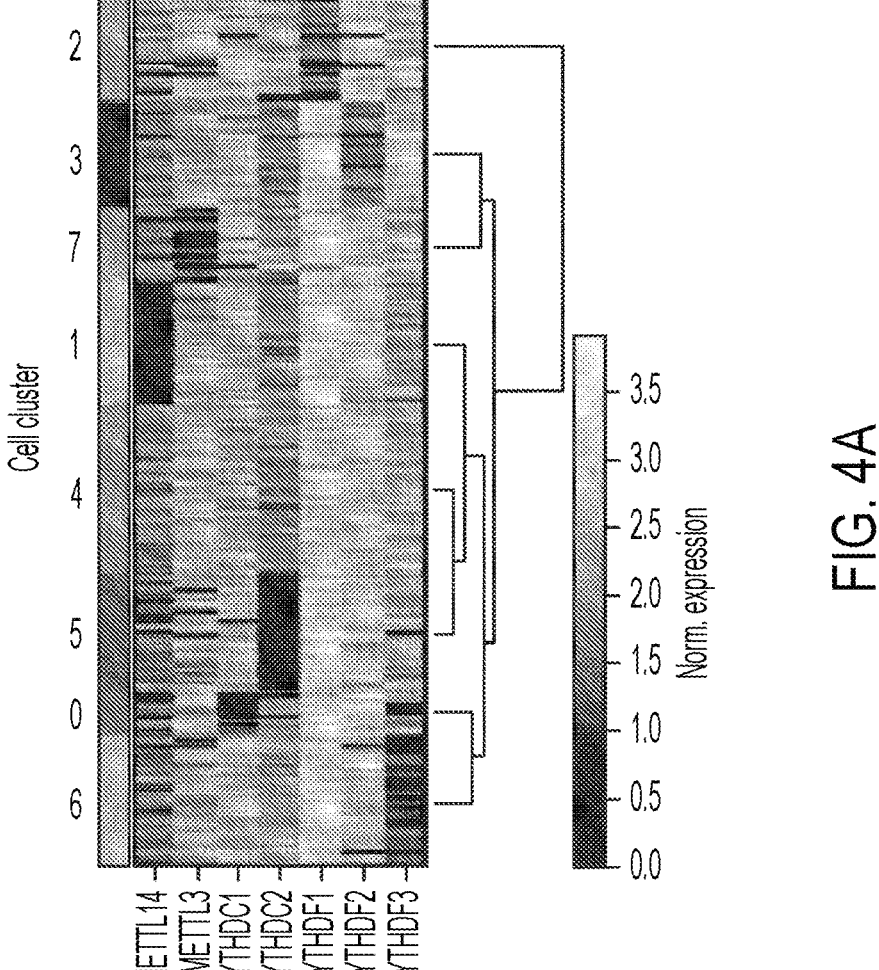
FIGS. 4A-4B show STARmap analyses of knockdown of seven $N^6$-methyladenosine ($m^6A$) writers or readers by siRNA transfection.
Figure 4B:
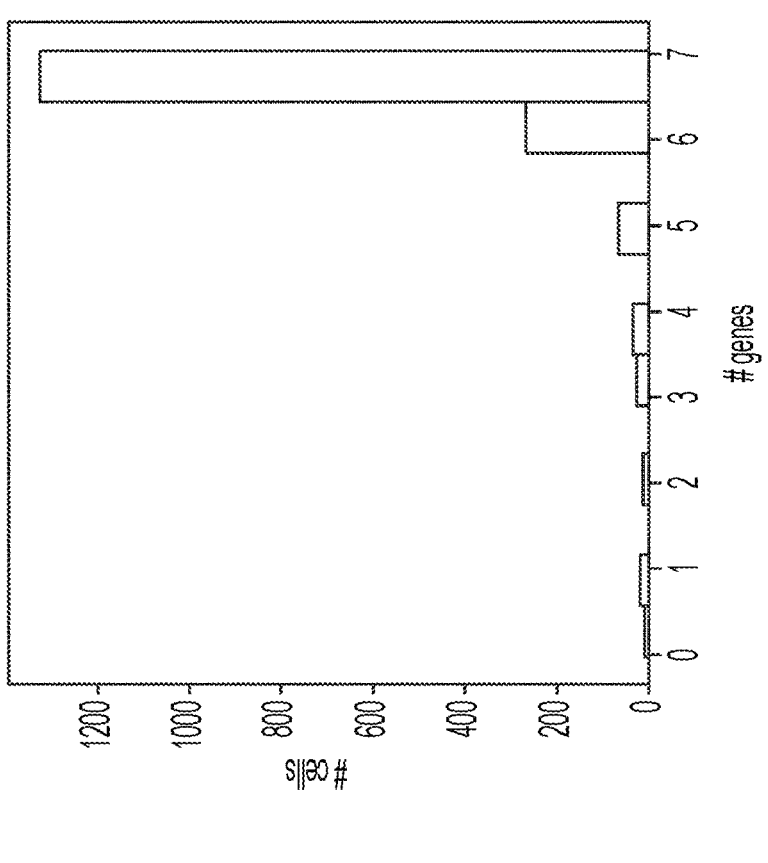
Figure 4B:
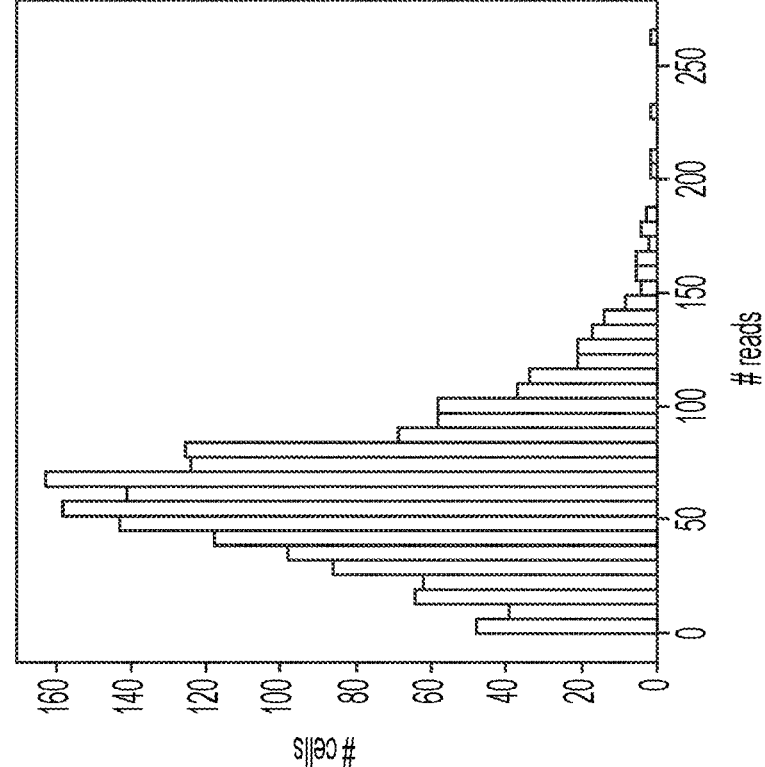

To validate the efficiency of gene knockdown by these siRNAs, an initial test was conducted using STARmap to detect the expression (or a lack of expression) of the siRNA-targeting genes, and this test was compared with the untreated wild-type cells. Each well of cultured cells was first treated with one type of siRNA, and after the cells had grown for 2 days, all the cells were pooled together in one well and allowed to grow overnight. The STARmap protocol was then applied to detect the expression of the seven genes in single cells using two rounds of in situ sequencing. Eight distinct clusters of HeLa cells were discovered after analyzing gene expression, with seven clusters representing YTHDF1-3, YTHDC1-2, and METTL14/3 knockdown cells and one cluster without siRNA transfection (FIG. 4). This method can be expanded to profile gene expression of 1000 genes when treated with the same group of siRNAs.

After the success of siRNA transfection was confirmed, the knockdown experiments of the seven genes (plus a control siRNA transfection) were repeated in HeLa cells. After 6 hours of transfection, the eight populations of cells were pooled together and equally divided into six groups. One group was then labeled with 200 μM 5-EU for ~15 hours before fixation. On the next day, the remaining five groups of unlabeled cells were incubated with 200 μM 5-EU for 1 h each and replaced with fresh media (with 200 μM 5-EU) for 0, 1, 2, 4 and 6 h, respectively. Subsequently, TEMPOmap was carried out, and the experiment was scaled to detect 1000 genes. Raw images of SEDAL sequencing were collected.

Figure 5:
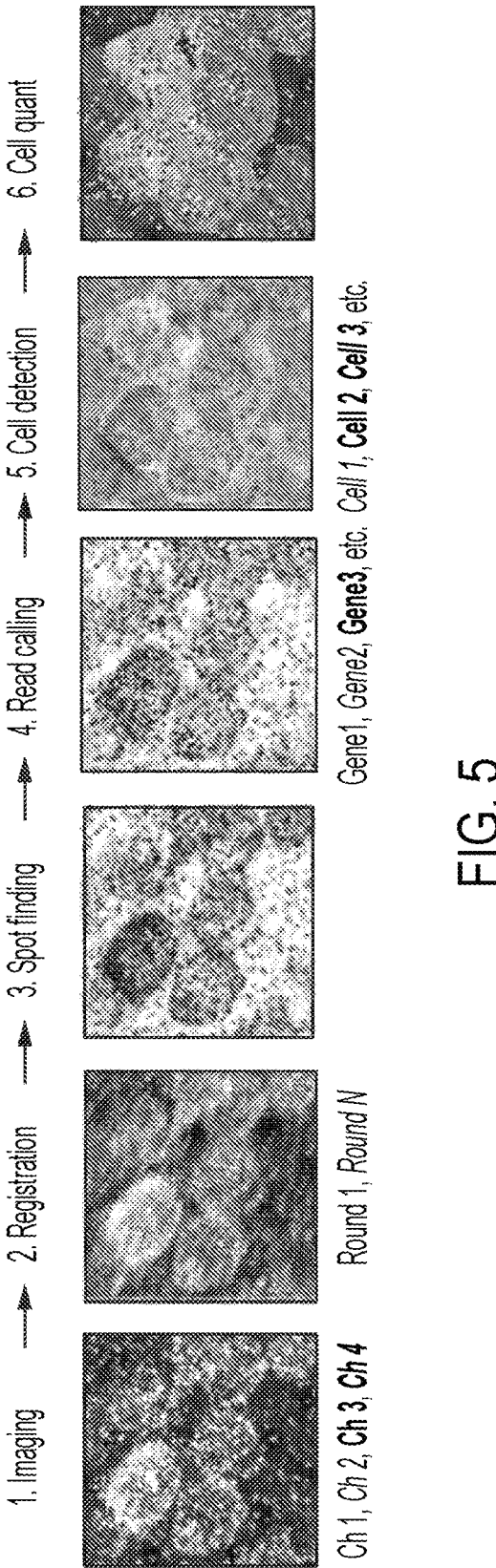
FIG. 5 shows the data processing pipeline. This processing pipeline, originally designed for STARmap, shows the typical computational workflow of extracting reads from raw imaging data.

After collecting the raw images from the six groups of cells treated with different lengths of pulse-chase, the images were first pre-processed using a computational workflow (FIG. 5) to extract the reads and quantify the genes detected. The multi-layered information in the data was then analyzed. TEMPOmap is the first experimental method that enables spatiotemporally resolved multiplexed in situ RNA detection.

Analysis of the data is divided into two layers: analyzing the RNAs in unperturbed cells only and analyzing the changes of RNAs in cells with gene knockdown. In the first layer, changes in RNA translocation and half-lives are examined by comparing the locations and quantification of RNA reads from different times. The pulse-chase data is also compared with the 15 h labeling data, which represents RNAs in the cellular steady state. Gene enrichment is then examined in specific subcellular regions at one time point and/or RNA mobility/immobility to different subcellular regions is examined. Interesting colocalization or co-translocation of genes can also be used to dissect the data. Similarly, RNA half-lives or rates of degradation can be calculated, and peculiar association between half-life and location can be examined further. It is similarly possible to determine whether translocating to a specific subcellular region is linked with long/short half-lives or if the rate of translocation itself is associated with half-lives. Subsequently, it is analyzed whether a specific group of RNAs that share similar activities or behavior is enriched in GO terms, or whether different "clusters" of RNAs have distinct biochemical roles, and from there, a more in-depth mechanistic study of the m$^6$A-processing pathway is conducted from the perspective of RNA localization.

In the second layer, analyses of unperturbed cells in the first layer are combined with those of the gene-knockdown cells to explore whether any of the m$^6$A writers and readers are involved in RNA subcellular trafficking, localization, and/or stability. It has been well verified that YTHDF1 promotes ribosome occupancy of target mRNA and YTHDF2 influences RNA stability, and it is highly likely that these observed causalities can be partially explained by spatial RNA localization and trans-localization, which are yet to be discovered. Besides looking for changes induced by specific gene knockdown, it is also possible that repressing any genes along the m$^6$A processing pathway leads to a universal change in the spatial transcriptome profile.

This Example demonstrates the analysis of mRNA levels, half-lives, and translocation for up to 1000 genes relating to m$^6$A metabolism. Beyond post-transcriptomic modification, this method can be used to study any biological phenomena that are influenced by the spatial context of biomolecules and morphological context of cells.

Example 3: Visualization of RNA in Neurons and 3D Intact Tissues

TEMPOmap can also be applied to solve important questions in neuroscience. Since axons and dendrites of neurons span space up to tens of millimeters away from the cell body, it is quite remarkable that the proteome in these regions senses stimuli and respond to them with no delay. TEMPOmap can be used to visualize neuronal mRNA transport and distal RNA-protein interactions. TEMPOmap can be applied to cultured neurons, and the workflow of TEMPOmap can be optimized for treating intact tissue. TEMPOmap enabled uniform detection of 100-micron thick tissues, equivalent to ten layers of cells. TEMPOmap can be used on mouse brain slices upon treating mice with an external stimulus.

To demonstrate the ability of TEMPOmap in neurons, the current experimental workflow can be applied in fixed neuronal culture, and an initial test can be conducted to detect ACTB mRNAs only. The neurons can be stimulated with KCl, and a pulse-chase experiment can be conducted after KCl stimulation. TEMPOmap probes that target the most highly expressed activity-regulated genes after neuronal stimulation are used and capture of the dynamic of these genes is tested. Genome-wide CRISPR screens can be performed in neurons and approximately 1000 gene probes targeting mRNAs relating to mRNA trafficking, RNA-protein interaction, and local translation can be designed to systematically provide an image-based study of the mechanism of distant RNA translocation and translation machinery. In addition, epitranscriptome processing in synapses can be explored. The use of TEMPOmap can provide more insights into the relationship between mRNA processing and neuronal activities such as synaptogenesis and experience-dependent plasticity.

Alternatively, the experimental workflow of TEMPOmap can be optimized to enable the possibility of 3D in situ sequencing since RNA dynamics is also critical to tissue physiology. Thus, leveraging the advantage of spatial transcriptomics, the method can differentiate and categorize cells from a new dynamic perspective and allow mapping of cells to tissue. Individual chemical and enzymatic steps in the workflow can be modified to make it compatible to 3D visualization.

Example 4: Spatiotemporally Resolved Transcriptomics at Subcellular Resolution Gene expression is dynamically regulated at multiple steps of the RNA life cycle: transcription, processing, export, translation, and degradation. Understanding gene regulation mechanisms in functionally diverse cell-types within multi-cellular organisms requires cell-type-specific measurements of RNA localization and kinetics. Single-cell RNA sequencing (scRNA-seq) technologies have enabled transcriptomic measurements at the single-cell level and redefined cell types by transcriptomic profiles. The recent development of spatial transcriptomic methods has further enabled simultaneously counting cellular transcripts and tracking their spatial information in situ for spatially resolved molecular cell typing in the context of tissue architecture.[1-11] In parallel, single-cell metabolic labeling experiments have revealed that separating the nascent transcriptome from existing RNAs is necessary to identify RNA metabolic programs and immediate regulatory changes in response to external stimuli.[12]

However, there still lacks an integrated method to simultaneously measure the spatial localization of RNAs and the kinetics of RNA biogenesis, export, and degradation at the transcriptome scale, limiting the ability to comprehend dynamic regulatory schemes triggered by developmental, environmental, metabolic, and pathological signals.

Figure 6A:
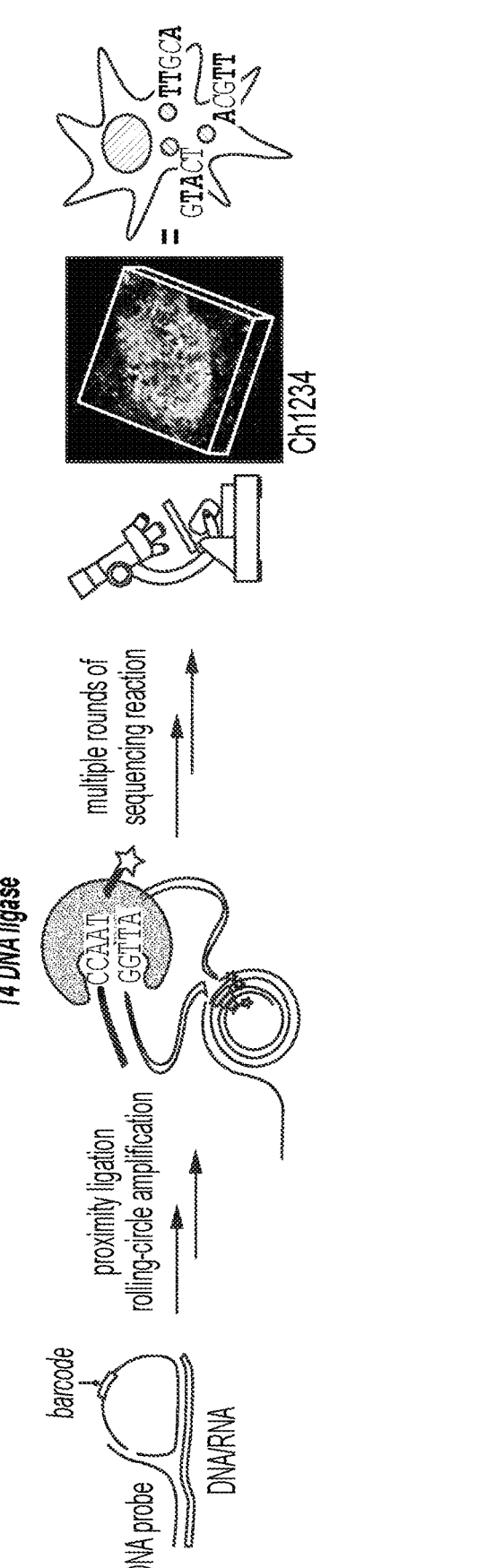
FIGS. 6A-6B provide schematics for temporally resolved STARmap at sub-hour and subcellular resolution.

To fill such a technology gap, a spatiotemporally resolved transcriptomic method has been developed. Previously, a method for spatially resolved transcript amplicon readout mapping (STARmap, FIG. 6A)[1] was developed in which chemically functionalized cDNA amplicons were covalently linked to a polyacrylamide matrix to allow stringent tissue clearing and biomolecule processing. This Example described the addition of the time dimension to STARmap. mRNAs are metabolically labeled with chemically modified polymerizable nucleosides, and modified transcripts are directly linked to the polymer matrix.

Figure 6B:
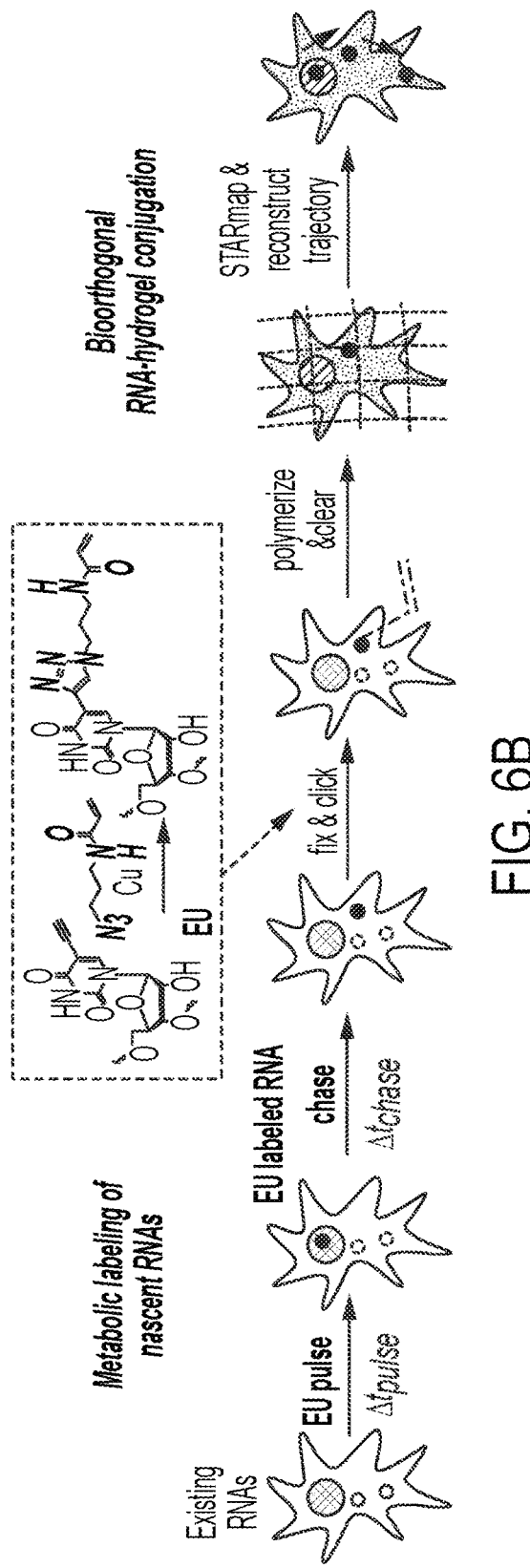

The current STARmap protocol covalently links acrylate-modified DNA amplicons to polyacrylamide hydrogel matrices, a crosslinking method that demonstrates a limited capability of mRNA retention. In this example, metabolically labeled RNA was directly linked to the hydrogel. This method provided a solution to increase the efficiency of crosslinking, and by preferentially linking labeled RNAs, is compatible with pulse-chase experiments[12] for the analysis of samples over a time course (FIG. 6B, t-STARmap). mRNAs are first metabolically labeled with 5-EU, and labeled transcripts are crosslinked with a polyacrylamide hydrogel via a 2-step synthesis including click chemistry. The synthesis scheme is comprised of high-yielding reactions that are commonly found in bioorthogonal labeling strategies, which help modified RNAs to link to the acrylamide gel via an acrylate group at the end of the linker. The acrylate group participates in free radical polymerization of the polyacrylamide matrix, serving as a link to lock RNAs onto polyacrylamide hydrogels during polymerization. The chemical reactions provide efficient RNA-hydrogel crosslinking so that more designated RNA molecules can be visualized by STARmap.

Pulse and chase experiments (FIG. 2B) are then performed with mammalian cell culture and animal models. The data is then analyzed to reconstruct the spatiotemporal trajectory of individual RNAs further computationally inside cells. The t-STARmap method can be used to study important biological questions such as cell state changes in response to a stimulus (e.g., cell cycle, neural activity, viral infections, etc.) and cell-type-specific gene regulation programs in functional organs.

Example 5: Further Use of Nascent RNA Labeling Chemistry for Spatiotemporally Resolved Transcriptomics This Example describes a novel image-based in situ RNA sequencing method that provides a system for detecting and quantifying genetic and metabolic activities in single cells and builds a platform for understanding the composition and changes of cell types, cell states, and cell-cell interactions in tissues and organs. By providing spatial and temporal resolution to single-cell RNA sequencing, the technology provides high-throughput multimodal "omics" information of the cellular activities of interest.

Methods of in situ RNA hybridization and sequencing have been invented and developed, providing tools to uncover genome-wide profiling of gene expression in single cells and significantly accelerate the capability to understand diseases. However, there remains a pressing need for measuring and foreshadowing RNA synthesis, transport, and turnover in single cells to profile gene expression over a certain time frame. The methodology described herein is unique due to its nature of providing spatial, temporal, and single-molecule information about RNA in a high-throughput manner. DNA-transcript proximity ligation is combined with various existing biotechnological tools such as metabolic labeling, DNA barcoding, and SEDAL sequential sequencing[1].

Figure 7:
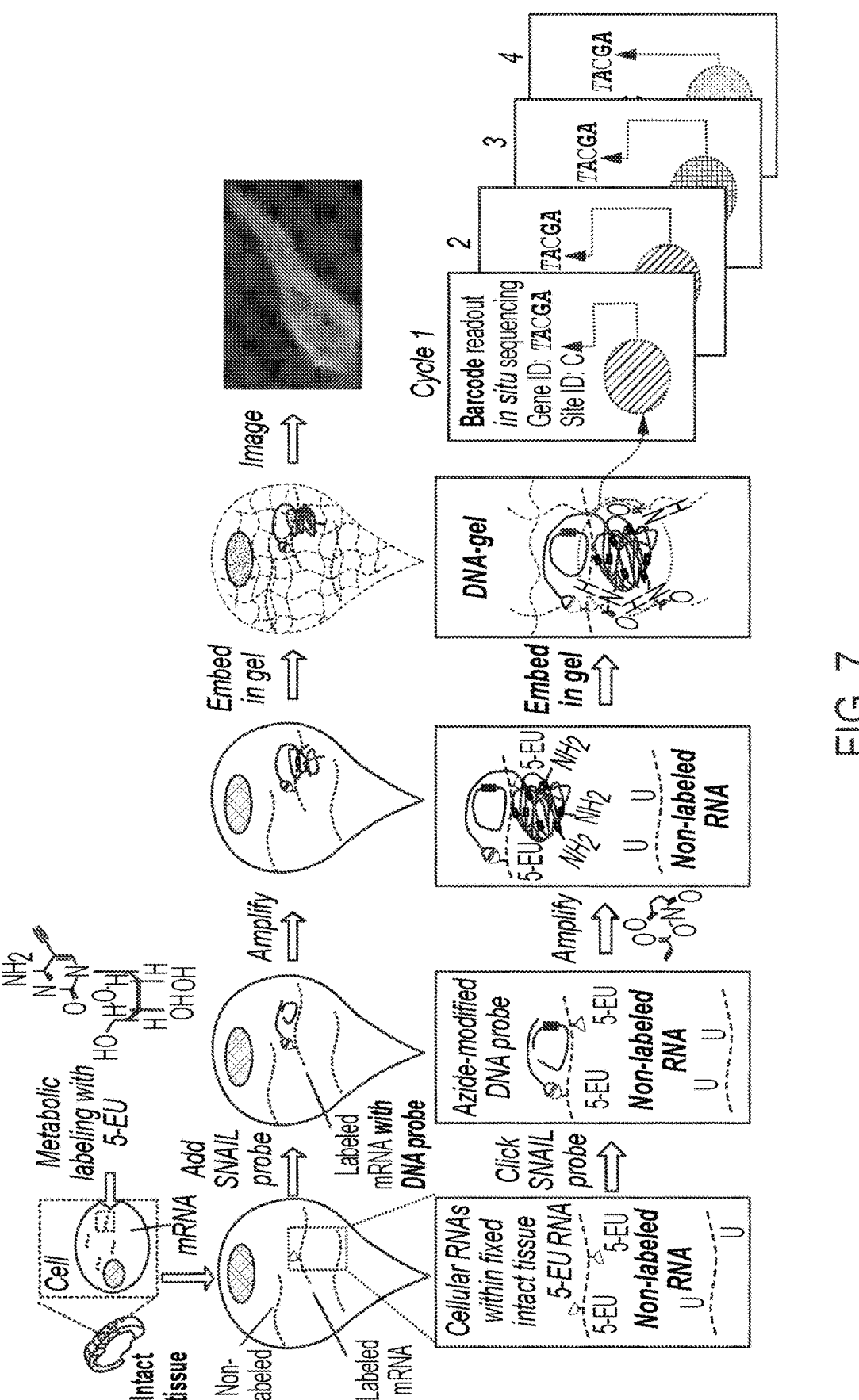
FIG. 7 provides an additional schematic showing the workflow of the TEMPOmap method. Functionalized cDNA amplicons are covalently linked to a polyacrylamide matrix to allow tissue clearing and biomolecule processing.

Spatially resolved transcript amplicon readout mapping (STARmap)[1] has been developed and is a robust in situ transcriptomic tool for spatial mapping of gene expression. This Example describes an alternative method that not only visualizes transcriptomes in single cells but also tracks the changes in transcriptomes within a time frame. This strategy (FIG. 7) is achieved by metabolically labeling mRNAs with a chemically modified nucleoside, 5-ethynyl-uridine (5-EU) and ligating the labeled mRNAs with azide-modified DNA primer via copper(I)-catalyzed azide-alkyne cycloaddition (CuAAC). This RNA-primer crosslinking event is then recognized by a padlock probe that hybridizes to the mRNA and amplified by rolling-cycle amplification. Subsequently, the amplified signals are retained in a hydrogel scaffold. A gene-unique identifier was encoded in each padlock probe and the identity of mRNAs is visualized and decoded by SEDAL sequencing.

Figure 8A:
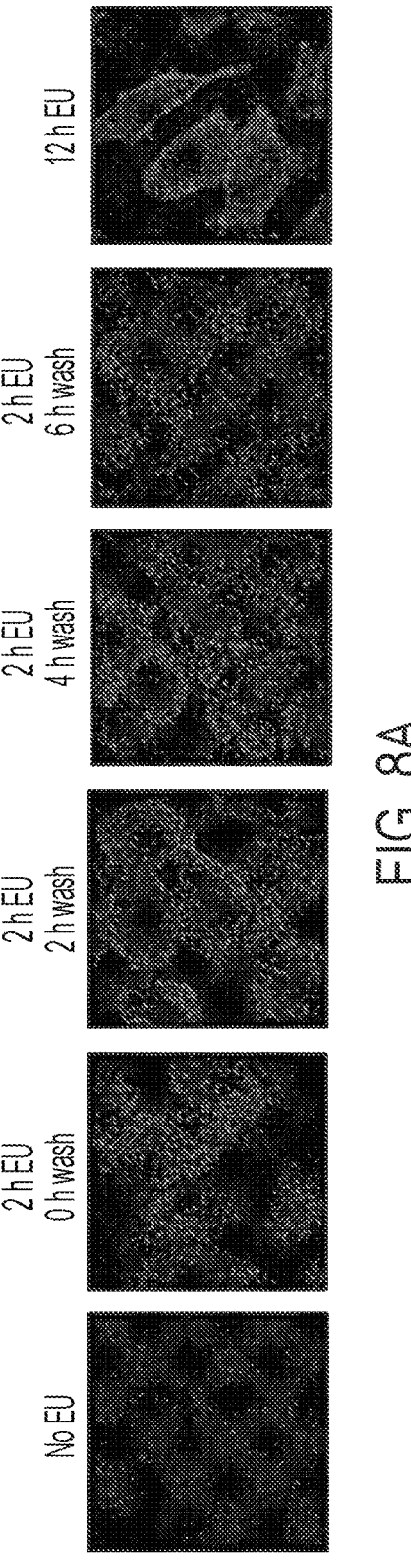
FIGS. 8A-8B show targeting of hACTB in HeLa cells in pulse-chase experiments.
Figure 8B:
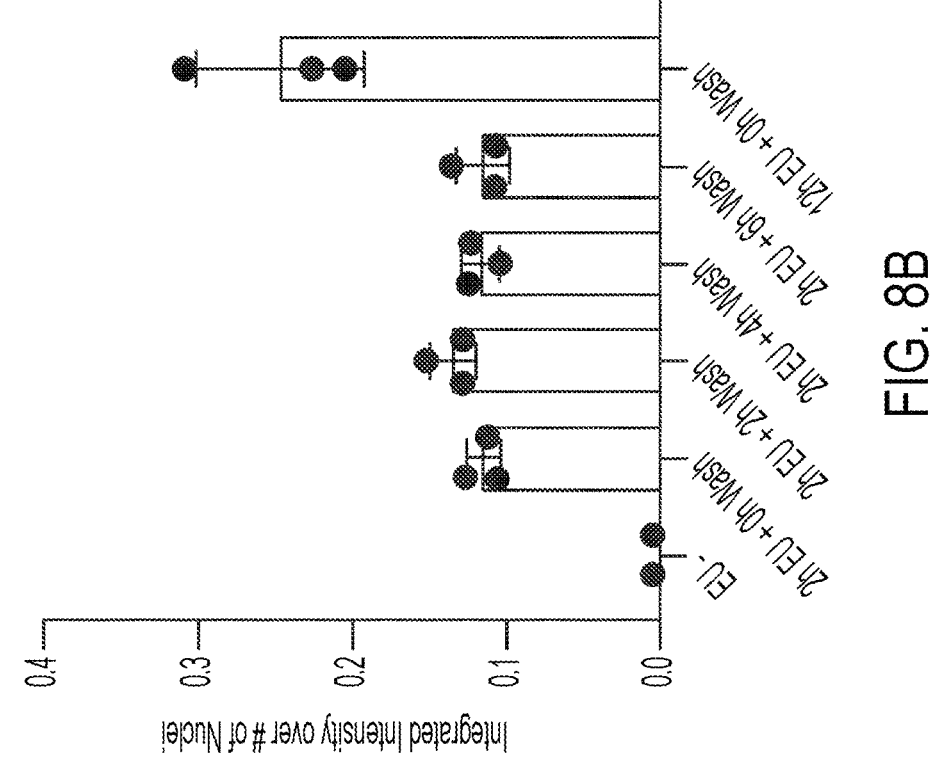

The approach achieves near-genome-wide transcriptome enrichment and selective retention of metabolically labeled transcripts and will be able to robustly detect changes in gene expression over a specific time course. The targeting of human beta-actin genes (hACTB) in HeLa cells is shown in FIG. 8, which demonstrates the significant enrichment of retained transcripts compared to the 5-EU unlabeled transcripts, as well as the ability to detect transcripts over different time frames.

Figure 9A:
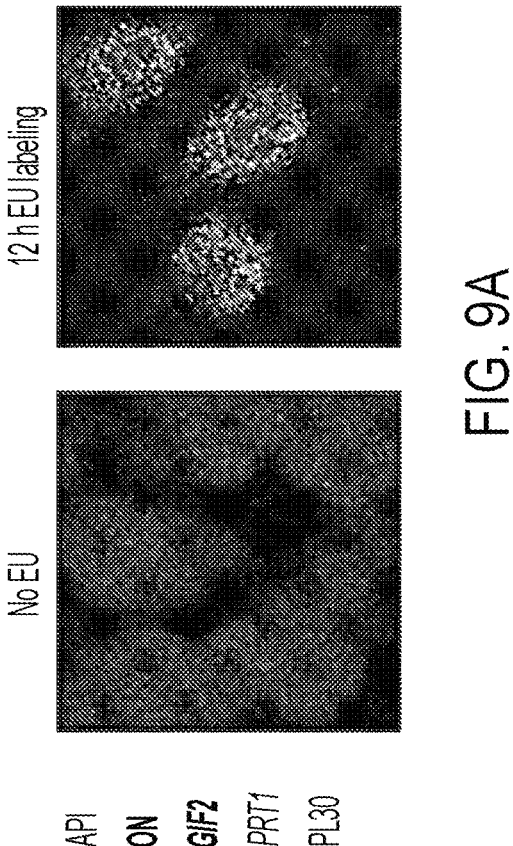
FIGS. 9A-9B show targeting of four m⁶A-related RNAs in HeLa cells during a time course.
Figure 9B:
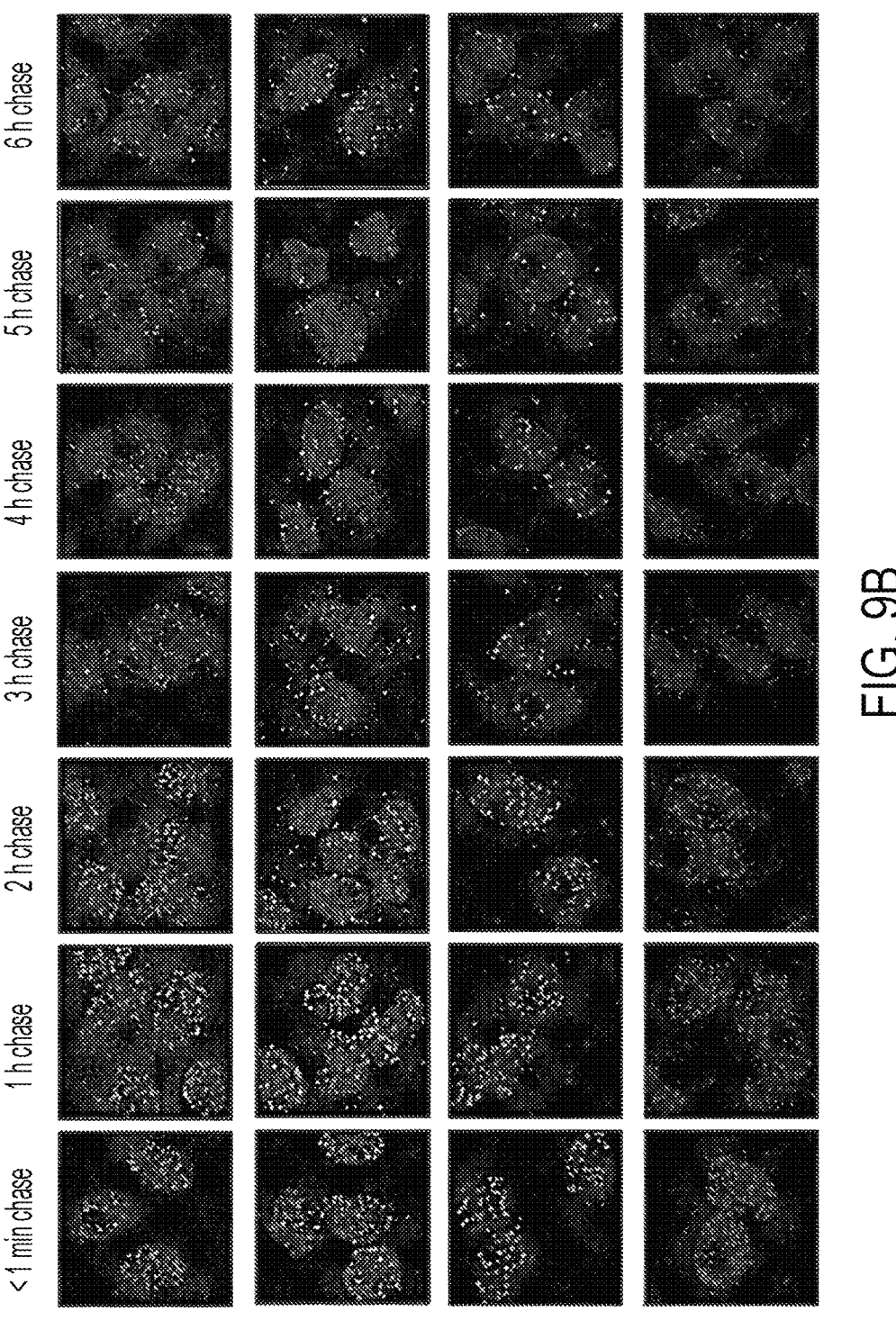

The dynamics of RNAs with or without N6-methyladenosine (m[6]A), an abundant epitranscriptomic mark that was shown to influence RNA processing, translation, and degradation, were also quantified. The influence of this RNA modification was studied by detecting the dynamics of four representative RNAs, two of which contain m[6]A, whereas the other two do not contain m[6]A (FIG. 9). It was demonstrated that four genes, which are represented by four colors in the images, were simultaneously detected. The image-based measurement of RNA degradation reasonably correlates with the previously measured RNA half-life using second-generation sequencing, and the images clearly show a trend of RNA translocation for all four RNAs.

Example 6: Spatiotemporally Resolved Single-Cell Transcriptomics Reveals Kinetic Sculpting of RNA Life Cycle Spatiotemporal regulation of the cellular transcriptome is crucial to instruct protein expression to the ultimate execution of cellular function. The intricate intracellular dynamics of RNA synthesis, decay, export, and translocation have been obscured due to the limitations of existing transcriptomics methods. A method for temporally resolved in situ sequencing and mapping (TEMPOmap) is described herein. This method represents a highly multiplexed three-dimensional in situ mapping technique to uncover subcellular gene expression across time and space in single cells. Using TEMPOmap, critical kinetic parameters of thousands of genes were determined throughout the RNA life cycle in human cells, revealing multi-step kinetic shaping of gene expression in the context of gene function, subcellular organization, and cell cycle progression. These spatiotemporally resolved transcriptomics measurements deepen the understanding of how regulatory strategies enable precise gene expression in time and space through kinetic sculpting.

Introduction

Cell state and function are shaped by spatiotemporally heterogeneous regulation of gene expression. The ability to systematically profile single-cell resolved transcriptome-wide information in time and space is critical to understanding transcriptional and post-transcriptional gene regulation mechanisms in cells and tissues. Spatially resolved transcriptomics methods have enabled integrated profiling of gene expression from heterogeneous cell types in the context of tissue morphology[13-19]. However, these spatial transcriptomics approaches only provide static snapshots of cells and tissues, obscuring the dynamic flow of gene expression[20]. In contrast, metabolic RNA labeling approaches have enabled profiling of the nascent single-cell transcriptome but lack spatial information[21-25]. In addition, live-cell imaging can directly track RNA trajectory inside cells, but simultaneously visualizing multiplexed transcripts remains challenging[26]. Thus, there exists a pressing need for a time-resolved, highly multiplexed spatial mapping method to profile gene expression that tracks nascent mRNAs in situ from birth to death at subcellular and single-cell resolutions.

Figure 10A:
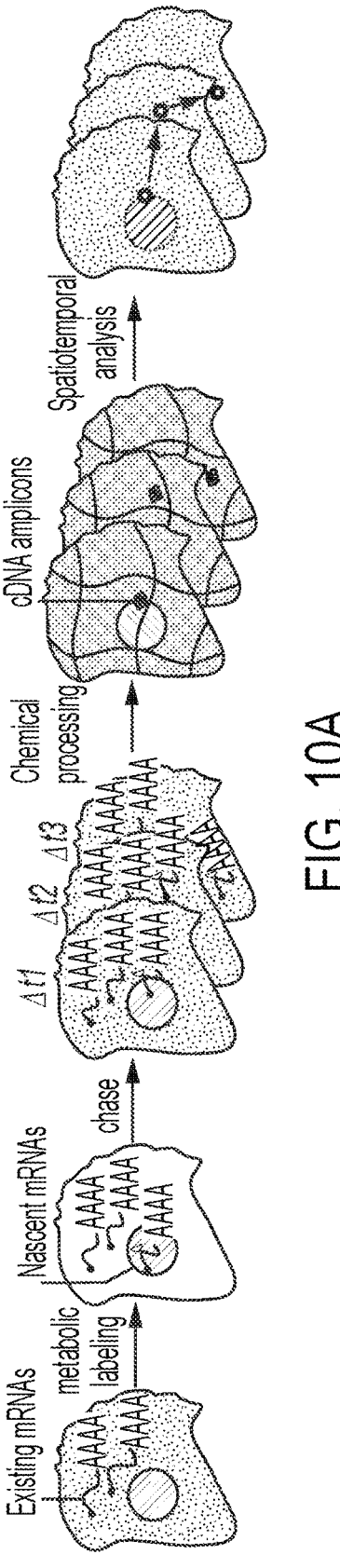
FIGS. 10A-10D show TEMPOmap schematics and validation.

Here, to provide a system-wide single-cell analysis of RNA life cycle in time and space, TEMPOmap (temporally resolved in situ sequencing and mapping), a method that tracks the spatiotemporal evolution of the nascent transcriptomics over time at subcellular resolution, was developed (FIG. 10A). TEMPOmap integrates metabolic labeling and selective amplification of time-gated nascent transcriptome with the current state-of-art three-dimensional (3D) in situ RNA sequencing at 200 nm resolution within the hydrogel-cell scaffold[13]. By designing precisely controlled pulse-chase labeling experiments, for the first time, a full collection of kinetic parameters for thousands of genes during the RNA life cycle was tracked simultaneously, including rates of transcription, decay in subcellular regions, nuclear export, and cytoplasmic translocation. In light of these spatiotemporal parameters, it was discovered that mRNAs of different genes are kinetically sorted at different steps of RNA life cycle and across different cell-cycle phases, which ultimately serves molecular and cellular functions.

TEMPOmap for Spatiotemporally Resolved Transcriptomics

Figure 10B:
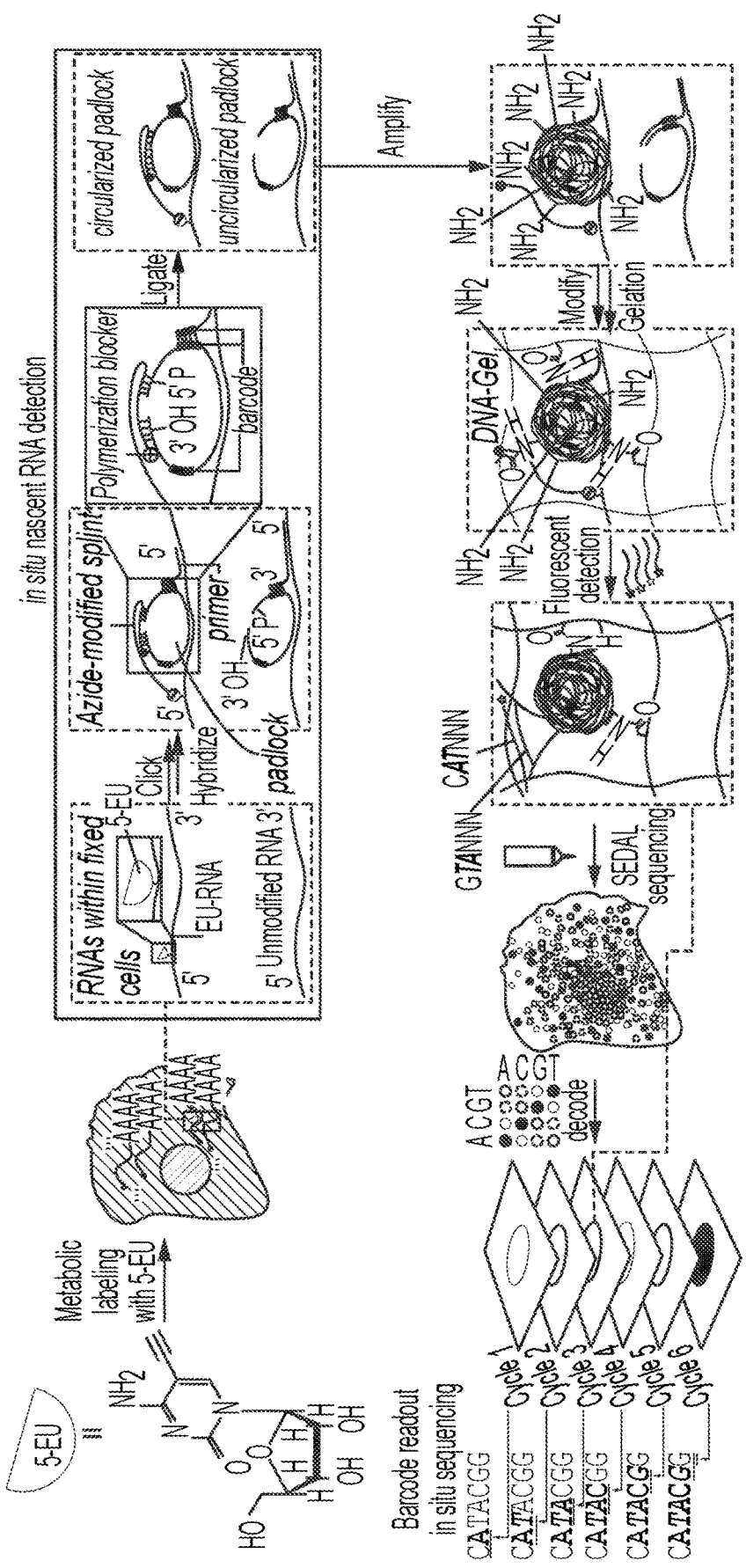
Figure 10C:
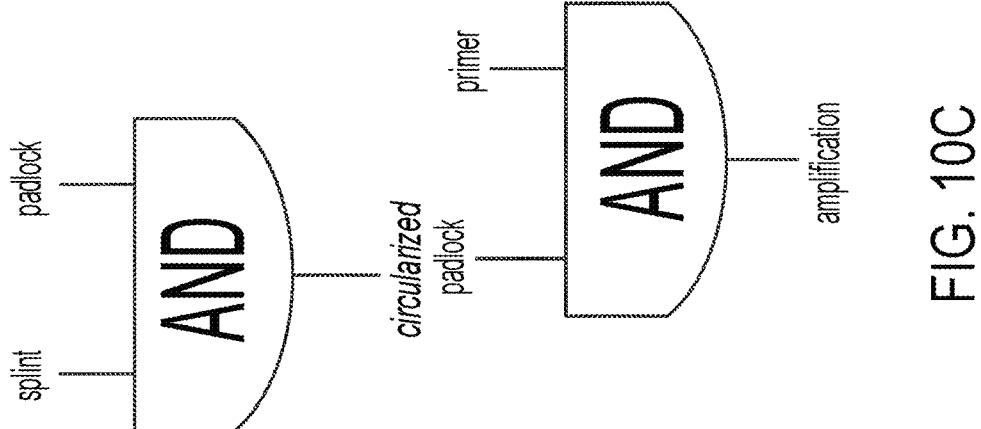
Figure 10D:
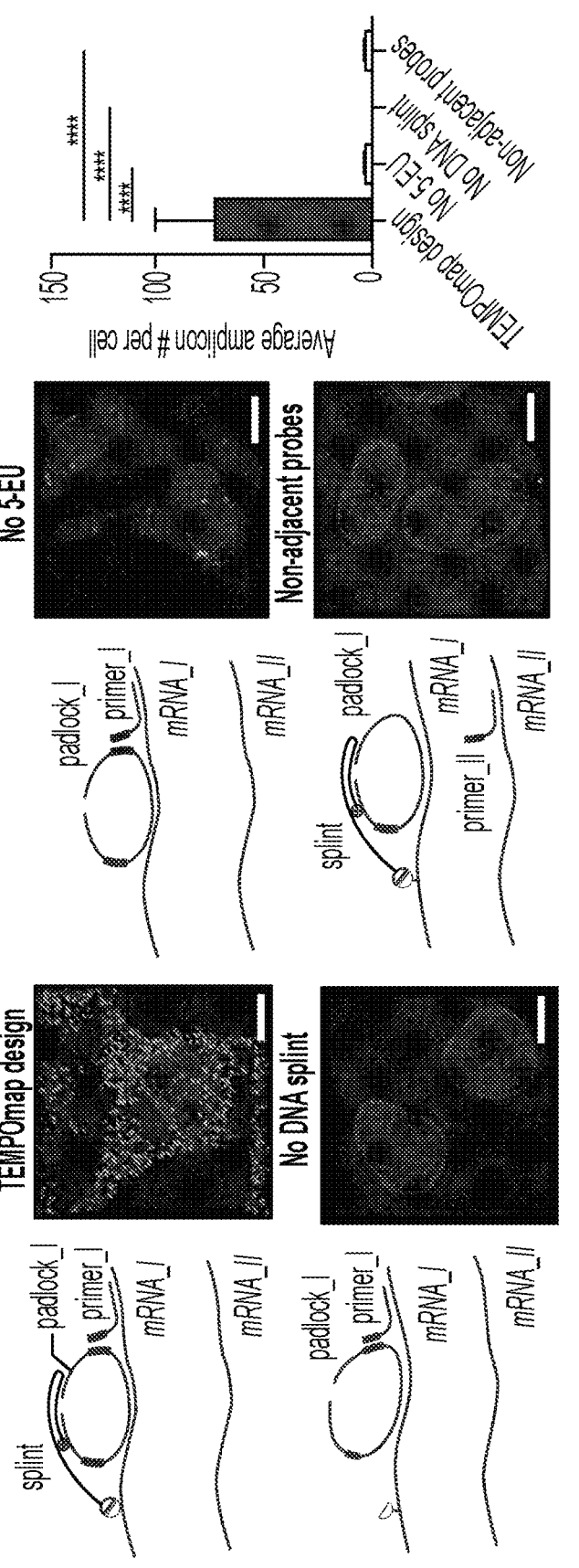

TEMPOmap starts with metabolic labeling of cells by 5-ethynyl uridine (5-EU)[2527], which adds a bioorthogonal chemical handle on the labeled mRNAs (FIG. 10B). Next, a tri-probe set (splint, padlock, and primer) was designed for each gene to selectively generate complementary DNA (cDNA) amplicons derived from metabolically labeled RNAs (FIGS. 10B-10C and 14B-14C): (1) the splint probe is an azide- and chain-terminator modified DNA oligonucleotide that is covalently conjugated to the 5-EU labeled mRNAs via copper(I)-catalyzed azide-alkyne cycloaddition (CuAAC, FIG. 14A) and thus excludes unlabeled RNAs from subsequent cDNA amplification; (2) the padlock probes recognize mRNA targets with 20-25 nucleotide (nt) cDNA sequence and gene barcodes, which can be circularized when the splint probe is in proximity; (3) the primer probes target the neighboring 20-25 nt next to the padlock probes, which serve as the primer to amplify circularized padlocks in situ via rolling cycle amplification (RCA), forming cDNA nanoballs (amplicons) that overcome auto-fluorescence and scattering in standard fluorescent in situ hybridization (smFISH); (4) in combination, only mRNAs that are bound by all three types of probes will be amplified for selective detection of labeled mRNA population in a label- and sequence-controlled manner via a two-step thresholding strategy (FIGS. 10C-10D).

Figures 14A, 14B:
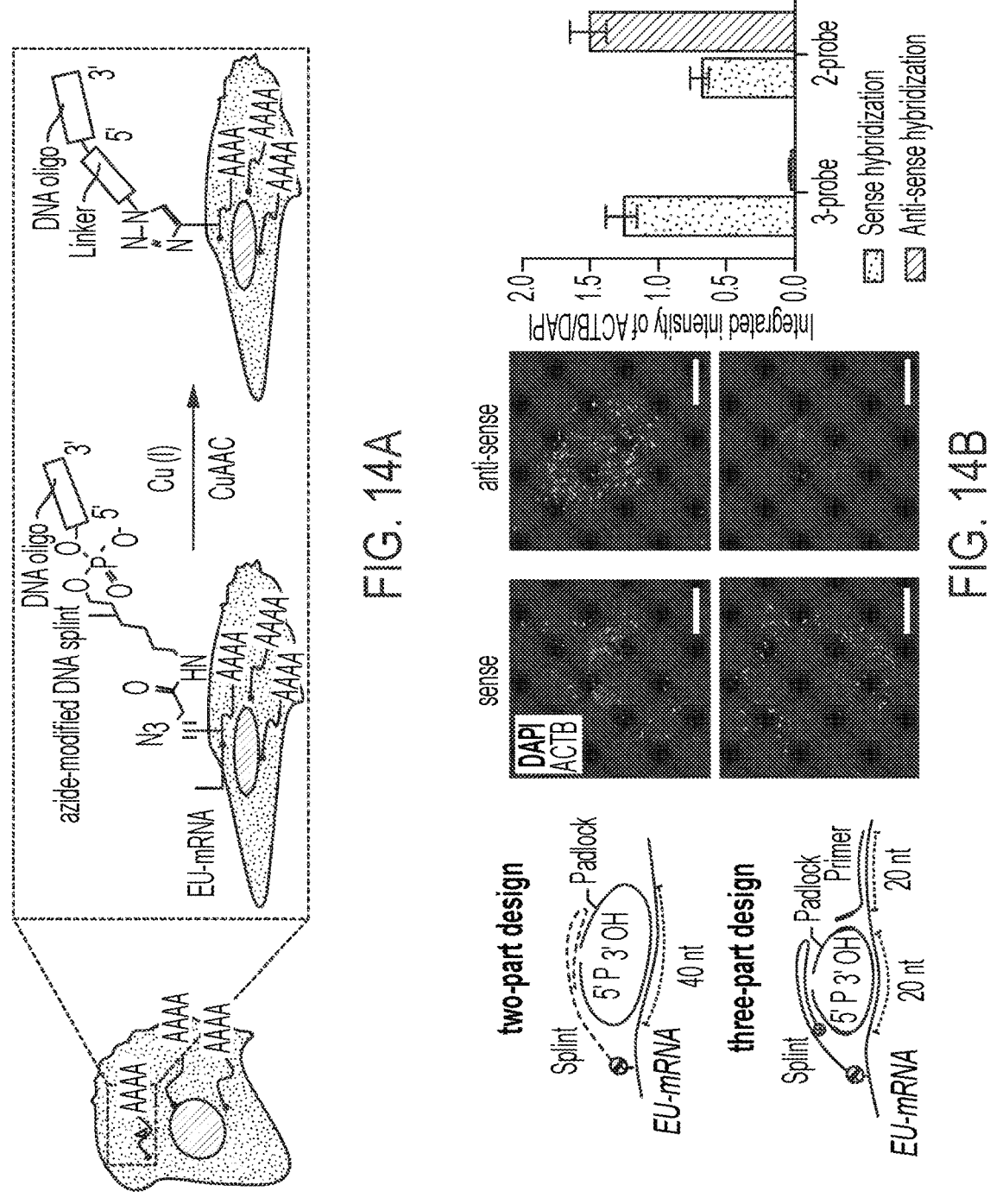
FIGS. 14A-14E show TEMPOmap experimental design and optimization.

It is noteworthy that the bi-probe sets that were initially designed recognize 5-EU-labeled RNAs via one gene-targeting padlock probe and one general azide-modified probe without chain terminator that plays the dual role of splint and primer (FIG. 14B). However, the bi-probe design resulted in strong background signals of amplicons (FIG. 14B), suggesting that a single gene-targeting padlock probe achieves less specific gene detection, and the dual gene-targeting primer and padlock pair in the tri-probe design may be ideal under some circumstances[13]. It was observed that the TEMPOmap protocol specifically enriches metabolically labeled transcripts (FIG. 10D) and robustly detects changes in beta-actin mRNA (ACTB) subcellular localization over a tunable time course (FIG. 14D).

Figure 11B:
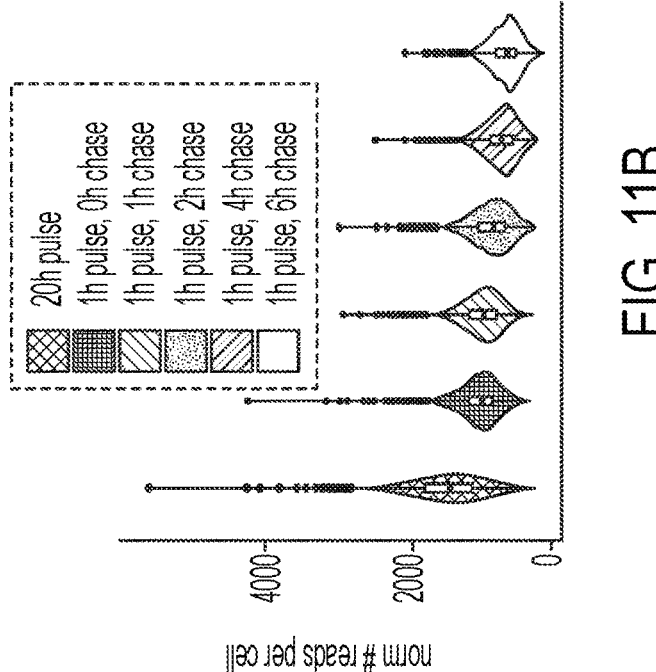
FIGS. 11A-11E shows spatiotemporal partitioning of single-cell and subcellular transcriptome.
Figure 11A:
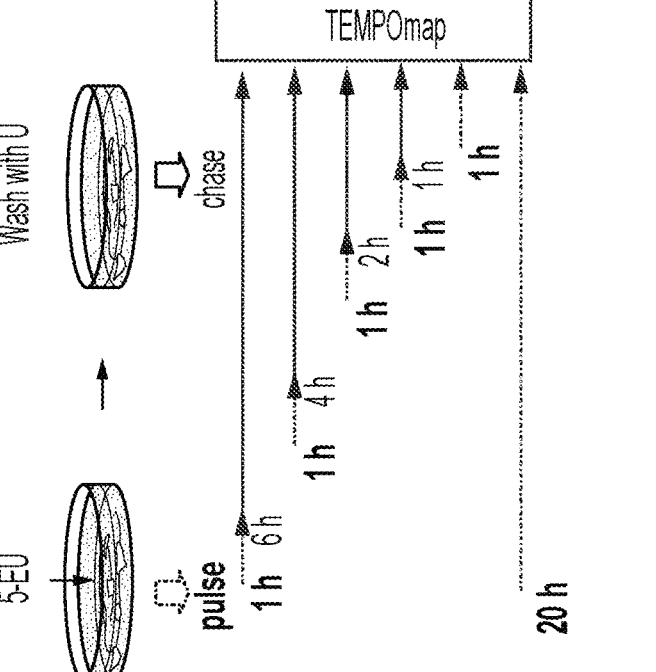

The in situ generated cDNA amplicon libraries are subsequently embedded in a hydrogel matrix for multiple cycles of fluorescent imaging to decode the gene-encoding barcodes via SEDAL (sequencing with error-reduction by dynamic annealing and ligation) (FIGS. 10B and 14C)[13] to simultaneously detect hundreds to thousands of genes. After the completion of sequencing cycles, the amplicon reads are next registered, decoded, and subjected to 3D segmentation for subcellular and single-cell resolved analysis (FIG. 11A).

RNA Life Cycle in Time and Space at Single-Cell Resolution

Figure 11C:
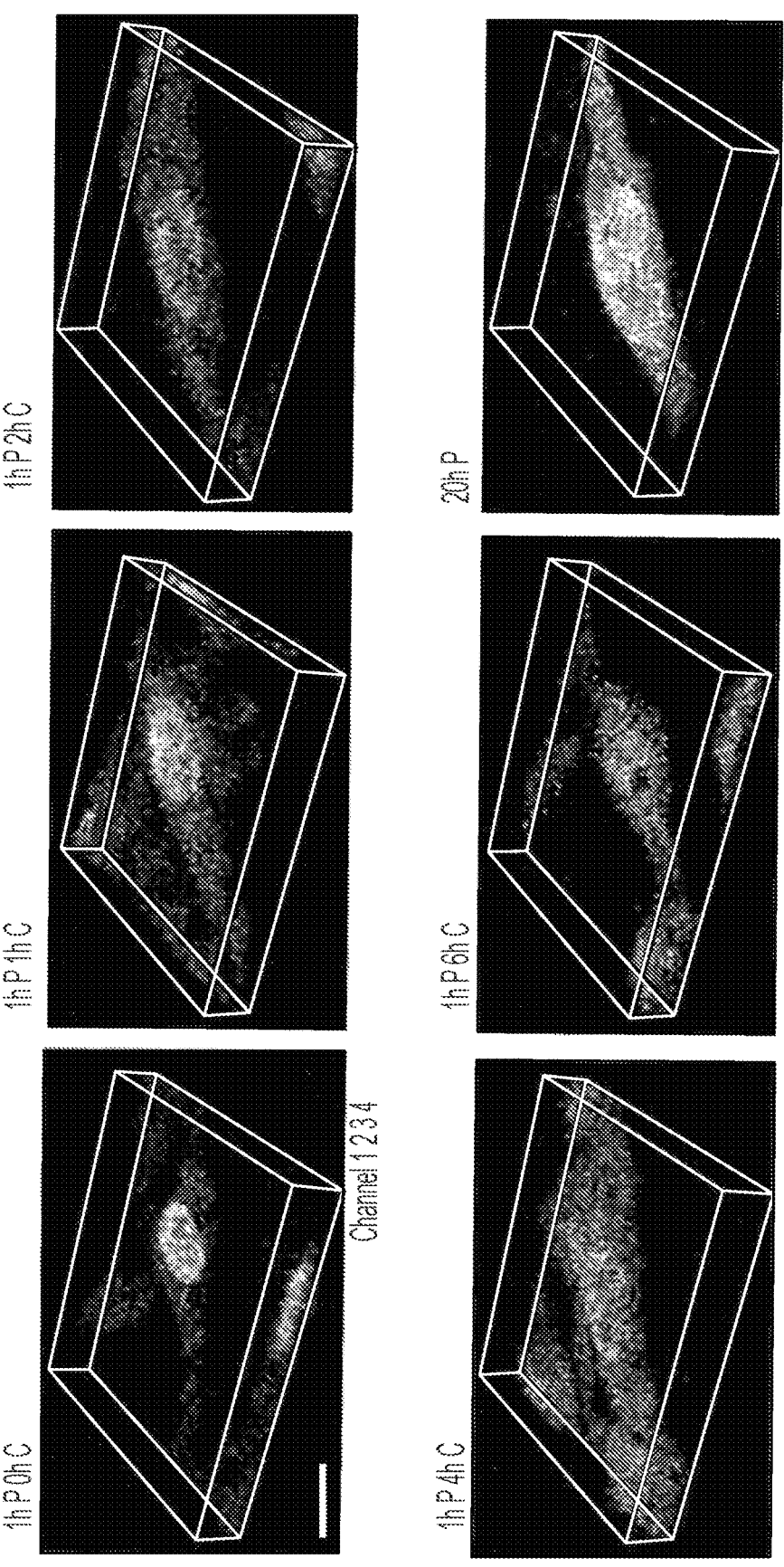
Figure 11D:
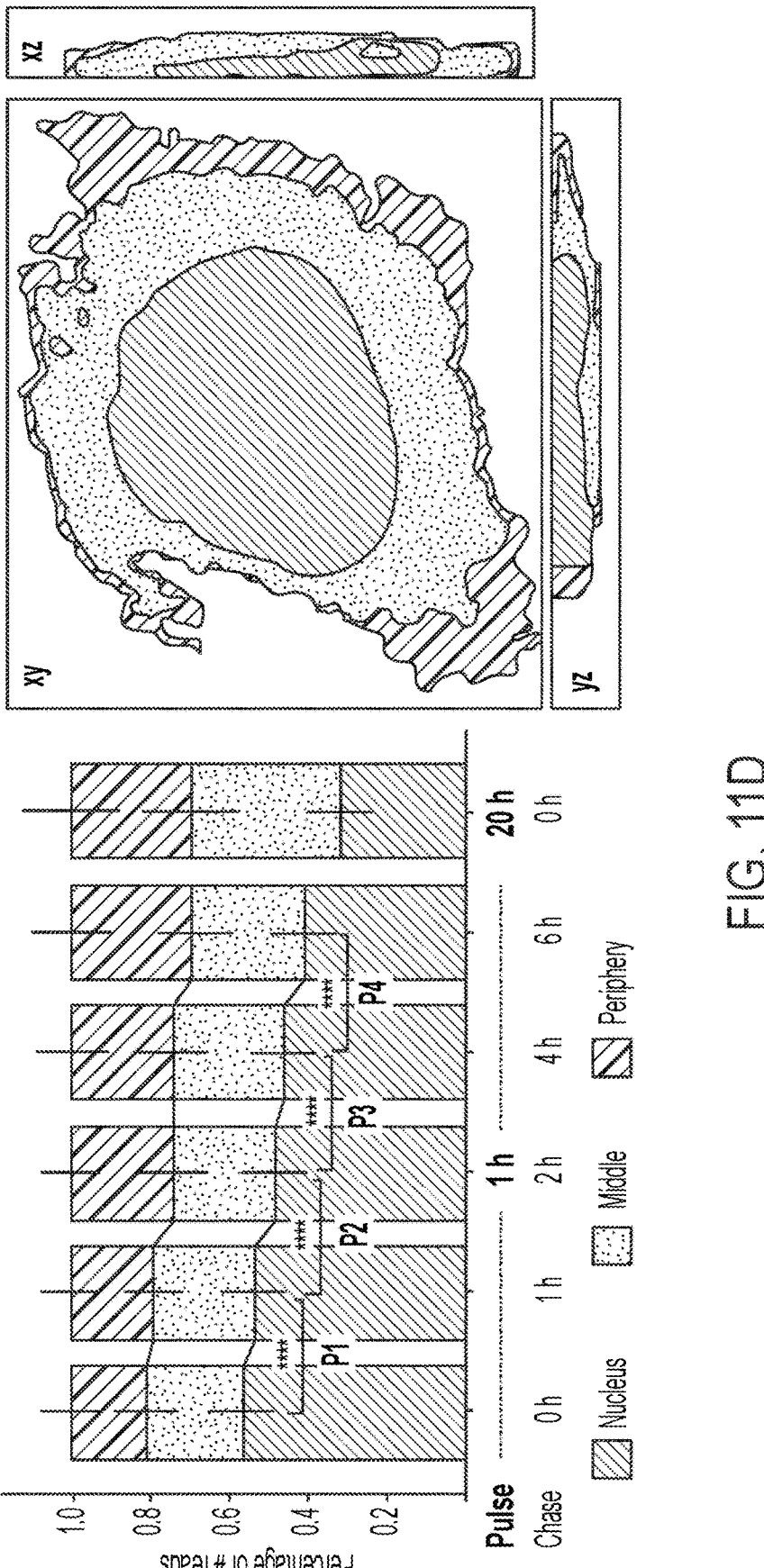
Figure 14E:
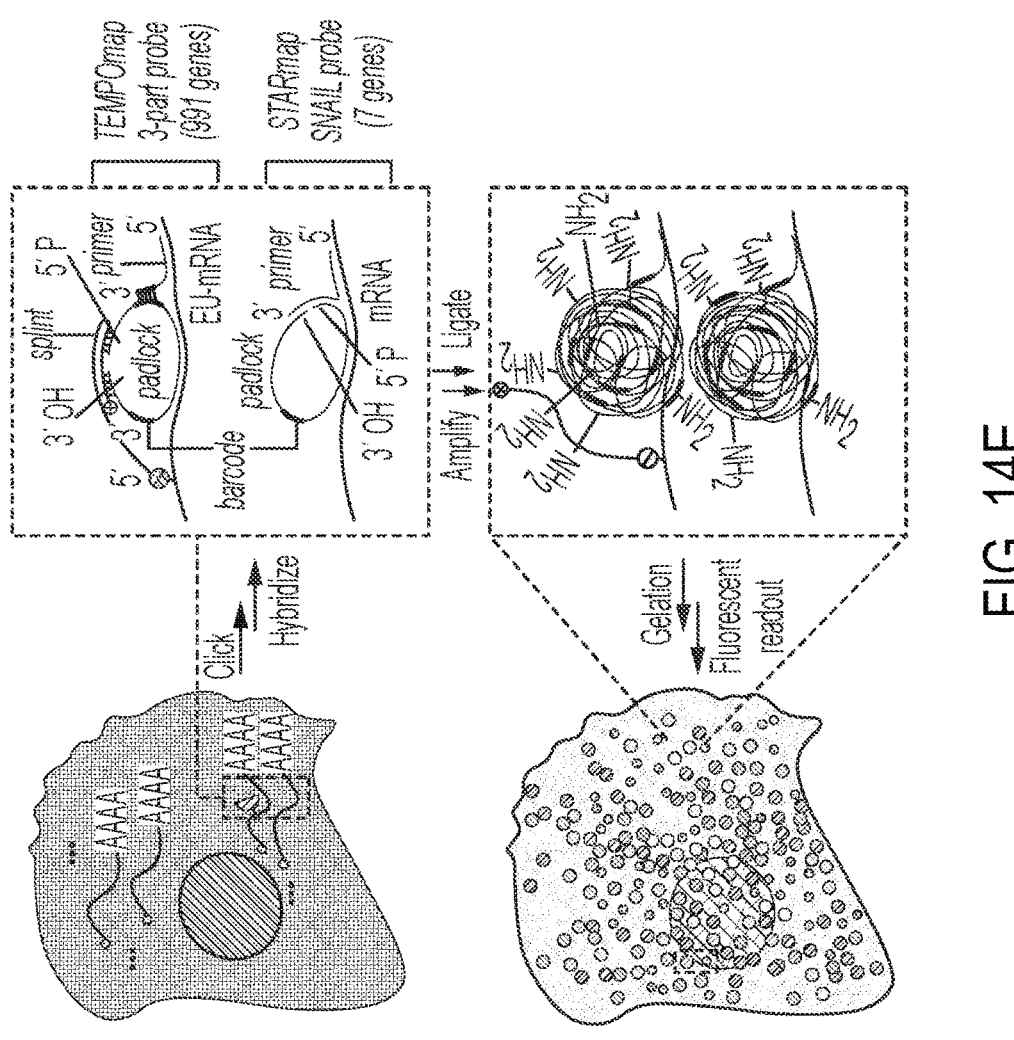
Figure 15A:
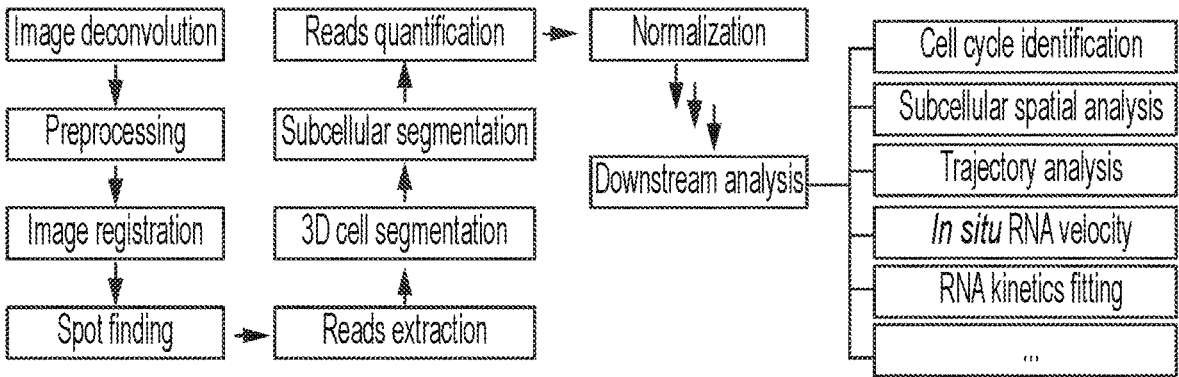
FIGS. 15A-15D shows TEMPOmap data processing and analysis.

TEMPOmap was next applied to profile a focused list of 991 genes (981 coding, 10 non-coding RNA) in human HeLa cells. Another seven genes by STARmap probes[13] were also included during amplicon preparation, which hybridize to both labeled and unlabeled RNAs as the internal control for batch correction and data normalization (FIG. 14E). A pulse-chase experiment[15,28] was then conducted with one hour (hr) pulse labeling and various chasing times (0, 1, 2, 4, and 6 hrs), as well as one steady-state reference with 20-hour pulse labeling (FIG. 11A). The barcodes in all samples were sequenced over six rounds of in situ sequencing, followed by the final round of subcellular compartment staining (nuclei and cytoplasm) to segment cell bodies and assign the subcellular locations of amplicons in 19,856 cells in 3D (FIGS. 11B-11C). The cytoplasmic space was further segmented into the middle region ("middle") and the periphery using a distant ratio (DR)-based method (FIG. 11D): each amplicon is measured by its shortest distances to the nuclear membrane (dn) and to the cell membrane (dc) in 3D, respectively, and a DR value is calculated as the ratio of dn to dn+dc. From 0 hr to 6 hr chase time post the 1 hr pulse labeling, a decline of total RNA reads per cell, a gradual shift of RNA distribution from nuclei to cytoplasm, and further allocation from middle cytoplasmic region to periphery region, was observed (FIGS. 11B-11C). Notably, a significant fraction of reads (~40%) retained in the nucleus were still observed even after 6 hr chase. A closer inspection into the retained RNA molecules revealed that RNAs with the highest nuclear-to-cytoplasm read ratio included long non-coding RNAs (NEAT1, MALAT1), supported by deep sequencing of RNA from cellular fractions (FIG. 15A)[29,30]. Notably, nucleus-retained mRNAs (KIF13A, LENG8, CCNL2, COL7A) were also found. This observation validates the previous discovery of wide-range nuclear retention of mRNA, which may serve as a regulatory role to buffer cytoplasmic gene expression noise[31,32].

Figure 11E:
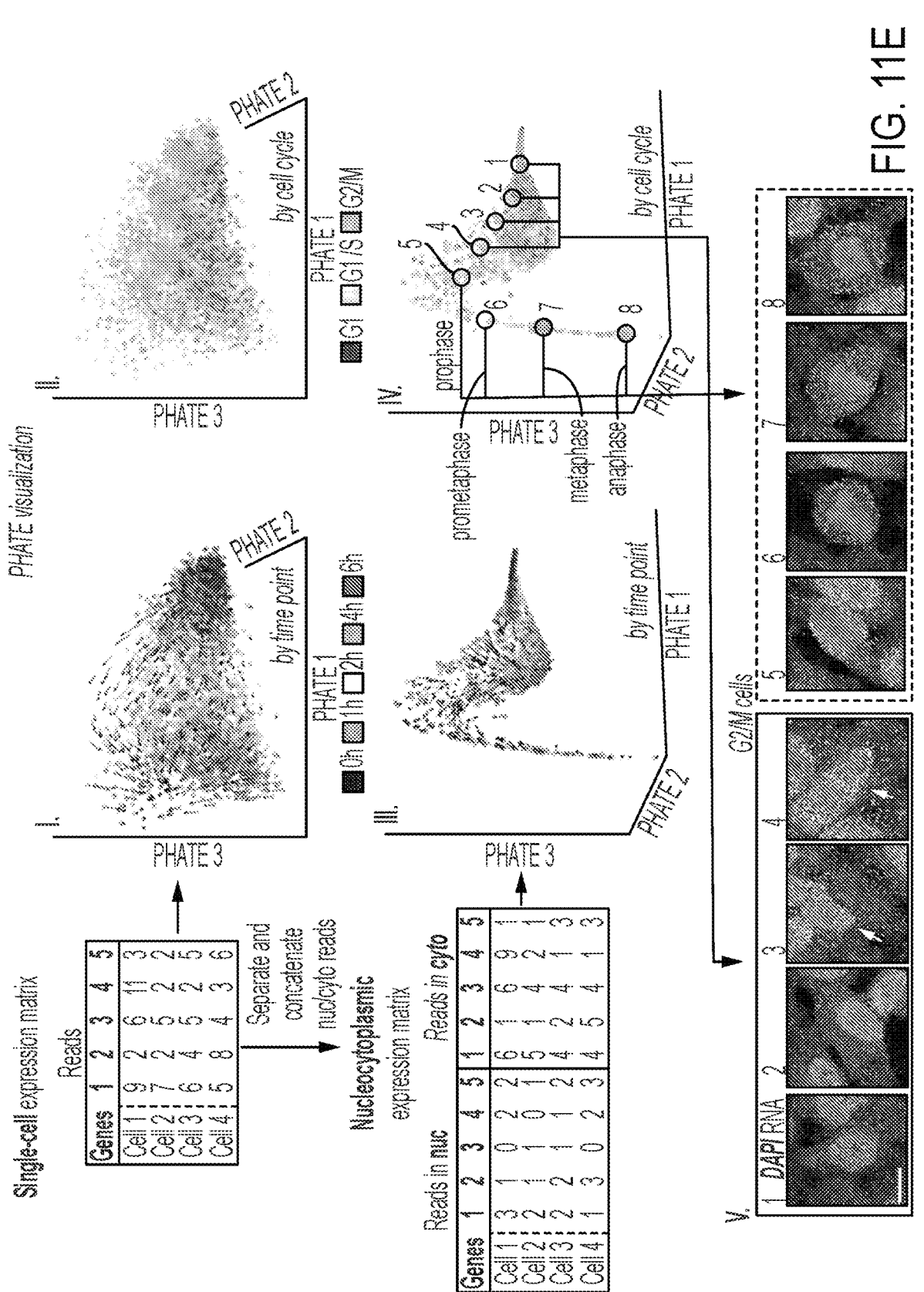

Next, all the cells under the 1 hr pulse condition were pooled with various chase time points (18,176 cells) for single-cell resolved dynamic trajectory analysis using PHATE and Dynamo (FIG. 11E, I)[33,34]. The results showed a clear trajectory along the progression of chase time, which suggests that the temporally resolved single-cell transcriptional states could be readily distinguished and aligned in the gene expression space. Overlaying the same PHATE coordinates with RNA degradation kinetics vectors further recapitulated the single-cell trajectory along RNA life cycle progression[34-36]. It was then asked how the RNA life cycle defined by pulse-chase timeline aligns with cell-cycle progression. To this end, the cells were classified into three cell cycle phases (G1, G1/S, and G2/M) based on their nascent expression of marker genes (FIGS. 16B-16C) using cell-cycle scoring[37]. Interestingly, the direction of cell-cycle progression is orthogonal to the pulse-chase time point progression (FIG. 11E, II). This observation suggests that TEMPOmap can provide independent temporal information regarding RNA life cycle in addition to the cell cycle.

Subcellular dynamics from the TEMPOmap dataset were then further probed. To this end, a nucleocytoplasmic gene-by-cell matrix was generated by concatenating single-cell nuclear expression with cytoplasmic expression for trajectory analysis (FIG. 11E, bottom). Apart from recovering the unidirectional trajectory of single cells along with labeling time points (FIG. 11E, III), it was found that a small fraction of G2/M cells formed a narrow trajectory and projected into a distinct space, suggesting that the nucleocytoplasmic RNA distribution in this group of G2/M cells drastically differs from the rest of the G2/M cells. It was suspected that these spatially distinct cells were the cells undergoing mitosis with their unique RNA nucleocytoplasmic distribution[38]. Indeed, the cells on this trajectory had been in different phases of mitosis, during which RNAs were mostly excluded from the chromatin regions compared to that in G2 cells (FIG. 11E, V). Furthermore, the uniform direction of this distinct trajectory well aligns with the time progression of mitosis (FIG. 1E, V, 5-8), indicating that the temporal mitotic transitions could be inferred by subcellular RNA localization patterns. As a result, by jointly making use of the time-gated nucleocytoplasmic distribution, this method not only separates G2 and M cells but also traces the trajectory of mitosis, providing a higher temporal resolution of cell-cycle progression on top of the single-cell transcript expression, which had been shown to have few changes of RNA copy numbers in G2/M but undergo drastic RNA eviction from chromosomes during mitosis[39].

Quantifying Subcellular RNA Kinetics Across Cell Cycle

Figures 12A, 12B:
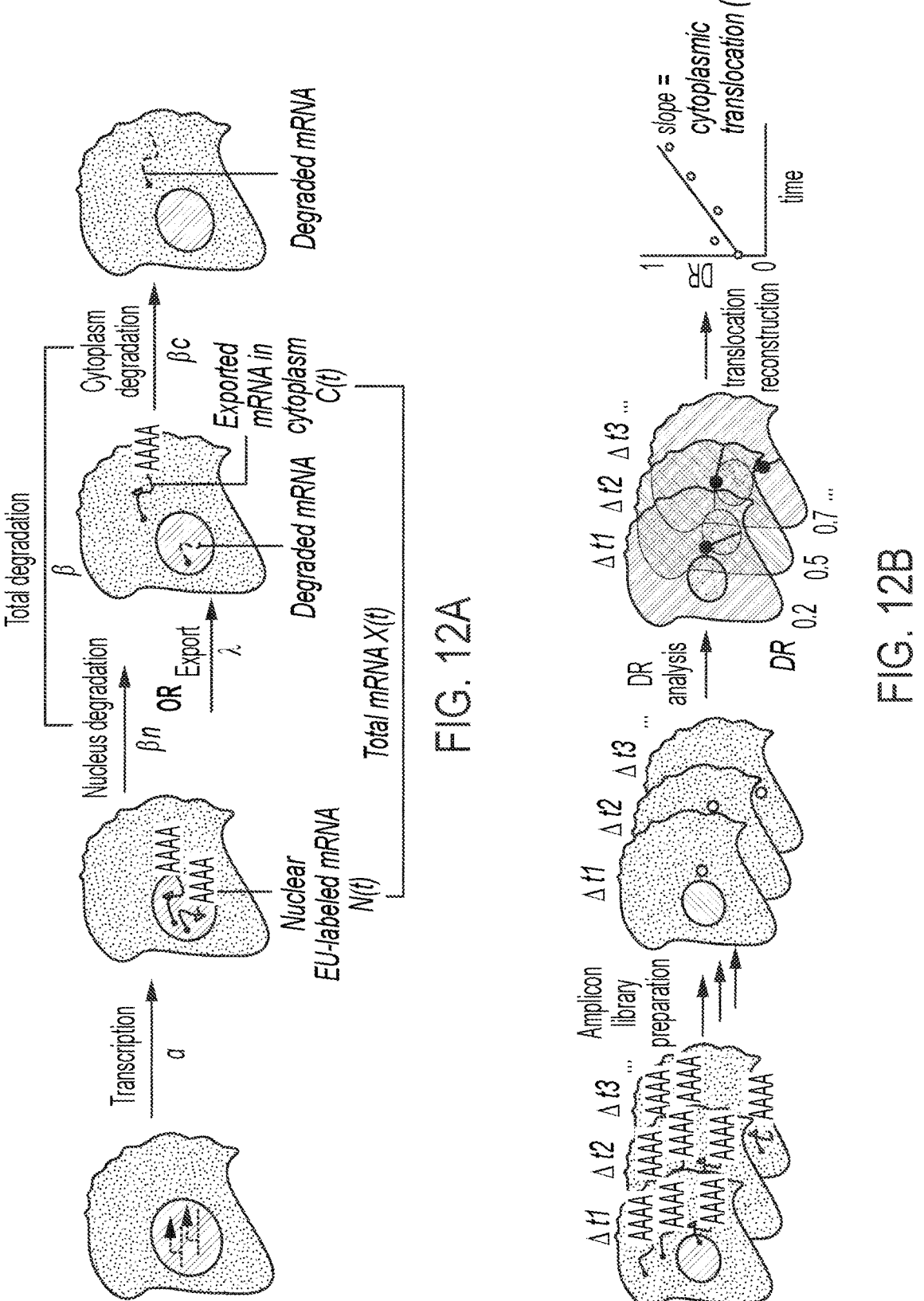
FIGS. 12A-12G show quantitative estimation of RNA subcellular dynamics across cell cycle.
Figures 17A, 17B:
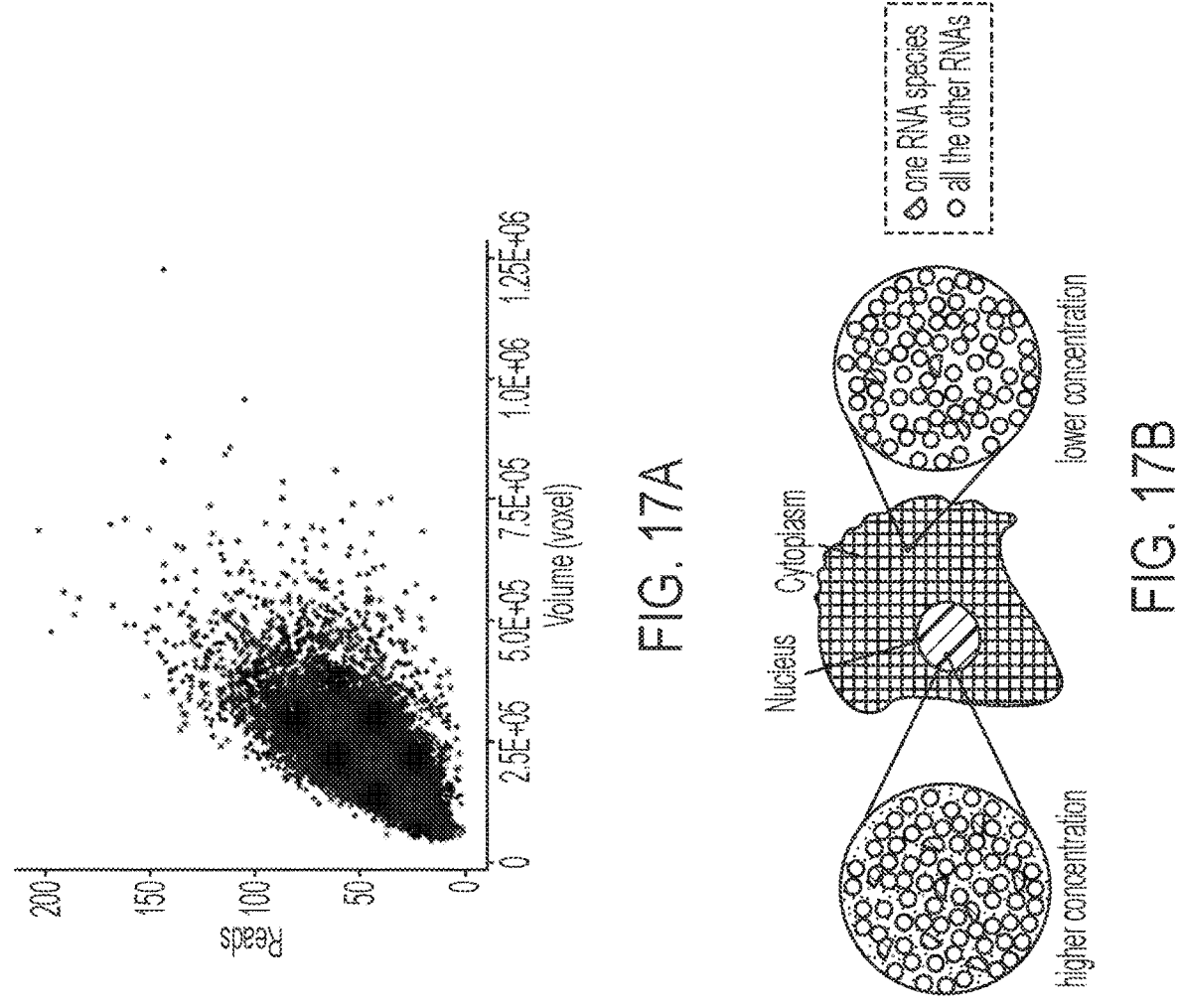
Figure 17C:
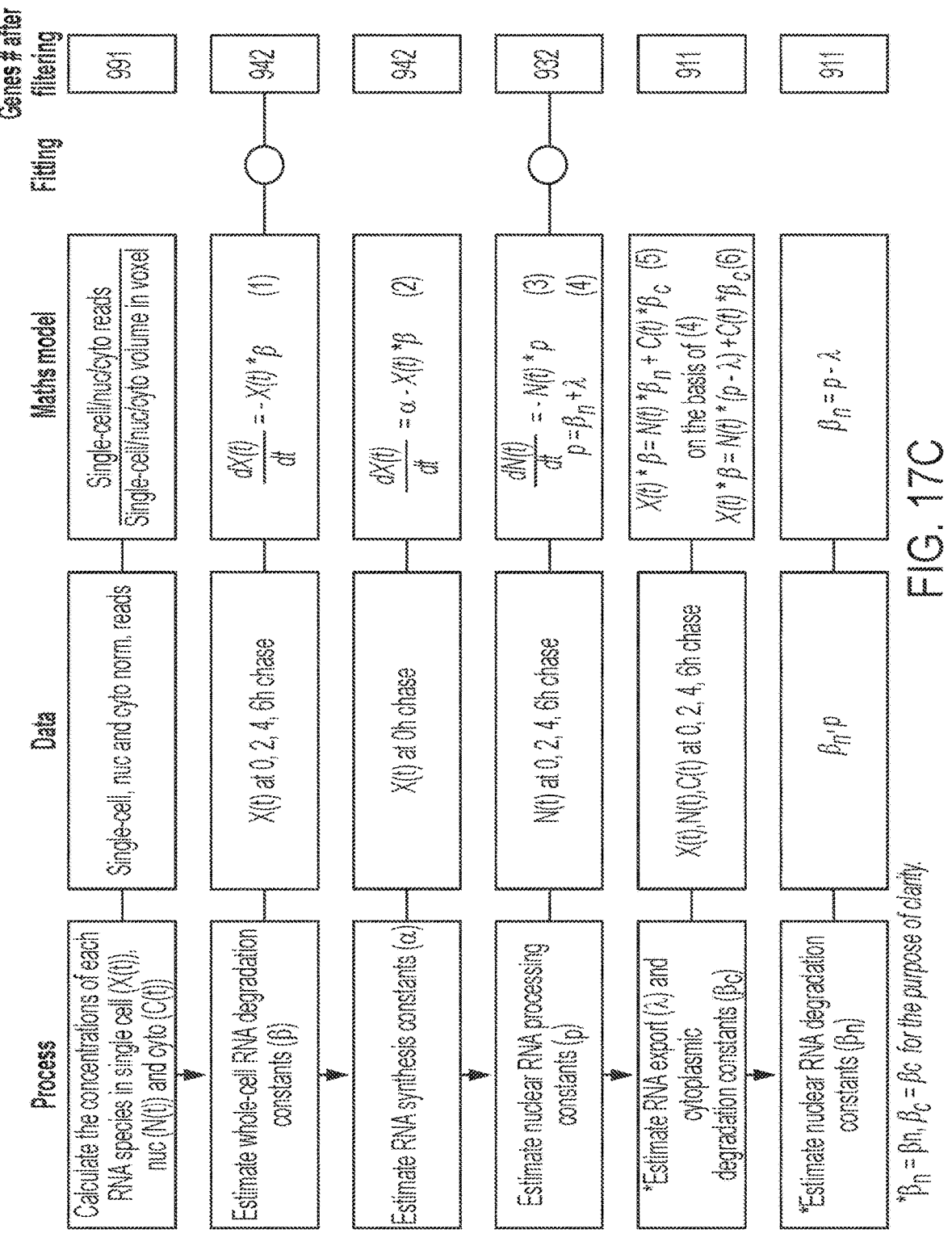

To further quantify individual dynamic steps during RNA life cycle, a model was developed to estimate six key kinetic constants for each gene—synthesis ($\alpha$), whole-cell degradation ($\beta$), nuclear degradation ($\beta n$), nuclear export ($\lambda$), cytoplasmic degradation ($\beta c$) (FIG. 12A), and cytoplasmic translocation ($\gamma$) (FIG. 12B). To minimize potential bias of physical cell volumes on subcellular RNA reads, the constants were estimated based on the concentration of each RNA species (reads/voxel) in the whole cell, nucleus, and cytoplasm (FIGS. 17A-17B). In the model, $\alpha$ and $\beta$ were first estimated using the averaged whole-cell RNA concentrations, and then $\beta n$, $\beta c$, and $\lambda$ were estimated by jointly using the averaged nuclear and cytoplasmic RNA concentrations (FIG. 17C). The model assumed zero-order kinetics for $\alpha^{28,40}$ and first-order kinetics for $\beta^{28,40}$, $\beta n$, $\beta c^{32}$, and $\lambda^{32,41}$ with fitting thresholding (911 genes out of 991 genes with $R^2 >= 0.5$) for quality control (FIG. 17C). In parallel, the DR values of each gene were calculated across different times, and $\gamma$ was fitted assuming a constant translocation rate for all genes (FIG. 12B).

Figure 17F:
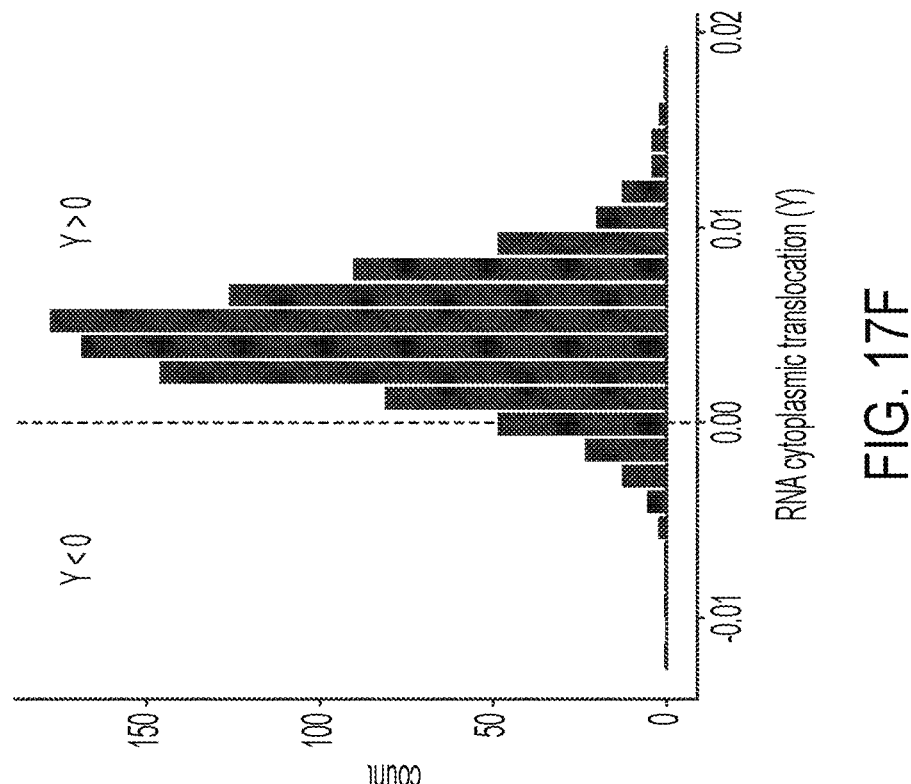
Figure 17G:
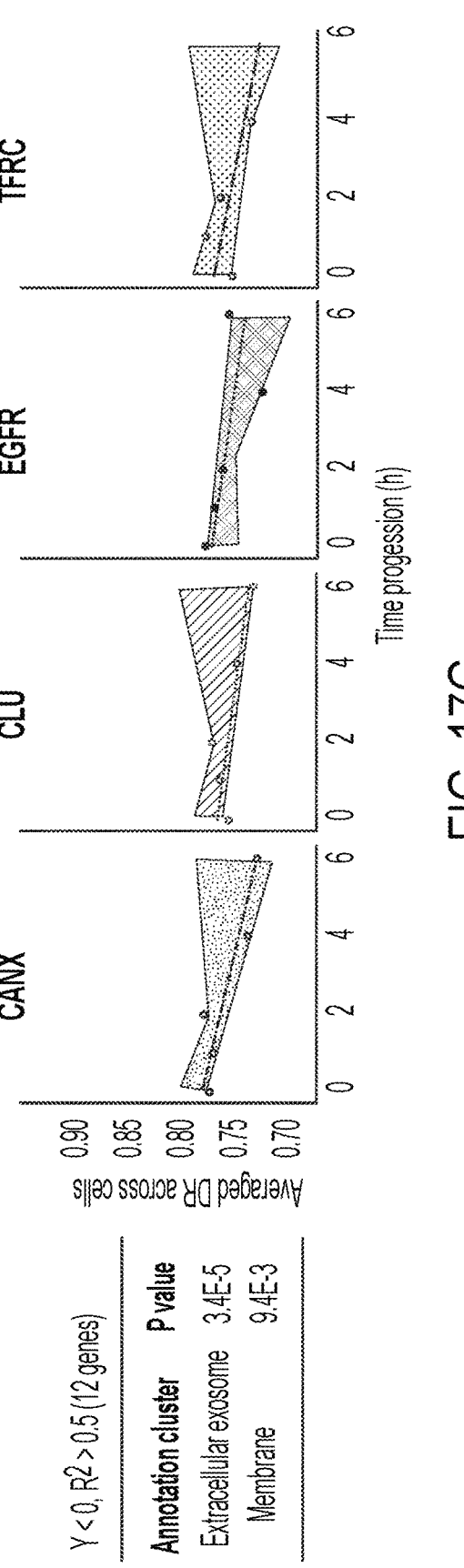
Figure 17H:
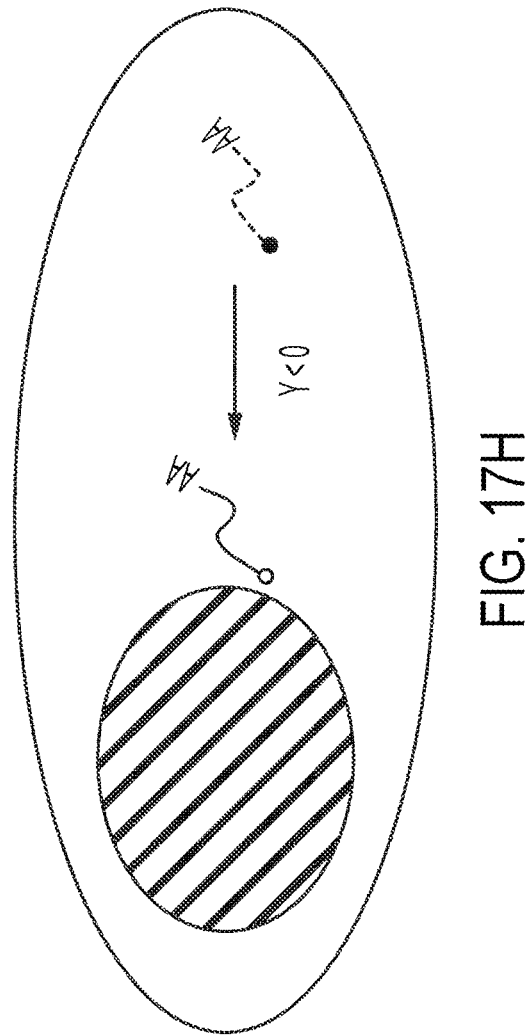

Notably, while nuclear export of RNA had been considered constant in a previous RNA velocity-based model[40], this result suggested that $\lambda$ under the first-order assumption[41] varies substantially across different RNA species, which could regulate the homeostasis of nucleocytoplasmic transcript abundance. In addition, for the first time, cytoplasmic translocation of RNAs of a large number of genes could be systematically studied simultaneously at 1 hr resolution. The majority of genes had $\gamma > 0$ (FIGS. 17E-17F), suggesting a translocating direction from nuclear membrane to the cytoplasmic membrane. However, a small subset of genes with $\gamma < 0$ ($R^2 > 0.5$) were significantly enriched in exosome and membrane proteins (FIG. 17G), indicating possible relocation events from the cytosol to the endoplasmic reticulum or faster degradation rates for non-ER anchored RNAs than ER-associated ones. Further studies need to be conducted to investigate the kinetic mechanism that directs the cytoplasmic translocation of different RNA molecules (FIG. 17H).

Figure 12C:
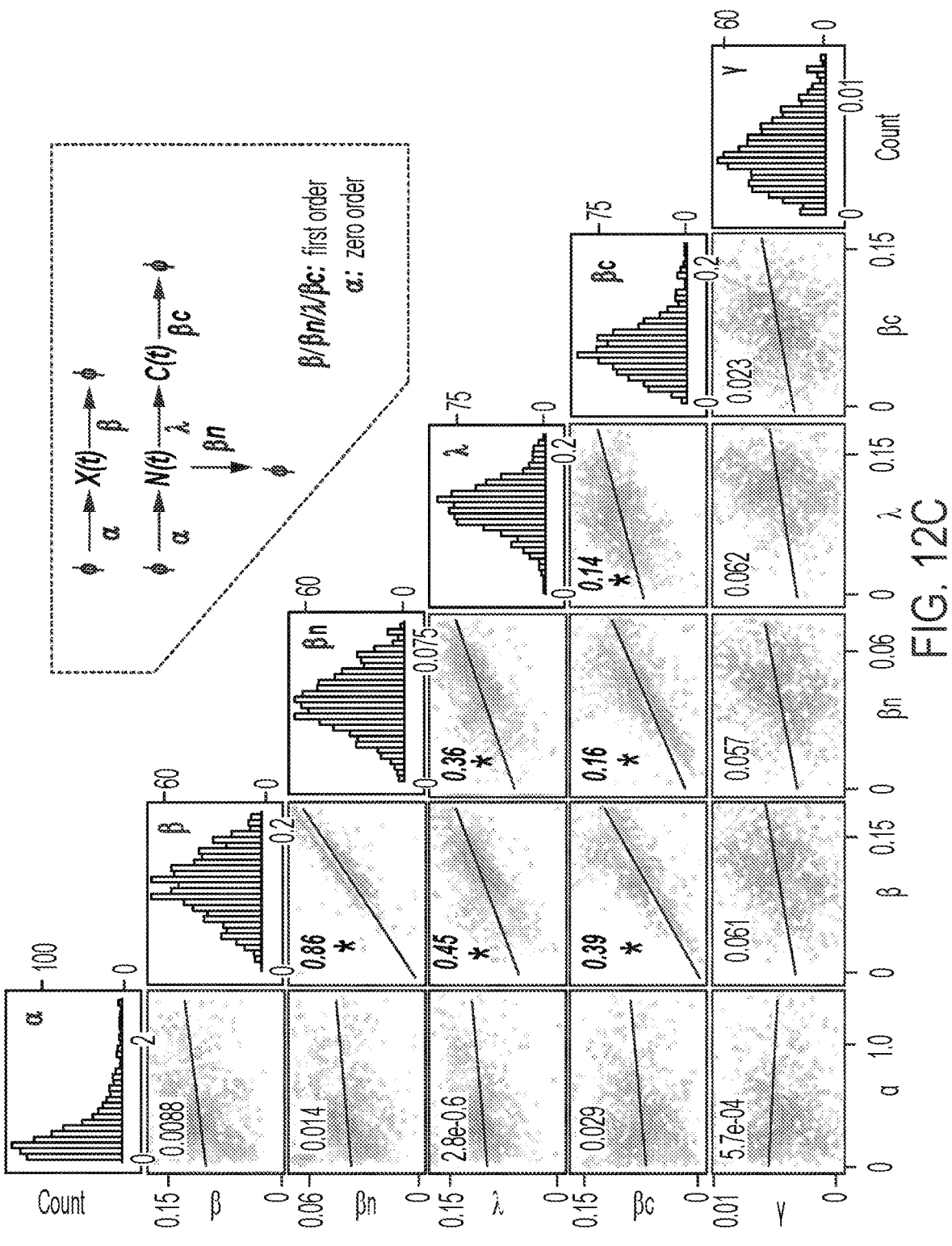

The relationship among these kinetic parameters was next explored by plotting their pairwise correlations with a matrix consisting of 911 genes (FIG. 12C). The gene set showed positive correlations among the three degradation constants ($\beta$ versus $\beta n$, $\beta n$ versus $\beta c$, and $\beta n$ versus $\beta c$, R=0.86, 0.39, and 0.14, respectively), while the highest correlation was $\beta$ and $\beta n$ (R=0.86). This observation suggested that, while RNA stability is mainly shaped by the intrinsic features (sequences, motifs, etc.), different genes have different allocations of nuclear versus cytosolic RNA degradation. In addition, significant correlations between degradation and nuclear export were observed (R=0.45, 0.36, and 0.14 for $\lambda$ versus $\beta$, $\beta n$, and $\beta c$, respectively), suggesting potential kinetic coupling between RNA decay and nuclear export. Despite the aforementioned correlations, the correlations between other pairs of kinetic parameters are weak (R<0.1), which demonstrated that individual steps of synthesis, transport, decay, and translocation at different subcellular regions are subject to distinct kinetic regulations during RNA life cycle.

Figures 12D, 12E:
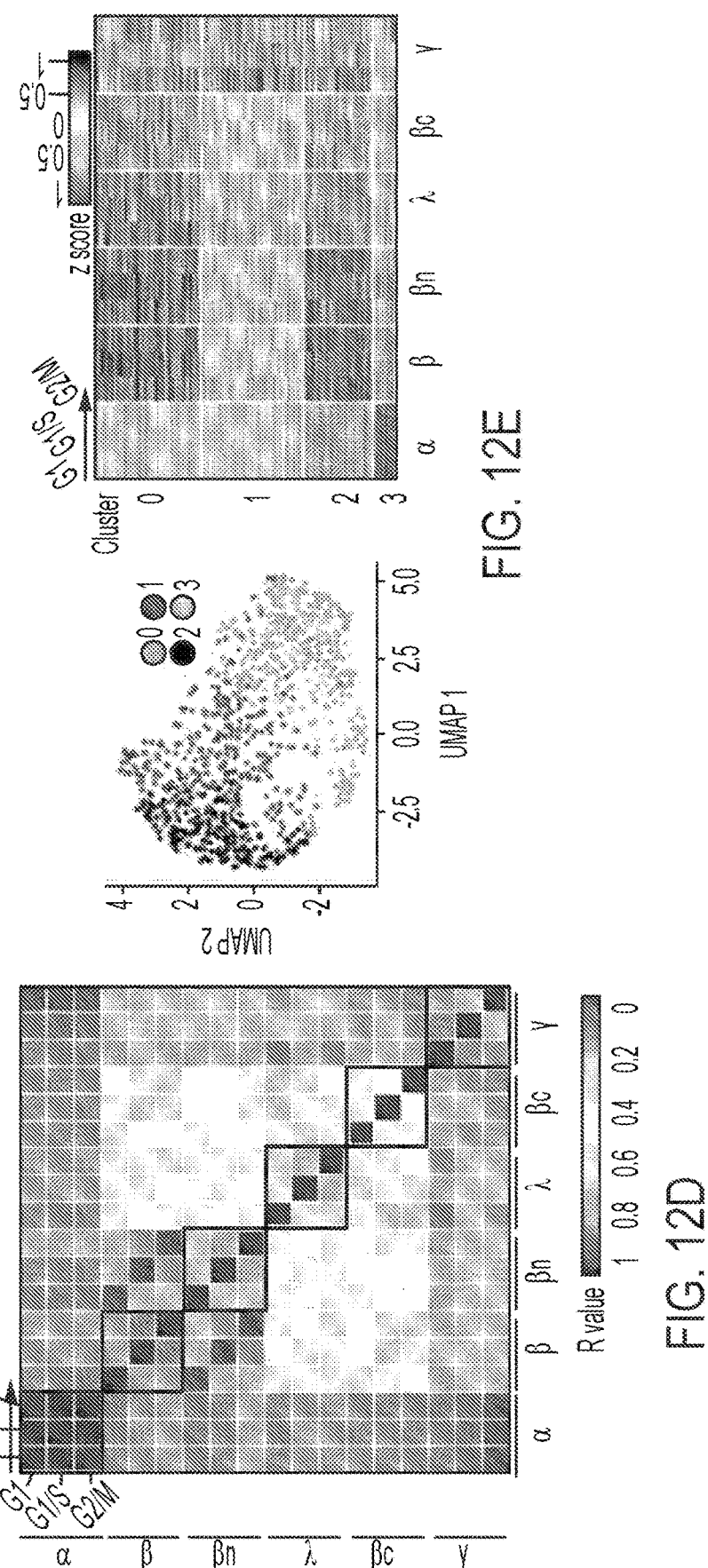
Figures 18A, 18B:
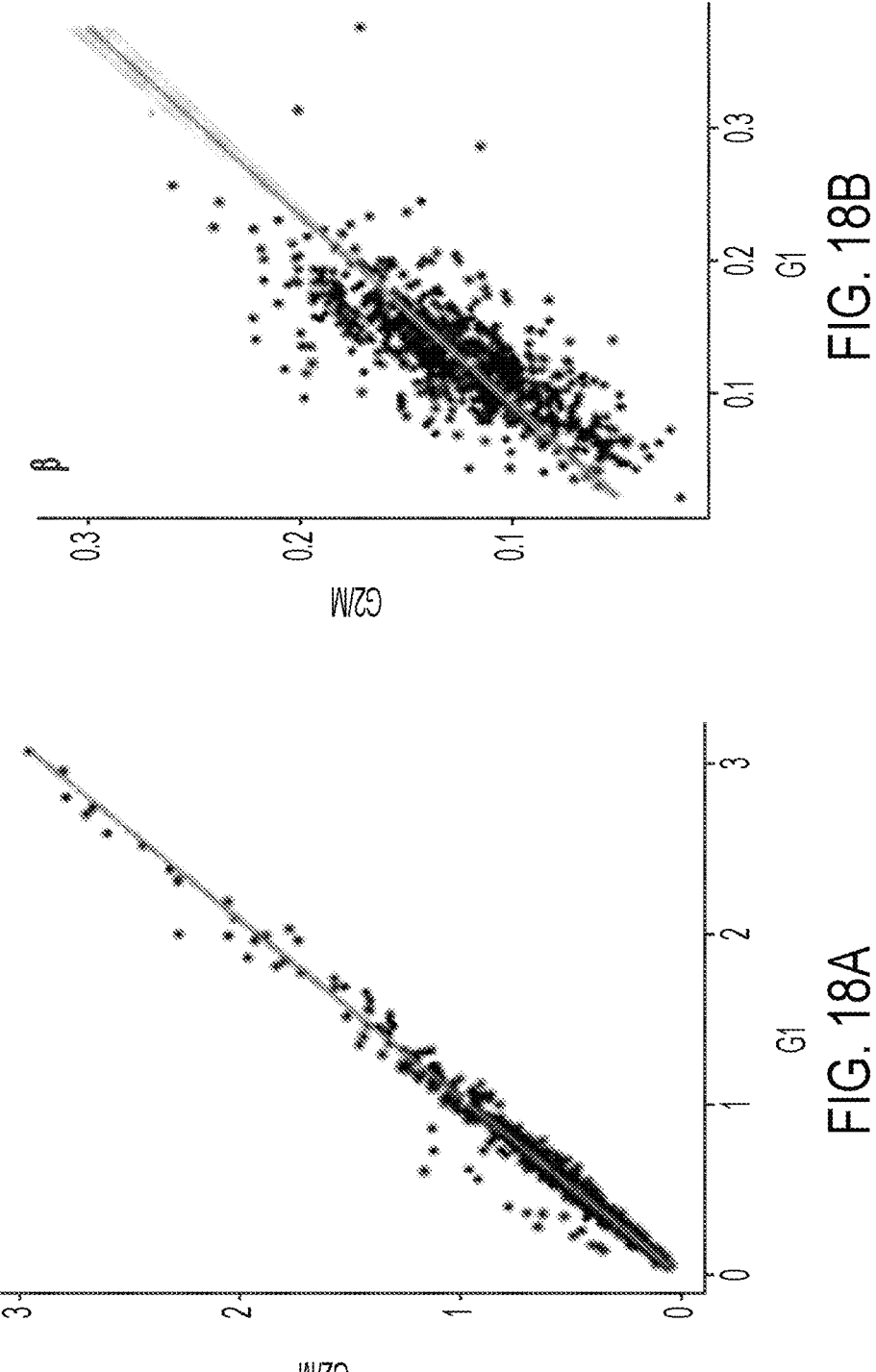
FIGS. 18A-18K shows RNA kinetic parameters across cell-cycle stages.
Figures 18C, 18D:
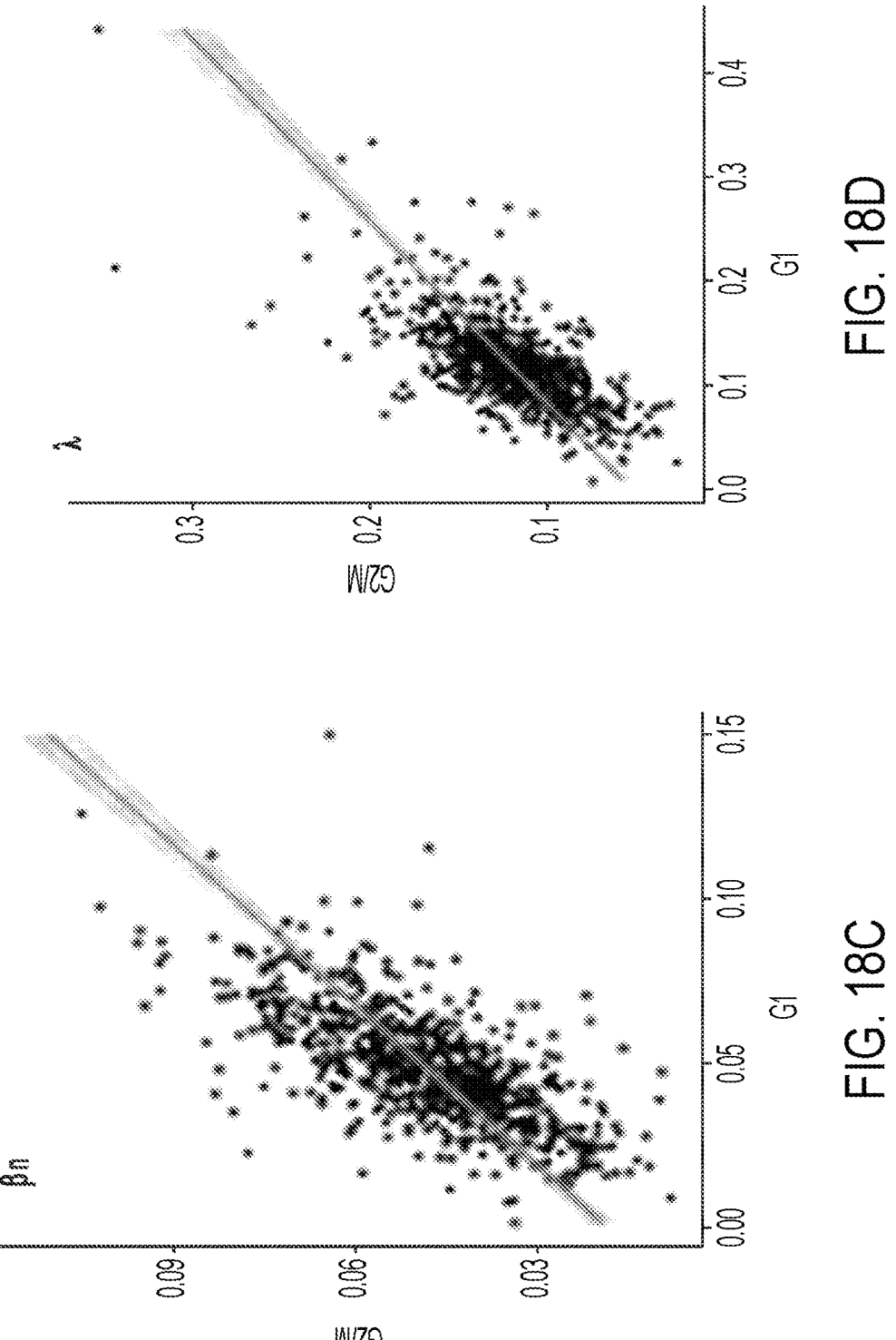
Figure 18F:
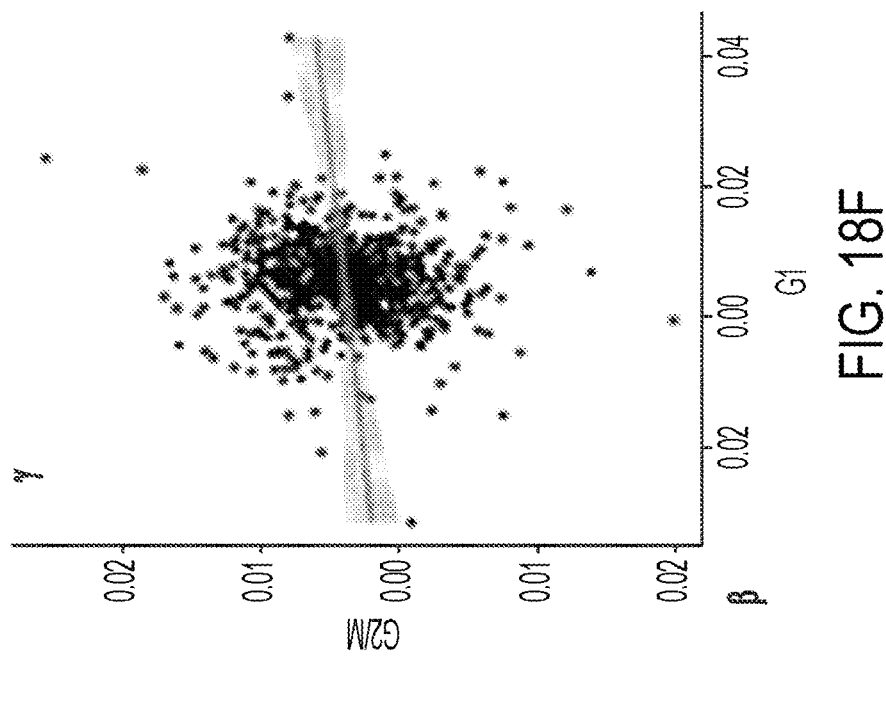
Figure 18E:
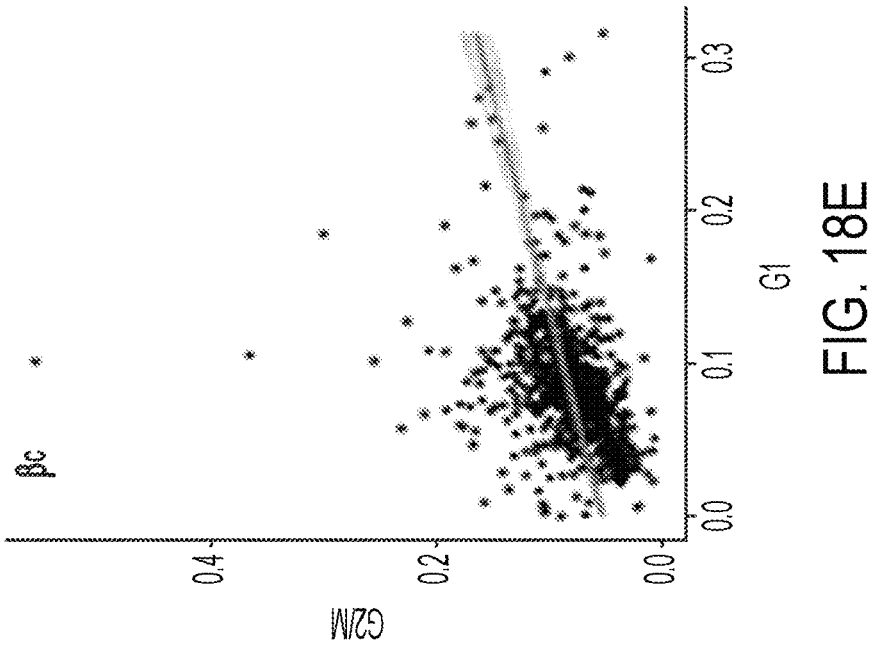

It was then asked whether RNA dynamics differ across cell cycle phasing. To this end, a second pairwise correlation analysis of six parameters was performed in the different cell-cycle phases (808 genes passed quality control; FIG. 12D). Interestingly, it was observed that, following the spatiotemporal sequence of RNA life cycle, a trend of decreasing correlation in cell cycle phases showed up: at the early stage of RNA production, $\alpha$ in the three states were highly correlated (R~1, FIG. 18A); during post-transcriptional processing in the nucleus, both $\beta n$ and $\lambda$ have moderate correlations (R~0.7 and 0.6, FIGS. 18C-18D); finally, near the end of RNA life cycle, cytoplasmic constants $\beta c$ and $\gamma$ have much weaker correlations (R~0.3 and 0.1, FIGS. 18E-18F). This observation revealed that the kinetic sorting in different RNA stages gradually diverted along the progression of cell cycle, and that RNA, along its spatiotemporal regulation, is subject to a shift from the universal direction of regulation to independent regulation in different cell states. From profiling the cell-cycle-dependent RNA kinetic landscape, a linkage was thus demonstrated between regulating the life cycles of cells and those of RNAs.

Figures 18G, 18H:
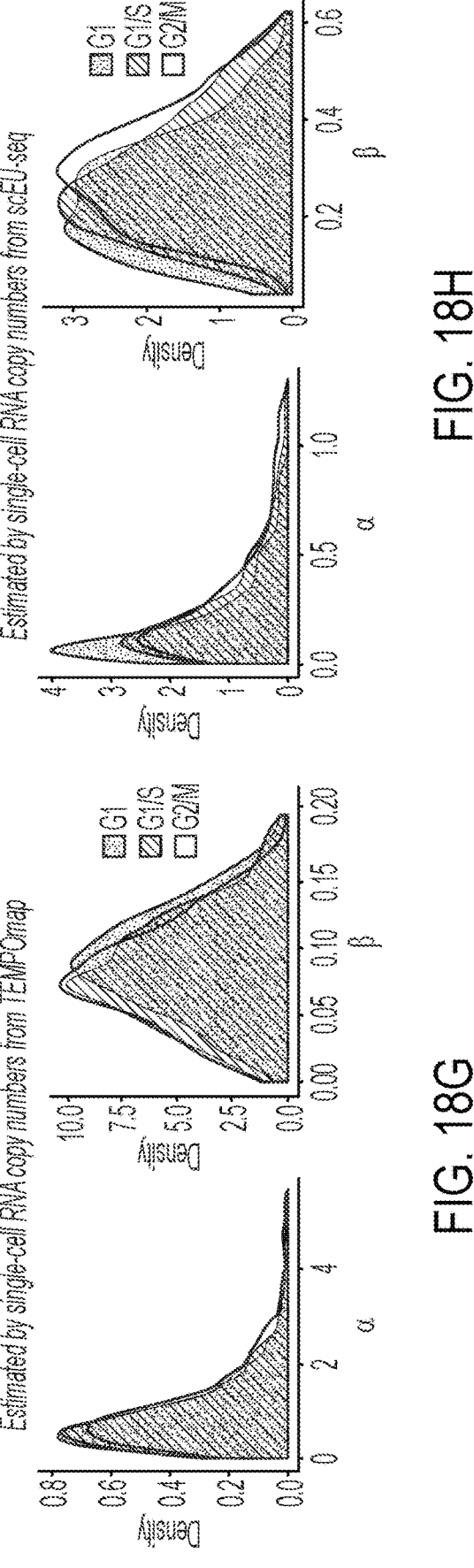
Figure 18I:
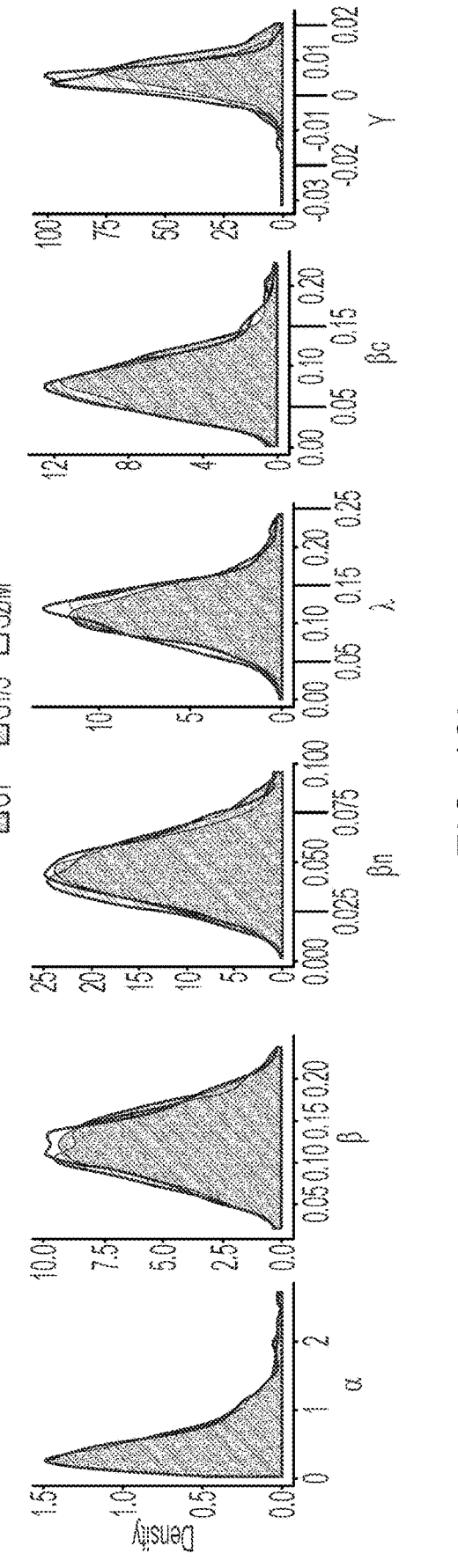
Figures 18J, 18K:
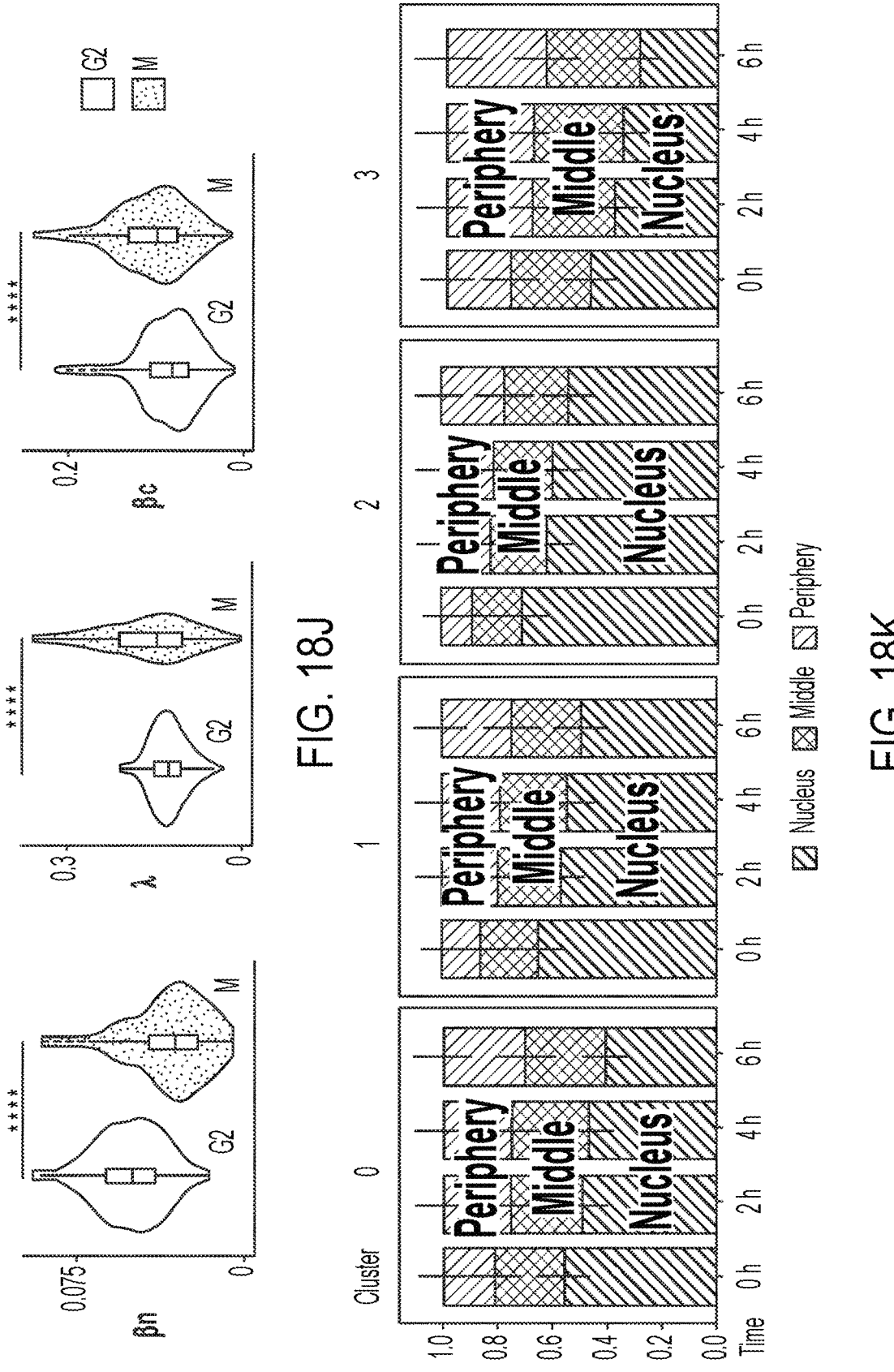

It is noteworthy that previous studies reported that RNA synthesis rate is higher in G2/M phase than G1[42]. When repeating the calculation of $\alpha$ and $\beta$ using RNA copy numbers per cell from the TEMPOmap data and published scEU-seq data[25], consistent results were observed showing that RNA synthesis rate is higher by ~15% in G2/M, whereas degradation rates across cell cycle have different trends between the two datasets, potentially because of different cell lines (FIGS. 18G-18H). However, when estimating $\alpha$ and $\beta$ using RNA concentrations (RNA copy numbers per unit nuclei volume for $\alpha$, and RNA copy numbers per unit cell volume for $\beta$), no significant changes in the distribution of $\alpha$ and $\beta$ values at different cell-cycle stages were observed (FIG. 18I). The contrast of estimated $\alpha$ and $\beta$ by RNA copy number per cell versus RNA concentrations agrees with previous works that showed that transcription rate is proportional to available sites of the chromosomes and that gene expression homeostasis is regulated by cell size[43]. In addition, when subsetting cells in G2 and M phase from single-cell nucleocytoplasmic PHATE embedding (FIG. 16D), a significantly higher $\lambda$ was found in M phase, which further confirms the observation of RNA eviction from chromosomes during mitosis (FIG. 18J, FIG. 11E, V).

Figures 12F, 12G:
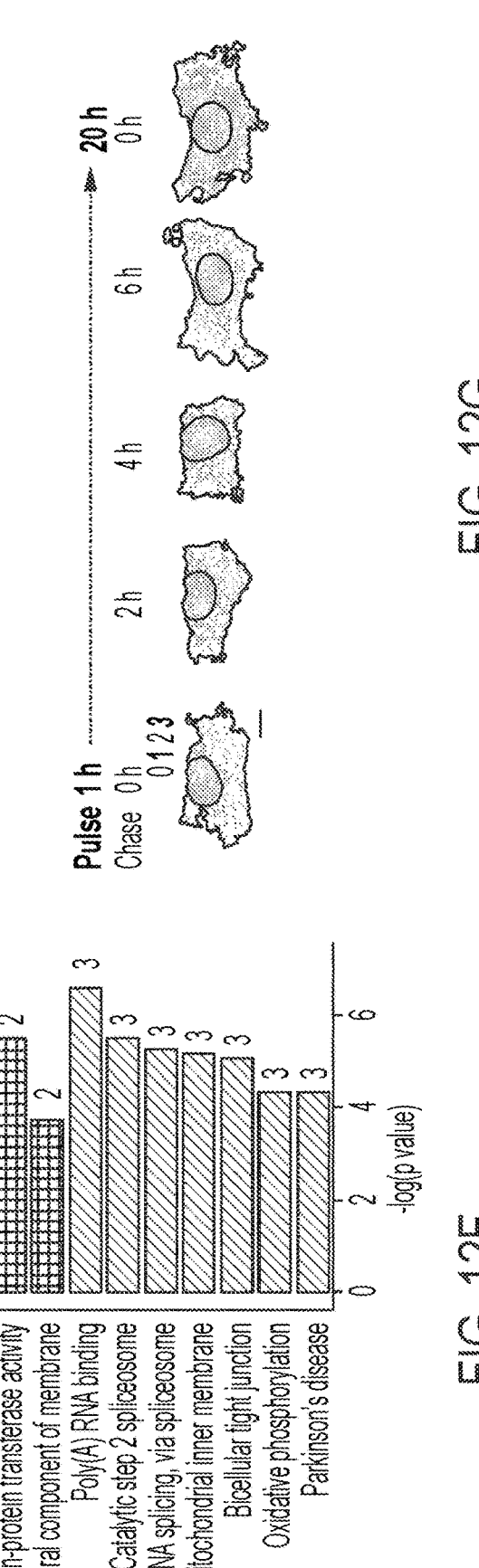

Given the correlation between kinetic constants and potential co-regulation mechanisms (e.g., shared RNA motifs and RNA-binding proteins), it was next asked if different genes may have evolved shared kinetic patterns in the context of RNA life cycle and cell cycle. Clustering analysis using the 18 parameters (six kinetic constants across three cell cycle stages) revealed four groups of distinct kinetic landscape (FIG. 12E). A closer inspection of the clusters shows that genes with slower synthesis (low $\alpha$), greater stability (low $\beta$), and slower export ($\lambda$) were enriched in helicase activity and other ATP-binding functions (Cluster 0); genes with lower a and moderate $\beta$ and $\lambda$ (Cluster 1) were strongly enriched in transcription; genes with unstable and rapidly-exported RNAs (high $\beta$ and $\lambda$) (Cluster 2) were enriched in terms related to ubiquitination and membrane proteins; genes with faster synthesis (high $\alpha$), greater stability (low $\beta$), and faster export (high $\lambda$) (Cluster 3) were enriched in constitutive cellular processes like mRNA splicing and mitochondrial functions (FIG. 12F). In addition, the spatial patterns of these groups of genes were compared (FIG. 12G). It was observed that genes in clusters 0 and 3 appeared to be more predominant in cytoplasm, whereas clusters 1 and 2 were more retained in the nucleus over the course of time. RNA reads of the four clusters in the three subcellular regions further supported this observation, indicating that kinetically-sorted genes may result in distinct spatiotemporal distributions (FIG. 18H).

Differential RNA Kinetic Sorting by Gene Function

Given the differential enrichment of GO terms from gene clusters defined by RNA kinetics (FIG. 12F), it was further investigated how the kinetic features of RNA life cycle serve gene function. Potentially co-regulated RNAs were first identified through a pairwise single-cell covariation analysis of 991 genes from the aforementioned pulse-chase HeLa cell samples (1 hr pulse, 0-6 hr chase, FIG. 13A). Using a joint gene sorting in the matrix across all time points on the heat map, two groups of genes were identified with significant inter-gene correlation whose correlation coefficients kept increasing from 0 to 6 hr chase (FIG. 13B, FIG. 19A), indicating potential kinetic sculpting of gene co-regulation patterns by RNA processing and decay. Notably, while both Group 1 and 2 genes are enriched with cell-cycle-related functions (FIG. 13C, bottom right, $p<0.05$ for Group 1; $p<1e-04$ for Group 2), they differ significantly in RNA kinetics: Group 1 was comprised of genes in kinetic Clusters 2 and 3 with faster RNA processing whose gene co-variation pattern was immediately evident from 0 to 2 hrs post synthesis; in contrast, Group 2 is enriched with genes from kinetic Clusters 0 and 1 with slower RNA processing (FIG. 12E, FIGS. 13B and 13D) whose co-variation patterns gradually emerged from 2 hrs to 6 hrs post-synthesis. This observation suggests that RNAs with distinct dynamic features at transcriptional and post-transcriptional steps orchestrate to jointly shape cell cycle progression.

Figures 13A, 13B:
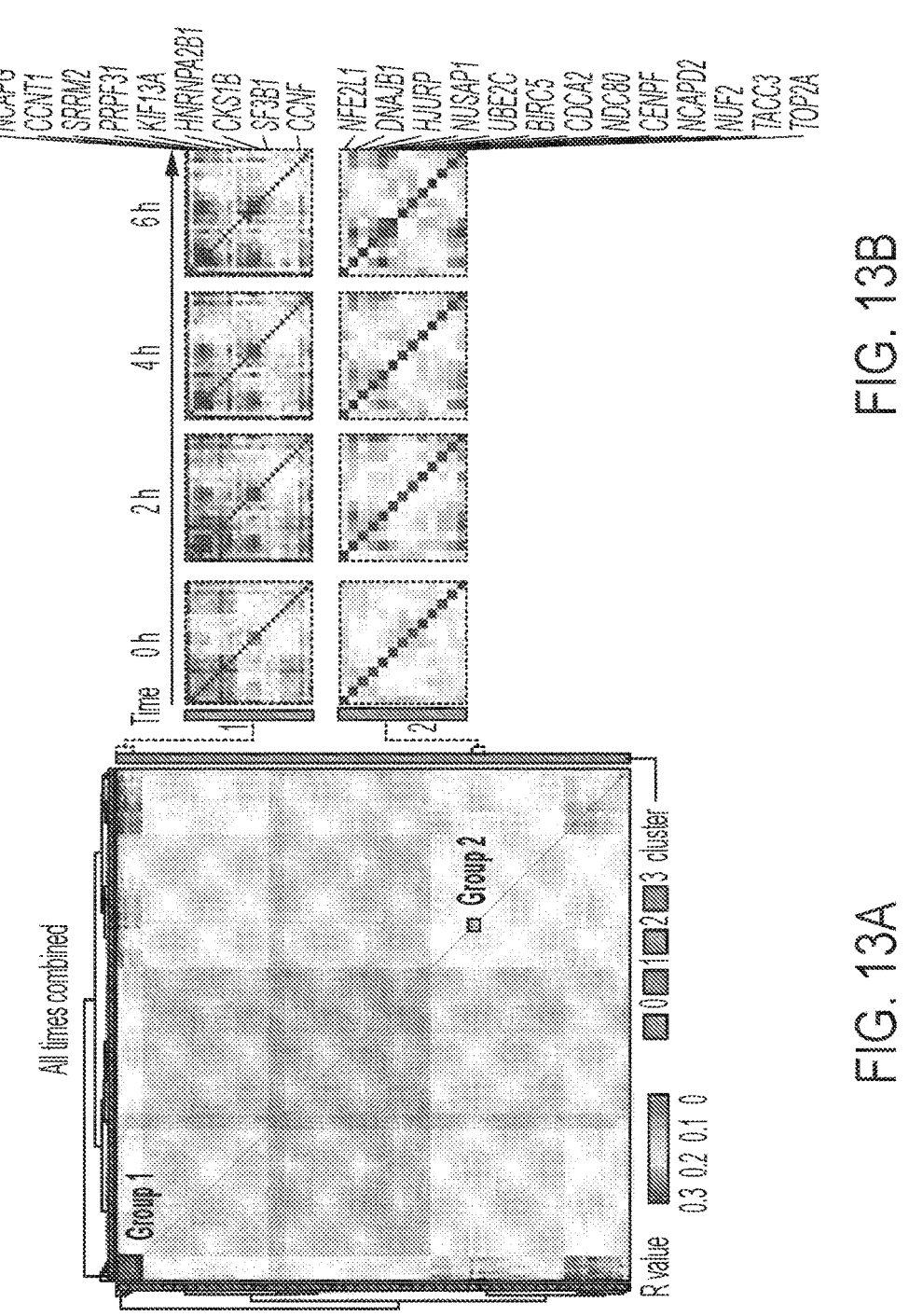
FIGS. 13A-13G show differential RNA dynamics by gene function and post-transcriptional characteristics.
Figure 13D:
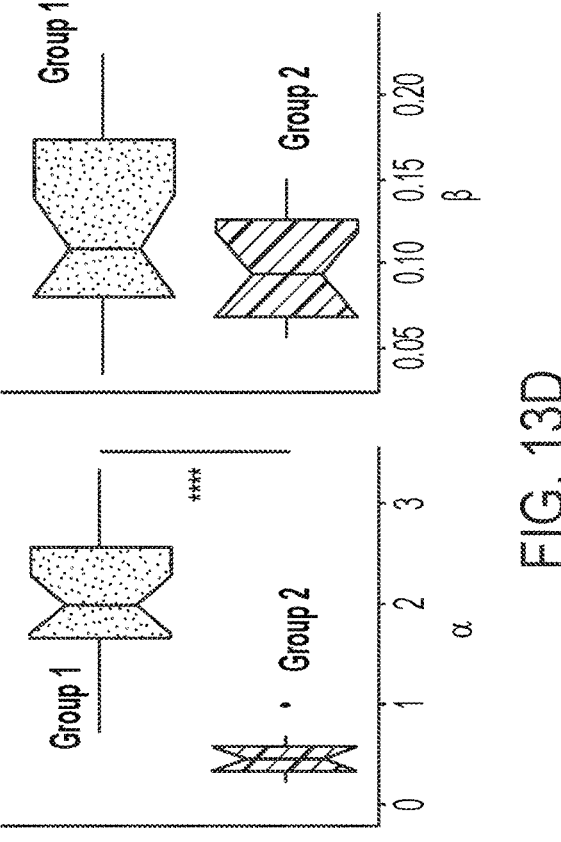
Figure 13C:
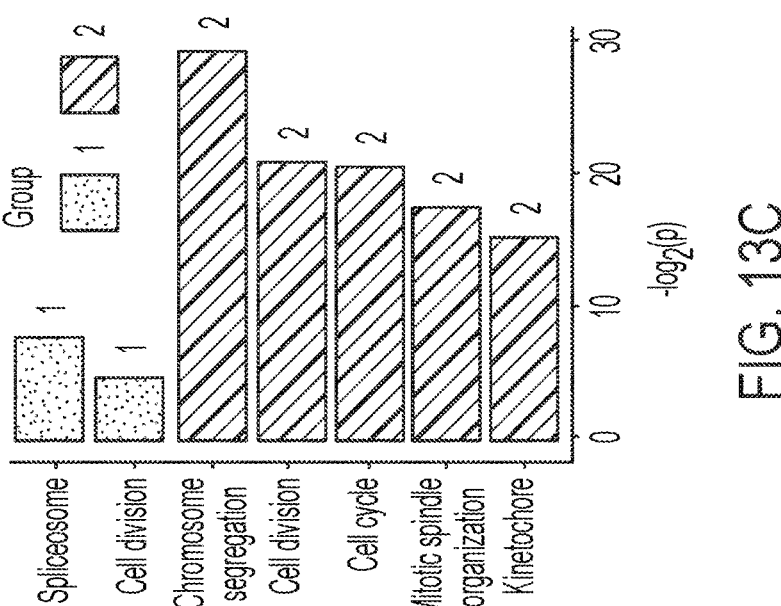
Figure 13E:
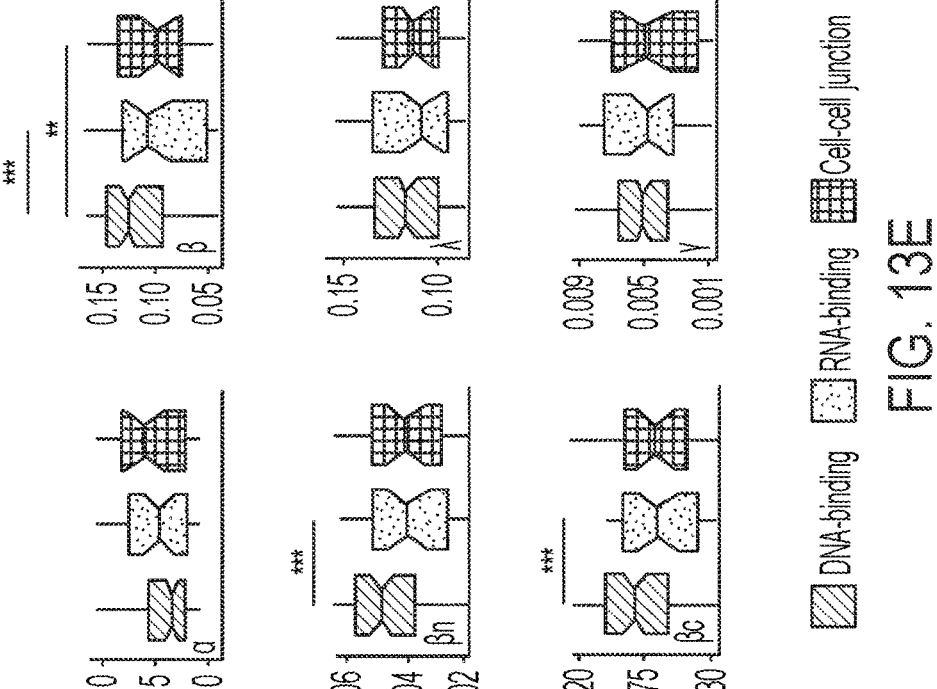

Next, the kinetic landscape of RNAs was systematically compared across different categories of molecular functions. The top three functional categories in the 991-gene list (FIG. 19B) are DNA-binding (97 genes), RNA-binding (28 genes), and cell-cell junction (25 genes). Comparing the six kinetic parameters across the three gene categories, it was found that DNA-binding genes have significantly faster RNA decay than RNA-binding genes and genes with the molecular function of cell-cell junction (FIG. 13E, $p=4.6e-03$ and $0.036$).

Figure 13F:
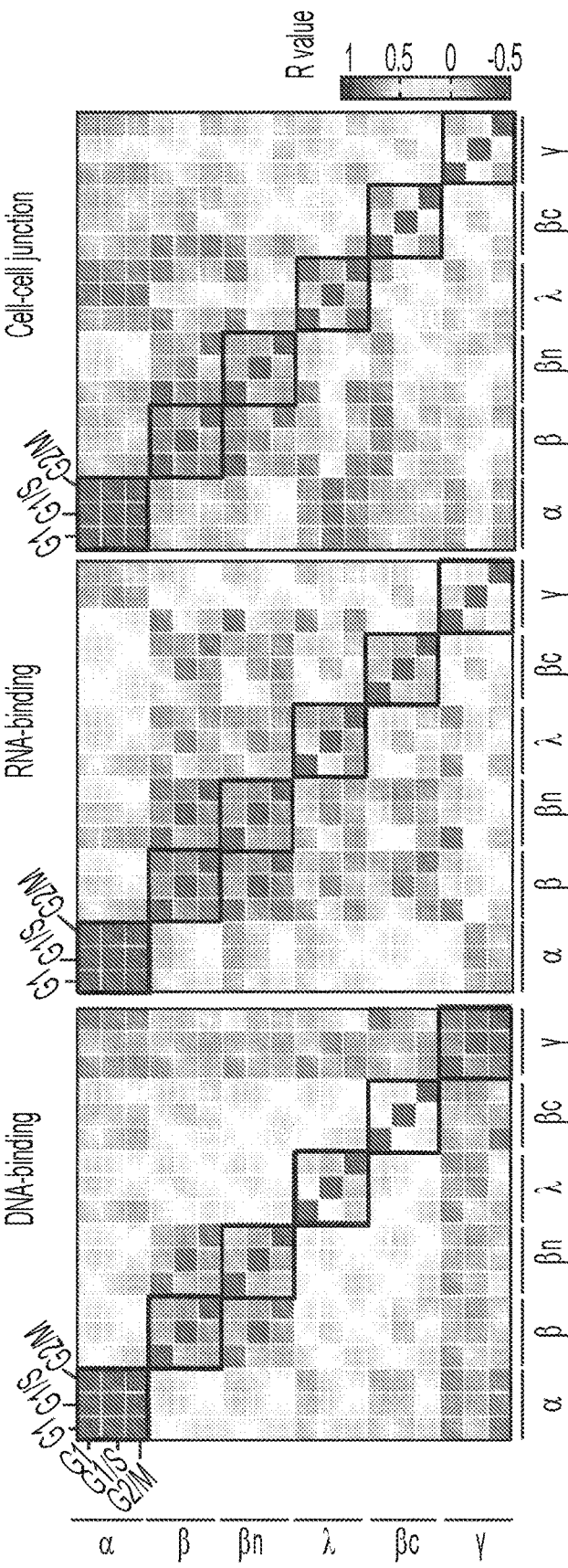

Further gene correlation analysis of the kinetic parameters from the three functional categories across cell cycle stages reveals distinct co-regulatory patterns of RNA kinetics (FIG. 13F). Specifically, from the upstream to the downstream of the RNA life cycle, genes functioning as DNA-binding proteins had high correlation until nuclear RNA degradation ($\beta n$, R~0.8); genes of RNA-binding function were kinetically correlated until cytoplasmic RNA degradation ($\beta c$, R~0.6), whereas genes for cell-cell junction showed an extended high correlation in cytoplasmic translocation ($\gamma$, R~0.5), indicating that those genes have additional co-regulation in cytoplasmic RNA decay and localization in comparison with DNA-binding proteins. Those observations further support the notion that RNAs are kinetically sorted to serve their molecular functions.

Figure 13G:
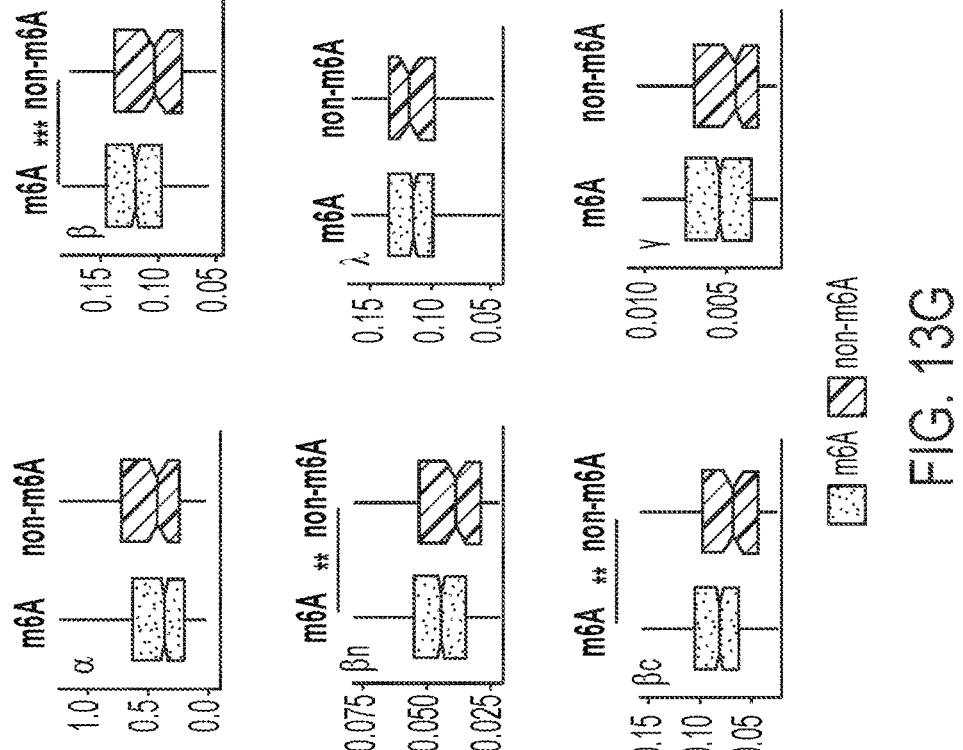
Figure 19A:
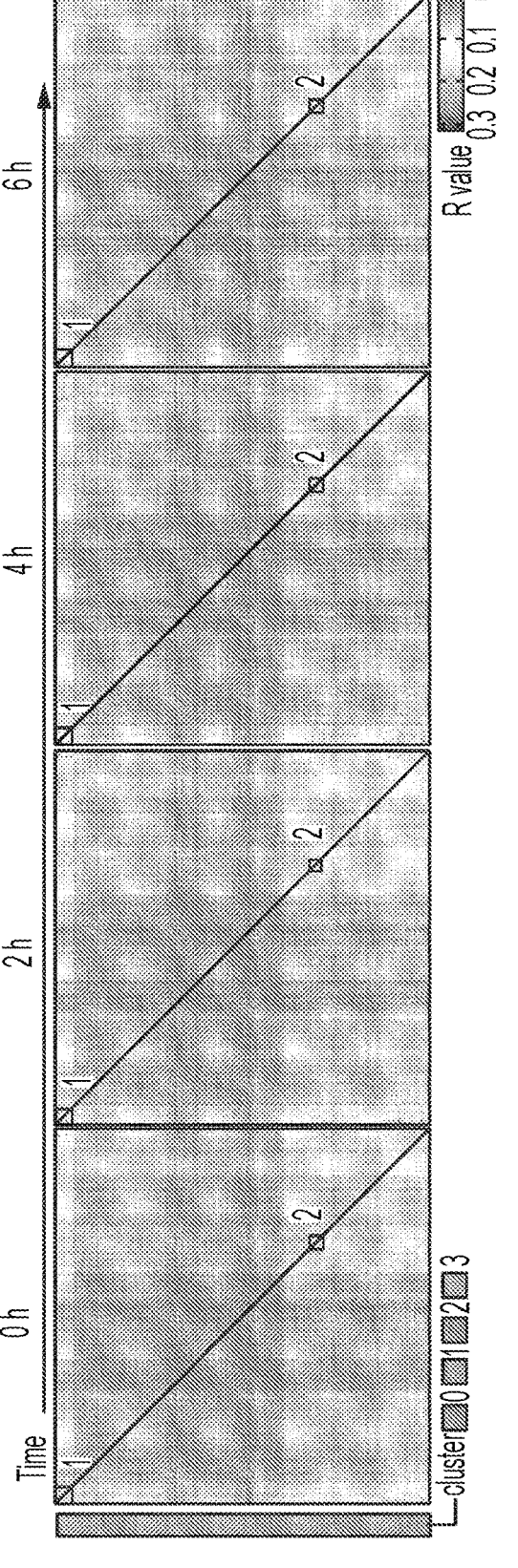
FIGS. 19A-19H show variations of RNA kinetics in gene functions and post-transcriptional modification status.
Figures 19B, 19C, 19D:
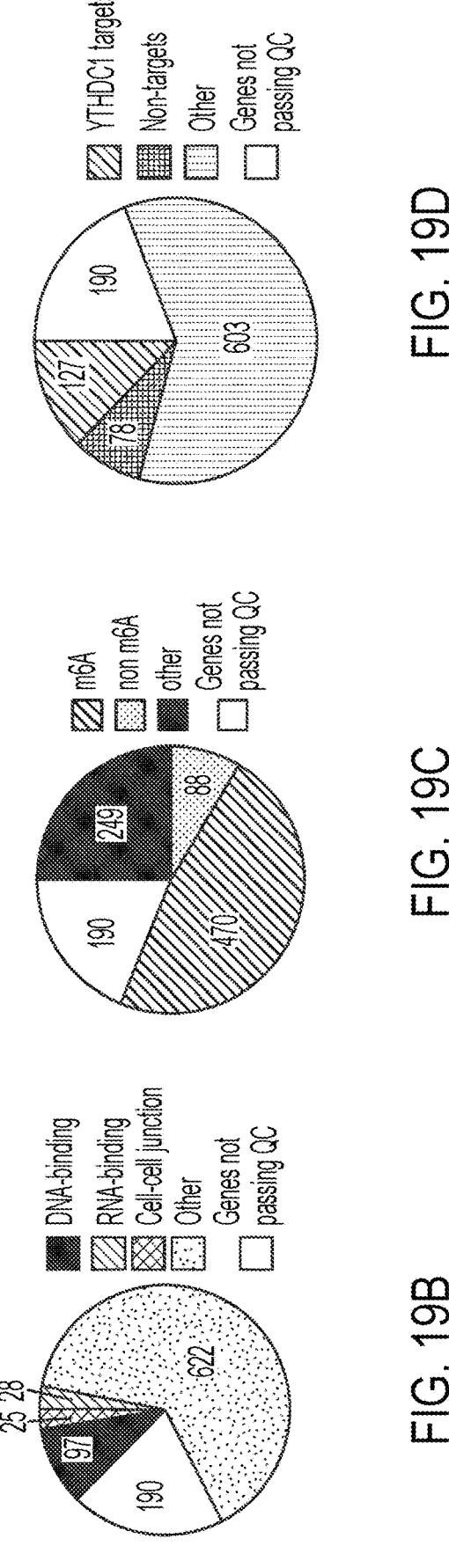
Figure 19E:
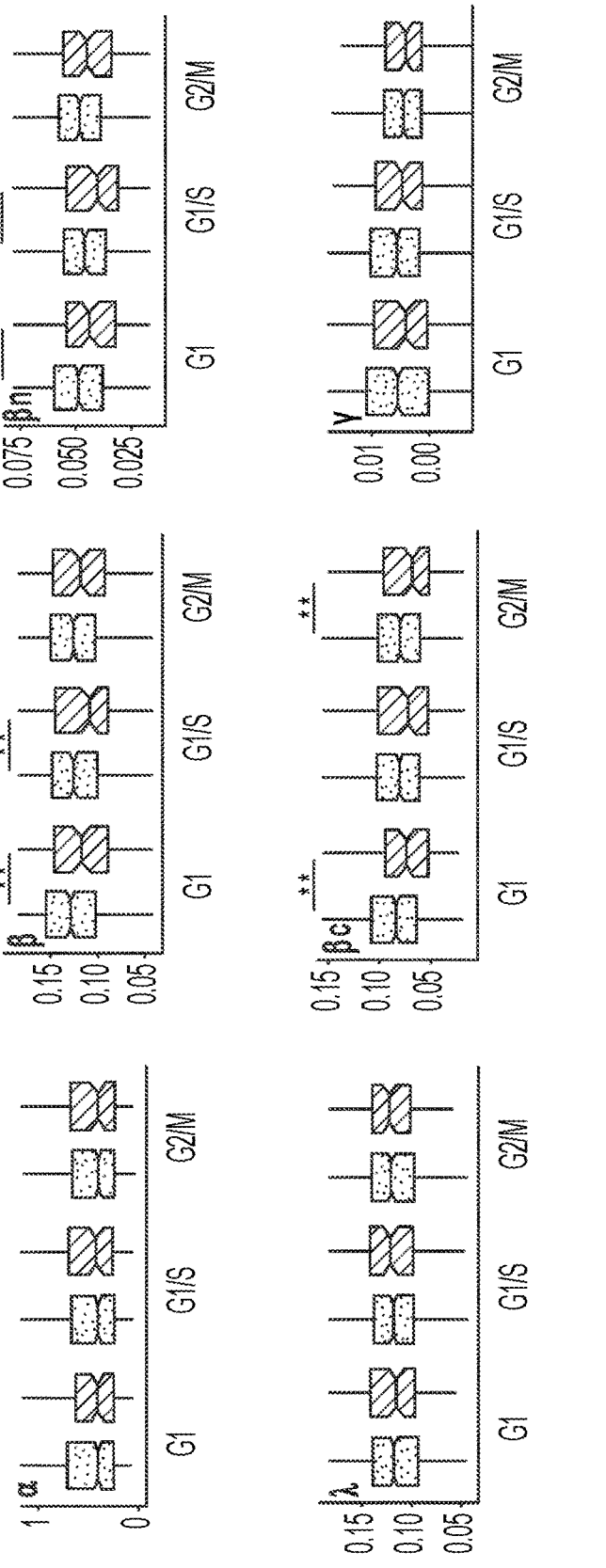
Figure 19F:
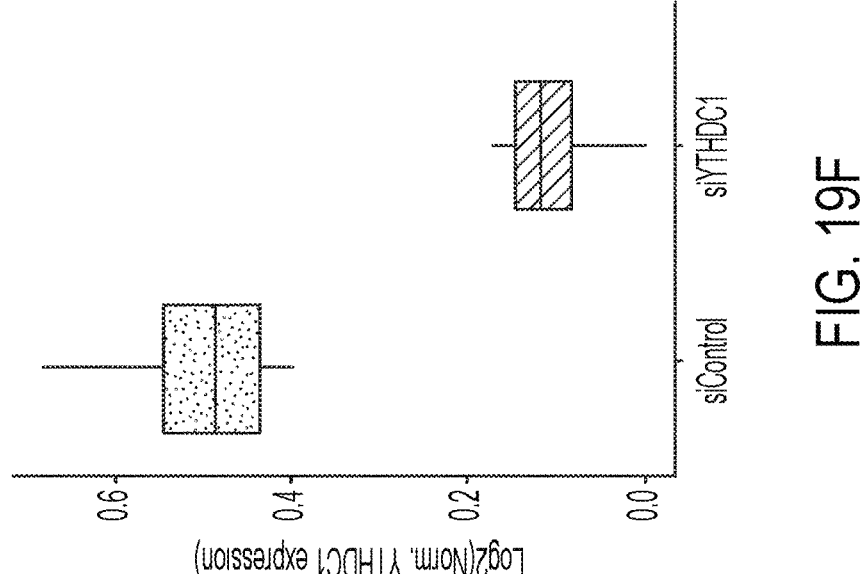
Figure 19G:
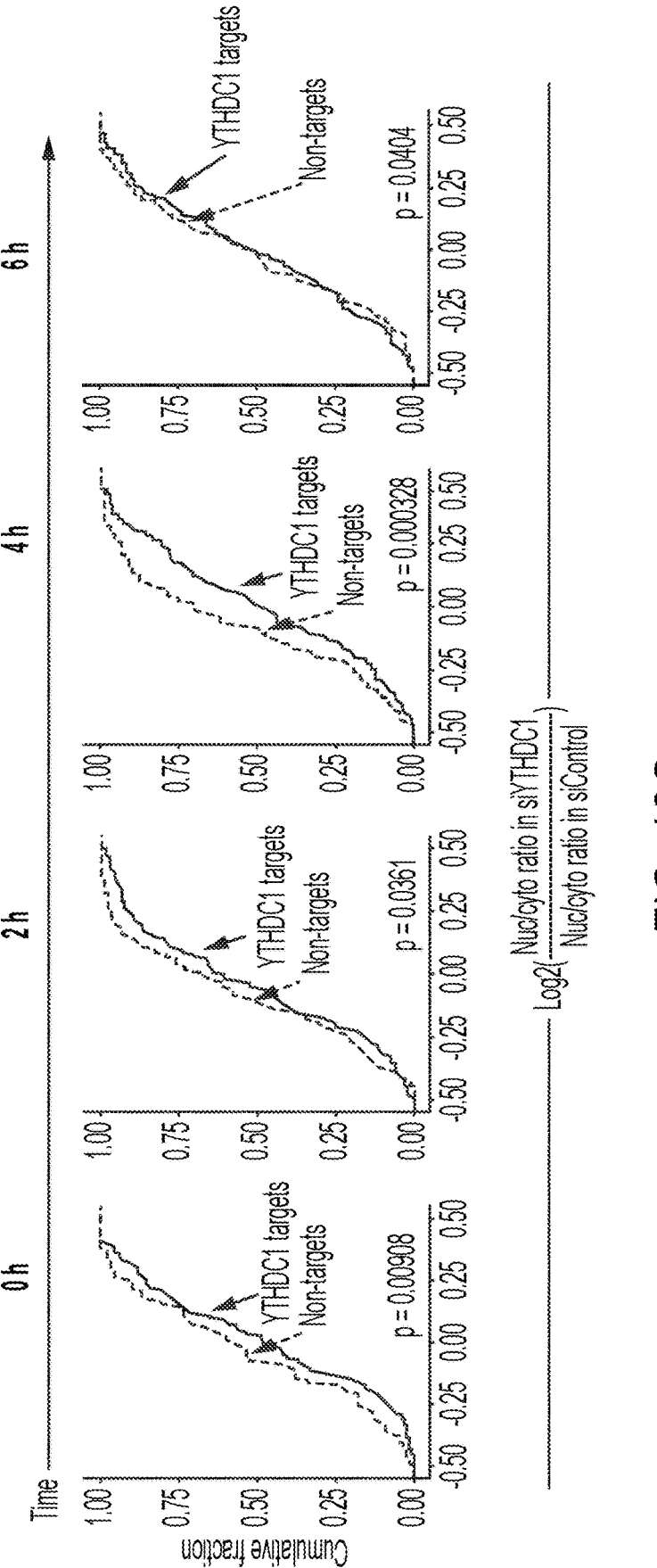
Figure 19H:
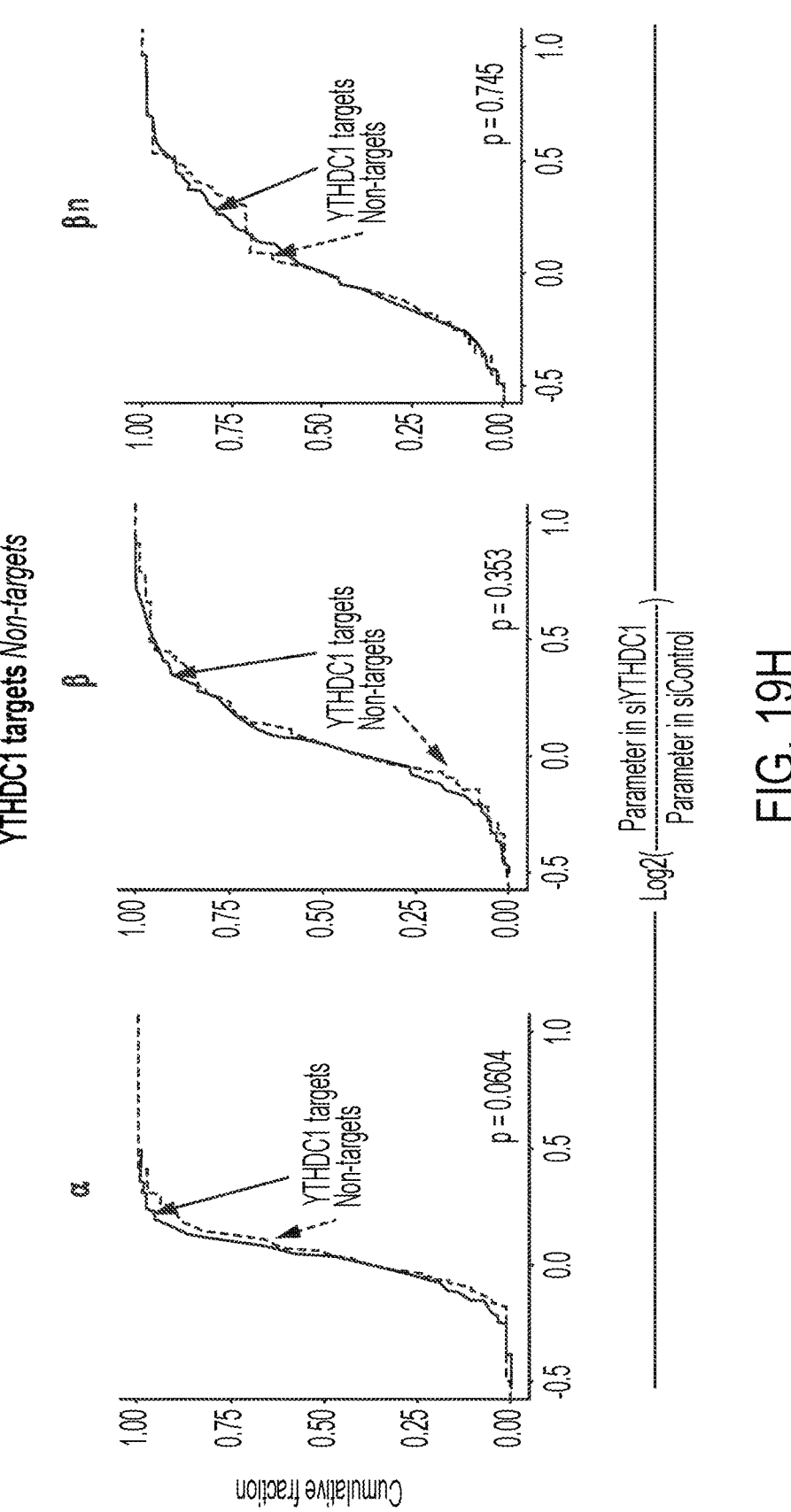
Figure 19H:
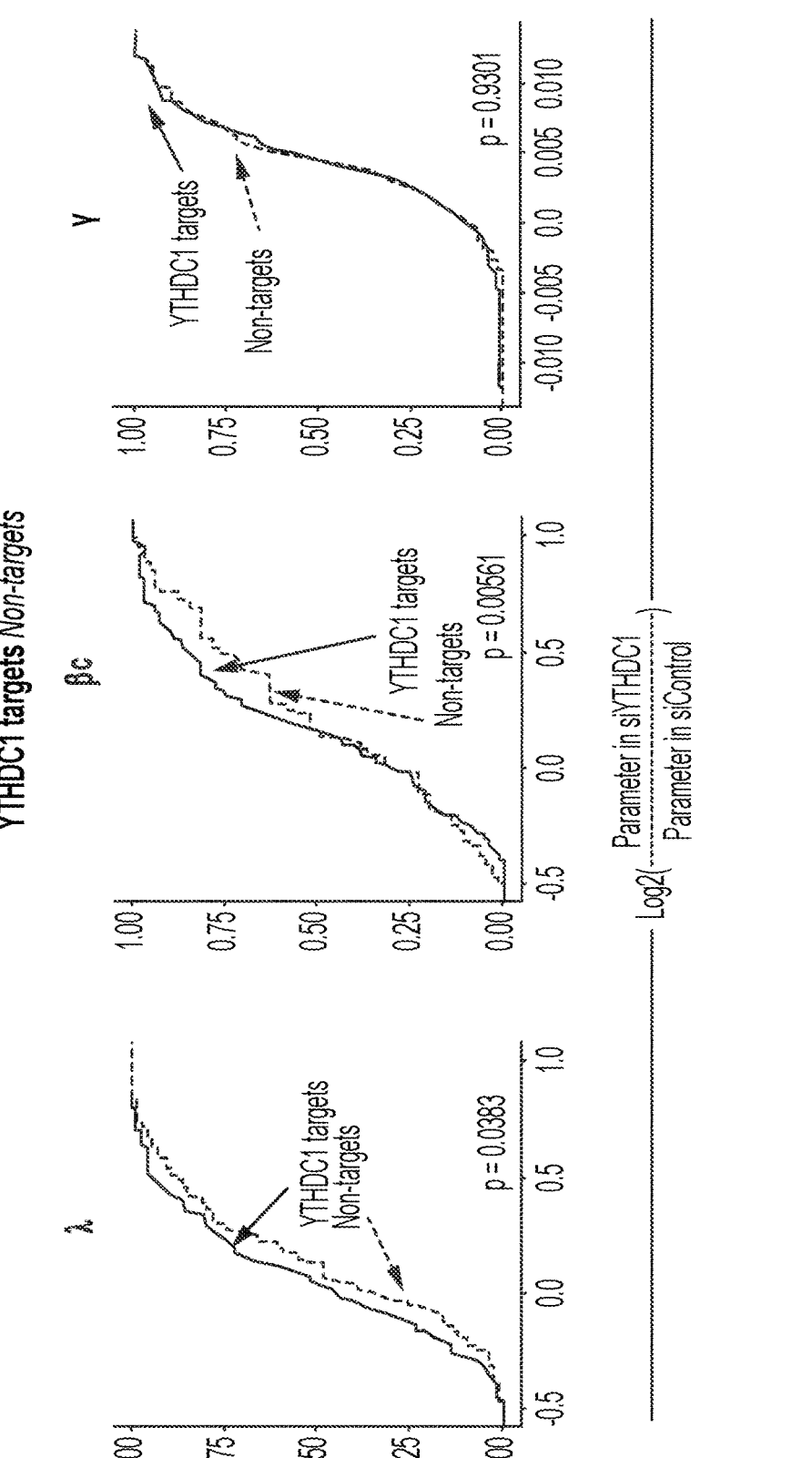

Finally, RNA kinetics were explored in the context of $N^6$-methyladenosine modifications ($m^6A$), a critical post-transcriptional chemical modification of RNA that plays vital roles[44,45]. $m^6A$ is known to accelerate RNA decay, however, the full landscape of kinetic regulation on $m^6A$-RNA has not been systematically addressed. To this end, the genes encoding RNAs with and without $m^6A$ modifications ($m^6A$- or non-$m^6A$-RNAs, FIG. 19C) were separated. Consistent with the previous report, $m^6A$-RNAs were less stable (higher $\beta$, FIG. 13G)[46]. In addition, the same trend was observed when comparing $\beta n$ and $\beta c$ of $m^6A$ vs non-$m^6A$, respectively, suggesting that the regulation of $m^6A$-methylation is achieved by both nuclear and cytoplasmic RNA decay, which is also consistent across cell-cycle phases (FIG. 19E). In contrast, a significant difference in $\lambda$ was not observed between the two groups. The previous work proposed a regulatory role of $m^6A$ in mRNA export mediated by YTHDC1[47]. Thus, to confirm the cellular role of YTHDC1, HeLa cells were treated with a control siRNA and with siRNA against YTHDC1 mRNA, and control and knock-down cells were separated based on single-cell YTHDC1 reads normalized against the expression of the other six functionally related genes (METTL3/14, YTHDF1-3, YTHDC2, FIG. 19F). In agreement with previous work, the nuclear-to-cytoplasmic ratio of YTHDC1-targeting genes was consistently higher than that of non-targets across time, suggesting nuclear accumulation of RNA upon YTHDC1 knockdown (FIGS. 19D, 19G). In addition, these results confirmed that such change of nuclear-to-cytoplasmic induced by YTHDC1 knockdown is attributed to the varied rate of nuclear RNA export (FIG. 19H). This study exemplifies that TEMPOmap can be combined with genetic perturbations (e.g., RNAi) to delineate functions of RNA-binding proteins at unprecedented resolution.

Discussion

TEMPOmap builds a novel in situ transcriptomic platform that simultaneously profiles time- and spatially-resolved transcriptomics in single cells, a multimodal single-cell transcriptomics technology at subcellular resolution that has not been achieved before. Using TEMPOmap, the studies described herein provide a comprehensive description of cell and RNA regulations over a tunable time course and unravel the laws governing how cell cycle and RNA cycle are configured for the complex machinery of life. A strong correlation of RNA kinetic patterns with gene functions was observed, and such function-oriented regulation of RNA life cycle might have evolved under survival and energy constraints to control spatiotemporal gene expression in a precise and economic way[48]. TEMPOmap can also be combined with high-throughput single-cell functional genomics (e.g., CRISPR screens[49]) to determine key molecular factors that impact the kinetic landscape of RNA life cycle. Furthermore, with optimization of metabolic labeling conditions[27,50,51], such methodology can be adapted for ex vivo or in vivo tissue samples to systematically profile dynamic events in tissue biology.

Methods

Chemicals and enzymes. Chemicals and enzymes listed as name (supplier, catalog number): Gel Slick Solution (Lonza, 50640). PlusOne Bind-Silane (GE Healthcare, 17-1330-01). Poly-D-lysine solution, 50 μg/mL (ThermoFisher, A3890401). Ultrapure distilled water (Invitrogen, 10977-015). Glass bottom 24-well plates (Greiner Bio-One, 662892, and MatTek, P24G-1.5-13-F). #2 Micro coverglass, 12 mm diameter (Electron Microscope Sciences, 72226-01). 16% PFA, EM grade (Electron Microscope Sciences, 15710-5). Methanol for HPLC (Sigma-Aldrich, 34860-1L-R). PBS, 7.4 (Gibco, 10010-023 for 1× and 70011-044 for 10×). Tween-20, 10% solution (Calbiochem, 655206). Triton-X-100, 10% solution (Sigma-Aldrich, 93443). OmniPur Formamide (Calbiochem, 75-12-7). 20×SSC buffer (Sigma-Aldrich, S6639). Ribonucleoside vanadyl complex (New England Biolabs, S1402S). Yeast tRNA (Invitrogen, AM7119). SUPERase•In (Invitrogen, AM2696). 5-Ethynyl Uridine (5-EU) (Invitrogen, E10345). 1.5× Click buffer (Lumiprobe, 61150). L-ascorbic acid (Sigma-Aldrich, A5960). T4 DNA ligase, 5 Weiss U/µL (Thermo Scientific, EL0011). Phi29 DNA polymerase (Thermo Scientific, EP0094). 10 mM dNTP mix (Invitrogen, 100004893). BSA, molecular biology grade (New England Biolabs, B9000S). 5-(3-aminoallyl)-dUTP (Invitrogen, AM8439). BSPEG9 (Thermo Scientific, 21582). Methacrylic acid NHS ester, 98% (Sigma-Aldrich, 730300). DMSO, anhydrous (Molecular Probes, D12345). Acrylamide solution, 40% (Bio-Rad, 161-0140). Bis Solution, 2% (Bio-Rad, 161-0142). Ammonium persulfate (Sigma-Aldrich, A3678). N,N,N',N'-Tetramethylethylenediamine (Sigma-Aldrich, T9281). OmniPur SDS, 20% (Calbiochem, 7991). *Antarctica* Phosphatase (New England Biolabs, M0289S). DAPI (Molecular Probes, D1306). Flamingo Fluorescent Protein Gel Stain (Bio-Rad, 1610491). DMEM (ThermoFisher, 11995). FBS (HyClone, SH3007103). Lipofectamine RNAiMAX (Invitrogen, 13778075). Azidobutyric acid NHS ester (Lumiprobe, 63720). Bio-Spin® P-6 Columns, SSC buffer (Bio-Rad, 7326002).

Design and construction of TEMPOmap tri-probes. TEMPOmap tri-probes were designed to contain a set of three separate DNA oligonucleotide probes: splint, primer and padlock. DNA splint was prepared by incubating 40 µM 5' amino-modified splint oligo (manufactured by Integrated DNA Technologies (IDT)) with 25 mM Azidobutyric acid NHS ester (azide-NHS) in 0.1 M NaHCO₃ at r.t. overnight. The product was purified by ethanol precipitation and run through Bio-Spin® P-6 Columns (SSC buffer).

Figure 14C:
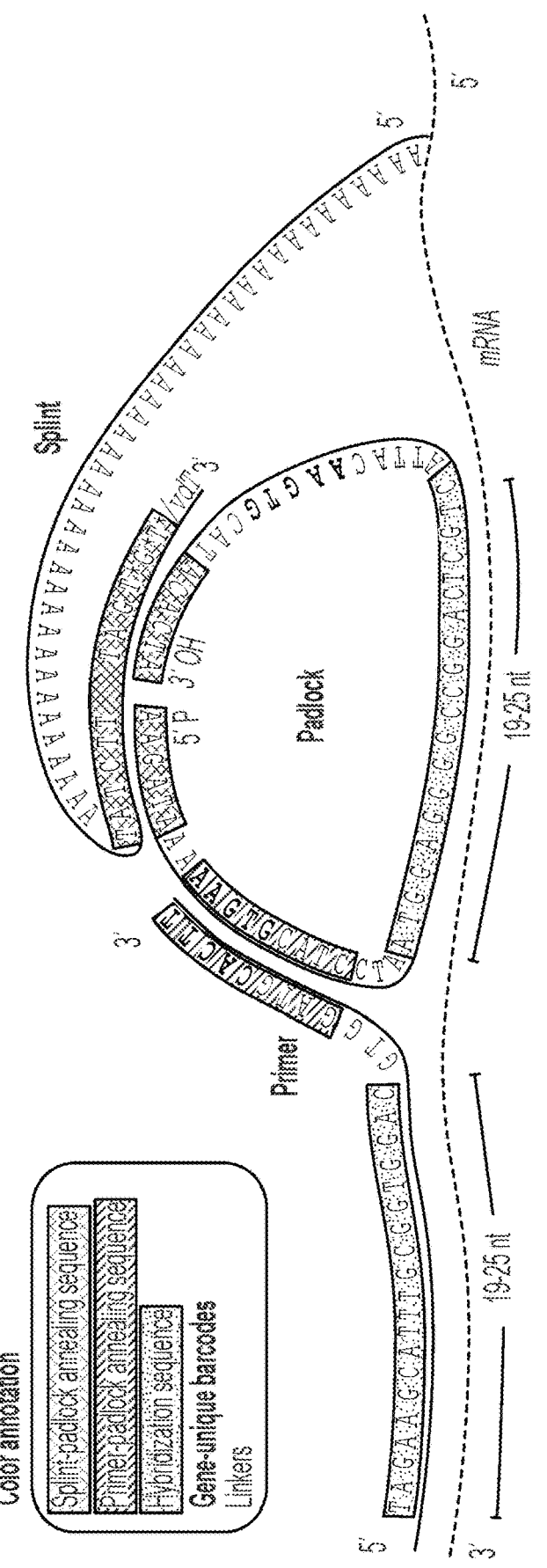
Figure 14D:
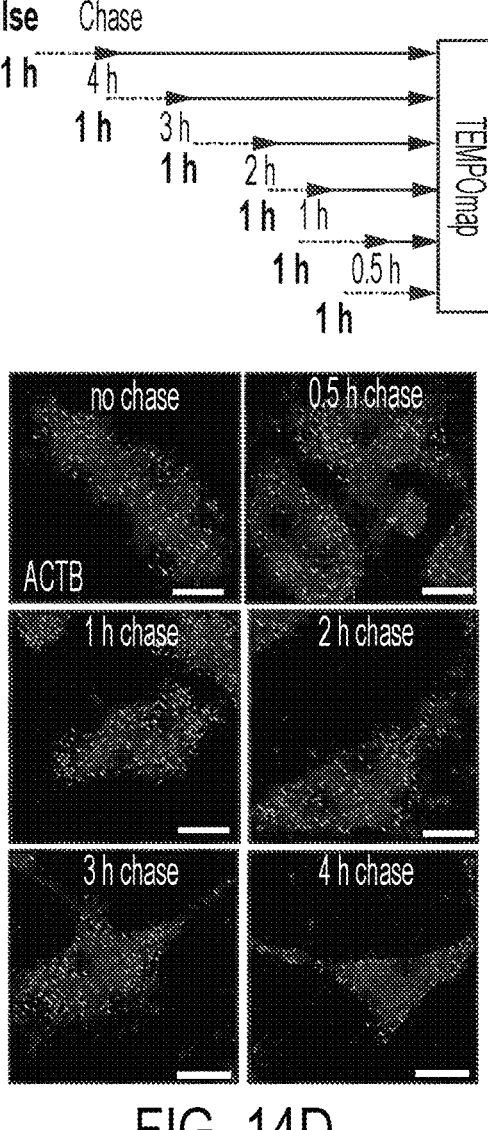

A representative sequence graph is shown in FIG. 14C. The probes were designed as follows: (1) The 5' azide-modified splint is divided into two regions: a linker containing 50 adenosine nucleotides connected to a 12-nt splint-padlock annealing sequence. In order to be protected from enzymatic amplification, the splint contains a 3' terminal inverted dT and the phosphorothioate bonds on the last three nucleotides at the 3'-end of the oligo. The splint-padlock annealing sequence enables the hybridization of the splint with padlock on the same RNA, creating a double-strand DNA region with a "nick" that can be sealed in the ligation step. (2) The 5' phosphorylated padlock is comprised of the complementary splint-padlock annealing sequence, two regions of the same 5-nt barcode, a 10-nt primer-padlock annealing sequence, a 19-25 nt target region for specific RNA binding, and several short linkers. (3) The primer contains another 19-25 nt target region, 2-nt mismatch bases, a 5-nt linker, and a 5-nt gene-unique sequence that is reverse complementary to the barcode on the matching padlock. The two target regions in each set of the primer and the padlock reside 1-2 bases next to each other on the same mRNA species.

The detailed procedure of target region selection on primer and padlock was applied as previously described[13]. In brief, only the shortest isoforms and the coding regions except for non-coding RNAs were considered. Picky 2.2 was used to design the target sequence on each probe pair with the length range of 40-46 nt, and 6 sequences were selected for each gene. The complementary DNA (cDNA) sequences of the selected regions were split into halves of 20-25 nt separated by 0-2 nt, which contained the best match of melting temperature. The probes were pooled, ordered, and manufactured by IDT. The reading and decoding probes used in SEDAL sequencing were designed and ordered according to Wang et al., 2018.

Design and construction of TEMPOmap bi-probes. For constructing TEMPOmap bi-probes (splint and padlock), the design of the splint probe was the same as described in the tri-probe section. Each padlock probe contains a 40-nt target region selected as described in the tri-probe design, and 5 sequences were selected for each gene.

HeLa cell culture and siRNA knockdown. The human HeLa cell line used in this study was purchased from ATCC (CCL-2) and grown in DMEM (Gibco, 11995) media supplemented with 10% FBS. The cells were plated on 24-well pre-treated glass bottom plates (treatment described in the next section) and grown at 37° C. with 5% CO₂ prior to siRNA knockdown. Allstars negative control siRNA from Qiagen (SI03650318) was used as control siRNA in knockdown experiments. YTHDC1 siRNA was ordered from Qiagen (SI04225851). Transfection was conducted by using Lipofectamine RNAiMAX (Invitrogen) for siRNA following the manufacturer's protocol.

For the downstream analyses comparing siControl vs siYTHDC1 (KD) cells, after in situ sequencing and TEMPOmap dataset processing (see below), control and KD cells were first separated based on single-cell YTHDC1 reads normalized against the average RNA expression of the other six functionally related genes targeted by STARmap probes (METTL3/14, YTHDF1-3, YTHDC2, FIG. 14E). The cells were then used with the top 25% normalized YTHDC1 reads as control cells (n~5000), and the bottom 25% as KD cells (n 5000).

TEMPOmap experimental procedure. 24-well glass bottom plates were treated with 1% methacryloxypropyltrimethoxysilane (Bind-Silane) and poly-D-lysine solution sequentially prior to cell plating. Cells were then plated on the coated plates and maintained in growth media (DMEM containing 10% FBS) in a humid culture incubator with 5% CO₂ at 37° C. Pulse-chase experiments were performed with 200 µM 5-EU and washed with cell media for a designated amount of time. After metabolic labeling and washing, the cells were fixed with 1.6% PFA in PBS for 10 min and permeabilized with pre-chilled (−20° C.) methanol for 30 min at −80° C. The samples were then taken from −80° C., equilibrated to r.t., and quenched with buffer containing PBSTR (0.1% Tween-20, 0.1 U/µL SUPERase•In in PBS) supplemented with 10 mM Tris pH 7.5 and 0.1 mg/mL yeast tRNA for 10 min.

To functionalize the nascently ethynylated RNAs, 5' azide-modified DNA splint (5 µM) was added to 1× Lumiprobe click chemistry buffer. CuAAC was initiated by adding ascorbate (800 µM). The reaction mixture was incubated at 37° C. for 1 hr with gentle shaking. The samples were then washed with PBSTR at 37° C. for 10 min twice.

A library of TEMPOmap primer and padlock probes (targeting 991 genes) and a set of STARmap SNAIL probes (targeting METTL3/14, YTHDF1-3) were separately pooled and ordered from IDT. All of the four probe pools were dissolved in ultrapure RNase-free water to 100 nM per oligo for storage. The probe mixtures were then heated at 90° C. for 5 min and cooled on ice. Subsequently, the samples were incubated in 1× hybridization buffer (2×SSC, 10% formamide, 1% Tween-20, 20 mM RVC, 0.1 mg/mL yeast tRNA, 0.2 U/µL SUPERase•In) supplemented with TEMPOmap probes at 2 nM per oligo and STARmap probes at 10 nM per oligo in a 40° C. humidified oven with gentle shaking for 14-16 hr. The samples were then washed with PBSTR twice and high salt buffer (4×SSC in PBSTR) once at 37° C. for 20 min in each wash, and one more PBSTR rinse after the wash. The samples were then incubated with T4 DNA ligation mixture (1:20 dilution of T4 DNA ligase, 1× BSA, and 0.2 U/μL SUPERase•In) in r.t. for 2 hr with gentle shaking, followed by PBSTR wash twice. Subsequently, the samples were incubated with RCA mixture (1:20 dilution of Phi29 DNA polymerase, 250 μM dNTP, 20 μM 5-(3-aminoallyl)-dUTP, 0.2 U/μL SUPERase•In, 1×BSA) at 30° C. for 2 hr with gentle shaking, followed by PBST (0.1% Tween-20 in PBS) wash twice. Next, the samples were treated with 25 mM Methylacrylic acid NHS ester (MA-NHS) in 0.1 M NaHCO₃ in r.t. for 2 hr, followed by PBST wash once.

To cast the gel, the samples were first incubated with monomer buffer (4% acrylamide, 0.2% bis-acrylamide, 2×SSC) supplemented with 0.2% TEMED in r.t. for 15 min. The buffer was removed, and 30 μL polymerization mixture (0.2% ammonium sulfate, 0.2% TEMED dissolved in monomer buffer) was slowly added to the center of the sample, which was immediately covered with Gel Slick-coated coverslip. The sandwiched polymerization mixture was incubated for 1 hr in N₂ followed by PBST wash twice. The gelated samples were then treated with dephosphorylation mixture (1:100× dilution of Antarctic phosphatase, 1×BSA) at r.t overnight, followed by PBST wash twice.

TEMPOmap sample imaging and in situ sequencing. TEMPOmap imaging and in situ sequencing were carried out as described by Wang et al. (2018) with modifications. In brief, six rounds of four-color confocal imaging were performed for 998 gene measurements, plus one last round including the nucleus detection stained with DAPI, cell morphology stained with flamingo, and endoplasmic reticulum (ER) region with Concanavalin A as described by the manufacturers' instructions. Each round of imaging began by incubating the samples with the sequencing mixture (1:25 dilution of T4 DNA ligase, 1×BSA, 10 μM reading probe and 5 μM fluorescent decoding oligos) at r.t. for 3 hr, followed by rinsing with washing and imaging buffer (2×SSC, 10% formamide) three times for 5 min each before imaging. After image acquisition, the samples were treated with the stripping buffer (60% formamide, 0.1% Triton X-100) twice for 10 min, followed by PBST wash three times. After six rounds of imaging, the cell nucleus stained with DAPI, the cytoplasm stained with flamingo fluorescent gel stain, and the ER stained with Concanavalin A were then imaged. Images were acquired using Leica SP8 confocal microscopy with a 405 diode, white light laser, and 40× oil-immersed objective (NA 1.3). For each round, images were acquired with 488 nm, 546 nm, 594 nm, and 647 nm illumination at 30 focal planes. The voxel size of the imaging was 200 nm×200 nm×350 nm.

Image processing and amplicon decoding. Image processing was performed as described in Wang et al. (2018) with modifications. First, an image deconvolution was applied with Huygens Essential v20.10.1p2. The deconvolved images were then normalized by the Min-Max strategy and further adjusted with histogram equalization where images in the first sequencing round were used as reference. In addition, a customized tophat filtering was applied to enhance fluorescence signals. To better identify the barcode of each cDNA amplicon, both a global registration and a non-rigid registration were performed on the preprocessed images. Global image registration was accomplished using a three-dimensional fast Fourier transform (FFT) to compute the cross-correlation between two image volumes at all translational offsets. The position of the maximal correlation coefficient was identified and used to translate image volumes to compensate for the offset. The non-rigid registration was achieved by the 'imregdemons' function in MATLAB 2020b. After registration, individual amplicons were identified in each color channel on the first round of sequencing. For this experiment, amplicon dots were identified by finding local maxima in 3D with MATLAB function 'imregionalmax'. Dots with intensity at their centroids less than the threshold were removed. Based on the estimation of amplicon size, the dominant color for each dot across all four channels on each round was determined by a 5×5×3 voxel volume surrounding the dot centroid. The integrated intensity of the voxel volume in each channel was used for color determination. In this case, each dot in each round had a L2 normalized vector with four elements. The color of each dot was determined by the corresponding channel with the highest value in the vector. Dots with multiple maximum values in the vector were discarded. Then, dots were first filtered based on quality scores (average of −log(color vector value in dominant channel) across all sequencing rounds). The quality score quantified the extent to which each dot on each sequencing round came from one color rather than a mixture of colors. The barcode codebook was converted into color space based on the expected color sequence following the 2-base encoding of the barcode DNA sequence. Dots passed the quality threshold and with a matched barcode sequence in the codebook were kept; all other dots were rejected. Both the physical locations and gene identities of the filtered dots were saved for downstream analysis.

Image segmentation for single cells and subcellular regions. Image segmentation was performed using CellProfiler v4.1.3 and other customized scripts in MATLAB. A 2D reference segmentation mask was generated by a customized pipeline for both the DAPI staining image and the composite image combining amplicon channels and flamingo fluorescent gel staining image.

For 3D segmentation, the images targeting different cellular compartments were first processed by a median filter and binarized with Otsu's method. All connected components (objects) that have fewer than 100 pixels were removed from the binary image. Then, images were dilated with a disk structure element with radius equal to 3. Lastly, a 3D segmentation mask targeting each cellular region was generated by an element-wise multiplication process between the binary image and the 2D reference cell segmentation from the previous step. The nucleus regions were removed from the 3D cell segmentation masks to create the cytoplasm segmentation.

Figure 15B:
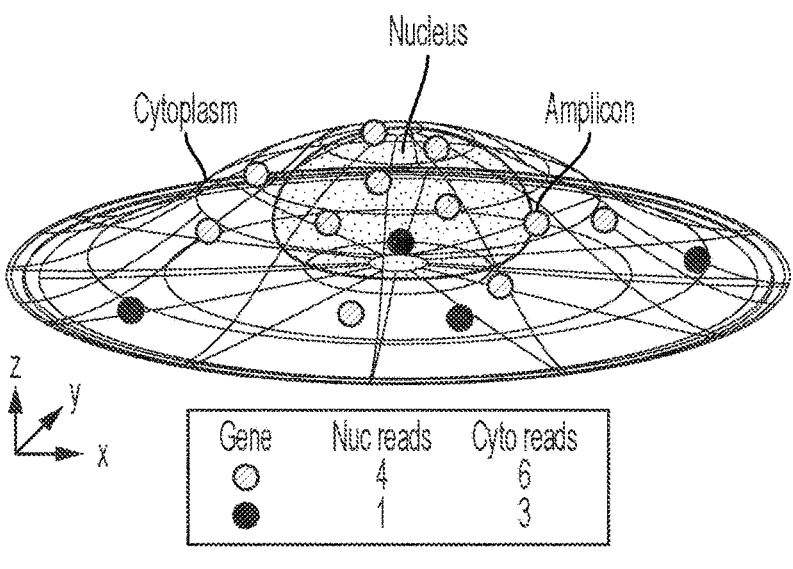
Figure 15C:
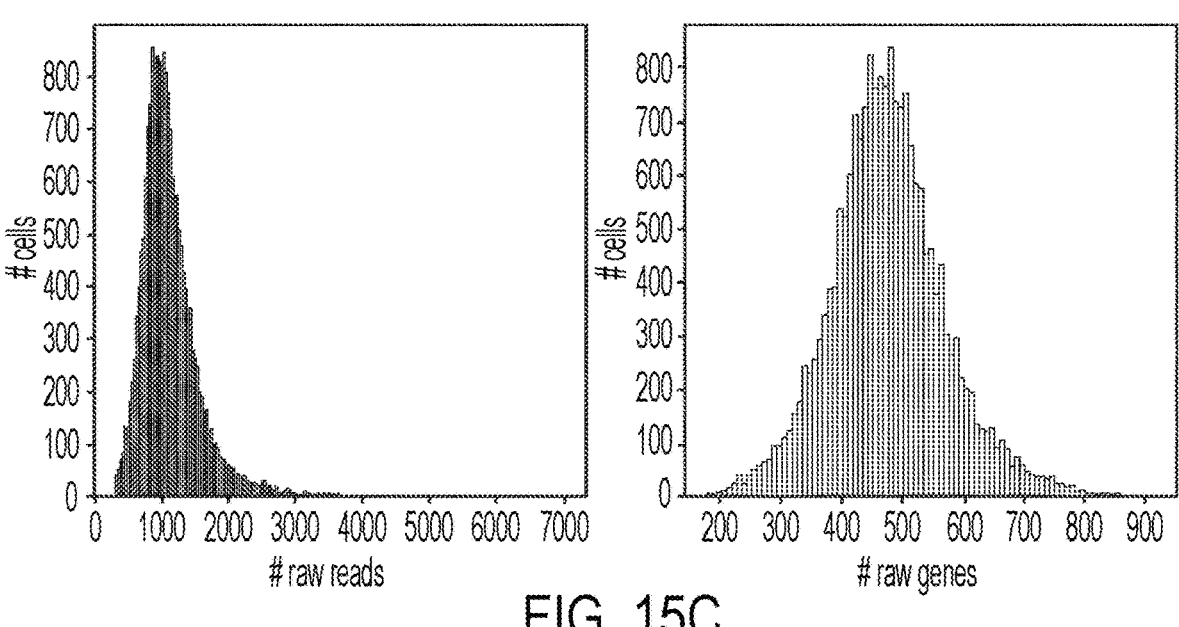

Filtered amplicons overlapping each segmented cell region in 3D were then assigned to the specific subcellular region (FIG. 15B), to compute a per-cell gene expression matrix in each cellular compartment.

Figure 15D:
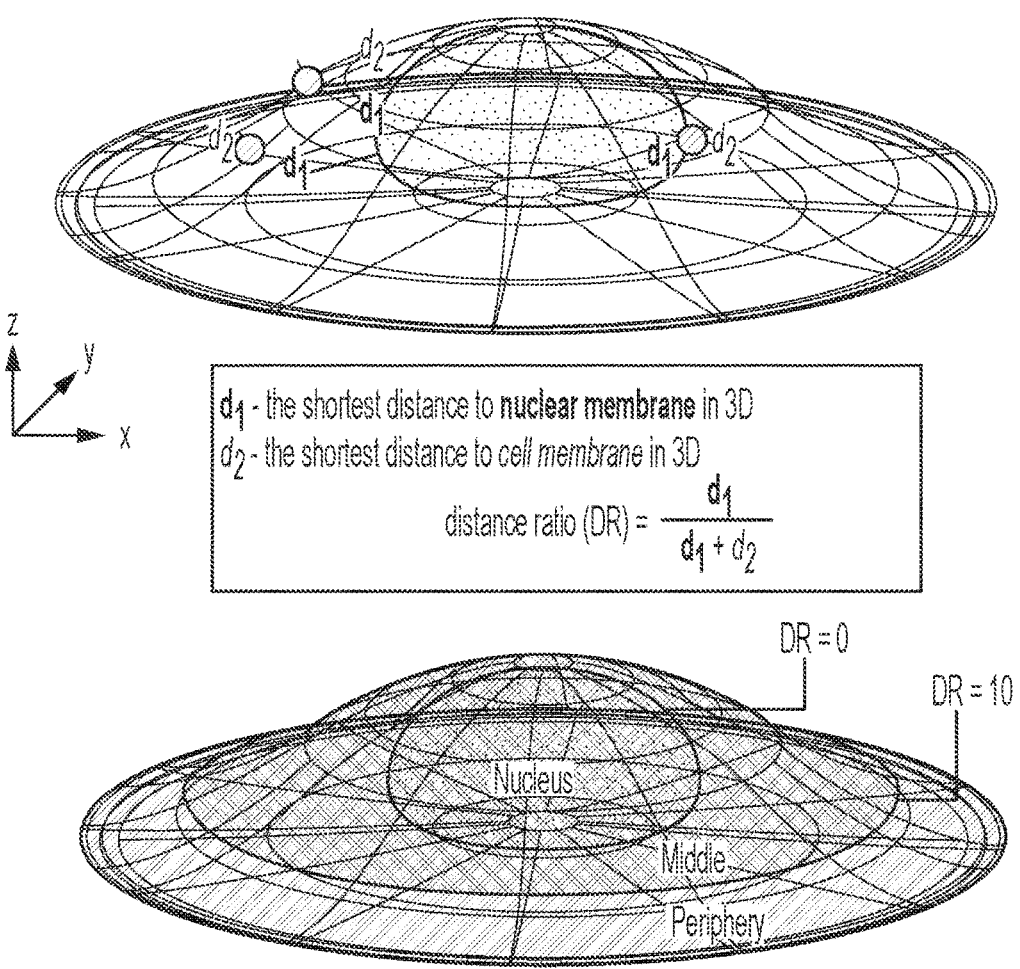

RNA subcellular distribution analysis via distance-ratio (DR) calculation. To quantify the relative location of reads inside the cytoplasm, a distance-ratio (DR) was calculated for each of the cytoplasmic reads. The DR value for an RNA read within a cell was defined as the shortest distance of the read to the nucleus (d₁), defined by nucleus segmentation, normalized by the sum of this distance and the shortest distance to the cell membrane (d₂), defined by cell segmentation (FIG. 15D). The shortest distance was calculated with a Euclidean distance transform function provided in Scipy. A cutoff DR value of 10 was used to further segment the cytoplasmic region into 'middle' and 'periphery' for a detailed examination of the subcellular distribution RNA reads across time points in TEMPOmap dataset.

Figure 16A:
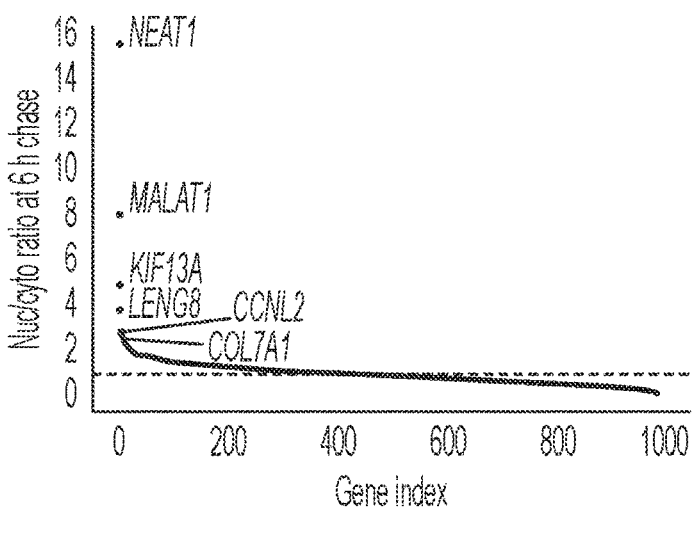
FIGS. 16A-16D show RNA subcellular analysis and cell-cycle phase identification.
Figures 16B, 16C:
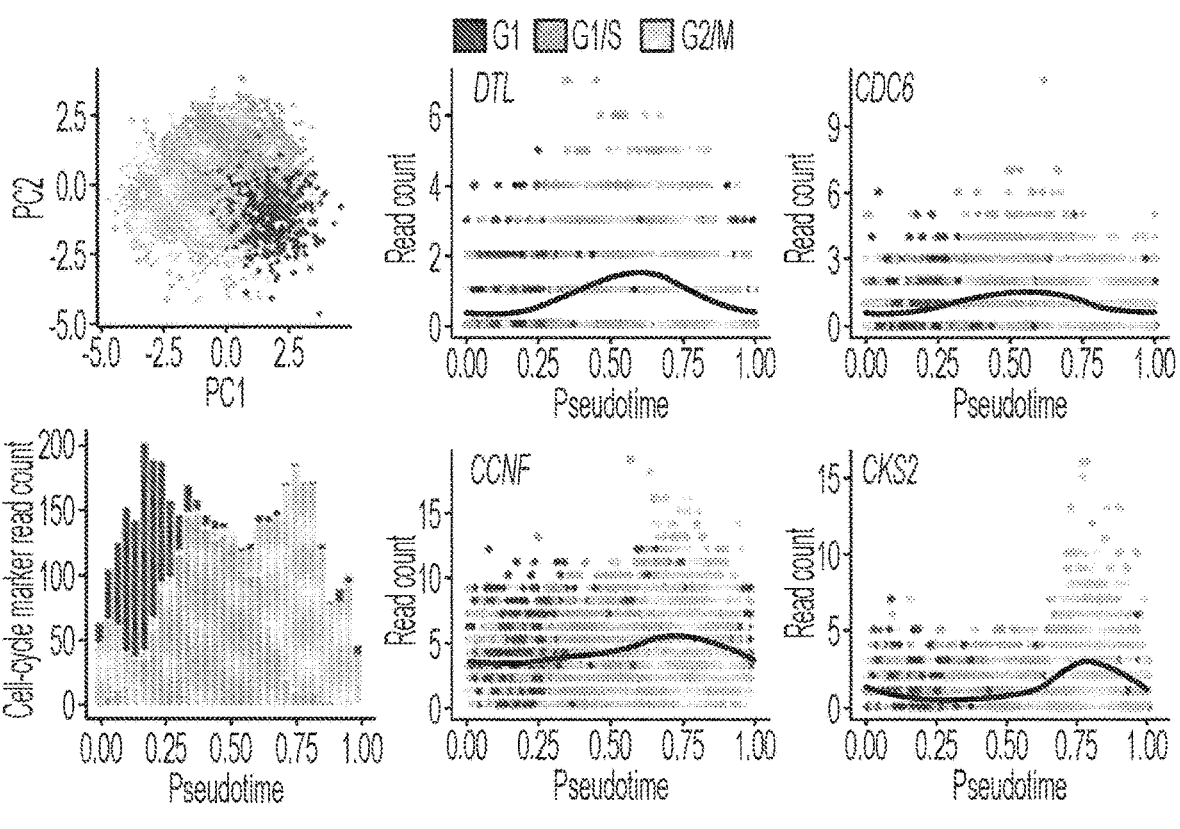
Figure 16D:
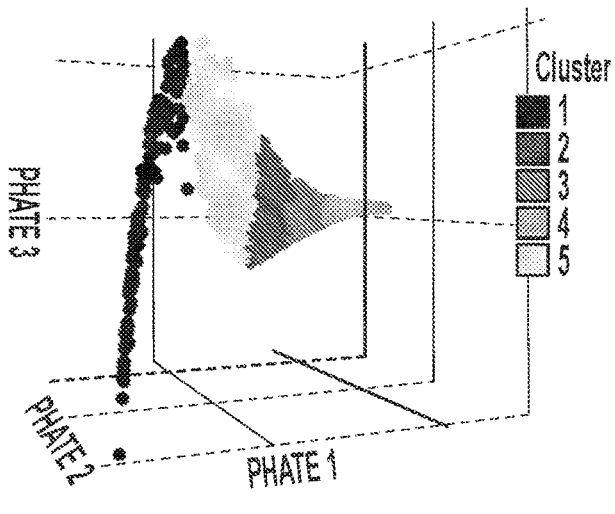

Dynamic modeling of RNA cytoplasmic translocation (γ). RNA cytoplasmic translocation parameter γ was estimated with a linear regression on mean DR value (details described above) for each gene across different pulse-chase time points (FIG. 16B). For each gene, the DR values of all the reads in all of the corresponding cells were averaged for the mean DR value to represent its cytoplasmic localization at a particular time point. Linear regression was performed across all time points for each gene using the 'linregress' function of Scipy in Python.

Cell clustering visualization via PHATE based on single-cell and subcellular-resolved gene expression matrix. Single cell clustering was performed on the cell-by-gene expression matrix, normalized to a same number of cell total reads. Subcellular-resolved clustering was performed on a horizontally concatenated nuclear and cytoplasmic expression matrix, both of identical dimension as the cell-by-gene expression matrix, and normalized in the same method as above. For both matrices, PHATE (Potential of Heat-diffusion for Affinity-based Trajectory Embedding) was used as the clustering and visualization method, which has been shown to preserve both local and global structure of the data. A neighbor parameter of 30 in PHATE was used in both analyses.

RNA degradation kinetics vector visualization and transcriptomic vector field animation by dynamo. The arrows overlaid with dots on the PHATE coordinates (FIG. 11E, I and III) were constructed by modeling the transcriptomic dynamics considering total RNA degradation kinetics in single cells. The total RNA degradation rates for vector visualization were estimated by −degradation rate*nascent RNAs.

The transcriptome vector field animation was constructed from the same RNA degradation kinetics as described above using dynamo[35].

Cell-cycle phase classification and validation. The three cell-cycle phases of single cells (G1, G1/S, G2/M) were classified using the TEMPOmap nascent RNA expression via the cell-cycle scoring function 'score_genes_cell_cycle' in scanpy. To validate whether 1 hr-labeled nascent transcriptome can accurately assign cell-cycle phases, the cell-cycle scoring analysis was repeated using 1 hr-pulse and total transcripts (22 hr-pulse and 0 hr-chase) from the previously published scEU-seq dataset, and a correlation analysis of the assigned cell-cycle results was conducted (FIG. 16C).

Dynamic Modeling and Fitting of RNA Synthesis (α), Degradation (β, βn, βc) and Export (λ) Constants Calculating RNA concentrations. After obtaining RNA copy numbers of each of the 991 genes in the nucleus and cytoplasm of single cells, the reads were first normalized across different chase time points against the averaged reads of six control genes (i.e., genes targeted by STARmap probes: METTL3, METTL14, YTHDC2, YTHDF1-3), which were assumed to display uniform expression under different pulse-chase conditions since the total RNAs of each gene were targeted. Normalized RNA copy numbers in each assigned region (FIG. 15B) were then divided by unit cell volume (in voxels), unit nuclear volume (in voxels), and unit cytoplasmic volume (in voxels), in order to calculate the RNA concentrations in single cell (X(t)), nucleus (N(t)), and cytoplasm (C(t)), respectively. RNA concentrations have a unit in reads/voxel and will be denoted as [RNA] in the following section.

Modeling. Let a be the transcription constant ([RNA]/h), β be the whole-cell degradation constant (1/h), βn be the nuclear degradation constant (1/h), λ be the export constant (1/h), and βc be the cytoplasmic degradation constant (1/h).

X(t) at 1 hr pulse is described by a first-degree dynamic equation:

$$dX(t)dt = \alpha - \beta * X(t) \tag{1}$$

and the time evolution of X(t) during the subsequent chase time points is described by:

$$dX(t)dt = -\beta * X(t) \tag{2}$$

where it was assumed that there is no new RNA synthesized after 1 hr pulse. Using equations (1) and (2), time-dependent α and β from whole-cell RNA concentration were estimated for each gene, where it was assumed that α and β are approximately constant during the pulse and chase period.

Next, to estimate the rest of the dynamic parameters (βn, λ, and βc), it was assumed that after transcription, RNA can be either degraded in nucleus or exported to cytoplasm, which can be mathematically combined into one parameter p (nuclear processing constant). Thus, the time evolution of N(t) is described by:

$$dN(t)dt = -p * N(t) \tag{3}$$

whereas $$p = \beta n + \lambda \tag{4}$$

where it was assumed that (1) all cellular RNAs travel unidirectionally from nucleus to cytoplasm, so the values of λ are all positive; (2) βn, λ, and βc are time-dependent and constant. Using equation (3), p was estimated for each gene. Next, an assumption that the whole-cell degradation rate is equal to the sum of nuclear degradation and cytoplasmic degradation was made. Therefore, the following formula is given:

$$X(t) * \beta = N(t) * \beta n + C(t) * \beta c \tag{5}$$

On the basis of (4), $$X(t) * \beta = N(t) * (p - \lambda) + C(t) * \beta c \tag{6}$$

The cytoplasmic degradation (βc) and export (λ) were thus estimated. With p estimated for each gene, the nuclear degradation (βn) was then calculated. It should be noted that the data at 1 hr pulse-1 hr chase condition was found to be an outlier of the linear model, potentially because of residual EU in the cells after washing. Therefore, the cells were removed from 1 hr chase, and only the cells from 0, 2, 4, 6 hr chase were used for modeling.

Fitting and thresholding. For the estimated β and p, the fitting of the model to the data was evaluated using $R^2$. The model was thus restricted to genes that (1) exhibit positive values of all the estimated parameters, thereby removing all the genes that have at least one parameter of negative value; and (2) have $R^2 >= 0.5$ when fitting equation (2) and (3) to estimate β and p to the corresponding data, respectively.

Constant degradation ($\beta$) and nuclear processing (p) coefficient in RNA concentration over time were thus assumed. 915 genes that passed the fitting threshold for all 5 parameters were obtained when all cell-cycle phases were combined, and 808 genes for all 15 parameters (5 parameters across three phases) were obtained when cells were separated into different phases.

Validation of kinetic parameter estimation. To validate these models, the calculation of synthesis ($\alpha$) and whole-cell degradation ($\beta$) was repeated using RNA copy numbers per cell of TEMPOmap dataset and the published scEU-seq dataset (1 hr pulse, 0, 2, 4, 6 hr chase), where 549 overlapping genes were obtained. The results from these two datasets were then compared by dimensionality reduction and gene clustering, and the z-scores derived from the variation of estimated rates of the gene clusters were visualized by heat map (FIGS. 18H-18J). The method details of gene clustering and visualization are described in the next section.

Kinetic parameter correlation and clustering analyses. Matrices describing pairwise correlation coefficients of the estimated kinetic parameters were constructed for both cell-cycle-combined 6 parameters (consisting of 915 genes) and cell-cycle-resolved 18 parameters (consisting of 808 genes) using R, which were then visualized by scatter plot matrix (FIG. 12C) and heat map (FIG. 12D), respectively. Some key examples of the correlations of cell-cycle-resolved 18 parameters were also visualized as scatter plots in FIGS. 18A-18F.

Dimensionality reduction was next performed on the cell-cycle-resolved 18 kinetic parameters of 808 genes using UMAP and then gene clustering by Louvain embedded in Seurat v4 based on UMAP, where four gene clusters were identified. It was noted that the range across kinetic parameters varies more greatly than the variance of the same parameter in different cell-cycle phases. Therefore, to better visualize the kinetic differences among the four clusters, z-scores were computed for each kinetic parameter calculated of all genes among the three cell-cycle phases, and the z-scores were plotted as a heat map in FIG. 12E, right.

For each of the four clusters identified by UMAP analysis, gene ontology (GO) was performed on the genes in each of the four clusters identified by UMAP analysis against TEMPOmap 991-gene list as the background using DAVID (david.ncifcrf.gov/content.jsp?file=citation.htm). All the GO terms with statistical significance (p value is close to or below 0.05) are shown in FIG. 12F.

Visualization of the four clusters in representative cells was performed using customized scripts in Python.

Co-variation analysis of single-cell nascent RNA expression over time. For the co-variation analysis in single-cell RNA expression across time (FIG. 13A, FIG. 19A), a matrix describing the correlation of expression level between each gene pair was first constructed using all the cells from 0, 2, 4 and 6 hr chase. A hierarchical clustering was then conducted to organize the genes based on their correlation coefficients in these time-combined cells using R. The matrix was re-ordered by the clustering result and visualized by heat map (FIG. 13A, left). Heat maps describing the correlation coefficients of expression level in each individual time point were then created while retaining the same grouping and ordering of the genes in all of the matrices (FIG. 19A). Comparing the heat maps across the four time points, two small gene clusters were identified (annotated as 1 and 2 in FIG. 13A) that showed correlated expressions when combining all the time points but also varied along individual time points (FIG. 19A). GO analysis was performed on the genes in each of the two clusters against the background gene list as described above using DAVID.

m$^6$A and YTHDC1 target identification in TEMPOmap gene list. For m$^6$A-related gene labels, genes encoding high-confidence m$^6$A-modified transcripts were identified by previously reported PAR-CLIP and immunoprecipitation (IP) data. Briefly, m$^6$A-RNA was defined as (1) having an enrichment at least one-fold in non-fragmented m$^6$A RIP-seq, and (2) transcripts that were bound in each replicate of PAR-CLIP. Similarly, non m$^6$A-RNA was defined as (1) having an enrichment <0 in non-fragmented m$^6$A RIP-seq and (2) transcripts that have no peak in either replicate of PAR-CLIP. Using these criteria, 573 genes encoding m$^6$A-RNA and 111 genes encoding non m$^6$A-RNA were identified from the TEMPOmap gene list.

For YTHDC1 target-related gene labels, genes encoding high-confidence targets were identified by previously reported YTHDC1 PAR-CLIP and IP data. Briefly, YTHDC1 targets were defined as (1) having an enrichment at least one-fold in YTHDC1-IP measurements and (2) p value is significant in IP measurements and (3) transcripts that were bound in each replicate of PAR-CLIP. Then, non-targets were defined as (1) having an enrichment <0 in non-fragmented m$^6$A RIP-seq and (2) transcripts that have no peak in either replicate of PAR-CLIP. Using these criteria, 158 genes encoding target transcripts and 160 genes encoding non-targets were identified.

Example 7: In Vivo TEMPOmap

Figure 20A:
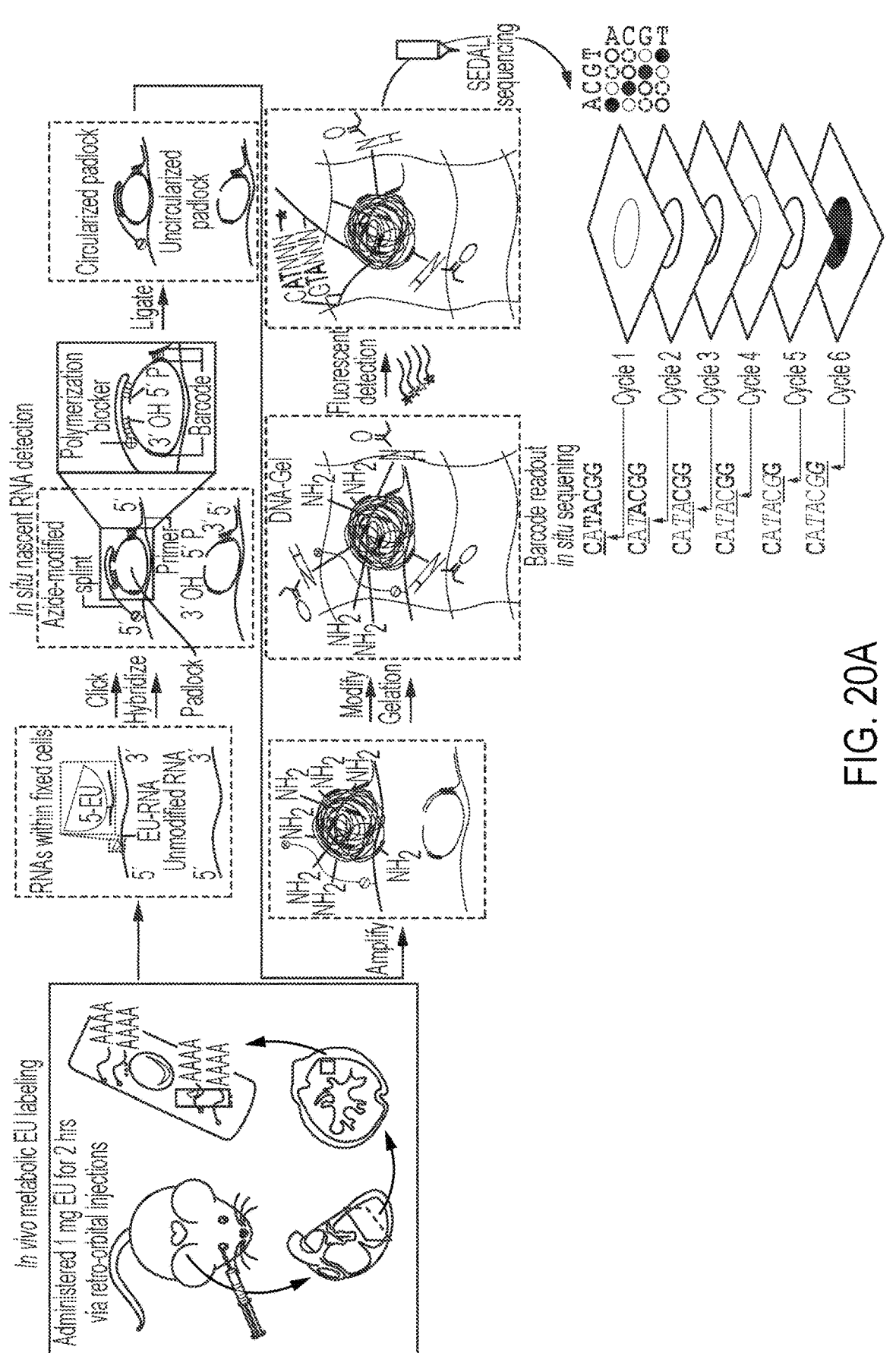
FIGS. 20A-20B show the principles of in vivo TEM-POmap. Nascent RNA labeling chemistry in tissue sections for spatiotemporally resolved transcriptomics of metaboli-cally-labeled live animals is shown.
Figure 20B:
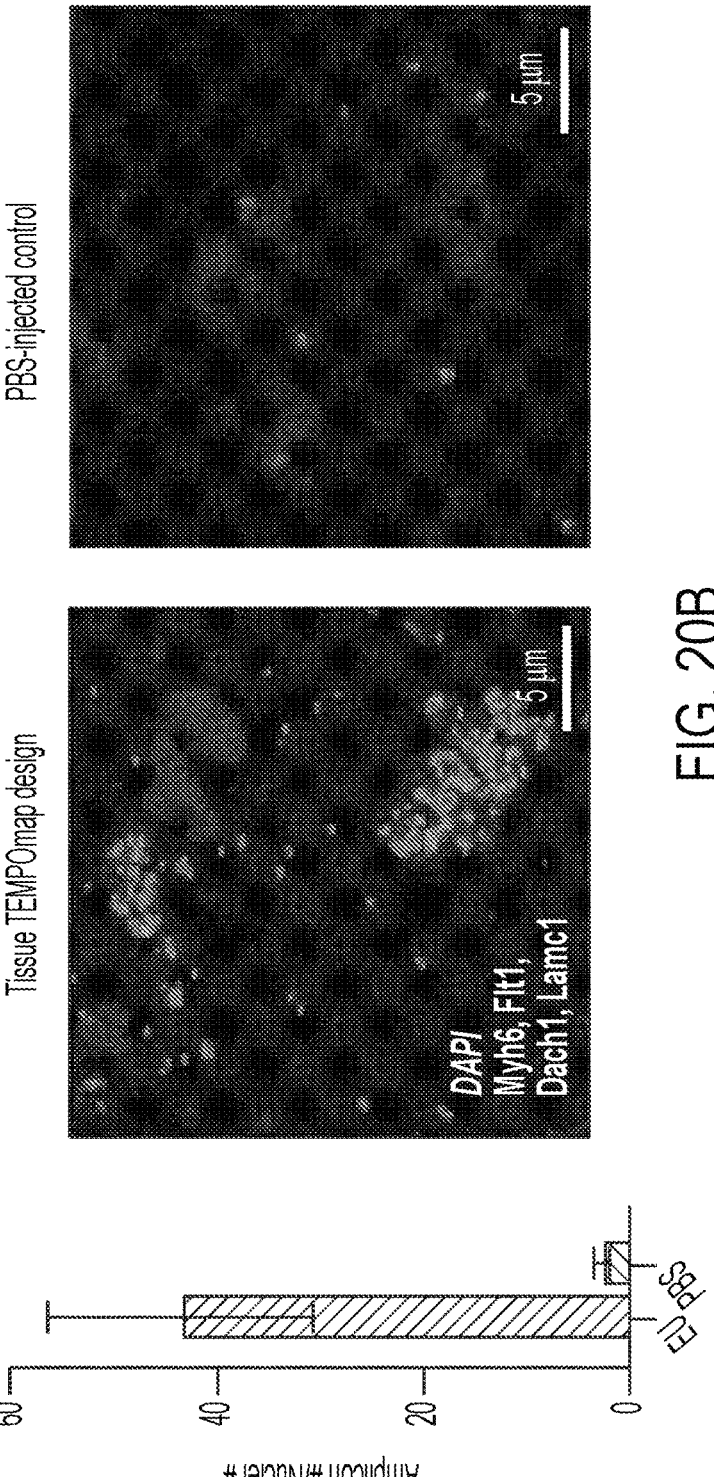

TEMPOmap was next tested in vivo in order to resolve spatiotemporal transcriptomics in tissues (e.g., heart tissue) of whole animals. To this end, 1 mg of EU was injected into a mouse via retro-orbital administration, and organs were harvested two hours later. A PBS-administered mouse was used as a control. The organs (e.g., the heart) were cryosectioned into 20 μm tissues, which were chemically processed using the TEMPOmap workflow (FIG. 20A). The applicability of TEMPOmap in vivo in heart tissue sections is shown. Targeting of four genes that are highly expressed in the heart (Myh6, Flt1, Dach1, and Lamc1) is shown in FIG. 20B. The results showed significant enrichment of nascently-transcribed RNA signals compared to PBS-administered control tissues, and thus demonstrate the capability of TEMPOmap for detecting and measuring metabolically-labeled RNAs on tissue sections of living animals. The TEMPOmap method can thus be applied in vivo to resolve multiplexed spatiotemporal transcriptomics in systems, tissues, organoids, and organs.

REFERENCES

1. Wang, X. et al. Three-dimensional intact-tissue sequencing of single-cell transcriptional states. *Science* 361, eaat5691 (2018).
2. Codeluppi, S. et al. Spatial organization of the somatosensory cortex revealed by osmFISH. *Nat. Methods* 15, 932 (2018).
3. Moffitt, J. R. et al. Molecular, spatial, and functional single-cell profiling of the hypothalamic preoptic region. *Science* 362, eaau5324 (2018).
4. Shah, S., Lubeck, E., Zhou, W. & Cai, L. In situ transcription profiling of single cells reveals spatial organization of cells in the mouse hippocampus. *Neuron* 92, 342 (2016).

5. Achim, K., Pettit, J., Saraiva, L. et al. High-throughput spatial mapping of single-cell RNA-seq data to tissue of origin. *Nat Biotechnol* 33, 503 (2015).

6. Lee, J. et al. Highly Multiplexed Subcellular RNA Sequencing in Situ. *Science* 343, 1360 (2014).

7. Stahl, P. et al. Visualization and analysis of gene expression in tissue sections by spatial transcriptomics. *Science* 353, 78 (2016).

8. Zechel, S., Zajac, P., Lönnerberg, P. et al. Topographical transcriptome mapping of the mouse medial ganglionic eminence by spatially resolved RNA-seq. *Genome Biol* 15, 486 (2014).

9. Gao, S., Yan, L., Wang, R. et al. Tracing the temporal-spatial transcriptome landscapes of the human fetal digestive tract using single-cell RNA-sequencing. *Nat Cell Biol* 20, 721 (2018).

10. Chen, K. et al. Spatially resolved, highly multiplexed RNA profiling in single cells. *Science* 348, 6233 (2015).

11. Crosetto, N., Bienko, M. & van Oudenaarden, A. Spatially resolved transcriptomics and beyond. *Nat Rev Genet* 16, 57 (2015).

12. Battich, N. et al. Sequencing metabolically labeled transcripts in single cells reveals mRNA turnover strategies. *Science* 367, 1151 (2020).

13. Wang, X. et al. Three-dimensional intact-tissue sequencing of single-cell transcriptional states. *Science* (80), 361 (2018).

14. Chen, K. H., Boettiger, A. N., Moffitt, J. R., Wang, S. & Zhuang, X. Spatially resolved, highly multiplexed RNA profiling in single cells. *Science* (80), 348, aaa6090-aaa6090 (2015).

15. Codeluppi, S. et al. Spatial organization of the somatosensory cortex revealed by osmFISH. *Nat. Methods* 15, 932-935 (2018).

16. Stihl, P. L. et al. Visualization and analysis of gene expression in tissue sections by spatial transcriptomics. *Science* vol. 353, 78-82 (2016).

17. Lee, J. H. et al. Highly multiplexed subcellular RNA sequencing in situ. *Science* (80). 343, 1360-1363 (2014).

18. Shah, S., Lubeck, E., Zhou, W. & Cai, L. In Situ Transcription Profiling of Single Cells Reveals Spatial Organization of Cells in the Mouse Hippocampus. *Neuron* 92, 342-357 (2016).

19. Stickels, R. R. et al. Highly sensitive spatial transcriptomics at near-cellular resolution with Slide-seqV2. *Nat. Biotechnol.* 39, 313-319 (2021).

20. Buxbaum, A. R., Haimovich, G. & Singer, R. H. In the right place at the right time: Visualizing and understanding mRNA localization. *Nature Reviews Molecular Cell Biology* vol. 16 95-109 (2015).

21. Erhard, F. et al. scSLAM-seq reveals core features of transcription dynamics in single cells. *Nature* 571, 419-423 (2019).

22. Qiu, Q. et al. Massively parallel and time-resolved RNA sequencing in single cells with scNT-seq. *Nat. Methods* 17, 991-1001 (2020).

23. Cao, J., Zhou, W., Steemers, F., Trapnell, C. & Shendure, J. Sci-fate characterizes the dynamics of gene expression in single cells. *Nat. Biotechnol.* 38, 980-988 (2020).

24. Hendriks, G.-J. et al. NASC-seq monitors RNA synthesis in single cells. *Nat. Commun.* 10, 3138 (2019).

25. Battich, N. et al. Sequencing metabolically labeled transcripts in single cells reveals mRNA turnover strategies. *Science* (80). 367, 1151 (2020).

26. Braselmann, E., Rathbun, C., Richards, E. M., & Palmer, A. E. Illuminating RNA Biology: Tools for Imaging RNA in Live Mammalian Cells. *Cell Chem. Biol.* 27, 891-903 (2020).

27. Jao, C. Y. & Salic, A. Exploring RNA transcription and turnover in vivo by using click chemistry. *Proc. Natl. Acad. Sci.* 105, 15779-15784 (2008).

28. Rabani, M. et al. Metabolic labeling of RNA uncovers principles of RNA production and degradation dynamics in mammalian cells. *Nat. Biotechnol.* 29, 436-442 (2011).

29. Djebali, S. et al. Landscape of transcription in human cells. *Nat.* 2012 4897414 489, 101-108 (2012).

30. Bhatt, D. M. et al. Transcript Dynamics of Proinflammatory Genes Revealed by Sequence Analysis of Subcellular RNA Fractions. *Cell* 150, 279-290 (2012).

31. Battich, N., Stoeger, T., & Pelkmans, L. Control of Transcript Variability in Single Mammalian Cells. *Cell* 163, 1596-1610 (2015).

32. Bahar Halpern, K. et al. Nuclear Retention of mRNA in Mammalian Tissues. *Cell Rep.* 13, 2653-2662 (2015).

33. Moon, K. R. et al. Visualizing structure and transitions in high-dimensional biological data. *Nat. Biotechnol.* 2019 3712 37, 1482-1492 (2019).

34. Qiu, X. et al. Mapping transcriptomic vector fields of single cells. *Cell* (2022) doi:10.1016/J.CELL.2021.12.045.

35. La Manno, G. et al. RNA velocity of single cells. *Nature* 560, 494-498 (2018).

36. Bergen, V., Lange, M., Peidli, S., Wolf, F. A. & Theis, F. J. Generalizing RNA velocity to transient cell states through dynamical modeling. *Nat. Biotechnol.* 38, 1408-1414 (2020).

37. Tirosh, I. et al. Dissecting the multicellular ecosystem of metastatic melanoma by single-cell RNA-seq. *Science* (80), 352, 189-196 (2016).

38. Sharp, J. A., Perea-Resa, C., Wang, W. & Blower, M. D. Cell division requires RNA eviction from condensing chromosomes. *J. Cell Biol.* 219 (2020).

39. Tanenbaum, M. E., Stern-Ginossar, N., Weissman, J. S., & Vale, R. D. Regulation of mRNA translation during mitosis. *Elife* 4 (2015).

40. Xia, C., Fan, J., Emanuel, G., Hao, J., & Zhuang, X. Spatial transcriptome profiling by MERFISH reveals subcellular RNA compartmentalization and cell cycle-dependent gene expression. *Proc. Natl. Acad. Sci. U.S.A.* 116, 19490-19499 (2019).

41. Chen, T. & Steensel, B. van. Comprehensive analysis of nucleocytoplasmic dynamics of mRNA in Drosophila cells. *PLOS Genet.* 13, e1006929 (2017).

42. Berry, S., Müller, M., & Pelkmans, L. Nuclear RNA concentration coordinates RNA production with cell size in human cells. *bioRxiv* 2021.05.17.444432 (2021) doi: 10.1101/2021.05.17.444432.

43. Padovan-Merhar, O. et al. Single Mammalian Cells Compensate for Differences in Cellular Volume and DNA Copy Number through Independent Global Transcriptional Mechanisms. *Mol. Cell* 58, 339-352 (2015).

44. Shi, H., Wei, J. & He, C. Where, When, and How: Context-Dependent Functions of RNA Methylation Writers, Readers, and Erasers. *Mol. Cell* 74, 640-650 (2019).

45. Roundtree, I. A., Evans, M. E., Pan, T. & He, C. Dynamic RNA Modifications in Gene Expression Regulation. *Cell* 169, 1187-1200 (2017).

46. Wang, X. et al. N6-methyladenosine-dependent regulation of messenger RNA stability. *Nature* 505, 117-120 (2014).

47. Roundtree, I. A. et al. YTHDC1 mediates nuclear export of N6-methyladenosine methylated mRNAs. *Elife* 6, (2017).

48. Schwanhüusser, B. et al. Global quantification of mammalian gene expression control. *Nature* 473, 337-342 (2011).

49. Dixit, A. et al. Perturb-Seq: Dissecting Molecular Circuits with Scalable Single-Cell RNA Profiling of Pooled Genetic Screens. *Cell* 167, 1853-1866.e17 (2016).

50. Akbalik, G. et al. Visualization of newly synthesized neuronal RNA in vitro and in vivo using click-chemistry. *RNA Biol.* 14, 20-28 (2017).

51. Sant, L. J. van't, White, J. J., Hoeijmakers, J. H. J., Vermeij, W. P. & Jaarsma, D. In vivo 5-ethynyluridine (EU) labelling detects reduced transcription in Purkinje cell degeneration mouse mutants, but can itself induce neurodegeneration. *Acta Neuropathol. Commun.* 2021 91 9, 1-20 (2021).

INCORPORATION BY REFERENCE

The present application refers to various issued patent, published patent applications, scientific journal articles, and other publications, all of which are incorporated herein by reference. The details of one or more embodiments of the invention are set forth herein. Other features, objects, and advantages of the invention will be apparent from the Detailed Description, the Figures, the Examples, and the Claims.

EQUIVALENTS AND SCOPE

In the articles such as "a," "an," and "the" may mean one or more than one unless indicated to the contrary or otherwise evident from the context. Embodiments or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claims that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the embodiments. Because such embodiments are deemed to be known to one of ordinary skill in the art, they may be excluded even if the exclusion is not set forth explicitly herein. Any particular embodiment of the invention can be excluded from any embodiment, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended embodiments. Those of ordinary skill in the art will appreciate that various changes and modifications to this description may be made without departing from the spirit or scope of the present invention, as defined in the following claims.

What is claimed is:

1. A method for profiling spatiotemporal gene expression in a cell, the method comprising:

a) incubating a cell in the presence of a pool of nucleoside analogs for an amount of time $t_1$ to metabolically label nucleic acids synthesized by the cell, wherein each nucleoside analog in the pool of nucleoside analogs comprises a reactive chemical moiety;

b) contacting the metabolically labeled nucleic acids with a population of first oligonucleotide probes, wherein each first oligonucleotide probe in the population of first oligonucleotide probes comprises a chemical moiety that reacts with the reactive chemical moiety of the nucleoside analogs;

c) contacting the metabolically labeled nucleic acids with one or more pairs of oligonucleotide probes comprising a second oligonucleotide probe and a third oligonucleotide probe, wherein:

i) the second oligonucleotide probe comprises a barcode sequence and a portion that is complementary to a metabolically labeled nucleic acid of interest; and ii) the third oligonucleotide probe comprises a portion that is complementary to the metabolically labeled nucleic acid of interest, a first barcode sequence, a portion that is complementary to a first oligonucleotide probe in the population of first oligonucleotide probes, and a second barcode sequence, wherein the first barcode sequence of the third oligonucleotide probe is complementary to the barcode sequence of the second oligonucleotide probe;

d) ligating the 5' end and the 3' end of the third oligonucleotide probe together to produce a circular oligonucleotide;

e) performing rolling circle amplification to amplify the circular oligonucleotide using the second oligonucleotide probe as a primer to produce one or more concatenated amplicons;

f) embedding the one or more concatenated amplicons in a polymer matrix;

g) contacting the one or more concatenated amplicons embedded in the polymer matrix with a fourth oligonucleotide probe comprising a sequence that is complementary to the second barcode sequence of the third oligonucleotide probe; and h) imaging the fourth oligonucleotide probe to determine the location of the one or more concatenated amplicons embedded in the polymer matrix.

2. The method of claim 1 further comprising repeating steps (a)-(h) at least one time for a different amount of time $t_2$ to profile the spatiotemporal expression of the labeled nucleic acids of interest.

3. The method of claim 1, wherein spatiotemporal gene expression is profiled in multiple cells simultaneously.

4. The method of claim 3, wherein the cells comprise a plurality of cell types.

5. The method of claim 1, wherein the cell is present within an intact tissue.

6. The method of claim 5, wherein the tissue is in vivo during the incubating of step (a) and prior to the contacting of step (b).

7. The method of claim 1, wherein spatiotemporal gene expression is profiled for up to 1000 metabolically labeled nucleic acids of interest simultaneously.

8. The method of claim 1, wherein the metabolically labeled nucleic acid of interest is nascent RNA, messenger RNA (mRNA), transfer RNA (tRNA), or ribosomal RNA (rRNA).

9. The method of claim 1, wherein the reactive chemical moiety of each nucleoside analog in the pool of nucleoside analogs is a reactive bioorthogonal functional group, and wherein the chemical moiety of each first oligonucleotide probe in the population of first oligonucleotide probes is a reactive bioorthogonal functional group.

10. The method of claim 1, wherein each first oligonucleotide probe in the population of first oligonucleotide probes further comprises a polymerization blocker.

11. The method of claim 1, wherein each first oligonucleotide probe in the population of first oligonucleotide probes comprises the structure:

5'-[reactive chemical moiety]-[poly-A linker sequence]-[portion complementary to third oligonucleotide probe]-[polymerization blocker]-3', wherein ]-[ comprises an optional nucleotide linker.

12. The method of claim 1, wherein the second oligonucleotide probe comprises the structure:

5'-[portion complementary to metabolically labeled nucleic acid of interest]-[barcode sequence]-3', wherein ]-[ comprises an optional nucleotide linker.

13. The method of claim 1, wherein the portion of the third oligonucleotide probe that is complementary to a first oligonucleotide probe in the population of first oligonucleotide probes is split between the 5' end and the 3' end of the third oligonucleotide probe.

14. The method of claim 1, wherein the third oligonucleotide probe comprises the structure:

5'-[first portion complementary to a first oligonucleotide probe]-[first barcode sequence]-[portion complementary to metabolically labeled nucleic acid of interest]-[second barcode sequence]-[second portion complementary to a first oligonucleotide probe]-3', wherein ]-[ comprises an optional nucleotide linker.

15. The method of claim 1, wherein the step of performing rolling circle amplification further comprises providing amine-modified nucleotides, wherein the amine-modified nucleotides are incorporated into the one or more concatenated amplicons.

16. The method of claim 15, wherein the step of embedding the one or more concatenated amplicons in a polymer matrix comprises reacting the amine-modified nucleotides of the one or more concatenated amplicons with methacrylic acid N-hydroxysuccinimide and co-polymerizing the one or more concatenated amplicons and the polymer matrix.

17. The method of claim 1, wherein the second barcode sequence of the third oligonucleotide probe is a gene-specific sequence used to identify the metabolically labeled nucleic acid of interest.

18. The method of claim 1, wherein the step of contacting the one or more concatenated amplicons embedded in the polymer matrix with the fourth oligonucleotide probe is performed to identify the metabolically labeled nucleic acid of interest.

19. A plurality of oligonucleotide probes comprising a first oligonucleotide probe, a second oligonucleotide probe, and a third oligonucleotide probe, wherein i) the first oligonucleotide probe comprises a reactive chemical moiety;

ii) the second oligonucleotide probe comprises a barcode sequence and a portion that is complementary to a metabolically labeled nucleic acid of interest; and iii) the third oligonucleotide probe comprises a portion that is complementary to the metabolically labeled nucleic acid of interest, a first barcode sequence, a portion that is complementary to the first oligonucleotide probe, and a second barcode sequence, wherein the first barcode sequence of the third oligonucleotide probe is complementary to the barcode sequence of the second oligonucleotide probe.

20. A system for profiling spatiotemporal gene expression in a cell comprising a) a cell;

b) a pool of nucleoside analogs, wherein each nucleoside analog in the pool of nucleoside analogs comprises a reactive chemical moiety;

c) a population of first oligonucleotide probes, wherein each oligonucleotide probe in the population of first oligonucleotide probes comprises a chemical moiety that reacts with the reactive chemical moiety of the nucleoside analogs; and d) one or more pairs of oligonucleotide probes comprising a second oligonucleotide probe and a third oligonucleotide probe, wherein:

i) the second oligonucleotide probe comprises a barcode sequence and a portion that is complementary to a nucleic acid of interest; and ii) the third oligonucleotide probe comprises a portion that is complementary to the nucleic acid of interest, a first barcode sequence, a portion that is complementary to a first oligonucleotide probe in the population of first oligonucleotide probes, and a second barcode sequence, wherein the first barcode sequence of the third oligonucleotide probe is complementary to the barcode sequence of the second oligonucleotide probe.

* * * * *